US009243057B2

(12) United States Patent
Marks et al.

(10) Patent No.: US 9,243,057 B2
(45) Date of Patent: Jan. 26, 2016

(54) ANTIBODIES FOR BOTULINUM NEUROTOXINS

(75) Inventors: James D. Marks, Kensington, CA (US); Maria Consuelo Garcia Rodriguez, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 168 days.

(21) Appl. No.: 13/813,623

(22) PCT Filed: Aug. 31, 2011

(86) PCT No.: PCT/US2011/050050
§ 371 (c)(1),
(2), (4) Date: Aug. 9, 2013

(87) PCT Pub. No.: WO2012/047427
PCT Pub. Date: Apr. 12, 2012

(65) Prior Publication Data
US 2015/0030600 A1    Jan. 29, 2015

Related U.S. Application Data

(60) Provisional application No. 61/430,084, filed on Jan. 5, 2011, provisional application No. 61/378,862, filed on Aug. 31, 2010.

(51) Int. Cl.
*C07K 16/12* (2006.01)
*G01N 33/569* (2006.01)
*G01N 33/573* (2006.01)
*A61K 39/00* (2006.01)

(52) U.S. Cl.
CPC ...... *C07K 16/1282* (2013.01); *G01N 33/56911* (2013.01); *G01N 33/573* (2013.01); *A61K 2039/505* (2013.01); *A61K 2039/507* (2013.01); *C07K 2317/21* (2013.01); *C07K 2317/24* (2013.01); *C07K 2317/33* (2013.01); *C07K 2317/54* (2013.01); *C07K 2317/55* (2013.01); *C07K 2317/76* (2013.01); *C07K 2317/92* (2013.01); *G01N 2333/33* (2013.01)

(58) Field of Classification Search
None
See application file for complete search history.

(56) References Cited

U.S. PATENT DOCUMENTS

| 4,689,299 | A | 8/1987 | Insel et al. |
| 5,231,003 | A | 7/1993 | Coughlin et al. |
| 5,306,730 | A | 4/1994 | Nagai et al. |
| 5,599,539 | A | 2/1997 | Carroll et al. |
| 5,719,267 | A | 2/1998 | Carroll et al. |
| 5,731,161 | A | 3/1998 | Aoki et al. |
| 5,807,741 | A | 9/1998 | Brown et al. |
| 5,919,665 | A | 7/1999 | Williams |
| 5,932,449 | A | 8/1999 | Emanuel et al. |
| 6,331,402 | B1 | 12/2001 | Nussbaum et al. |
| 6,416,947 | B1 | 7/2002 | Balasubramanian et al. |
| 6,461,617 | B1 | 10/2002 | Shone et al. |
| 6,495,143 | B2 | 12/2002 | Lee et al. |
| 6,656,468 | B1 | 12/2003 | Carroll et al. |
| 6,667,158 | B1 | 12/2003 | Bavari et al. |
| 6,730,324 | B2 | 5/2004 | Troczynski et al. |
| 6,762,280 | B2 | 7/2004 | Schmidt et al. |
| 6,794,128 | B2 | 9/2004 | Marks et al. |
| 6,841,156 | B2 | 1/2005 | Aoki et al. |
| 6,932,449 | B2 | 8/2005 | Collins et al. |
| 7,049,085 | B2 | 5/2006 | Bavari et al. |
| 7,081,529 | B2 | 7/2006 | Smith et al. |
| 7,157,562 | B1 | 1/2007 | Olsen, II et al. |
| 7,192,596 | B2 | 3/2007 | Shone et al. |
| 7,214,787 | B1 | 5/2007 | Smith et al. |
| 7,244,826 | B1 | 7/2007 | Marks et al. |
| 7,332,580 | B2 | 2/2008 | Adams et al. |
| 7,332,585 | B2 | 2/2008 | Adams et al. |
| 7,341,843 | B2 | 3/2008 | Atassi |
| 7,563,874 | B2 | 7/2009 | Marks et al. |
| 7,700,738 | B2 | 4/2010 | Marks et al. |
| 7,999,079 | B2 | 8/2011 | Marks et al. |
| 8,198,034 | B2 | 6/2012 | Fernandez-Salas et al. |
| 8,263,747 | B2 | 9/2012 | Marks et al. |
| 8,299,218 | B2 | 10/2012 | Marks et al. |
| 8,329,873 | B2 | 12/2012 | Adams et al. |
| 8,476,024 | B2 | 7/2013 | Mahrhold et al. |
| 8,598,321 | B2 * | 12/2013 | Marks et al. ............. 530/388.15 |
| 8,618,261 | B2 | 12/2013 | Ester et al. |

(Continued)

FOREIGN PATENT DOCUMENTS

| EP | 0578515 | 1/1994 |
| WO | WO 9410332 | 5/1994 |

(Continued)

OTHER PUBLICATIONS

Gessler et al, Applied and Environmental Microbiology, Dec. 2005, 71/12:7897-7903.*
Brown et al, Hybridoma, 1997, 16/5:447-456.*
Garcia et al, Human monoclonal antibodies binding botulinum neurotoxin types C, D, and mosaic neurotoxins C-D and D-C, Abstracts Toxins 2011 / Toxicon 68 (2013) 86-87 abstract only.*
Lou et al, Human Antibody Engineering for Prevention and Treatment of Botulinum Neurotoxin (BONT) Intoxication, Abstracts / Toxicon 93 (2015) S40-S41, Abstract #131.*
Paul, Wlilliam, E., (1993), "Fundamental Immunology", Raven Press, 9:292-295.
Zhang et al., (2012), "Simultaneous and sensitive detection of six serotypes of botulinum neurotoxin using enzyme-linked immunosorbent assay-based protein antibody microarrays", Analytical Biochemistry, 430:185-192.
Przedpelski et al., (2013), "Enhancing the Protective Immune Response against Botulism", Infection and Immunity, 81(7):2638-2644.

(Continued)

*Primary Examiner* — Nita M Minnifield
(74) *Attorney, Agent, or Firm* — Carol L. Francis; Brian E. Davy; Bozicevic, Field & Francis LLP

(57) ABSTRACT

The present disclosure provides antibodies that specifically bind to botulinum neurotoxins (e.g., BoNT/A, BoNT/B, BoNT/C, BoNT/D, BoNT/E, BoNT/F, BoNT/G, etc.) and the epitopes bound by those antibodies. The antibodies and derivatives thereof that specifically bind to the neutralizing epitopes provided herein can be used to neutralize botulinum neurotoxin and are therefore also useful in the treatment of botulism.

23 Claims, 39 Drawing Sheets

(56) References Cited

U.S. PATENT DOCUMENTS

| | | | |
|---|---|---|---|
| 8,974,792 | B2* | 3/2015 | Marks et al. ............... 424/179.1 |
| 9,000,131 | B2* | 4/2015 | Marks et al. ............... 424/167.1 |
| 9,023,352 | B2 | 5/2015 | Shoemaket et al. |
| 2002/0155114 | A1 | 10/2002 | Marks et al. |
| 2004/0009172 | A1 | 1/2004 | Fischkoff et al. |
| 2004/0137601 | A1 | 7/2004 | Von Eichel-Streiber et al. |
| 2004/0265935 | A1 | 12/2004 | Atassi |
| 2005/0147610 | A1 | 7/2005 | Ghayur et al. |
| 2006/0147471 | A1 | 7/2006 | Borodic et al. |
| 2006/0177881 | A1 | 8/2006 | Bavari et al. |
| 2006/0246071 | A1 | 11/2006 | Green et al. |
| 2006/0251658 | A1 | 11/2006 | Ledbetter et al. |
| 2008/0125328 | A1 | 5/2008 | Wyrick et al. |
| 2010/0166773 | A1 | 7/2010 | Marks et al. |
| 2010/0222555 | A1 | 9/2010 | Dessain et al. |
| 2011/0059079 | A1 | 3/2011 | Babuka et al. |
| 2011/0200615 | A1 | 8/2011 | Marks et al. |
| 2012/0121581 | A1 | 5/2012 | Babuka et al. |
| 2012/0177663 | A1 | 7/2012 | Marks et al. |
| 2012/0225436 | A1 | 9/2012 | Fernandez-Salas et al. |
| 2012/0269822 | A1 | 10/2012 | Marks et al. |
| 2013/0040368 | A1 | 2/2013 | Fernandez-Salas et al. |
| 2014/0105910 | A1* | 4/2014 | Marks et al. ............... 424/167.1 |
| 2015/0030600 | A1* | 1/2015 | Marks ................. C07K 16/1282 424/139.1 |
| 2015/0197559 | A1* | 7/2015 | Marks ................. C07K 16/1282 424/167.1 |

FOREIGN PATENT DOCUMENTS

| | | |
|---|---|---|
| WO | WO 9625669 | 8/1996 |
| WO | WO 9956129 | 11/1999 |
| WO | WO 0069891 | 11/2000 |
| WO | WO 0069895 | 11/2000 |
| WO | WO 0119992 | 3/2001 |
| WO | WO 03057857 | 7/2003 |
| WO | WO 2004106376 | 12/2004 |
| WO | WO 2005084361 | 9/2005 |
| WO | WO 2005118635 | 12/2005 |
| WO | WO 2007094754 | 8/2007 |
| WO | WO 2008097866 | 8/2008 |
| WO | WO 2009105150 | 8/2009 |
| WO | WO 2009131605 | 10/2009 |
| WO | WO 2011028961 | 3/2011 |
| WO | WO 2011028962 | 3/2011 |

OTHER PUBLICATIONS

U.S. Appl. No. 13/614,771, filed Sep. 13, 2012, Marks et al.
Amersdorfer & Marks (2000) "Phage libraries for generation of anti-botulinum scFv antibodies" *Meth. Mol. Biol.* 145:219-240.
Arndt, et al. (2005) "The structure of the neurotoxin-associated protein HA33/A from *Clostridium botulinum* suggests a reoccurring beta-trefoil fold in the progenitor toxin complex" *J. Mol. Biol.* 346(4):1083-1093.
Baldwin, et al. (2005) "Characterization of the antibody response to the receptor binding domain of botulinum neurotoxin serotypes A and E" *Infect. Immun.* 73(10): 6998-7005.
Bendig (1995) "Humanization of Rodent Monoclonal Antibodies by CDR Grafting" *Methods: Companion to Methods in Enzymology* 8:83-93.
Black & Dolly (1986) "Interaction of 125I-labeled botulinum neurotoxins with nerve terminals. I. Ultrastructural autoradiographic localization and quantitation of distinct membrane acceptors for types A and B on motor nerves" *J. Cell Biol.* 103(2):521-534.
Bowmer (1963) "Preparation and Assay of the International Standards for *Clostridium botulinum* Types A, B, C, D and E Antitoxins" *Bull. World Health Organ.* 29:701-709.
Brown, et al. (1997) "Identification and Characterization of a Neutralizing Monoclonal Antibody against Botulinum Neurotoxin Serotype F, Following Vaccination with Active Toxin" *Hybridoma* 16(5):447-456.
Byrne & Smith (2000) "Development of vaccines for prevention of botulism" *Biochimie* 82(9-10): 955-966.

Casset, et al. (2003) "A peptide mimetic of an anti-CD4 monoclonal antibody by rational design" *Biochem Biophys. Res Comm.* 307(1):198-205.
Cenci Di Bello, et al. (1994) "Antagonism of the Intracellular Action of Botulinum Neurotoxin Type A with Monoclonal Antibodies That Map to Light-Chain Epitopes" *Eur. J. Biochem.* 219(1-2):161-169.
Chen, et al. (1998) "Biophysical characterization of the stability of the 150-kilodalton botulinum toxin, the nontoxic component, and the 900-kilodalton botulinum toxin complex species" *Infect. Immun.* 66(6):2420-2425.
Colcher et al. (1990) "In vivo tumor targeting of a recombinant single-chain antigen-binding protein" *J. Natl. Cancer Inst.* 82(14):1191-1197.
Daniels-Holgate & Dolly (1996) "Productive and non-productive binding of botulinum neurotoxin A to motor nerve endings are distinguished by its heavy chain" *J. Neurosci. Res.* 44(3):263-271.
Dixit et al. (2005) "Characterization of *Clostridium* sp. RKD producing botulinum-like Neurotoxin" *Syst. Appl. Microbiol.* 28(5):405-414.
Dixit et al. (2006) Development of an immunodetection test for a botulinum-like neurotoxin produced by *Clostridium* sp. *Indian J Med Res*. 124(3):355-362.
Doellgast, et al. (1993) "Sensitive enzyme-linked immunosorbent assay for detection of *Clostridium botulinum* neurotoxins A, B, and E using signal amplification via enzyme-linked coagulation assay" *J. Clin. Microbiol.* 31(9):2402-2409.
Doellgast, et al. (1997) "Sensitive assay for measurement of antibodies to *Clostridium botulinum* neurotoxins A, B, and E: use of hapten-labeled-antibody elution to isolate specific complexes" *J. Clin. Microbiol.* 35(3):578-583.
Dolly, et al. (1984) "Acceptors for botulinum neurotoxin reside on motor nerve terminals and mediate its internalization" *Nature (London)* 307(5950):457-460.
Emanuel, et al. (1996) "Directing antigen specificity towards botulinum neurotoxin with combinatorial phage display libraries" *J. Immunol. Meth.* 193(2):189-197.
Ferreira, et al. (1987) "Monoclonal Antibody for the Detection of *Clostridium botulinum* Type A toxin" *Mol. Cell Probes* 1(4):337-345.
Ferreira, et al. (1990) "Monoclonal antibody to type F *Clostridium botulinum* toxin" *Appl. Environ Microbiol.* 56(3):808-811.
Fitzsimmons, et al. (2000) "Inhibition of tetanus toxin fragment C binding to ganglioside G(T1b) by monoclonal antibodies recognizing different epitopes" *Vaccine* 19(1):114-121.
Foote & Milstein (1991) "Kinetic maturation of an immune response" *Nature* 352(6335):530-532.
Fotinou, et al. (2001) "The crystal structure of tetanus toxin Hc fragment complexed with a synthetic GT1b analogue suggests cross-linking between ganglioside receptors and the toxin" *J. Biol. Chem.* 276(34):32274-32281.
Garcia-Rodriguez, et al. (2007) "Molecular evolution of antibody specificity and cross reactivity for type A botulinum neurotoxins" *Nature Biotech.* 25(1):107-116.
Gibson, et al. (1988) "Evaluation of a monoclonal antibody-based immunoassay for detecting type B *Clostridium botulinum* toxin produced in pure culture and an inoculated model cured meat system" *J. Appl. Bacterial.* 64(4):285-291.
Gill (1982) "Bacterial Toxins: A Table of Lethal Amounts" *Mol. Biol. Rev.* 46(1):86-94.
Hallis, et al. (1993) "Characterization of Monoclonal Antibodies to Botulinum" *Botulinum and Tetanus Neurotoxins: Neurotransmission and Biomedical Aspects*, ed. DasGupta, B. R. Plenum, New York., pp. 433-436.
Hathaway, et al. (1984) "Antitoxin levels in botulism patients treated with trivalent equine botulism antitoxin to toxin types A, B, and E" *J. Infect. Dis.* 150(3):407-412.
Hatheway & Dang (1994) "Immunogenicity of the Neurotoxins of *Clostridium botulinum*" *Therapy with Botulinum Toxin* ed. Jankovic & Hallet, Marcel Dekker, New York, pp. 93-107.
Hildebrand & Archer (1961) "Evidence Concerning Liquid Structure" *PNAS USA* 47(12):1881-1882.

(56) References Cited

OTHER PUBLICATIONS

Hildebrand, et al. (1961) "Distribution and Particle Size of Type A Botulinum Toxin in Body Fluids of Intravenously Injected Rabbits" *Proc. Soc. Exp. Biol. Med.* 107(2):284-289.
Huston, et al. (1996) "Single-chain Fv radioimmunotargeting" Q. J. Nucl. Med. 40(3):320-333.
Koriazova & Montal (2003) "Translocation of botulinum neurotoxin light chain protease through the heavy chain channel" *Nat. Struct. Biol.* 10(1):13-18.
Kozaki, et al. (1986) "The use of monoclonal antibodies to analyze the structure of *Clostridium botulinum* type E derivative toxin" *Infect Immun.* 52(3):786-791.
Lacy, et al. (1998) "Crystal structure of botulinum neurotoxin type A and implications for toxicity" *Nat. Struct. Biol.* 5(10): 898-902.
Lang, et al. (1993) "Immunotherapy with human monoclonal antibodies. Fragment A specificity of polyclonal and monoclonal antibodies is crucial for full protection against tetanus toxin" *J. Immunol.* 151(13):466-472.
Levy, et al. (2007) "Fine and domain-level epitope mapping of botulinum neurotoxin type A neutralizing antibodies by yeast surface display" *J. Mol. Biol.* 365(1):196-210.
Lipps & Khan (2000) "Antigenic cross reactivity among the venoms and toxins from unrelated diverse sources" *Toxicon.* 38(7):973-980.
MacCallum, et al. (1996) "Antibody-antigen Interactions: Contact Analysis and Binding Site Topography" *J. Mol. Biol.* 262(5):732-45.
Mahant, et al. (2000) "The current use of botulinum toxin" *J. Clin. Neurosci.* 7(5):389-394.
Marchev & Marcheva (1982) "[Production of MonoSpecific Type A Botulinum Toxin and Antiserum Using a Column Chromatographic Method]" *Vet. Med. Nauki.* 19(1):57-63.
Middlebrook & Brown (1995) "Immunodiagnosis and immunotherapy of tetanus and botulinum neurotoxins" *Curr. Top. Microbiol. Immunol.* 195:89-122.
Montecucco & Schiavo (1995) "Structure and function of tetanus and botulinum neurotoxins" *Q. Rev. Biophys.* 28(4):423-472.
Montecucco (1986) "How do Tetanus and Botulinum Toxins Bind to Neuronal Membranes?" *Trends Biochem. Sci.* 11(8):314-317.
Montero-Julian, et al. (1995) "Pharmacokinetic study of anti-interleukin-6 (IL-6) therapy with monoclonal antibodies: enhancement of IL-6 clearance by cocktails of anti-IL-6 antibodies" *Blood* 85(4): 917-924.
Noah, et al. (1995) "Production of Monoclonal Antibodies Specific to *Clostridium botulinum* Type B Neurotoxin" *J. AOAC Int.* 78(2):381-385.
O'Connell, et al. (2007) "Production of a recombinant antibody fragment in whole insect larvae" *Mol Biotechnol.* 36(1): 44-51.
Oguma, et al. (1982) "Four different monoclonal antibodies against type C1 toxin of *Clostridium botulinum*" *Infect. Immun.* 38(1):14-20.
Oguma, et al. (1984) "Analysis of antigenicity of *Clostridium botulinum* type C1 and D toxins by polyclonal and monoclonal antibodies" *Infect Immun.* 43(2):584-588.
Palys, et al. (2006) "Conversion of a mouse Fab into a whole humanized IgG antibody for detecting botulinum toxin" *Hum Antibodies* 15(4):125-132.
Park, et al. (2003) "Immunologic characterization of spasmodic dysphonia patients who develop resistance to botulinum toxin" *J. Voice.* 17(2):255-264.
Pless, et al. (2001) "High-affinity, protective antibodies to the binding domain of botulinum neurotoxin type A" *Infect. Immun.* 69(1):570-574.
Reichert (2001) "Monoclonal antibodies in the clinic" *Nat. Biotechnol.* 19(9):819-822.
Schengrund (1999) "What is the Cell Surface Receptor(s) for the Different Serotypes of Botulinum Neurotoxin?" *J Toxicol.—Toxin Rev.* 18(1):35-44.
Schiavo, et al. (1992) "Tetanus and botulinum-B neurotoxins block neurotransmitter release by proteolytic cleavage of synaptobrevin" *Nature (London)* 359(6398):832-835.

Schiavo, et al. (1993) "Identification of the nerve terminal targets of botulinum neurotoxin serotypes A, D, and E" *J. Biol. Chem.* 268(32):23784-23787.
Schier, et al. (1995) "In vitro and in vivo characterization of a human anti-c-erbB-2 single-chain Fv isolated from a filamentous phage antibody library" *Immunotechnology*, 1(1):73-81.
Schmidt & Stafford (2005) "Botulinum neurotoxin serotype F: identification of substrate recognition requirements and development of inhibitors with low nanomolar affinity" *Biochemistry* 44(10):4067-4073.
Sharma, et al. (2006) "Detection of type A, B, E, and F *Clostridium botulinum* neurotoxins in foods by using an amplified enzyme-linked immunosorbent assay with digoxigenin-labeled antibodies" *Appl Environ. Microbiol.* 72(2):1231-1238.
Simpson (1980) "Kinetic studies on the interaction between botulinum toxin type A and the cholinergic neuromuscular junction" *J. Pharmacol. Exp. Ther.* 212(1):16-21.
Tacket et al. (1984) "Equine antitoxin use and other factors that predict outcome in type A foodborne botulism" *Am. J. Med.* 76(5):794-798.
Tsuzuki, et al. (1988) "Establishment of a monoclonal antibody recognizing an antigenic site common to *Clostridium botulinum* type B, C1, D, and E toxins and tetanus toxin" *Infect Immun.* 56(4):898-902.
Volk, et al. (1984) "Neutralization of tetanus toxin by distinct monoclonal antibodies binding to multiple epitopes on the toxin molecule" *Infect. Immun.* 45(3):604-609.
Williams, et al. (1983) "Radioiodination of botulinum neurotoxin type A with retention of biological activity and its binding to brain synaptosomes" *Eur. J. Biochem.*, 131(2):437-445.
Wu, et al. (2001) "Characterization of neutralizing antibodies and identification of neutralizing epitope mimics on the *Clostridium botulinum* neurotoxin type A" *Appl. Environ. Microbiol.* 67(7):3201-3207.
Arnon (1993) "Clinical Trial of Human Botulism" *Botulinum and Tetanus Neurotoxins: Neurotransmission and Biomedical Aspects*, ed. DasGupta, B. R. Plenum, New York., pp. 477-482.
Arnon et al. (2001) "Botulinum toxin as a biological weapon: medical and public health management" *JAMA* 285(8):1059-1070.
Berzofsky, et al. (1993) "Immunogenicity and Antigen Structure" *Fundamental Immunology* 3rd edition, Ed. William E. Paul, Chapter 8, p. 242.
Black & Gunn (1980) "Hypersensitivity reactions associated with botulinal antitoxin" *Am. J. Med.* 69(4): 567-570.
Franz, et al. (1993) "Efficacy of Prophylactic and Therapeutic Administration of Antitoxin for Inhalation Botulism" *Botulinum and Tetanus Neurotoxins: Neurotransmission and Biomedical Aspects*, ed. DasGupta, B. R. Plenum, New York., pp. 473-476.
Hatheway (1995) "Botulism: the present status of the disease" *Curr Top. Microbiol. Immunol*, 195:55-75.
Hibbs, et al. (1996) "Experience with the use of an investigational F(ab')2 heptavalent botulism immune globulin of equine origin during an outbreak of type E botulism in Egypt" *Clin. Infect. Dis.* 23(2):337-340.
Kozaki, et al. (1998) "Characterization of *Clostridium botulinum* type B neurotoxin associated with infant botulism in japan" *Infect. Immun.* 66(10):4811-4816.
Lacy & Stevens (1999) "Sequence homology and structural analysis of the clostridial neurotoxins" *J. Mol. Biol.* 291(5):1091-1104.
Middlebrook & Franz (1997) "Botulinum Toxins" *Medical Aspects of Chemical and Biological Warfare* Ed. Sidell, et al. TMM publications, Washington, D.C., Chapter 33, pp. 643-654.
Oguma et al. (1990) "Infant botulism due to *Clostridium botulinum* type C toxin" *Lancet* 336(8728):1449-1450.
Siegel (1988) "Human immune response to botulinum pentavalent (ABCDE) toxoid determined by a neutralization test and by an enzyme-linked immunosorbent assay" *J. Clin. Microbiol.* 26(11):2351-2356.
Sonnabend, et al. (1981) "Isolation of *Clostridium botulinum* type G and identification of type G botulinal toxin in humans: report of five sudden unexpected deaths" *J. Infect. Dis.* 143(1):22-27.

(56) References Cited

OTHER PUBLICATIONS

Almquist, et al. (2006) "Expression of an anti-botulinum toxin A neutralizing single-chain Fv recombinant antibody in transgenic tobacco" *Vaccine* 24(12):2079-2086.

Amersdorfer (1997) "Molecular Characterization of Murine Humoral Immune Response to Botulinum Neurotoxin Type A Binding Domain as Assessed by Using Phage Antibody Libraries" *Infect. Immun.* 65(9):3743-3752.

Amersdorfer, et al. (2002) "Genetic and Immunological Comparison of Anti-Botulinum Type A Antibodies from Immune and Non-Immune Human Phage Libraries" *Vaccine* 20(11-12):1640-1648.

Atassi, et al. (1996) "Mapping of the Antibody-Binding Regions on Botulinum Neurotoxin H-Chain Domain 855-1296 with Antitoxin Antibodies from Three Host Species" *J. Protein Chem.* 15(7):691-699.

Bartels et al. (1994) "Specific Antibodies against the Zn(2+)-Binding Domain of Clostridial Neurotoxins Restore Exocytosis in Chromaffin Cells Treated with Tetanus or Botulinum A Neurotoxin" *J Biol Chem* 269(11):8122-8127.

Bavari, et al. (1998) "Identifying the principal protective antigenic determinants of type A botulinum neurotoxin" *Vaccine* 16(19):1850-1856.

Boder, et al. (2000) "Directed Evolution of Antibody Fragments withMonovalent Femtomolar Antigen-Binding Affinity" PNAS USA 97(20):10701-10705.

Boles, et al. (2006) "Recombinant C Fragment of Botulinum Neurotoxin B Serotype (rBoNTB(HC)) Immune Response and Protection in the Rhesus Monkey" *Toxicon* 47(8):877-884.

Caton, et al. (1986) "Structural and functional implications of a restricted antibody response to a defined antigenic region on the influenza virus hemagglutinin" *EMBO J.* 5(7):1577-1587.

Chen, et al. (1997) "Antibody Mapping to Domains of Botulinum Neurotoxin Serotype A in the Complexed and Uncomplexed Forms" *Infect. Immun.* 65(5):1626-1630.

Coleman et al. (2004) "Methods: Recombinant DNA Technology" *FASEB Journal* 18(8):Suppl. S:C174, Meeting abstract, Abstract Only.

Colman (1994) "Effects of Amino Acid Sequence Changes on Antibody-Antigen Interactions" Res. Immunol. 145(1):33-36.

Dolimbek, et al. (2008) "Immune recognition of botulinum neurotoxin B: Antibody binding regions on the heavy chain of the toxin" *Mol. Immunol.* 45(4):910-924.

Dong et al. (2010) "A Single-Domain Llama Antibody Potently Inhibits the Enzymatic Activity of Botulinum Neurotoxin by Binding to the Non-Catalytic Alpha-Exosite Binding Region" *J Mol Biol* 397(4):1106-1118.

Emanuel, et al. (2000) "Recombinant antibodies: a new reagent for biological agent detection" *Biosen. Bioelectron.* 14(10-11):751-759.

Gilsdorf et al. (2006) "Expression Purification, and Characterization of Clostridium Botulinum Type B Light Chain" *Protein Expr Purif* 46(2):256-267.

Goldman et al. (2008) "Thermostable Llama Single Domain Antibodies for Detection of Botulinum A Neurotoxin Complex" *Anal Chem* 80(22):8583-8591.

Gonzales, et al. (2005) "Minimizing the Immunogenicity of Antibodies for Clinical Application" Tumour Biol. 26(1):31-43.

Hall (2004) "Novel Application of an In Vitro Technique to the Detection and Quantification of Botulinum Neurotoxin Antibodies" *J. Immunol. Methods* 288(1-2):55-60.

Jung & Plückthun (1997) "Improving In Vivo Folding and Stability of a Single-Chain Fv Antibody Fragment by Loop Grafting" *Protein Eng.* 10(8):959-66.

Kozaki, et al. (1995) "Immunological characterization of the neurotoxin produced by *Clostridium botulinum* type A associated with infant botulism in Japan" *Microbiol. Immunol.* 39(10):767-774.

Lebecque & Gearhart (1990) "Boundaries of somatic mutation in rearranged immunoglobulin genes: 5' boundary is near the promoter, and 3' boundary is approximately 1 kb from V(D)J gene" *J. Exp. Med.* 172(6):1717-1727.

Lee et al. (2008) "Production and characterization of monoclonal antibody to botulinum neurotoxin type B light chain by phage display" *Hybridoma (Larchmt)* 27(1):18-24.

Levy, et al. (1989) "Early onset of somatic mutation in immunoglobulin VH genes during the primary immune response" *J. Exp. Med.* 169(6):2007-2019.

Liu et al. (2007) "Isolation of Anti-Toxin Single Domain Antibodies from a Semi-Synthetic Spiny Dogfish Shark Display Library" *BMC Biotechnol* 7:78.

Mah, et al. (2003) "Recombinant anti-botulinum neurotoxin A single-chain variable fragment antibody generated using a phage display system" *Hybrid Hybridomics.* 22(5):277-283.

Marks (2004) "Deciphering antibody properties that lead to potent botulinum neurotoxin neutralization" *Mov. Disord.* 19(Suppl. 8):S101-S108.

Mcheyzer-Williams (1993) "B Lymphocyte Biology" *Fundamental Immunology*, 3rd Edition, Ed. William E. Paul Raven Press: NY, Chapter 9, pp. 292-295.

McKean, et al. (1978) "Mechanisms of antibody diversity: multiple genes encode structurally related mouse κ variable regions" *PNAS USA* 75(8):3913-3917.

Meng et al. (2012) "Engineered domain-based assays to identify individual antibodies in oligoclonal combinations targeting the same protein" *Anal Biochem* 430(2):141-150.

Mowry, et al. (2004) "Production and purification of a chimeric monoclonal antibody against botulinum neurotoxin serotype A" *Protein Expr. Purif.* 37(2):399-408.

Mullaney, et al. (2001) "Epitope Mapping of Neutralizing Botulinum Neurotoxin A Antibodies by Ohage Display" *Infect. Immun.* 69(10):6511-6514.

Nowakowski, et al. "Potent Neutralization of Botulinum Neurotoxin by Recombinant Oligoclonal Antibody" *PNAS USA* 99(17):11346-11350.

Oshima (1997) "Immune Recognition of Botulinum Neurotoxin Type A: Regions Recognized by T cells and Antibodies against the Protective H(C) Fragment (residues 855-1296) of Toxin" *Mol. Immunol.* 34(14):1031-1040.

Padlan et al. (1989) "Structure of an antibody-antigen complex: crystal structure of the HyHEL-10 Fab-lysozyme complex" *Proc Natl Acad Sci USA* 86:5938-5942.

Razai, et al. (2005) "Molecular evolution of antibody affinity for sensitive detection and neutralization of botulinum neurotoxin type A" *J. Mol. Biol.* 351(1):158-169.

Rudikoff, et al. (1982) "Single Amino Acid Substitution Altering Antigen-Binding Specificity" *PNAS USA* 79(6):1979-1983.

Schier, et al. (1996) "Isolation of picomolar affinity anti-c-erbB-2 single-chain Fv by molecular evolution of the complementarity determining regions in the center of the antibody binding site" *J. Mol. Biol.* 263(4):551-567.

Scotcher, et al. (2009) "Characterization of the Epitope Region of F1-2 and F1-5, Two Monoclonal Antibodies to Botulinum Neurotoxin Type A" Hybridoma 28(5):315-325.

Shone, et al. (1985) "Monoclonal antibody-based immunoassay for type A *Clostridium botulinum* toxin is comparable to the mouse bioassay" *Appl Environ Microbiol.* 50(1):63-67.

Smith, et al. (2005) "Sequence variation within botulinum neurotoxin serotypes impacts antibody binding and neutralization" *Infect. Immun.* 73(9):5450-5457.

Stark & Caton (1991) "Antibodies that are specific for a single amino acid interchange in a protein epitope use structurally distinct variable regions" *J. Exp. Med.* 174(3):613-624.

Swaminathan & Eswaramoorthy (2000) "Structural Analysis of the Catalytic and Binding Sites of Clostridium Botulinum Neurotoxin B" *Nat Struct Biol* 7(8):693-699.

Thanongsaksrikul et al. (2010) "A V H H That Neutralizes the Zinc Metalloproteinase Activity of Botulinum Neurotoxin Type A" *J Biol Chem* 285(13):9657-9666.

Weigert, et al. (1978) "Rearrangement of genetic information may produce immunoglobulin diversity" *Nature* 276(5690):785-790.

Yang et al. (2004) "Isolation and characterization of a neutralizing antibody specific to internalization domain of Clostridium botulinum neurotoxin type B" *Toxicon* 44(1):19-25.

Zwick, et al. (2001) "Neutralization synergy of human immunodeficiency virus type 1 primary isolates by cocktails of broadly neutralizing antibodies" *J. Virol.* 75(24):12198-12208.

\* cited by examiner

A. Create $V_L$ gene repertoire by PCR 
B. Add scFv linker, section of $V_H$ FR4 and restriction sites by PCR
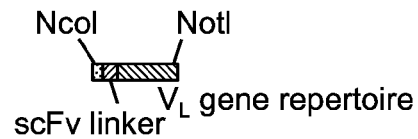
C. Clone, $V_H$ FR4-scFv linker-$V_K$ repertoire into Nco1-Not1 digested pYD2
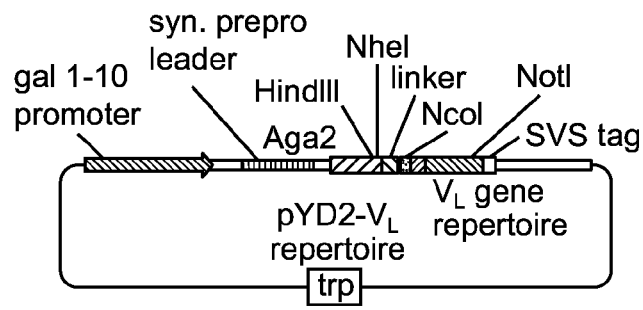
D. Amplify $V_H$ gene from wildtype scFv gene in pYD2 with 5' and 3' overhangs
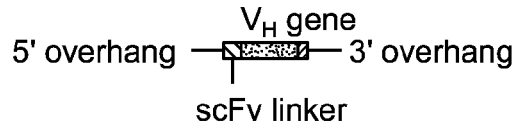
E. Clone $V_H$ gene by gap repair into NheI-NcoI pYD2-VL repertoire vector
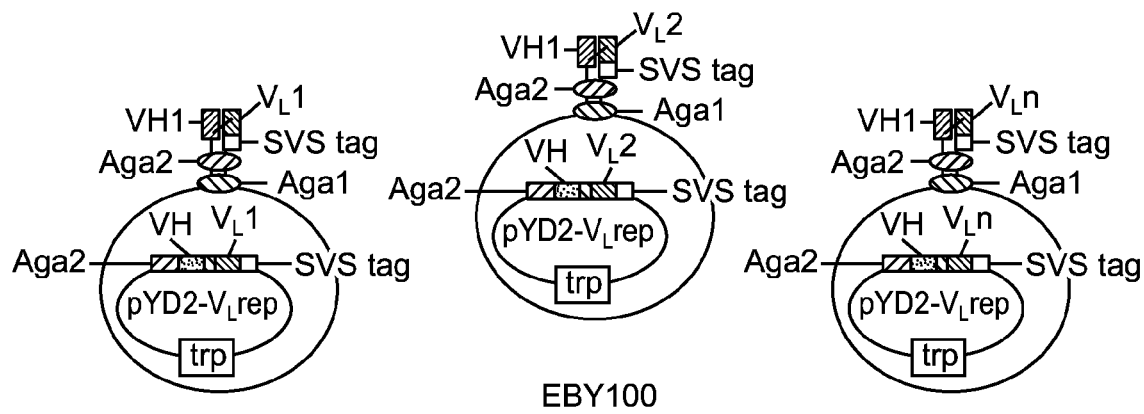
FIG. 2

BoNT/A LC binder (17 clones)

| VH/Clone | Framework1 | CDR1 | Framework2 | CDR2 | Framework3 |
|---|---|---|---|---|---|
| 6A1M | LQLKQSGPGLVKPSQSLSLTCSVTGYSITS | GYYWY | WIRQFPGNKLEWMG | YISYDGSNNYNPSLKN | RISITRDTSKNQFFLKLNSVTTEDTATYYCAR |
| 6A2M | EVQLQQSGAELVRPGTSVKLSCKKSSGYTFT | SDWMH | WVIQRPGQGLEWIG | VIDPSDSYTNYNQKFKG | KATLTVDTSSSTAYMHLSSLTSEDSAVYFCAR |
| 6A3M | EVQLQQSGAELVKPGASVKLSCKASGYTFT | SYWMH | WLKQRPGQGLEWIG | VIDPSDSYTNYNQKFKG | KATLTVDTSSSTAYMQLSSLTSEDSAVYYCAR |
| 6A4M | EVQLQQSGAELVRPGTSVKLSCKASGYTFT | SYWMH | WVKQRPGQGLEWIG | VIDPSDSYTNYNQKFKG | KATLTVDTSSSTAYMQLSSLASEDSAVYYCAR |
| 6A5M | DVQLQESGPGLVKPSQSLSLTCSVTGYSIT | GGYYWN | WIRQFPGNKLEWMG | YISYDGSNNYNPSLKN | RISITRDTSKNQFFLKLNSVTTEDTATYYCAR |
| 6A6M | QVQLKESGAELMKPGASVKLSCKATGYTFT | GYWIE | WVKQRPGHGLEWIG | EILPGSGSTNYNEKFKG | KATFTADTSSNTAYMQLSSLTTEDSAIYYCAS |
| 6A7M | EVKLVESGGDLVKPGGSLKLSCAASGFTFS | SYGMS | WVRQTPDKRLEWVA | TISSGGSYTTYYPDNVKG | RFTISRDNAKNNLFLQMSHLKSEDTAMYYCAR |
| 6A8M | QVQLKESGPGLVKPSQTVSLITCTVTGYSIT | NGNHWWN | WIRQVSGSKLEWIG | YISSSGYTDINPSLKS | RISITRDTSKNQLFLQLNSVTTEDIATYYCAR |
| 6A9M | QIQLLQSGAELVKPGASVKLSCTASGFNIK | DYYMH | WVKQRPEQGLEWIG | RIDPEDGDTEYAPKFQG | KATMTADTSSNTAYLQLSSLTSEDSAVYFCAR |
| 1C7 | EVQLQQSGAELVRPGASVKMSCKASGYTFT | SYNMH | WVKQTPRQGLEWIG | AIYPGNGDTSYNQKFKG | KATLTVDKSSSTAYMQLSSLTFEDSAVYYCAR |
| 1C10 | QIQLLQPGTELVRPGTSVKLSCKASGYTFT | NYWMH | WVKQRPGQGLEWIG | VIDPSDSYTNYNQKFKG | KATLTVDTSSSTAYMQLSSLTFEDSAVYYCAR |
| 1D8 | EVQLQQSGAELVRPGTSVKLSCKASGYTFT | SYWMH | WVKQRPGQGLEWIG | VIDPSDSYTNYNQKFKG | KATLTVDTSSSTAYMQLSSLTFEDSAVYYCAR |
| 1G11 | EVQLQQSGAELVRPGTSVKLSCKASGYTFT | SYWMH | WVKQRPGQGLEWIG | VIDPSDSYTNYNQKFKG | KATLTVDTSSSTAYMQLSSLTFEDSAVYYCAR |
| 1H5 | EVQLQQSGAELVRPGTSVKLSCKASDYTFT | NYWTH | WVKQRPGQGLEWIG | VIDPSDSYTNYNQKFKG | KATLTVDTSSSTAYMQLSSLTSEDSAVYYCAR |
| 9B2 | QVQLQQSGAELVKPGASVKLSCTASGFNIE | DDYMH | WVKQRPEQGQLEWIG | RIDPANGNTEYAPKFQD | KATTADTSSNTAYLQLSRLTSEDTAVYYCAR |
| 10C9 | QVQLQQSGAELVRPGTSVKLSCKASGYTFT | SHWMH | WVKQRPGQGLEWIG | VIDPSDSYTNYNQKFKG | KATLTVDTSSSTAYMQLSSLTSEDSAVYYCAR |
| 10H10 | QVQLQQSGAELVRPGTSVKLSCKASGYTFT | SYWMH | WVKQRPGQGLEWIG | VIDPSDSYTNYNQKFKG | KATLTVDTSSSTAYMQLSSLTSEDSAVYYCAI |

BoNT/A LC binder (17 clones)

| VH/Clone | CDR3 | Framework4 | | |
|---|---|---|---|---|
| 6A1M | NLGLWYFDV | WGTGTPLTVSS | | SEQ ID NO: 1 |
| 6A2M | REGHYYGKAMDY | WGQGTSVTVSS | | SEQ ID NO: 2 |
| 6A3M | GGNGFFDY | WGQGTTLTVSS | | SEQ ID NO: 3 |
| 6A4M | YPGNRAMDY | WGQGTSVTVSS | | SEQ ID NO: 4 |
| 6A5M | NMGLWYFDV | WGTGTPVTVSA | | SEQ ID NO: 5 |
| 6A6M | IYYGHDY | WGQGTTLTVSS | | SEQ ID NO: 6 |
| 6A7M | DWDYYYGSYWYFDV | WGTGTSVTVSS | | SEQ ID NO: 7 |
| 6A8M | DDGYYEALDY | WGQGTSVTVSS | | SEQ ID NO: 8 |
| 6A9M | LNYDYPYWYFDV | WGTGTTLTVSS | | SEQ ID NO: 9 |
| 1C7 | TAGFYFDY | WGQGTTLTVSA | | SEQ ID NO: 10 |
| 1C10 | YSGPYAMDY | WGQGTTLTVSS | | SEQ ID NO: 11 |
| 1D8 | GSSGYVNY | WGQGTTLTVSS | | SEQ ID NO: 12 |
| 1G11 | GGTGYFDY | WGQGTTVTVSS | | SEQ ID NO: 13 |
| 1H5 | GYYDTMDY | WGQGTTVTVSS | | SEQ ID NO: 14 |
| 9B2 | GGWLGNYYAMDY | WGQGTSVTVSS | | SEQ ID NO: 15 |
| 10C9 | RRNYGMDY | WGQGTSVTVSS | | SEQ ID NO: 16 |
| 10H10 | GGGRSSLDY | WGQGTSVTVSS | | SEQ ID NO: 17 |

FIG. 4 Panel A

FIG. 4 Panel A (Cont.)

FIG. 4 Panel B

BoNT/B LC binder (24 clones)

| VH/Clone | Framework1 | CDR1 | Framework2 | CDR2 | Framework3 |
|---|---|---|---|---|---|
| 16B3 | EVQLQQSGPELVKPGASVKITCKASGYTFT | DNNMD | WVKQSHGKSLEWIG | DINPNNGGSIYNQKFKG | KASLTLDKSSSTAYMELRSLTSEDTAVYYCAR |
| 16D5 | EVKLVESGAELVRPGASVKLSCTPSGFNIK | DDYMH | WVKRPEQGLEWIG | RIDPANGNTRYAPKFQD | KATLTADTSSNTAYLHLTSLTSEDTAVYYCAR |
| 18A6 | EVQLQQSGPELVKPGASVKISCKASGYTFT | DNYIN | WVKQRPGQGLEWIG | WIYPGSGNTKYNEKFKG | KATLTVDTSSNTAYMQLTGLASDDSAVFFCAR |
| 18A7 | DVQLQQSGIEVMKPGASVKLSCKASGYPFT | AYWIE | WVKQRPGHGLEWIG | EFLPGGISTNFNEKFKG | KATFSADTSSNSAYIQLNSLTTEDSAIYCVL |
| 18D10 | QVQLKQSGIEVMKPGASVKLSCKASGYPFT | AYWIE | WVKQRPGHGLEWIG | EFLPGGISTNFNEKFKG | KATFSADTSSNSAYIQLNSLTTEDSAIYCVL |
| 18E5 | EVQLQESGPELVKPGASVKISCKASGYTFT | DHNMD | WVKQSLGKSLEWIG | DINPNNGGAVYNQNFKG | KATLTVDKSSSTAYMELRSLTSEDTAVYYCAR |
| 18F2 | EVQLQQSGPELMKPGASVKISCKASGYAFS | RSWMN | WVKQRPGKGLEWIG | RIYPGDGDTNYNGKFKD | KASLTADTSSSTAYMQLSSLTSEDSAVFFCAR |
| 19A9 | EVQLQQPGSELARPGASVKLSCKASGYTFT | SYPIT | WVKQTTGQLEWIG | RIYPRSGNTYYNEKFKG | KATLTADKSSSTAYMELRSLTSEDSAVFFCAR |
| 19B6 | QVQLQQSGAELVKPGASVKISCKASGYTFT | DNYIN | WVKQRPGQGLEWIG | EIYPRSGNTYYNENFQG | KATLTVDTSSNTAYMQLSSLTSEDSAVFFCAR |
| 19D2 | EVQLQQSGGELARPGSSVKLSCKASGYSFT | GYSLT | WVKQTPGQGLEWIG | EIYPRSGNTYYNEKFKG | KATTTADESSSTAYMELRSLTSEDSAVFFCAR |
| 19D22 | QIQLLQSGAELVRPGTSVKMSCKAAGYPFT | SYWMG | WVKQRPGHGLEWIG | DIYPGGPYTNYNEKFKG | KATLTADTSSSTAYMQFSSLTSEDSAIYYCAL |
| 19D22.4 | QIQLLQSGAELVRPGTSVKMSCKAAGYPFT | SYWMG | WVKQRPGHGLEWIG | DIYPGGPYTNYNEKFKG | KATLTADTSSSTAYMQFSSLTSEDSAIYYCAL |
| 19G6 | QVQLQESGPELVKPGASVKMSCKASGYPFT | IYWIT | WVKQRPGQGLEWIG | EIYPGSGFTKYNEKFRS | KATLTVDTSSSTAYMQLSSLTSEDSAVYYCAL |
| 31A5 | DVQLQESGPELVKPGASVKISCKASGYSFT | DYNMN | WVKQSNGKSLEWIG | VINPNYGTTSYNQKFKG | KATLTVDQSSSTAYMQLNSLTSEDSAVYYCAR |
| 31A5.1 | DVQLQESGPELVKPGASVKISCKASGYSFT | DYNMN | WVKQSNGKSLEWIG | VINPNYGTTSYNQKFKG | KATLTVDQSSSTAYMQLNSLTSEDSAVYYCAR |
| 31C3 | EVKLVETGPELKKPGETVKISCKASGYTFT | NYGMN | WVKQAPGKGLKWMG | WINTNTGEPTYAEEFKG | RFAFSLETSASTAFLQINNLKNEDTATYFCAR |
| 31C3.5 | EVKLVETGPELKKPGETVKISCKASGYTFT | NYGMN | WVKQAPGKGLKWMG | WINTNTGEPTYAEEFKG | RFAFSLETSASTAFLQINNLKNEDTATYFCAR |
| 31C3.6 | EVKLVETGPELKKPGETVKISCKASGYTFT | NYGMN | WVKQAPGKGLKWMG | WINTNTGEPTYAEEFKG | RFAFSLETSASTAFLQINNLKNEDTATYFCAR |
| 31E2 | EVKLVESGAELVRPGASVKLSCTASGFNIK | DDYVH | WVKQRPEQGLEWIG | RIDPEDGETKYAPKFQG | KATITADTSSNTAYIQLSSLTSEDTAVYYCAL |
| 31E2.20 | EVKLVESGAELVRPGASVKLSCTASGFNIK | DDYVH | WVKQRPEQGLEWIG | RIDPEDGETKYAPKFQG | KATITADTSSNTAYIQLSSLTSEDTAVYYCAL |
| 31G2 | QVQLQQSGAELVRPGASVKMSCKASGYPFT | DTYMH | WVKQRPGQGLEWIG | RIDPEDGETKYAPKFQG | KATITADTSSNTAYLQLSSLTSEDTAVYYCAR |
| 31H3 | EVQLQQSGAELVRPGASVKMSCKASGYPFT | IYWIT | WVKQRPGQGLEWIG | EIYPGSGFTKYNEKFRS | KATLTVDTSSSTAYMQLSSLTSEDSAVYYCAL |
| 34E8 | QVQLVESGPDLVKPSQSLSLTCTVTGYSIT | SGYSWH | WIRQFPGNKLEWMG | YIHYSGSTNYNPSLKS | RISITRDTSKNQFFLQLNSVTTEDTATYYCAV |
| 34E8B12 | QVQLVESGPDLVKPSQSLSLTCTVTGYSIT | SGYSWH | WIRQFPGNKLEWMG | YIHYSGSTNYNPSLKS | RISITRDTSKNQFFLQLNSVTTEDTATYYCAV |

BoNT/B LC binder (24 clones)

| VH/Clone | CDR3 | Framework4 | |
|---|---|---|---|
| 16B3 | WGYYGSLAY | WGQGTLVTVSS | SEQ ID NO:18 |
| 16D5 | SYYRAWFDY | WGQGTLVTVSS | SEQ ID NO:19 |
| 18A6 | VNFYVSWDY | WGQGTSVTVSS | SEQ ID NO:20 |
| 18A7 | TGTGFDY | WGQGTTLTVSS | SEQ ID NO:21 |
| 18D10 | TGTGFDY | WGQGTSVTVSS | SEQ ID NO:22 |
| 18E5 | YGYYGYFDY | WGQGTTLTVSS | SEQ ID NO:23 |
| 18F2 | SEGYYHNLGAY | WGQGTTVTVSS | SEQ ID NO:24 |
| 19A9 | DYDYAGGGRGY | WGQGTTLTVSS | SEQ ID NO:25 |
| 19B6 | VGFRVNFDY | WGQGTTLTVSS | SEQ ID NO:26 |
| 19D2 | DFYDYDGGGRGY | WGQGTTLTVSS | SEQ ID NO:27 |
| 19D22 | YGQVGSYAMDY | WGQGTSVTVSS | SEQ ID NO:28 |
| 19D22.4 | YGQVGSYAMDY | WGQGTSVTVSS | SEQ ID NO:29 |
| 19G6 | YGSNFDY | WGQGTTLTVSS | SEQ ID NO:30 |
| 31A5 | SGGTGYYFDY | WGQGTTLTVSS | SEQ ID NO:31 |
| 31A5.1 | SGGTGYYFDY | WGQGTTLTVSS | SEQ ID NO:32 |
| 31C3 | GPIYYGTSYRFFDV | WGTGTSVTVSS | SEQ ID NO:33 |
| 31C3.5 | GPIYYGTSYRFFDV | WGTGTSVTVSA | SEQ ID NO:34 |
| 31C3.6 | GPIYYGTSYRFFDV | WGTGTSVTVSA | SEQ ID NO:35 |
| 31E2 | WSNWYFDV | WGAGTTVTVSS | SEQ ID NO:36 |
| 31E2.20 | WSNWYFDV | WGAGTTVTVSA | SEQ ID NO:37 |
| 31G2 | WLLYYYAMDY | WGQGTSVTVSA | SEQ ID NO:38 |
| 31H3 | YGSNFDY | WGQGTTLTVSS | SEQ ID NO:39 |
| 34E8 | YYDYDGDYFDY | WGQGTTLTVSS | SEQ ID NO:40 |
| 34E8B12 | YYDYDGDYFDY | WGQGTTLTVSS | SEQ ID NO:41 |

FIG. 4 Panel B (Cont.)

BoNT/B Hc binder (16 clones)

| VH/Clone | Framework1 | CDR1 | Framework2 | CDR2 | Framework3 |
|---|---|---|---|---|---|
| 26A10 | EVQLQQSGPELVKPGTSVKISCKASGYAFT | GPFMN | WVKQSHGKSLEWIG | RINPYNGDAFYNQKFKD | KATLTVDKSSTAHMELRSLTSDDSAVYYCAR |
| 26B2 | DVQLQESGPELVKPGASVKISCKASGYTFA | DYYIN | WVKQSHGKSLEWIG | DFNPNNGDHSYNQKFKD | KATLTVDESSNTAYMELRSLTSEDSAVYYCTR |
| 26C2 | QVQLKQSGPELVKPGASVKLSCKASGYTFT | SYDIN | WVKQRPGQGLEWIG | WIYPRDDITKYNEKFKD | KATLTVDTSSTAYMELHSLTSEDSAVYFCAR |
| 26C4 | ELKIVESGGGLVQPGGSLELSCAASGFTFS | NYGMS | WIRQTPDKRLELVA | TINSNGGTYYPDRVKG | RFTISRDNAKNTLYLQMSSLRFEDTAMFYCAR |
| 26D1 | EVQLKQSGAELVKPGASVKLSCTASGFNIK | DYYMH | WVKQRTEQGLEWIG | RIDPEDGETKYAPKFQG | KATITADTSSNTAYLQLSSLTSEATAVYYCVT |
| 26D9 | DVQLQESGAELVKPGASVKLSCKASGFTFT | DYWMH | WVKQRPGQGLEWIG | MIHPYNGDNNYHEKFKS | KATLTVDKSSTAYMQLSSLTTEDSAVYYCVR |
| 26D10 | EVQLQESGPGLVQPSQSLITCTVSGFSLT | NHGVH | WIRQSPGKGLEWIG | VIWRSGSRDYNVTFKSR | LSITKDNSKSQVFFKLNSLQADDTAIYYCAKI |
| 26D11 | EVQLQESGPELVKPGASVKISCMASGYPFT | GPFMN | WVKQSHGKSLEWIG | RINPYNGDAFYNPKFNG | KATLTVDKSSTAHMELRSLTSGDSAVYYCAR |
| 26E1 | QVQLQQSGAELVRPGASVKLSCTASGFNIK | DDYMH | WVKQRPEQGLEWIG | RIDPANGNTKYAPKFQD | KATITADTSSNTAYLQLSSLTSEDTAVYYCAR |
| 26E2 | QVQLQQSGAELVKPGASVKLSCKASGYTFT | TYWMH | WVKQRPGQGLEWIG | MIHPNTGGINYNEKFKS | KATLTVDKSSTAYMQLSGLTSEDSAVFYCAI |
| 26E6 | EVQLQQSGPELVKPGASVKISCKASGYTFA | DYYIN | WVKQSHGKSLEWIG | DFNPNNGDHSYNQKFKD | KATLTVDESSNTAYMELRSLTSEDSAVYYCTR |
| 26G5 | EVQLQESGPGLAKPSQTLSLTCSVTGYSIT | SDYWN | WIRKFPGNKLEYMG | YISYSGSTYYNPSLKSR | ISITRDTSKNQYYLQLNSVTTEDTATYYCARS |
| 26G11 | EVQLQQSGAELVKPGASVKISCKASGYAFT | GYNIN | WVKQSHGKSLEWIG | LVNPYYGSSTYNQMFKG | KATLTVDKSSTAYMQLNSLTSEDSAVYYCAK |
| 26H11 | EVQLLESGPELVKPGASVKISCKASGYAFT | GPFMN | WVKQSHGESLEWIG | RINPYNGDSFYNQKFKG | KATLTVDKSSTAHMELRSLTSDDSAVYYCAR |
| 1B12.3 | QVNLRESGGGVQPGRSLRLSCAASGFTFS | SYALH | WVRQTPGKGLEWVA | LISYDGSNKYYADSVKG | RFTISRDNSKNMLYLQMNSLRAEDTAVYYCAK |
| 1B12.4 | QVNLRESGGGVQPGRSLRLSCAASGFTFS | SYALH | WVRQTPGKGLEWVA | LISYDGSNKYYADSVKG | RFTISRDNSKNMLYLQMNSLRAEDTAVYYCAK |

FIG. 4 Panel C

BoNT/B Hc binder (16 clones)

| VH/Clone | CDR3 | Framework4 | |
|---|---|---|---|
| 26A10 | EYDGSYPYYDTLDY | WGQGTSVTVSS | SEQ ID NO:42 |
| 26B2 | EFYYYFDV | WGTGTSVTVSS | SEQ ID NO:43 |
| 26C2 | GDYYGSLDY | WGQGTTLTVSS | SEQ ID NO:44 |
| 26C4 | DGYYVYDY | WGQGTTLTVSS | SEQ ID NO:45 |
| 26D1 | SRAGAVY | WGQGTTLTVSS | SEQ ID NO:46 |
| 26D9 | NDYDPYYYALDY | WGQGTSLTVSA | SEQ ID NO:47 |
| 26D10 | GPRLGYFDV | WGAGTSVTVSS | SEQ ID NO:48 |
| 26D11 | EYDGRYPYYSTLDY | WGQGTSVTVSS | SEQ ID NO:49 |
| 26E1 | EGVYYYDGSYMRAMDY | WGQGTSVTVSS | SEQ ID NO:50 |
| 26E2 | LRVVPEAY | WGQGTLVTVSA | SEQ ID NO:51 |
| 26E6 | EFYYYFDV | WGTGTTVTVSS | SEQ ID NO:52 |
| 26G5 | FYDGYLYFDY | WGQGTTVTVSS | SEQ ID NO:53 |
| 26G11 | DYGNSYPYYFDF | WGQGTTLTVSS | SEQ ID NO:54 |
| 26H11 | EYGGSYPYYSTLDY | WGQGTSVTVSS | SEQ ID NO:55 |
| 1B12.3 | DRSHYGDYVGYLDY | WGQGTLVTVSS | SEQ ID NO:56 |
| 1B12.4 | DRSHYGDYVGYLDY | WGQGTLVTVSS | SEQ ID NO:57 |

FIG. 4 Panel C (Cont.)

BoNT/C, BoNT C/D, BoNT D/C, or /BoNT/D binder (47 clones)

| VH/Clone | Framework1 | CDR1 | Framework2 | CDR2 | Framework3 |
|---|---|---|---|---|---|
| 1C1 | QVQLQESGSGLVKPSQSLSLTCAVSGGSIS | SGDYSWS | WIRQPPGEGLEWIG | YIFPRGSTYYNPSLRS | RVTMSVDRSKNQFSLSLNSVTAADTAVYYCAR |
| 1C1.1 | QVQLQESGSGLVKPSQSLSLTCAVSGGSIS | SGDYSWS | WIRQPPGEGLEWIG | YIFPRGSTYYNPSLRS | RVTMSVDRSKNQFSLSLNSVTAADTAVYYCAR |
| 1C2 | QVQLQQSGAEVRKSGASVKVSCKTSGYTFT | TYYIH | WVRQAPGQGLEWMG | MIDPRGGSASYAQRFQG | RVTMTRDTSTTVFLALNSLESNDTAVYYCAR |
| 1C3 | QVQLQQSGAEVRKPGASVKVSCKTSGYTFT | TYYIH | WVRQAPGQGLEWMG | MIDPRGGSASYAQRFQG | RVTMTRDTSTTVFLALNSLESNDTAVYYCAR |
| 1C4 | QVQLQQSGAEVRKPGASVKVSCKTSGYTFT | TYYIH | WVRQAPGQGLEWMG | MIDPRGGSASYAQRFQG | RVTMTRDTSTTAFLALNSLESNDTAVYYCAR |
| 1C8 | QVQLQQSGAEVKKPGASVKVSCKASAFTFN | SNYIH | WVRLAPGQGPEWMG | IINPDGGRTTYAQKFQG | RITMTTDISTYAVYMELSSLRSEDTAVYYCAR |
| 87C1 | QVQLQQSGGGVVQPGRSLRLSCAGSGFTLS | TYGMH | WVRQAPGKGLEWVA | VISNDGSKEYYADSVKG | RFAISRDNSKNTLSLQMNGLRAEDTAIYYCAK |
| 87C2 | QVQLQESGGGVVQTGRSXRLSCEASGFTFS | TYGMH | WVRQPPGKGLEWVA | AVSNDGSDKYTDSVRG | RFTISRDNSKNAGYLQMNSLRAEDTAMYCAK |
| 87C78 | QVQLVESGGGVVQPGKSLRLSCVTSTFTLG | TYAMH | WVRQAPGKGLQWVA | VLSYDGRYADYADSVKS | RFNISRDNSKNTLYLQMHSLTTEDTALYYCAK |
| 4C1 | QVQLQESGPGLVQPGTLSLTCAVSGGSIN | SGDYWT | WIRQHPGKGLEWIG | NIYYTGRTYYNPSLQS | RLTMSVDTSRTHFSLKLSAVTAADTAVYYCAR |
| 4C2 | EVQLVQSGGNLVQPGGSLRLSCTASGFIFS | NHWMQ | WVRQIPGKGLMWVS | RINDGSRSTSYAGFVKG | RFTMSRDNAKNTLFLQMNSLTAEDTGVYYCVR |
| 4C3 | EVQLVQSGAEVKKPGSSVKVSCKASGNSLN | NYAIT | WVRQAPGQGLEWMG | GINPLFGTANYAQKFQD | RVTMTADESTNIAYLDLSLLTADTAVYFCAV |
| 4C4 | QVQLVESGPGLVKPSQTLSLTCSVSGASIN | NSPYFWN | WFRQFPGKGLEWIG | YIYWSGSTNYNPSLKS | RLAMSVDTSKNQFSLKLTSATAADTAVYYCAR |
| 4C4.1 | QVQLVESGPGLVKPSQTLSLTCSVSGASIN | NSPYFWN | WFRQFPGKGLEWIG | YIYWSGSTNYNPSLKS | RLAMSVDTSKNQFSLKLTSATAADTAVYYCAR |
| 4C4.2 | QVQLVESGPGLVKPSQTLSLTCSVSGASIN | NSPYFWN | WFRQFPGKGLEWIG | YIYWSGSTNYNPSLKS | RLAMSVDTSKNQFSLKLTSATAADTAVYYCAR |
| 4C5 | QVQLVESGGADVKKPGASVRVSCKASGYTIS | TYAMS | WVRQAPGQGLEWMG | WISGYNGNTNYAQFQG | RVTMTRDTSTNTAYMELRSLRSDDTAFYYCAR |
| 4C6 | QVQLVESGGADVKKPGASVRVSCKASGYTIS | SFALS | WVRQAPGRGLEWMG | WISGYNGNTNYAQDFQG | RVTMTRDTSTNTAYLELRSITSDDMALYYCAR |
| 4C7 | QVQVVQSGGGLVQPGGSLRLSCAGSGFTFS | TYAMS | WVRQAPGKGLELVS | GISFGGDNTHQADSVKG | RFTISRVDSKSTLYLQMNRMRTEDTVVYYCEK |
| 4C8 | QVQLVESGGGLVQPGRSLRLSCAASGLTLS | NYWMN | WVRQAPGKGLEWVA | NIHQDGVEKYYVDSVKG | RFTISRDNAKNSLYLQMSSLRAEDTAVYYCAR |
| 4C9 | QVQLVESGAEVKKPGASVKVSCTASGLTLS | GYYMD | WVRQAPGQGLEWMG | RINPKSGDPNYEQKFQG | RVTLTRDKSINTVYMELSRLKSDDTAIYYCAR |
| 4C10 | QVQLVESGGGAVQPGESLRLSCAASGFTFS | GFDMH | WVRQSPGRGLEWVA | RISHDGSMADYADSLRG | RFTISRDNPKNTLYLHMNSLRVEDTALYYCAK |
| 4C10.1 | QVQLVESGGGVVQPGRSLRLSCGASRFTFS | GFDMH | WVRQAPGKGLEWVA | RISHDGSMADYADSLRG | RFTISRDNSKNTLYLQMNSLRVEDTALYYCAK |

FIG. 4 Panel D

BoNT/C, BoNT C/D, BoNT D/C, or /BoNT/D binder (47 clones)

| VH/Clone | Framework1 | CDR1 | Framework2 | CDR2 | Framework3 |
|---|---|---|---|---|---|
| 4C10.2 | QVQLVESGGGAVQPGESLRLSCAASGFTFS | GFDMH | WVRQSPGRGLEWVA | RISHDGSMADYADSLRG | RFTISRDNPKNTLYLHMNSLRVEDTALYYCAK |
| 8C1 | QVQLQESGGGLVQPGGSLRLSCAASGITLS | SYMMN | WVRQVPGKGLEWLA | NINQDANEKYYVDSVKG | RFTISRDNAKNSLYLQMNNLRVEDTAIYYCAR |
| 8C2 | QVNLRESGPGLVKPSQTLSLITCTVSGGSIN | TGEFYWG | WIRQLPGKGLEWIG | YTHHTGSPYYKSSLKS | RVSISIDRSKNQFSLELRSVTAADTAVYYCVR |
| 8C3 | QVQLQESGPGLVKPSQTLSLTCTVSGGPIN | NSPYFWN | WFRQHPGKGLEWIG | YIYYSGSTYYNPSLKS | RVSMAVDTSKNQFTLRLSSVTAADTAMYFCAR |
| 8C4 | EVQLVESGGGLVQPGRSLRLSCAASGFTFD | DYAMH | WVRQAPGKGLEWVS | GISWNSGSIGYADSVKG | RFTVSRDNGKNSLYLQMNSLRAEDTALYFCAK |
| 8C5 | EVQLVESGAEVKKPGASVKVSCKAFGYTLI | NYAMH | WVRQAPGQRLEWMG | LIKAGNGNTKYSQKFQG | RVTITRDPSASTAYMELSSLRSEDTAVYYCAR |
| 8C6 | QVQLQESGGGLVQPGGSLRLSCAASGFSFR | SYDMT | WVRQAPGRGLVWVS | SITSTGSSTYYADSVKG | RFTISRDNSKNTVYLQMNSLRAEDTAVYYCAK |
| 8D1 | QVQLVESGAEVRKPGASVKVSCWTSGYPFT | DFYIH | WVRQAPGQGLEWMG | VINPTVGNTAYAERFQG | RVTMTRNTSISTAYMELSSLRSEDTAVYYCAR |
| 8D2 | QVQLVQSGAEVKKPGESLKISCKGSGYSFT | SYWIG | WVRQMPGKGLEWMG | IIYPGDSDTRYSPSFQG | QVTISADKSISTAYLQWSSLKASDTAMYYCVS |
| 8DC1 | QVTLKESGGGLVQPGRSLITLSCPLSGFTSS | DYVLH | WVRQAPGTGLDWVA | VISSDGTKAYYGDSVKG | RFTISRDTSKNTLLLQMNSPRAEDTAIYYCAI |
| 8DC1.2 | QVTLKESGGGLVQPGRSLITLSCPLSGYSFT | DYVLH | WVRQAPGTGLDWVA | VISSDGTKAYYGDSVKG | RFTISRDTSKNTLLLQMNSPRAEDTAIYYCAI |
| 8DC2 | QVQLVQSGAEVKKPGSSVKVSCKTSGGTFR | NFAIS | WVRQAPGQGLEWMG | GIIPMFGKGHYAQNFQG | RVTITADDSTTTAYMELSSLRYEDTAVYYCAR |
| 8DC3 | QVQLVQSGGGLVKPGGSLRLSCAASGFTFS | SHSMN | WVRQAPGKGLEWVS | SISSSSYIYYADSVKG | RFTISRDNSKNSLYLQLNSLRAEDTAVYYCAR |
| 8DC4 | QVQLQESGPGLVKPSQTLSLTCTVSGGSIS | SDNYFWT | WIRQSPGKGLEWLG | HISYSGRSYSNLSLKR | RLTISVDTSKNQFSLNLNSVTAADTAVYYCAR |
| 8DC4.1 | QVQLQESGPGLVKPSQTLSLTCTVSGGSIS | SDNYFWT | WIRQSPGKGLEWLG | HISYSGRSYTNLSLKR | RLTISVDTSKNQFSLNLNSVTAADTAVYYCAR |
| 8DC5 | QLQLVESGGGLVQPGGSLRLSCEASGFNFR | TYGMH | WVRQAPGKGLEWVA | VIWFDGSKIYYADPVKG | RFTISKDNSKNTILYLQMSSLRGEDTAVYYCAR |
| 8DC6 | EVQMVESGGGVVQPGRSLRLSCAASGFTFT | SYAMH | WVRQAPGKGLEWVS | MISNDESNTKYADSVKG | RFTISRDNSKNTLFLQMNSLRAEDTAMYSCAR |
| 8DC7 | QVQLVQSGGRLVRPGGSLRLSCAASGFVFS | NYGMH | WVRQAPGKGLEWVA | FLTHGGTNKYYSDSVKG | RLTISRDNAKSTLFLEVNSLRVEDTALYYCVK |
| 8DC8 | QVQLQQSGSGLVKPSETLSLTCTVSGGSIS | SAGYSWS | WIRQSPGKGLECIG | YIYQTGSTFYNLSLKG | RVTMSLDRSKNQISLRLTSVVAADTAVYYCAR |
| 8DC10 | QVQLVQSGAEAKKPGASVKLSCQASGYTFT | GYAIH | WVRQAPGQRLEWLG | WINCVNGNTKYSPKLPG | RVTITRDTSATTAYLELNSLTSEDTAVYYCAR |
| 8DC11 | QVQLVESGPGLVKPSQTLSLSCTVSGGSVN | HYYWN | WIRQPPGKGLEWIG | YIFYNGRTNYNPSLKS | RVTMSVDTSKNQISLKLRSVTAADTAVYYCAR |
| 8DC12 | QVQLVQSGGGVVQPGRSLRLSCAASGFTFS | SYGMH | WVRQAPGKGLEWVA | AISYDGSNKYYADSVKG | RFTISRDNSKNTLYLQMNSLRAEDTAVYYCAK |
| 8DC13 | QVQLVQSGAEVKKPGASVKVSCKASGYTFT | GYYIH | WVRQAPGQGLEWMG | RINPNSGGANYAHKFQG | RVTMTRDTSSNTAYMEVSRLKSDDTAVYYCAR |
| 8DC14 | QVQLVQSGGGVVQPGRSLRLSCVASGFTFS | SYTMH | WVRQAPGEGLEWVA | GISNDGRNQYYSDSVKG | RATISRDNSKDTLYLQMHSLRAEDTAVYYCAK |
| 8DC15 | QVQLQESGPGLLKPSQTLSLTCSVSGGSMI | TGGYYWT | WVRQLPGKGLEWIG | HVYYTGKTYYNPSLNG | RFTIAIDTSKNQFSLNLNSVTATDTAVFYCAR |

FIG. 4 Panel D (Cont. 1)

BoNT/C, BoNT C/D, BoNT D/C, or BoNT/D binder (47 clones)

| VH/Clone | CDR3 | Framework4 | |
|---|---|---|---|
| 1C1 | TKMGAAEGVFDY | WGQGTLVTVSS | SEQ ID NO:58 |
| 1C1.1 | TKMGAAEGVFDY | WGQGTLVTVSS | SEQ ID NO:59 |
| 1C2 | GGLPYQQLPL | WGQGTLVTVSS | SEQ ID NO:60 |
| 1C3 | GGLPYQQLPL | WGQGTLVTVSS | SEQ ID NO:61 |
| 1C4 | GGLPYQQLPL | WGQGTLVTVSS | SEQ ID NO:62 |
| 1C8 | GATNIPYGMSV | WGQGTLVTVSS | SEQ ID NO:63 |
| 87C1 | AIKSYSTIGGACNL | WGQGTMVTVSS | SEQ ID NO:64 |
| 87C2 | TLKFGLNYMDV | WGKGTTVTVSS | SEQ ID NO:65 |
| 87C78 | AIKAFRPVPPSFHMDV | WGIGTTVTVSS | SEQ ID NO:66 |
| 4C1 | GQDTSMVTRNFYYGLDV | WGQGTTVTVSS | SEQ ID NO:67 |
| 4C2 | ETWEVLGHLGYEVLDH | WGLGTLVTVSS | SEQ ID NO:68 |
| 4C3 | GAFTNYPF | WGQGTTVTVSS | SEQ ID NO:69 |
| 4C4 | DQGGGTVVKENWFDP | WGQGTLVTVSS | SEQ ID NO:70 |
| 4C4.1 | DQGGGTVVKENWFDP | WGQGTLVTVSS | SEQ ID NO:71 |
| 4C4.2 | DQGGGTVVKENWFDP | WGQGTLVTVSS | SEQ ID NO:72 |
| 4C5 | VKLTTMVRGGPFDY | WGQGTLVTVSS | SEQ ID NO:73 |
| 4C6 | VKLSTMVRGGPFDY | WGLGTMVTVSS | SEQ ID NO:74 |
| 4C7 | AIKGYSSRPVRAYEM | WGLGTMVTVSS | SEQ ID NO:75 |
| 4C8 | GGKYSNSSAMYQ | WGQGTLVTVSS | SEQ ID NO:76 |
| 4C9 | SVSGGAFDL | WGRGTLVTVSS | SEQ ID NO:77 |
| 4C10 | DRWRSGSYPAFEK | WGQGTMVTVSS | SEQ ID NO:78 |
| 4C10.1 | DRWRSGSYPAFEI | WGQGTMVTVSS | SEQ ID NO:79 |

FIG. 4 Panel D (Cont. 2)

BoNT/C, BoNT C/D, BoNT D/C, or BoNT/D binder (47 clones)

| VH/Clone | CDR3 | Framework4 | |
|---|---|---|---|
| 4C10.2 | DRWRSGSYPAFEK | WGQGTMVTVSS | SEQ ID NO:80 |
| 8C1 | GGKFSKSSPQWA | WGQGTLVTVSS | SEQ ID NO:81 |
| 8C2 | DRDGSGFFDN | WGRGTLVTVSS | SEQ ID NO:82 |
| 8C3 | DQGGGSVVGTNWFDP | WGQGTLVTVSS | SEQ ID NO:83 |
| 8C4 | DGGPEWELRGAFDI | WGQGTLVTVSS | SEQ ID NO:84 |
| 8C5 | VRDKRTTDVSNYYYGMDV | WGQGTTVTVSS | SEQ ID NO:85 |
| 8C6 | VLQPKWELPH | WGQGTLVTVSS | SEQ ID NO:96 |
| 8D1 | RGGRRRDAFDI | WGQGTMVTVSS | SEQ ID NO:87 |
| 8D2 | YSSLDAFDI | WGQGTMVTVSS | SEQ ID NO:88 |
| 8DC1 | STRGPFDI | WGQGTMVTVSS | SEQ ID NO:89 |
| 8DC1.2 | STRGPFDI | WGHGTMVTVSS | SEQ ID NO:90 |
| 8DC2 | GTRNGSLRDAFDI | WGQGTTVTVSS | SEQ ID NO:91 |
| 8DC3 | GDHDFRSGYYGMDV | WGQGTMVTVSS | SEQ ID NO:92 |
| 8DC4 | ERLPPGRGYDMDV | WGQGTTVTVSS | SEQ ID NO:93 |
| 8DC4.1 | ERLPPGRGYDMDV | WGQGTLVTVSS | SEQ ID NO:94 |
| 8DC5 | GGWFGTWRDNMDV | WGPGTTVTVSS | SEQ ID NO:95 |
| 8DC6 | GGYYTRPLAFDT | WGQGTLVTVSS | SEQ ID NO:96 |
| 8DC7 | EGQLDSKYFDS | WGQGTLVTVSS | SEQ ID NO:97 |
| 8DC8 | VVGVYPGWFDS | WGQGTLVTVSS | SEQ ID NO:98 |
| 8DC10 | SMLVAARVYYYGMDV | WGQGTMVTVSS | SEQ ID NO:99 |
| 8DC11 | EGARGYCSSTSCHDAFDI | WGRGTLVTVSS | SEQ ID NO:100 |
| 8DC12 | GEHFVVTAFAT | WGQGTLVTVSS | SEQ ID NO:101 |
| 8DC13 | RRAVANLDYHYYGMDV | WGQGTTVTVSS | SEQ ID NO:102 |
| 8DC14 | ANYHFILATTFHS | WGQGTLVTVSS | SEQ ID NO:103 |
| 8DC15 | AIWGGWYFDL | WGQGTLVTVSS | SEQ ID NO:104 |

FIG. 4 Panel D (Cont. 3)

BoNT/F binder (36 clones)

| VH/Clone | Framework1 | CDR1 | Framework2 | CDR2 | Framework3 |
|---|---|---|---|---|---|
| 6F1 | QVQLVESGGGLIQPGGSLRLSCAASGFTFS | SYAMR | WVRQAPGKGLEWVS | GISGSGGRKYYADSVKG | RFTISRDNSKNTLYLQMNSLRAEDTAIYYCAK |
| 6F3 | QVQLQQSGPEVVKPGASVKISCKASGYTFA | DYWIG | WTKQGPGHGLEWIG | HIYPGGGYINYNEKFKG | KATLTADMSSSTAYMQFSSLITSEDSAIYYCAR |
| 6F4 | EVQLQESGPELVKPGASVKISCKTSGYTFT | DYYMN | WVKQSHGKSLEWIG | DINPNNGGATYNQKFKG | KATLTVDKSSSRTLYMELRSLTSEDSAVHCAC |
| 6F5 | EVQLVQSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 39A1 | EVQQVQSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 41C2 | EVQQVQSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 43D3 | EVQLVQSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 39H6 | EVQLVPSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 41E2 | EVQLVPSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 41F7 | EVQLVPSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 42G8 | EVQLVPSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 39D1.1 | EVQLVQSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 41A4 | EVQLVQSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 41B7 | EVQLVQSGGNLVQPGGSLRLSCAATGPIGS | HWMT | WVRQAPGQGLEWVA | NINLDGTEKFYVDSVKG | RFTVSRDNRKSSVFLQMNLRVDDTAVYYCAR |
| 39D5.1 | EVQLVQSGGNLVQPGGSLRLSCAATGPIGS | HWMT | WVRQAPGQGLEWVA | SINLDGTEKFYVDSVKG | RFTVSRDNRKSSVFLQMNLRVDDTAVYYCAR |
| 41G8 | EVQLVQSGGNLVQPGGSLRLSCAATGPIGS | HWMT | WVRQAPGQGLEWVA | SINLDGTEKFYVDSVKG | RFTVSRDNRKSSVFLQMNLRVDDTAVYYCAR |
| 6F6 | EVQLLESGGGLVKPGGSRKLSCEASGFTFS | DYGMH | WVRQAPEKGLEWVG | YISSGSRIIYYADTVKG | RITISRDNAKNTLFLQMTSLRSEDTAMYCVR |
| 6F7 | QVQLQESGPGLVKPSQTVSLITCTVAGYSIT | NGNHWWN | WIRQVSGSKLEWIG | YITSSGSTDSNPSLKS | RISITRDTSKNQLFIQLNSVTTEDIATYCAR |
| 6F8 | QVQLKQSGAELVKSGASVKLSCTASGFNIK | DFYMH | WVKQRTEQGLEWIG | RIDPEDGETKYAPKFQG | KATITADTSNTAYLQLSSLITSEDTAVYYCVR |
| Hu6F8 | QVQLVQSGAEVKKPGASVKLSCKASGFNIK | DFYMH | WVRQAPGQGLEWIG | RIDPEDGETKYAPKFQG | RATITADTSTNTAYLELRSLRSDDTAVYYCVR |
| 6F9 | QVQLQQPGAELVKPGASVKLSCKASGNSFA | SSWMH | WVKQRPGQGLEWIG | MIHPYSGSTNFNEKFKS | KATLSVDKSSSTAYMQLSSLITSEDSAVYYCAM |
| Hu6F9 | QVQLVQSGAEVKKPGASVKLSCKASGNSFA | SSWMH | WVRQAPGQGLEWIG | MIHPYSGSTNFNEKFKS | RATLTVDKSTSTAYMELRSLRSDDTAVYYCAM |
| 6F10 | EVQLQESGGDLVQPGGSLRLSCAASGFTFS | YYGMS | WVRQTPDKRLEWVA | TISSGGTYTYYPDSVKG | RFTISRDNAKNTLYLQMSSLSSEDTAMYCAR |
| Hu6F10 | EVQLVESGGGLVKPGGSLRLSCAASGFTFS | YYGMS | WVRQAPGKGLEWVA | TISSGGTYTYYPDSVKG | RFTISRDNAKNSLYLQMNSLRAEDTAMYCAR |
| 28C9 | QVQLQESGPGLVRPSQSLSLITCSVTGYSIS | RSYYWN | WIRQFPGNKLEWMG | YISYDDSYDYNPSLKN | RISITRDTSKNQFFLKLSSVTTEDTATYCAR |
| 28H4 | EVQLQQSGAELAKPGASVKLSCKASGYTFT | SYMH | WVKQGPGQLEWIG | AIYPGNSDIGYNQKFKG | KAKLTAVTSASTAYMELSSLITNEDSAVYYCTR |
| 29A2 | EVQLLETGDLVKPGGSLRLSCAASGFTFS | YYGMS | WVRQTPDKRLEWVA | TISSGGSYTYYPDSVKG | RFTISRDNAKNTLYLQMSSLKSEDTAMYCAR |
| 29B8 | QVQLQESGAELVKPGASVKLSCTASGFNIK | DYYMH | WVKQRTEQGLEWIG | RIDPEDGETKYAPKFQG | KATITADTSSNTAYLQLSSLITSEDTAVYYCVS |
| 30C8 | EVQLKQSGTELVKPRSSVKMSCKASGYTFT | DYWIG | WTKQRPGHGLEWIG | HIYPGGGYTNYNEKFKG | KATLTADISSSAAYMQFSSPTSEDSAIYYCAR |
| 32G2 | QVQLVQSGGGLVRPGGSMKLSCVASGFTFS | NSWMN | WVRQSPEKGLEWVA | QIRSNDNYATHYMESVKG | RFTISRDDSKSCVYLQMNLWAEDTGIYYCTS |
| 37B4 | QVQLVQSGAEVKKPGSSVKVSCKASGGTFS | SYAIS | WVRQAPGQGLEWMG | GIPIFGTANYAQKFQG | RVTITDTSTSTAYMELRSLRSDDTAVYYCAR |
| 37B6 | QVQLVQSGRSLRLSCETSGFPFG | DYTMS | WFRQTPGMRPEWVG | FIKNKDYGDVTQYAASVRG | RFTISRDDSNSVTLYQMNSLKVDDSALYYCVR |
| 38B8 | EVQLVQSGGGLVQPGRSLRLSCAASGFTFS | SCWMS | WVRQAPGKGLEWVS | NIKQDGSVEQYVNSVKG | RFTISRDNANNSLYLQMNSLRAEDTAVYYCAI |
| 38C1 | QVQLVQSGGGVVQPGRSLRLSCEASGFNIK | NHGMH | WVRQAPGKGLEWVS | AISGSGGSTYYADSVKG | RFTISRDNSKNTLYLQMNSLRAEDTAVYYCAK |
| 38D11 | QVQLVQSGGGVVQPGRSLRLSCAASGFTFS | SYGMH | WVRQAPGKGLEWVA | VIWYDGSNKYYADSVKG | RFTISRDNSKNTLYLQMNSLRAEDTAVYYCAR |
| 38F8 | EVQLVQSGAEVKKPGSSVKVSCKASGGTFS | SYAIS | WVRQAPGQGLEWMG | GIPIFGTANYAQKFQG | RVTITADESTSTAYMELSSLRSEDTAVYYCAR |

FIG. 4 Panel E

BoNT/F binder (36 clones)

| VH/Clone | CDR3 | Framework4 | |
|---|---|---|---|
| 6F1 | DRWYSGYDFDY | WGQGTLVTVSS | SEQ ID NO:105 |
| 6F3 | VTMVESGDWYFDV | WGTGTTVTVSS | SEQ ID NO:106 |
| 6F4 | GPYFFDF | WGQGTTLTVSS | SEQ ID NO:107 |
| 6F5 | LQWGGYNGWLSP | WGQGTLVTVSS | SEQ ID NO:108 |
| 39A1 | LQWGGYNGWLSP | WGQGTLVTVSS | SEQ ID NO:109 |
| 41C2 | LQWGGYNGWLSP | WGQGTLVTVSS | SEQ ID NO:110 |
| 43D3 | LQWGGYNGWLSP | WGQGTLVTVSS | SEQ ID NO:111 |
| 39H6 | LQWGGYNGWLSP | WGQGTLVTVSS | SEQ ID NO:112 |
| 41E2 | LQWGGYNGWLSP | WGQGTLVTVSS | SEQ ID NO:113 |
| 41F7 | LQWGGYNGWLSP | WGQGTLVTVSS | SEQ ID NO:114 |
| 42G8 | LQWGGYNGWLSP | WGQGTLVTVSS | SEQ ID NO:115 |
| 39D1.1 | LQWGGYDGWLSP | WGQGTLVTVSS | SEQ ID NO:116 |
| 41A4 | LQWGGYDGWLSP | WGQGTLVTVSS | SEQ ID NO:117 |
| 41B7 | LQWGGYDGWLSP | WGQGTLVTVSS | SEQ ID NO:118 |
| 39D5.1 | LQWGGYNGWLSP | WGQGTLVTVSS | SEQ ID NO:119 |
| 41G8 | LQWGGYNGWLSP | WGQGTLVTVSS | SEQ ID NO:120 |
| 6F6 | GTWVFDY | WGQGTTLTVSS | SEQ ID NO:121 |
| 6F7 | SSNYFFHVLDY | WGQGTSVTVSS | SEQ ID NO:122 |

FIG. 4 Panel E (Cont. 1)

BoNT/F binder (36 clones)

| VH/Clone | CDR3 | Framework4 | |
|---|---|---|---|
| 6F8 | DRDYD | WGQGTTLTVSS | SEQ ID NO:123 |
| Hu6F8 | DRDYD | WGQGTTLTVSS | SEQ ID NO:124 |
| 6F9 | NWDWYFDV | WGTGTTVTVSA | SEQ ID NO:125 |
| Hu6F9 | NWDWYFDV | WGQGTTVTVSS | SEQ ID NO:126 |
| 6F10 | RRSYDSVYWYFDV | WGAGTSVTVSS | SEQ ID NO:127 |
| Hu6F10 | RRSYDSVYWYFDV | WGRGTLVTVSS | SEQ ID NO:128 |
| 28C9 | ASDFDV | WGTGTTVTVSS | SEQ ID NO:129 |
| 28H4 | HGYYIYALDY | WGQGTSVTVSS | SEQ ID NO:130 |
| 29A2 | RRVYYGSSYEDY | WGQGTTLTVSS | SEQ ID NO:132 |
| 29B8 | LLRSRTGYFDY | WGQGTTLTVSS | SEQ ID NO:133 |
| 30C8 | IIMVESGDWYFDV | WGTGTTLTVSS | SEQ ID NO:134 |
| 32G2 | YSDLAY | WGQGTLVTVSA | SEQ ID NO:135 |
| 37B4 | DEDYYDSSGYYDY | WGQGTLVTVSS | SEQ ID NO:136 |
| 37B6 | GGGQWWQNDAFDV | WGRGTMVTVSS | SEQ ID NO:137 |
| 38B8 | PHRSDYGLGV | WGQGTTVTVSS | SEQ ID NO:138 |
| 38C1 | PNPGKKWGAEWGASGN | WGQGTLVTVSS | SEQ ID NO:139 |
| 38D11 | DKGWELMTNTDAFDI | WGQGTLVTVSS | SEQ ID NO:140 |
| 38F8 | VAGTSRSAFDI | WGQGTMVTVSS | SEQ ID NO:141 |

FIG. 4 Panel E (Cont. 2)

BoNT/A LC binder (17 clones)

| VL/Clone | Framework1 | CDR1 | Framework2 | CDR2 | Framework3 |
|---|---|---|---|---|---|
| 6A1M | EIVLTQSPAILSASPGEKVTMTC | RASSSVRYMH | WYQQKPGSSPKPWIY | ATSNLAS | GVPARFSGSGSGTSYSLTISRVEAEDAATYYC |
| 6A2M | DIVMSQSPASLAVSLGQRATISC | RASESVDYDGDSYMN | WYQQKPGQPPKLLIY | AASNLES | GIPARFSGSGSGTDFTLNIHPVEEEDAATYYC |
| 6A3M | DIVLTQSPASLAVSLGQRATISC | RASESVDYDGDSYMN | WYQQKPGQPPKLLIY | AASNLES | GIPARFSGSGSGTDFTLNIHPVEEEDAATYYC |
| 6A4M | DIVLTQSPASLAVSLGQRATISC | RASESVDYDGDSYMN | WYQQKPGQPPKLLIY | AASNLES | GIPARFSGSGSGTDFTLNIHPVEEEDAATYYC |
| 6A5M | QIVLTQSPANLSASPGEKVTMTC | SASSSVSYMH | WYQQKPGSSPKPWIY | ATSNLAS | GVPARFSGSGSGTSYSLTISRMEAEDAATYYC |
| 6A6M | DIVMTQSPKFMSTSVGDRVSVTC | KASQNVGTNVA | WYQQKPGQSPKALIY | SASYRYS | GVPDRFTGSGSGTDFTLTISNVQSEDLAEYFC |
| 6A7M | ENVLTQSPAILSASPGEKVTMTC | RASSSVSYMH | WYQQKPGSSPRLLIY | DTSNLAS | GVPVRFSGSGSGTSYSLTISRMEAEDAATYYC |
| 6A8M | DIVMSQSPAIMSASPGEKVTLTC | SASSSVSSNYLY | WYQQKPGSSPKLWIY | STSNLAS | GVPARFSGSGSGTSYSLTISRVEAEDAATYYC |
| 6A9M | QIVLTQSPAIMSASPGEKVTMTC | SASSSVSYMY | WYQQKPGSSPRLLIY | DTSNLAS | GVPVRFSGSGSGTSYSLTISRMEAEDAATYYC |
| 1C7 | DIVMTQSPAIMSASPGEKVTMTC | SASSSVSYMY | WYQQKPGSSPRLLIY | YTSNLAP | GVPARFSGSGSGNSYSLTISSMEGEDAATYYC |
| 1C10 | EIVLTQSPASLAVSLGQRATISC | RACESVDYDGDSYMN | WYQQKPGQPPKLLIY | AASNLES | GIPARFSGSGSGTDFTLNIHPVEEEDAATYYC |
| 1D8 | DIVMSQSPASLAVSLGQRATISC | RASESVDYDGDSYMN | WYQQKPGQPPKLLIY | AASNLES | GIPARFSGSGSGTDFTLNIHPVEEEDAATYYC |
| 1G11 | DIVMTQTPASLAVSLGQRATISC | RASESVDYDGDSYMN | WYQQKPGQPPKLLIY | AASNLES | GIPARFSGSGSGTDFTLNIHSVEEEDAATYYC |
| 1H5 | DIVLTQSPASLAVSLGQRATISC | RASESVDYDGDSYMN | WYQQKPGQPPKLLIY | AASNLES | GIPARFSGSGSGTDFTLNIHPVEEEDAATYYC |
| 9B2 | DIVMTQTPLTLSVTIGQPASISC | RSSQSLLHNYGNTYLH | WYLQKPGQSPKLLIY | KVSNRFS | GVPDRFSGSGSGTDFTLKISRVEAEDLGVYFC |
| 10C9 | DIVMTQSPTSLAVSLGQRATISC | KASQSVDYDGDSFMN | WYQQKPGQPPKLLIY | GASNLES | GIPARFSGSGSRTDFTLTINPVEADDVATYYC |
| 10H10 | DVVMTQTPASLAVSLGQRATISC | KASQSVDYDGDSYMN | WYQQKPGQPPKLLIY | AASSLES | GIPARFSGSGSGTDFTLNIHPVEEEDAATYYC |

BoNT/A ALC binder (17 clones)

| VL/Clone | CDR3 | Framework4 | |
|---|---|---|---|
| 6A1M | QQWSGNAPT | FGGGTKLEIKR | SEQ ID NO:141 |
| 6A2M | LQSNEAPWT | FGGGTKLEIKR | SEQ ID NO:142 |
| 6A3M | LQSNEAPWT | FGGGTKLELKR | SEQ ID NO:143 |
| 6A4M | LQSNEAPWT | FGGGTKLEIKR | SEQ ID NO:144 |
| 6A5M | QQWSSYPPMYT | FGGGTKLELKR | SEQ ID NO:145 |
| 6A6M | QQYNSYPYT | FGGGTKLEIKR | SEQ ID NO:146 |
| 6A7M | QQWSSYPYT | FGGGTKLEIKR | SEQ ID NO:147 |
| 6A8M | QQWSSNPPT | FGGGTKLEIKR | SEQ ID NO:148 |
| 6A9M | QQWSSYPLT | FGAGTRLELKR | SEQ ID NO:149 |
| 1C7 | QQFTSSPYT | FGGGTKLEIKA | SEQ ID NO:150 |
| 1C10 | LQSNEAPWT | FGGGTKLEIKA | SEQ ID NO:151 |
| 1D8 | LQSNEAPWT | FGGGTKLEIKA | SEQ ID NO:152 |
| 1G11 | LQSNEAPWT | FGGGTKLEIKA | SEQ ID NO:153 |
| 1H5 | LQSNEAPWT | FGGGTKLEIKA | SEQ ID NO:154 |
| 9B2 | SQGTHVPWT | FGGGTKLEIKA | SEQ ID NO:155 |
| 10C9 | QQSNEDPLT | FGAGTKLELKA | SEQ ID NO:156 |
| 10H10 | QQSNEDPYT | FGGGTKLEIKA | SEQ ID NO:157 |

FIG. 4 Panel F

BoNT/B LC binder (24 clones)

| VL/Clone | Framework1 | CDR1 | Framework2 | CDR2 | Framework3 | CDR3 |
|---|---|---|---|---|---|---|
| 16B3 | QNVLTQSPAIMSASPGEKVTMTC | SASSSVSSRYLH | WYQQKSGASPKLWIY | GTSNLAS | GVPARFSGSGSGTSYSLTISSVEAEDAATYYC | QQYHSDPLT |
| 16D5 | QIVLTQSPATLSVTPGDSVSLSC | RASQSISNNLH | WYQQKSHESPRLLIK | YASQSIS | GIPSRFSGSGSGTDFTLSINSVETEDFGMYFC | QQSNSWPLT |
| 18A6 | EIVLTQSPAIMSASPGEKVTMTC | SASSSISYMH | WFQQKPGMSPKRRIF | DTSKLAS | GVPARFSGSGSGTSYSLTISSMEAEDAGTYYC | HQRSSYPFT |
| 18A7 | QIVLTQSPAIMSASPGEKVTITC | SASSSVSYMH | WFQQKPGTSPKLWIY | STSNLAS | GVPARFSGSGSGTSYSLTISSMEAEDVATYYC | QQWSSNPLI |
| 18D10 | ENVLTQSPAIMSASPGEKVTMTC | SASSSVSYMH | WYQQKSGTSPKRWIY | DTSKLAS | GVPARFSGSGSGTSYSLTISSMEAEDAATYYC | QQWSSNPLI |
| 18E5 | QIVLTQSPAIMSASPGEKVTMTC | RASSSVSSSYLH | WYQQKPGSSGTSPKLWIY | STSNLAS | GVPARFSGSGSGTSYSLTISSVEAEDAATYYC | QQYDSSPST |
| 18F2 | EIVLTQSPAIMSASPGQKVTITC | SASSSVSYMH | WYQQKSGTSPKRWIY | DTSKLAS | GVPARFSGSGSGTSYSLTIISSMEAEDAATYYC | QQYDSSPST |
| 19A9 | DIVLTQSPAIMSASPGGKITITC | SASSSVSYMH | WFQQKPGTSPKLWIY | DTSKLAS | GVPARFSGSGSGTSYSLTISSMEAEDAATYYC | QQWRSNPPT |
| 19B6 | QIVLTQSPAIMSASPGEKVTMTC | SASSSLSYVH | WYQQKPGSSPKPWIY | STSNLAS | GVPARFSGSRSGTSYSLTISSMEAEDAATYYC | QQRSSYPYT |
| 19D2 | DIVMTQTPAIMSASPGEKVTITC | SASSSVSYMY | WYQQKPGTSPKLMIY | ATSNLVS | GVPARFSGSGSGTSYSLTISSMEAEDAATYYC | QQRSSYPPT |
| 19D22 | QIVLTQSPAIMSASPGEKVTMTC | SASSSVSYMY | WYQQKPGSSPRLLIY | STSNLAS | GVPVRFSGSGSGTSYSLTISRMEAEDAATYYC | QQWSSYPPIT |
| 19D22.4 | ENVLTQSPAIMSASPGEKVTMTC | SASSSVNYMY | WYQQKPGSSPRLLIY | DTSNLAS | GVPVRFSGSGSGTSYSLTISRMKAEDAATYFC | QQWSSFPPT |
| 19G6 | No VL | | | | | |
| 31A5 | QIVLTQSPAILSASPGEKVTMTC | RASSSVSYMH | WYQQKPGSSPKAWIY | ATSNLAS | GVPARFSGSGSGTSYSLTISRVEAEDAATYYC | QQWSSYPPT |
| 31A5.1 | QIVLTQSPAILSASPGEKVAMTC | RASSSVSYMH | WYQQKPGSSPKLLIY | DTSNLAS | GVPVRFSGSGSGTSYSLTISRMEAEDAATYYC | QQWSSYPPT |
| 31C3 | QIVLTQSPAIMSASPGEKVTMTC | RASSSVSSSYLH | WYQQKPGSSPKLMIY | STSNLAS | GVPARFSGSGSGTSYSLTISSMEAEDAATYFC | QQWSSFPPT |
| 31C3.5 | DIVMTQSPVSITASRGEKVTITC | RASSSISSNYLH | WYQQKPGSSPKLLIY | RTSNLAS | GVPVRFSGSGNSYSLTISSMEAEDAASYFC | HQWSSYPPT |
| 31C3.6 | DIVMTQSPVSITASRGEKVTITC | RASSSISSNYLH | WYQQKPGSSPKLLIY | RTSNLAS | GVPARFSGSGSGNSYSLTISSMEAEDAASYFC | HQWSSYPPT |
| 31E2 | EIVLTQSPEILSASPGEKVTMTC | RASSSVSYMH | WYQQKPGSSPKPWIY | ATSNLAS | GVPARFSGSGSGTSYSLTISSMEAEDAATYYC | QQWTSNPPT |
| 31E2.20 | QIVLTQSPALMAASPGEKVTITC | RASSSVSYMH | WYQQKSETSPKPWIY | GTSNLAS | GVPARFSGSGSGTSYSLTISSMEAEDAATYYC | QQFHNYPPT |
| 31G2 | DIVMTQSPAIMSASPGEKVTMPC | SASSSVSYMH | WYQQKPGTSPKRWIY | DTSKLAS | GVPARFSGSGSGTSYSLTISRVEAEDAATYYC | HQRSSYPLI |
| 31H3 | No VL | | | | | |
| 34E8 | | | | | | QQWSSHPPT |
| 34E8B12 | DVVMTQSPAIMSASPGEKVTMTC | SASSSVSYMY | WFQQKPGSSPKPWIY | RTSNLAP | GVPARFSGSGSGTSYSLTISSMEAEDAATYYC | QQWSSNPEWT |

FIG. 4 Panel G

BoNT/B LC binder (24 clones)

| VL/Clone | Framework4 | | |
|---|---|---|---|
| 16B3 | FGGGTKLEIKA | SEQ ID NO:158 | |
| 16D5 | FGAGTKLELKA | SEQ ID NO:159 | |
| 18A6 | FGGGTKLEIKA | SEQ ID NO:160 | |
| 18A7 | FGGGTKLEIKA | SEQ ID NO:161 | |
| 18D10 | FGAGTKLELKA | SEQ ID NO:162 | |
| 18E5 | FGGGTRLEIKA | SEQ ID NO:163 | |
| 18F2 | FGGGTKLEIKA | SEQ ID NO:164 | |
| 19A9 | FGGGTKLEIKA | SEQ ID NO:165 | |
| 19B6 | FGAGTKLEIKA | SEQ ID NO:166 | |
| 19D2 | FGGGTKLEIKA | SEQ ID NO:167 | |
| 19D22 | FGAGTRLEIKA | SEQ ID NO:168 | |
| 19D22.4 | FGGGTRLEIKA | SEQ ID NO:169 | |
| 19G6 | No VL | | |
| 31A5 | FGSGTKLEIKA | SEQ ID NO:170 | |
| 31A5.1 | FGGGTKLEIKA | SEQ ID NO:171 | |
| 31C3 | FGGGTKLEIKA | SEQ ID NO:172 | |
| 31C3.5 | FGGGTKLEIKR | SEQ ID NO:173 | |
| 31C3.6 | FGGGTKLEIKA | SEQ ID NO:174 | |
| 31E2 | FGGGTKLEIKA | SEQ ID NO:175 | |
| 31E2.20 | FGAGTKLEIKA | SEQ ID NO:176 | |
| 31G2 | FGGGTKLEIKA | SEQ ID NO:177 | |
| 31H3 | FGAGTRLEIKA | SEQ ID NO:178 | |
| 34E8 | No VL | | |
| 34E8B12 | FGGGTKLEIKA | SEQ ID NO:179 | |

FIG. 4 Panel G (Cont.)

BoNT/B Hc binder (16 clones)

| VL/Clone | CDR1 | |
|---|---|---|
| 26A10 | ENVLTQSPAIMSASPGEKVTMTC | SASSSVSSSYLH |
| 26B2 | DIEMTQTPAIMSASPGEKVTMTC | SASSSVSSSRYLH |
| 26C2 | QIVLTQSPAIMSASPGEKVTMTC | SASSSVSSYMY |
| 26C4 | DIVLTQSPAIMSASPGEKVTISC | SASSSVSVSYMY |
| 26D1 | QIVLTQSPASLAVSLGQRATISC | RASESVDNYGISFMN |
| 26D9 | QIVLTQSPASLAVSLGQRATISC | RASSSVSVYY |
| 26D10 | QIVLTQSPASLAVSLGERATISC | RASESVSTSGYSYMH |
| 26D11 | DIVMTQSPAIMAASLGERVTMTC | TASSSVSSTSGYSYMH |
| 26E1 | No VL | |
| 26E2 | QIVLTQSPAIMSASPGEKVTMTC | SASSSVSVSYMH |
| 26E6 | DIVMSQSPLSLPVSLGDQAFISC | RFSQSIVHSNGNTYLE |
| 26G5 | EIVLTQSPAILSASPGEKVTMTC | SASSSVSVSYMH |
| 26G11 | QIVLTQSPAIMSASLGERVTMSC | RASSSVSVSYMY |
| 26H11 | QIVLTQSPSTLSASVGDRVTITC | TASSSVSSSYLH |
| 1B12.3 | DIVMTQSPSTLSASVGDRVTITC | RASQGISSWLA |
| 1B12.4 | DIVMTQSPSTLSASVGDRVTITC | RASQGISSWLA |

| Framework2 | CDR2 | Framework3 | CDR3 |
|---|---|---|---|
| WYQQKPGSSPKLWIY | STSNLAS | GVPARFSGSGSGTSYSLTISSVEAEDAATYYC | QQYDSSPLT |
| WYQQKSGASPKLWIY | GTSNLAS | GVPARFSGSGSGTSYSLTISSVEAEDAATYYC | QQYHSDPLT |
| WFQQKPGSSPKLWIY | DTSKLAS | GVPGRFSGSGSGNSYSLTISSMEAEDVATYYC | FQGSGYPLT |
| WYQQKPGSSPKPWIY | RTSNLAS | GVPARFSGSGSGTSYSLTISSMEAEDAATYYC | QQYHSYPPT |
| WFQQKPGQPPKLLIY | AASNQGS | GVPARFSGSGSGTDFSLNIHPMEEDTAMYFC | QQSKEVPYT |
| WYQQKPGSSPKPWIY | RTSNLAS | GVPVRFSGSGSGTSYSLTISRVEAEDAATYYC | QQWSSYPPT |
| WYQQKPGQPPKLLIY | LASNLES | GVPARFSGSGSGTDFTLNIHPVEEEDAATYYC | QHSRELYT |
| WYQQKPGSSPKLWIY | STSHLAS | GVPARFSGSGSGTSFSLTISSMEAEDAATYYC | QQWSSDLVT |
| WYQQKSTSPKLWIY | DTSKLAS | GVPARFSGSGSGTSYSLTISSMEAEDAATYYC | QQWSSNPPFT |
| WYLQKPGQSPKLLIY | KVSNRFS | GVPDRFSGSGSGTDFTLKISRVEAEDLGVYYC | FQGSHVPYT |
| WYQQKPGSSPRLLIY | DTSNLAS | GVPARFSGSGSGTSYSLTISRVEAEDAATYYC | QQRSSNPPT |
| WYQQKPGSSPKPWIY | ATSNLAS | GVPARFSGSGSGTSYSLTISSMEAEDAATYYC | HQRSSNPPT |
| WYQQKPGSSPKLWIY | STSNLAS | GVPVRFSGSGSGTSYSLTISSMEAEDAATYYC | QQWSSYPLT |
| WYQQKPGKAPKLLIY | KASSLES | GVPSRFSGSGSGTEFTLTISSLQPEDFATYYC | LQNHPYPRA |
| WYQQKPGKAPKLLIY | KPWGKES | GVPSRFSGSGSGTEFTLTISSLQPEDFATYYC | LQNHPYPRA |

FIG. 4 Panel H

BoNT/B    Hc binder (16 clones)

| VL/Clone | Framework4 | | |
|---|---|---|---|
| 26A10 | FGAGTKLEIKA | SEQ ID NO:180 | |
| 26B2 | FGAGTKLEIKA | SEQ ID NO:181 | |
| 26C2 | FGAGTKLEIKA | SEQ ID NO:182 | |
| 26C4 | FGGGTKLEIKA | SEQ ID NO:183 | |
| 26D1 | FGGGTKLEIKA | SEQ ID NO:184 | |
| 26D9 | FGGGTKLEIKA | SEQ ID NO:185 | |
| 26D10 | FGGGTKLEIKA | SEQ ID NO:186 | |
| 26D11 | FGAGTRLEIKA | SEQ ID NO:187 | |
| 26E1 | No VL | | |
| 26E2 | FGAGTKLELKA | SEQ ID NO:188 | |
| 26E6 | FGGGTKLEIKA | SEQ ID NO:189 | |
| 26G5 | FGDGTRLEIKA | SEQ ID NO:190 | |
| 26G11 | FGDGTRLEIKA | SEQ ID NO:191 | |
| 26H11 | FGAGTKLEIKA | SEQ ID NO:192 | |
| 1B12.3 | FGQGTKLEIKR | SEQ ID NO:193 | |
| 1B12.4 | FGQGTKLEIKR | SEQ ID NO:194 | |

FIG. 4 Panel H (Cont.)

BoNT/C, BoNT C/D, BoNT D/C, BoNT/D binder ( 47 clones)

| VL/Clone | Framework1 | CDR1 | Framework2 | CDR2 | Framework3 | CDR3 |
|---|---|---|---|---|---|---|
| 1C1 | DIVMTQSPSTLSASVGDRVTITC | RASQSVSTWLA | WYQQKPGKAPNLLIS | EASNLES | GVPSRFSGSGSGTEFTLTISSLQPDDFAIYYC | QQYNSYVWT |
| 1C1.1 | EIVLTQSPSSLPASVGDRVTITC | RASQSIGTYLN | WYQHKPGSAPKLLIN | AASSLQS | GVPSRFSGSGSGTDFTLTISSLQPDDFATYYC | QQYNSYWT |
| 1C2 | DIVMTQSPSSLSASVGDRVTITC | RASQSISSYLN | WYQQKPGKAPKLLIY | AASSLQS | GVPSRFSGSGSGTDFTLTISSLQPEDFATYYC | QQSYSTPYT |
| 1C3 | DIQMTQSPSTLSASIGDRVTITC | QASQDISNYLN | WYQQKPGKAPKLLIY | AASSLQS | GVPSRFSGSGSGTDFTLTISSLQPEDLATYYC | QQSYSTPLF |
| 1C4 | DIVMTQSPSSLSASVGDRVTITC | RASQSISSYLN | WYQQKPGKAPKLLIY | AASSLQS | GVPSRFSGSGSGTDFTLTISSLQPEDFATYYC | QQSYSTPYT |
| 1C8 | DIVMTQSPSSLSASVGDRVTITC | RASQAIRNDLG | WYQEPGKAPKLLIY | AASTLQS | GVPSRFSGRGRGSGTDFTLTISSLQPEDFATYYC | LQHNSYPLT |
| 87C1 | DIVMTQSPSFLSASVGDRVTITC | RASQSISSYLN | WYQQKPGKAPKLLIY | AASSLQS | GVPSRFSGSRSGTYFTLTISSLQPEDFATYYC | QQSYITWT |
| 87C2 | ETTLTQSPDTLSLSPGERATLSC | RASQSVSRSYLA | WYQQKPGQAPRLLIY | GASSRAT | GIPDRFSGSGSGTDFTLTISRLEPEDFAVYYC | QQYDSRIWT |
| 87C78 | DIVMTQSPSSLSASVGDRVTITC | RASQGISSYLA | WYQQKPGKAPQLLIY | KASILKS | GVPSRFSGSGSGTEFTLTISSLQPEDFATYFC | QQTFDTPLT |
| 4C1 | DIVMTQSPSFVSASVGDRVTITC | RASQGISSYLA | WYQQKPGKAPKLLIY | AASTLQS | GVPSRFSGSGSGTDFTLTISSLQPEDIATYYC | QELSSYPLT |
| 4C2 | DIVMTQSPSSLSASVGDRVTITC | RASQGISSYLA | WYQQKPGKAPKLLIY | AASTLQS | GVPSRFSGSGSGTEFTLTISSLQPEDFATYYC | QQLNSYPRT |
| 4C3 | SGLTQDPAVSEALGQTVRITC | QGDSLRSYYAS | WYQQKPGQAPLLVIY | AGNNRPS | GIPDRFSGSSSGNTASLTITGARAFDEADYYC | NSRDSSGNYL |
| 4C4 | ETTLTQSPSSLSASVGDRVSITC | RASQSISNYLN | WYQQKPGKAPKLLIY | AASSLQS | GVPSRFSGSGSGTDFTLTISSLQPEDFATYYC | QQSYSDPPT |
| 4C4.1 | DIQMTQSPSSLSASVGDRVTITC | RASQSIGTYLN | WYQQKPGRAPTLLVS | RTSNLHT | GVPSRFSGDGSGSHFSLTIDSLQPEDFATYYC | QQSHTSPVT |
| 4C4.2 | DIVMTQSPSSLSASVGDRLTMTC | QASQDIGKHLN | WYQQKPGKAGKPPKLLIY | GASNLKT | GVPSRFSAGVSWTDFTFTISNVQPEDVATYYC | QQSYSTPPT |
| 4C5 | EIVLTQSPSSLSATVGDRVTITC | RASQGIRNDLV | WYQQKPGKAPKRLTY | AASSLLS | GVPSRFSGSGSGTDFTLTISSLQPEDFATYYC | QQYNSYPPT |
| 4C6 | DIEMTQSPSSLSAVRDKVTISC | RASQGISSWLT | WYQQKPGKAPKLLIY | KASTLQS | GVPSRFRGSGSGTEFTLTISSLQPEDFATYYC | QQLGSFPLT |
| 4C7 | DIVMTQSPSSLSASVGDRVTISC | RASQDIRNDLN | WYQQKPGKAPKLLIY | *ASTLQS | GVPSRFSGSGSGTDFTLTISSLQPEDFATYYC | QQINSFPLT |
| 4C8 | DIVMTQSPSSLAASVGDRVTITC | RASQSISGYLN | WYQQKPGKAPNLLIY | AASSLQS | GVPSRFSGSGSGTDFTLTISSLQPDDFASYYC | QQSYDIPRT |
| 4C9 | DIVMTQSPSSLSASVGDRVTITC | RASQSINSYLN | WYQQKPGKVPRLLIY | SASSLQS | GVPSRFSGSGSGTDFTLTISSLQPDDFATYYC | QQYKRYSS |
| 4C10 | QSVPTQPASVSGSPGQSITISC | TGTSSDVGAYNYVS | WYQHPGKAPKLMIY | DVSDRPS | GVSNRFSGSKSGNTASLTISGLQAEDEADYYC | SSYTSSSTYV |
| 4C10.1 | DIVMTQSPSSLSASVGDRVTITC | RASQDINNRLA | WYQQKPGKAPKLLIY | GATSLQS | GVPSRFSGSGSGTEFTLAINLQPDDFATYYC | QQANSLPLT |
| 4C10.2 | QSALTQPASVSGSPGQSITISC | TGTSSDVGRYNLVS | WYQQHPGKPPKLMIY | DVSNRPS | GVSNRFSASKSGNTASLTVSGLQAEDEADYYC | SSYAGGNNLWV |
| 8C1 | QPVLTQPPSASGTPGQRVTISC | SGGSSNIGSNTVN | WYQQLPGTAPKLLIY | NNNQRPS | GVPDRFSGSKSGTSASLAISGLQSEDEADYYC | AAWDDSLNGWV |
| 8C2 | QPGLTQPPSASGTPGQRVTISC | SGSSSNIGSNTVN | WYQQLPGTAPKLLIY | SNNQRPS | GVPDRFSGSKSGTSASLAISGLQSEDEADYYC | AAWDVSLNAYV |

FIG. 4 Panel I

BoNT/C, BoNT C/D, BoNT D/C, BoNT/D binder ( 47 clones)

| VL/Clone | Framework1 | CDR1 | Framework2 | CDR2 | Framework3 | CDR3 |
|---|---|---|---|---|---|---|
| 8C3 | SYELTQPPSASGTPGQRVSISC | SGSSSNIGSNPVN | WYQQLPGTAPKLLIY | SNNHRPS | GVPDRFSGSKSGTSASLAISGLQSEDEADYYC | AAWDDSLSTVV |
| 8C4 | QPVLTQPPSASGTPGQRVTISC | SGSSSNIGSNTVN | WYQQLPGTAPKLLIY | SNNQRPS | GVPDRFSGSKSGTSASLAISGLQSEDEADYYC | AAWDDSLNAYV |
| 8C5 | DIVMTQTPSSLSASVGDRVTITC | RTSQGFTSALA | WYQQKSGEPPKLLIY | DASRLES | GVPSRFSGSGSGSDFALIISSLQPEDFATYYC | QQSNSYPLT |
| 8C6 | SSELTQDPAVSVALGQTVRITC | QGDSLRSSSAS | WYQQKPGQAPVLVIF | GENKRPS | GIPDRFSGSTSGNTVSLTITGAQAEDEADYYC | NSRDSSGNHL |
| 8D1 | DIVMTQSPSSLSASVGDRVTITC | RASQGISSYLN | WYQQKLGKAPKLLIY | AASSLQS | GVPSRFSGSGSGTDFTLTISSLQPEDFATYYC | QQSYGTPRT |
| 8D2 | EIVLTQSPSSLSASVGDRVTITC | QASQDISNSLC | WYQQKPGKAPKLLIY | DASNLET | GVPSRFSGSGSGTDFIFTISSLQPEDIATYYC | QQYDNLLRV |
| 8DC1 | EIVLTHSPSSLSASVGDRITITC | RASQGISNYLA | WYQQKPGKAPKVLIY | KASSLEN | GVPSRFSGSGSGTDFTLTITSLQPDDFATYYC | QQYNAYPLT |
| 8DC1.2 | DIQMTQSPSSLSAFVGDRITITC | RASRGVSNYLA | WYQQKPGKAPKLLIY | AASSLQS | GVPSRFSGSGSGTEFTLTISGLQPDDFATYYC | QQYNAYPLT |
| 8DC2 | ASVLTQDPSASGSPGQSVTISC | TGTSSDVGGYNYVS | WYQQHPGKAPKLMIY | DVSNRPS | EVPDRFSGSKSGNTASLTVSGLQAEDEADYYC | SSYAGSNKRV |
| 8DC3 | AELTQDPAVSVALGQTVRITC | QGDSLRNYYAS | WYQQKPGQAPVLVIY | GKNIRPS | GIPDRFSGSSSGNTASLTITGAQAEDEADYYC | NSRDSNGNHYV |
| 8DC4 | DVVMTQSPSSLSASVGDRVTITC | QASQDISSYLN | WYQQKPGKAPKLLIY | AASSLQS | GVPSRFSGSGSGTDFTLTISSLQPEDFATYYC | QQSYSTPLT |
| 8DC4.1 | EIVLTQSPSSLSASVGDRVTITC | RASQSISSYLN | WYQQKPGKAPKLLIY | AASSLQS | GVPSRFSGSGSGTDFTLTISSLQPEDFATYYC | QQSYNTPLT |
| 8DC5 | DIQMTQSPSSLSASVGDRVTITC | RASQGIRNDLG | WYQQKPGKAPKRLIY | AASSLQS | GVPSRFSGSGSGTDFTLTISSLQPEDFATYYC | LQHNSYPWT |
| 8DC6 | DVVMTQSPSSVSASVGDRVTITC | RASQGISSYLA | WYQQKPGKVPKLLIY | AASSLQR | GVPSRFSGSGSGTDFTLTISRLQPEDVATYYC | QKYNSAPLT |
| 8DC7 | EIVLTQSPSSLSASVGDRVTITC | RASQSISSYLA | WYQQKPGKAPELLIY | AASTLQS | GVPSRFSGSGSGTDFTLTISSVQPEDFATYYC | QQSYSTPFT |
| 8DC8 | DIVMTQSPSTLSASVGDRVTITC | RASQSINIWMA | WYQQKPGKAPKLLVY | KASSLES | GVPSRFSGSGSGTEFTLTISSLQPDDFATYYC | QQYNSYGT |
| 8DC10 | EIVLTQSPSSVSVSVGDRVTITC | RASQSISSYLN | WYQQKPGKAPKLLIY | AASSLQS | GVPSRFSGSGSGTDFTLTISSLQPEDFATYYC | QQSYSTPWT |
| 8DC11 | EIVLTQSPSFLSASVGDRVTITC | RASQGIRNDLA | WFQQKPGKAPKLLIY | ATSTLQS | GVPSRFSGSGSGTDFTLTISSLQPEDFADYYC | QQAASFPLT |
| 8DC12 | DIVMTQSPSFLSASIGDRVTITC | RASQSISNWLA | WYQQKPGKAPKVLVY | KASSLEN | GVPSRFSGSGSGTDFTLTITSLQPDDFATYYC | QQYNAYPLT |
| 8DC13 | DIVMTQSPSTLSASVGARVTITC | RASQNINTYLN | WYHQKPGKAPKLLIY | AASSLQS | GVPSRFSGSGSGTDFTLTISSLQPEDFATYYC | QQSYSTPHT |
| 8DC14 | DIVMTQSPSSVSASVGDRVTITC | RASQGISSWLA | WYQQKPGKAPKLLIY | AASSLQS | GVPSRFSGSGSGTDFTLTISRLQPEDVATYYC | QRYNSLPFT |
| 8DC15 | DIQMTQSPSSLSASVGDRITITC | RASRDIRDDLA | WYQQKPGKAPKLLIY | AASSLQS | GVPSRFSGSGSGTEFTLTISSLQPEDFATYYC | QQANSFPLT |

FIG. 4 Panel I (Cont. 1)

BoNT/C, BoNT C/D, BoNT D/C, BoNT/D binder (47 clones)

| VL/Clone | Framework4 | | |
|---|---|---|---|
| 1C1 | FGQGTKLEIKR | SEQ ID NO:195 |
| 1C1.1 | FGQGTKVGIKR | SEQ ID NO:196 |
| 1C2 | FGQGTKLEIKR | SEQ ID NO:197 |
| 1C3 | FGGGTKVEIKR | SEQ ID NO:198 |
| 1C4 | FGQGTKLEIKR | SEQ ID NO:199 |
| 1C8 | FGGGTKVDIKR | SEQ ID NO:200 |
| 87C1 | FGQGTRLEIKH | SEQ ID NO:201 |
| 87C2 | FGQGTKLEIKR | SEQ ID NO:202 |
| 87C78 | FGQGTKVEIKR | SEQ ID NO:203 |
| 4C1 | FGGGTKLEIKR | SEQ ID NO:204 |
| 4C2 | FGQGTKVDIKR | SEQ ID NO:205 |
| 4C3 | FGAGTKLTVLG | SEQ ID NO:206 |
| 4C4 | FGQGTKVEIKR | SEQ ID NO:207 |
| 4C4.1 | FGQGTKVEIKR | SEQ ID NO:208 |
| 4C4.2 | FGQGTKVEIKR | SEQ ID NO:209 |
| 4C5 | FGGGTKLEIKR | SEQ ID NO:210 |
| 4C6 | FGQGTKVEIKR | SEQ ID NO:211 |
| 4C7 | FGGGTKVEIKR | SEQ ID NO:212 |
| 4C8 | FGQGTKVEIKR | SEQ ID NO:213 |
| 4C9 | FGQGTKVEIKR | SEQ ID NO:214 |
| 4C10 | FGTGTKLTVLG | SEQ ID NO:215 |
| 4C10.1 | FGGGTKVDIKR | SEQ ID NO:216 |
| 4C10.2 | FGGGTKVTVLG | SEQ ID NO:217 |
| 8C1 | FGGGTQLTVLG | SEQ ID NO:218 |
| 8C2 | FGTGTKVTVLG | SEQ ID NO:219 |

FIG. 4 Panel I (Cont. 2)

BoNT/C, BoNT C/D, BoNT D/C, BoNT/D binder (47 clones)

| VL/Clone | Framework4 | | |
|---|---|---|---|
| 8C3 | FGGGTKLTVLG | SEQ ID NO: | 220 |
| 8C4 | FGTGTQLTVLG | SEQ ID NO: | 221 |
| 8C5 | FGGGTKVDIKR | SEQ ID NO: | 222 |
| 8C6 | FGGGTKVTVLG | SEQ ID NO: | 223 |
| 8D1 | FGQGTKVEIKR | SEQ ID NO: | 224 |
| 8D2 | FGGGTKLEIKR | SEQ ID NO: | 225 |
| 8DC1 | FGGGTKLEIKR | SEQ ID NO: | 226 |
| 8DC1.2 | FGGGTKLEIKR | SEQ ID NO: | 227 |
| 8CC2 | FGGGTKLTVLG | SEQ ID NO: | 228 |
| 8DC3 | FGTGTKVTVLG | SEQ ID NO: | 229 |
| 8DC4 | FSGGTKVTVLG | SEQ ID NO: | 230 |
| 8DC4.1 | FGGGTKVEIKR | SEQ ID NO: | 231 |
| 8DC5 | FGGGTKVEIKR | SEQ ID NO: | 232 |
| 8DC6 | FGGGTKVEIKR | SEQ ID NO: | 233 |
| 8DC7 | FGQGTKVEIKR | SEQ ID NO: | 234 |
| 8DC8 | FGKGTKVEIKR | SEQ ID NO: | 235 |
| 8DC10 | FGQGTKVDIKR | SEQ ID NO: | 236 |
| 8DC11 | FGGGTKVDIKR | SEQ ID NO: | 237 |
| 8DC12 | FGGGTKVEIKR | SEQ ID NO: | 238 |
| 8DC13 | FGGGTKLEIKR | SEQ ID NO: | 239 |
| 8DC14 | FGGGTKLEIKR | SEQ ID NO: | 240 |
| 8DC15 | FGGGTKVDIKR | SEQ ID NO: | 241 |

FIG. 4 Panel I (Cont. 3)

BoNT/F binder (36 clones)

| VL/Clone | Framework1 | CDR1 | Framework2 | CDR2 | Framework3 | CDR3 |
|---|---|---|---|---|---|---|
| 6F1 | SELTQDPAVSVALGQTVRITC | QGDSLRSYYAS | WYQQKPGQAPVLVIY | GKNNRPS | GIPDRFSGSSSGNTASLTITGAQAEDEADYFC | NSRDSNGHRI |
| 6F3 | ENVLTQSPAIMSASLGEEITLIC | SASSSVSYMH | WYQQKGTSPKLWIY | YTSNLAS | GVPARFSGSGSGTSYSLTISSMEAEDAATYYC | QQWSSNPYT |
| 6F4 | QIVLTQSPATMSASPGEKVTITC | SASSSVNYMH | WYQQKPGSSPKLWIY | DTSSLAP | GVPARFSGSGSGTSYSLTISSMEAEDAASYFC | HQWSSYPYT |
| 6F5 | DIEMTQSPPSLSASVGDRVSLTC | RASEYIGTSLN | WYQQKPGKAPKLLIY | AASALHS | GVPSRFSGSGSGTDFTLTISGLQPEDFATYYC | QQANDLPLT |
| 39A1 | DIVMTQSPPSLSASVGDRVSLTC | RASEYIGTSLN | WYQQKPGKAPKLLIY | AASALHS | GVPSRFSGSGSGTDFTLTISGLQPEDFATYYC | QQANDLPLT |
| 41C2 | DIVMTQSPPSLSASVGDRVSLTC | RASEYIGTSLN | WYQQKPGKAPKLLIY | AASALHS | GVPSRFSGSGSGTDFTLTISGLQPEDFATYYC | QQTNDLPLT |
| 43D3 | DIVMTQSPPSLSASVGDRVSLTC | RASEYIGTSLN | WYQQKPGKAPKLLIY | AASALHS | GVPSRFSGSGSGTDFTLTISGLQPEDFATYYC | QQANDLPLT |
| 39H6 | DIVMTQSPPSLSASVGDRVSLTC | RASEYIGTSLN | WYQQKPGKAPKLLIY | AASALHS | GVPSRFSGSGSGTDFTLTISGLQPEDFATYYC | QQANDLPLT |
| 41E2 | DILMTQSPPSLSASVGDRVSLTC | RASEYIGTSLN | WYQQKPGKAPKLLIY | AASALHS | GVPSRFSGSGSGTDFTLTISGLQPEDFATYYC | QQANDLPLT |
| 41F7 | DIVMTQSPPSLSASVGDRVSLTC | RASEYIGTSLN | WYQQKPGKAPKLLIY | AASALHS | GVPSRFSGSGSGTDFTLTISGLQPEDFATYYC | QQTNDLPLT |
| 42G8 | DIVMTQSPPSLSASVGDRVSLTC | RASEYIGTSLN | WYQQKPGKAPKLLIY | AASALHS | GVPSRFSGSGSGTDFTLTISGLQPEDFATYYC | QQANDLPLT |
| 39D1.1 | DIVMTQSPPSLSASVGDRVSLTC | RASEYIGTSLN | WYQQKPGKAPKLLIY | AASALHS | GVPSRFSGSGSGTDFTLTISGLQPEDFATYYC | QQTNDLPLT |
| 41A4 | DIVMTQSPPSLSASVGDRVSLTC | RASEYIGTSLN | WYQQKPGKAPKLLIY | AASALHS | GVPSRFSGSGSGTDFTLTISGLQPEDFATYYC | QQANDLPLT |
| 41B7 | DIVMTQSPPSLSASVGDRVSLTC | RASEYIGTSLN | WYQQKPGTAPKLLIY | AASALHS | GVPSRFSGSGSGTDFTLTISGLQPEDFATYYC | QQANDLPLT |
| 39D5.1 | DIVMTQSPPSLSASVGDRVSLTC | RASEYIGTSLN | WYQQKPGKAPKLLIY | AASALHS | GVPSRFSGSGSGTDFTLTISGLQPEDFATYYC | QQTNDLPLT |
| 41G8 | DIVMTQSPASLAVSLGQRATISC | RASENIGTSLN | WYQQKPGKAPKLLIY | AASNLES | GIPARFSGSGSGTDFTLTINPVEADDVATYYC | QQSNEDPYT |
| 6F6 | DIVMTQSPASLAVSLGQRATISC | RASESVDNYGISFMN | WFQQKPGQPPKLLIY | AASNLES | GIPARFSGSGSGTDFTLTINPVEADDVATYYC | QQSNEDPYT |
| 6F7 | DIVLTQTPAIMSASPGEKVTMTC | SASSSVSYMH | WFQQKPGTSPKLWIY | STSNLAS | GVPARFSGSGSGTSYSLTISRMEAEDAATYYC | QQRSSYPPT |

FIG. 4 Panel J

BoNT/F binder (36 clones)

| VL/Clone | Framework1 | CDR1 | Framework2 | CDR2 | Framework3 | CDR3 |
|---|---|---|---|---|---|---|
| 28C9 | DVLMTQTPLSLPVSLGDQASISC | RSSQSLVHSNGNTYLH | WYLQKPGQSPKLLIY | KVSNRFS | GVPDRFSGSGSGTDFTLKISRVEAEDLGVYFC | SQSTHVPYT |
| 28H4 | DIVLTQSPAIMSASPGEKVTMTC | SASSSVSYMY | WYQQKPGSSPKPWIY | RTSNLAS | GVPVRFSGSGSGTSYSLTISSMEAEDAATYYC | QQYHNFPPT |
| 29A2 | EIVLTQSPALMSASPGEKVTMTC | SASSSVSYMY | WYQQKPRSSPKPWIY | LTSNLAS | GVPARFSGSGSGTSYSLTISSMEAEDAATYYC | QQWSSNPYT |
| 29B8 | ENVLTQSPAIMSASPGEKVTMTC | SASSSVSYMH | WYQQKSGTSPKRWIY | DTSNLAP | GVPARFSGSGSGTSYSLTISSMEAEDAASYFC | HQWSSYPYT |
| 6F8 | DVVMTQTPSSLAVSLGQRATISC | RASESVDNYGISFMN | WFQQKPGQPPRLLIY | AASNQGS | GVPARFSGSGSGTDFRLNIHPMEEDDTAMYFC | QQSKEVPWT |
| Hu6F8 | DVVMTQSPLSLPVTLGQPASISC | RASESVDNYGISFMN | WFQQRPGQPPRLLIY | AASNQGS | GVPDRFSGSGSGTDFTLKISRMEAEDVAMYFC | QQSKEVPWT |
| 6F9 | DVVMTQSPKFMSTSVGDRVSITC | KASQDVGTAVA | WYQQKPGQSPKLLIY | WASTRHT | GVPDRFTGSGSGTDFTLTISDVLSEDLADYFC | QQYGGYPT |
| Hu6F9 | DVVMTQSPDSLATSLGERVTINC | KASQDVGTAVA | WYQQKPGQPPKLLIY | WASTRHT | GVPDRFSGSGSGTDFTLTISSVQAEDVADYFC | QQYGGYPT |
| 30C8 | DIVLTQSPAIMSASLGEEITLTC | SASSSVSYMH | WYQQKSGTSPKLLIY | STSNLAS | GVPSRFSGSGSGTSYSLTISNMEAEDAATYYC | QQWSSNPYT |
| 32G2 | DIVMTQTPLSLPVSLGDQASISC | RSSQSIVHSNGNTYLE | WYLQKPGQSPTLLIY | KVSNRFS | GVPDRFSGSGSGTDFTLKISRVEAEDLGVYYC | FQGSHVPYT |
| 6F10 | DIVLTQSPAITAASLGQKVTITC | SASSSGSYIH | WYQQKSGTSPKLLIY | RTSNLAS | GVPSRFSGSGSGTFYSLTISSVEAEDAADYFC | HQWSSYPT |
| Hu6F10 | DIQMTQSPSSLSASVGDRVTITC | SASSSGSYIH | WYQQKPGKVPKLLIY | RTSNLAS | GVPSRFSGSGSGTDYTLTISSVQPEDVADYFC | HQWSSYPT |
| 37B4 | QTVVTQEPSLTVAPGGTVTLTC | GSSAGAVTTDHYPS | WFQKKPGQAPTTIIY | DTTNKHSMTP | GPARFSGSLLGGKAALTLSGAQPEDEAEYYC | FLSYRGSRPV |
| 37B6 | SSELSQDPAVSVALGQTVRITC | QGDSLRSYYAS | WYQQKPGQAPVLVIY | GKNNRPS | GIPDRFSGSSSGNTASLTITGAQAEDEADYYC | SSRDSS |
| 38B8 | SSELSQDPAVSVALGQTVRITC | QGDSLRSYYAS | WYQQKPGQAPVLVIY | GKNNRPS | GIPDRFSGSSSGNTASLTITGAQAEDEADYYC | SSRDSS |
| 38C1 | SSELSQDPAVSVALGQTVRITC | QGDSLRSYYAS | WYQQKPGQAPVLVIY | GKNNRPS | GIPDRFSGSSSGNTASLTITGAQAEDEADYYC | SSRDSS |
| 38D11 | QPGLTQPPSASGTPGQRVTISC | SGSSSNIGSNTVN | WYQQLPGTAPKLLIY | SNNQRPS | GVPDRFSGSKSGTSASLAISGLQSEDEADYYC | AAWDDSLNGYV |
| 38F8 | SSELSQDPAVSVALGQTVRITC | QGDSLRSYYAS | WYQQKPGQAPVLVIY | GKNNRPS | GIPDRFSGSSSGNTASLTITGAQAEDEADYYC | SSRDSS |

FIG. 4 Panel J (Cont. 1)

BoNT/F binder (21 clones)

| VL/Clone | Framework4 | |
|---|---|---|
| 6F1 | FGGGTKLTVLG | SEQ ID NO:242 |
| 6F3 | FGGGTKLEIKR | SEQ ID NO:243 |
| 6F4 | FGGGTKLEIKR | SEQ ID NO:244 |
| 6F5 | FGGGTKLEIKR | SEQ ID NO:245 |
| 39A1 | FGGGTKLEIKR | SEQ ID NO:246 |
| 41C2 | FGGGTKLEIKR | SEQ ID NO:247 |
| 43D3 | FGGGTKLENKR | SEQ ID NO:248 |
| 39H6 | FGGGTKLEIKR | SEQ ID NO:249 |
| 41E2 | FGGGTKLEIKR | SEQ ID NO:250 |
| 41F7 | FGGGTKLEIKR | SEQ ID NO:251 |
| 42G8 | FGGGTKLEIKR | SEQ ID NO:252 |
| 39D1.1 | FGGGTKLEIKR | SEQ ID NO:253 |
| 41A4 | FGGGTKLEIKR | SEQ ID NO:254 |
| 41B7 | FGGGTKLEIKR | SEQ ID NO:255 |
| 39D5.1 | FGGGTKLEIKR | SEQ ID NO:256 |
| 41G8 | FGGGTKLEIKR | SEQ ID NO:257 |
| 6F6 | FGGGTKLEIKR | SEQ ID NO:258 |
| 6F7 | FGGGTRLEIKR | SEQ ID NO:259 |

FIG. 4 Panel J (Cont. 2)

BoNT/F binder (21 clones)

| VL/Clone | Framework4 | |
|---|---|---|
| 28C9 | FGGGTRLEIKA | SEQ ID NO:260 |
| 28H4 | FGGGTKLEIKA | SEQ ID NO:261 |
| 29A2 | FGGGTKLELKA | SEQ ID NO:262 |
| 29B8 | FGGGTKLEIKA | SEQ ID NO:263 |
| 6F8 | FGGGTKLEIKR | SEQ ID NO:264 |
| Hu6F8 | FGGGTKLEIKR | SEQ ID NO:265 |
| 6F9 | FGGGTKLEIKR | SEQ ID NO:266 |
| Hu6F9 | FGGGTKLEIKR | SEQ ID NO:267 |
| 30C8 | FGGGTKLELKA | SEQ ID NO:268 |
| 32G2 | FGGGTKLEIKA | SEQ ID NO:269 |
| 6F10 | FGGGTKLEIKR | SEQ ID NO:270 |
| Hu6F10 | FGGGTKLEIKR | SEQ ID NO:271 |
| 37B4 | FGGGTKVTVLA | SEQ ID NO:272 |
| 37B6 | GDPGTKLTVLA | SEQ ID NO:273 |
| 38B8 | GDPGTKLTVLA | SEQ ID NO:274 |
| 38C1 | GDPGTKLTVLA | SEQ ID NO:275 |
| 38D11 | FGTGTKVTVLA | SEQ ID NO:276 |
| 38F8 | GDPGTKLTVLA | SEQ ID NO:277 |

FIG. 4 Panel J (Cont. 3)

additional BoNT/B binder (2 Clones)

| VHClone | Framework1 | CDR1 | Framework2 | CDR2 |
|---|---|---|---|---|
| 4B19 | QVQLVQSGAEVKKPGASVNVSCKASGYTFT | GYYIY | WVRQAPGQGLEWMG | WINPNSGVTKYAQKFQG |
| 4B19.1 | QVQLVQSGAEVKKPGASVNVSCKASGYTFT | GYYIY | WVRQAPGQGLEWMG | WINPNSGVTKYAQKFQG |

| VH/Clone | Framework3 | CDR3 | Framework4 | |
|---|---|---|---|---|
| 4B19 | RVTMTIDTSTNTAYMELNRLRADDTAVYYCAR | EWTQLWSPYDY | WGQGTTVTVSS | SEQ ID NO:278 |
| 4B19.1 | RVTMTIDTSTNTAYMELNRLRADDTAVYYCAR | EWTQLWSPYDY | WGQGTTVTVSS | SEQ ID NO:279 |

| VL/Clone | Framework1 | CDR1 | Framework2 | CDR2 |
|---|---|---|---|---|
| 4B19 | EIVLTQSPSSFSASVGDRVTITC | RASQSISSYLN | WYQQKPGKAPKLLIY | AASSLQS |
| 4B19.1 | DIVLTQSPSTLSASVGDRVTISC | RASRSIGWYLN | WYQQRPGKAPKLLIY | AASSLHN |

| VL/Clone | Framework3 | CDR3 | Framework4 | |
|---|---|---|---|---|
| 4B19 | GVPSRFSGSGSGTDFTLTISSLQPEDFATYYC | QQSYSTPLT | FGGGTKLEIKR | SEQ ID NO:280 |
| 4B19.1 | GVPSRFSGSGSGTEFTLTISSLQPDDFATYYC | QQAFGFPRT | FGQGTKVEIKR | SEQ ID NO:281 |

FIG. 4 Panel K

BoNT/G binder (2 clones)

| VH/Clone | Framework1 | CDR1 | Framework2 | CDR2 |
|---|---|---|---|---|
| 7G1 | QVQLVQSGAEVKRPGASVKISCKTSGYSFN | DYSLQ | WVRQAPGQGPEWMG | MISPAGTGPVYTKNFRD |
| 7G2 | QVQLQQSGGGLIQPGGSLRLSCVASGLTVS | SNYMS | WVRQAPGKGLEWVS | AISGSGGTTYYADSVKG |

| VH/Clone | Framework3 | CDR3 | Framework4 | |
|---|---|---|---|---|
| 7G1 | RVTLTSDTSTGTAYMELRSLTSGDTAIYFCAR | GIHRSGWRKFFDF | WGQGTLVTVSS | SEQ ID NO:282 |
| 7G2 | RFTISRDNSKNTLYLQMNSLRAEDTAVYYCAR | LNNGEYDY | WGQGTLVTVSS | SEQ ID NO:283 |

| VL/Clone | Framework1 | CDR1 | Framework2 | CDR2 |
|---|---|---|---|---|
| 7G1 | DIQMTQSPSSVSASVGDRVTITC | RASQSISGYLN | WYQQKPGKAPKLLIY | ATSSLQS |
| 7G2 | EIVLTQSPSSLSASVGDRVTITC | RASQGISNYLA | WFQQKPGKVPKRLIY | AASSLHS |

| VH/Clone | Framework3 | CDR3 | Framework4 | |
|---|---|---|---|---|
| 7G1 | GAPSRFSGSGSGTDFTLTISSLQPEDFATYYC | QQANSFPLT | FGGGTKVEIKR | SEQ ID NO:284 |
| 7G2 | GVPSRFSGSGSGTEFTLTISGLQPEDFATYYC | QHLNSYPLT | FGGGTKVEIKR | SEQ ID NO:285 |

FIG. 4 Panel L panel A

| VH/Clone | Framework1 | CDR1 | Framework2 | CDR2 | Framework3 |
|---|---|---|---|---|---|
| 2B23K1 | EVQLLESGGGLVQPGGSLRLSCAASGFTFS | NYPMS | WVRQAPGKGLAWVS | SLTASGDNTFYADSVKG | RFTISRDNSKNTLYLQMHSLRAEDTAVYYCAK |
| 2B23K2 | EVQLLESGGGLVQPGGSLRLSCAASGFTFS | NYPMS | WVRQAPGKGLAWVS | SLTASGDNTFYADSVKG | RFTISRDNSKNTLYLQMHSLRAEDTAVYYCAK |
| 2B23K4 | EVQLLESGGGLVQPGGSLRLSCAASGFTFS | NYPMS | WVRQAPGKGLAWVS | SLTASGDNTFYADSVKG | RFTISRDNSKNTLYLQMHSLRAEDTAVYYCAK |
| 2B23K7 | EVQLLESGGGLVQPGGSLRLSCAASGFTFS | NYPMS | WVRQAPGKGLAWVS | SLTASGDNTFYADSVKG | RFTISRDNSKNTLYLQMHSLRAEDTAVYYCAK |
| 2B23K11 | EVQLLESGGGLVQPGGSLRLSCAASGFTFS | NYPMS | WVRQAPGKGLAWVS | SLTASGDNTFYADSVKG | RFTVSRDNRKSSVFLQMNNLRVDDTAVYYCAK |
| 6F5.1 | EVQLVPSGGNIVQPGGSLRLSCAATGPIGS | HWMT | WVRQAPGQGPEWMG | NINLDGTEKFYVDSVKG | RVTLTSDTSIGTAYMELRSLTSGDTAIYFCAR |
| 7G1.1 | QVQLQQSGAEVKRPGASVKISCKTSGYSFN | DYSLQ | WVRQAPGQGPEWMG | MISPAGTGPVYTKNFRD | RVTITADESTSTTYMELSSLRSEDTAVYYCAR |
| 7G2.1 | QVQLQQSGGLIQPGGSLRLSCVASGLTVS | SNYMS | WVRQAPGKGLEWVS | AISGSGGTTYYADSVKG | RFTISRDNSKNTLYLQMNSLRAEDTAVYYCAR |
| 7G3 | QVTLKESGAEVKKPGSSVKVSCKASGGTFS | RHGIS | WVRQVPGQGLEWMG | GIIPIFGTAKYAQKFQG | RVTITADESTSTTYMELSSLRSEDTAVYYCAR |
| 7G4 | QVQLVQSGAEVKKPGESLKISCKGSGYTFA | NEWIA | WVRQMPGKGLDYMG | MIWPGVSETRYSPSFQG | QVTISADKSSNTAYLHWSSLKASDSAMYYCVR |
| 7G5 | EVQLVQSGAEVKKPGASVKVSCKASGGTFS | SYAIS | WVRQAPGQGLEWMG | GIIPIFGTANYAQKFQG | RVTITADESTSTAYMELSRLRSDDTAVYYCAR |
| 7G6 | EVQLVQSGAEVKKPGSSVKVSCKASGGTFS | SYAIS | WVRQAPGQGLEWMG | GIIPIFGTANYAQKFQG | RVTITADESTSTAYMELSSLRSEDTAVYYCLY |
| 7G7 | EVQLVQSGAEVRKPGASVKLSCKASGYTFT | DYYVH | WMRQAPGQGLEWMG | WIDPNGGGTNSAQKFRG | RVTLTRDTSISTAYMELRRLKSDDTAVYYCAR |
| 7G8 | QVQLQESGPGLVKPSETLSLICTVSGAFMD | GYFLN | WIRQTPGKGLEWIG | YIYYTGRTSYSPSLNS | RLTMSVDTSKTQFSLKLTSMAAADTAIYCAR |
| 7G9 | EVQLVQSGAEVKKPGSSVKVSCKASGGTFS | TYTEN | WVRQAPGQGLEWIG | GIIPLFRTSHYAQKFQG | RVTISADESTSTAYMELTSLRPEDTAVYYCAR |
| 7G10 | QVQLVQSGGGVVQPGRSXRLSCAASGFTFS | KYVMH | WVRQAPGKGLEWVA | VIWHDGSHRFYGDSVKG | RFTISRDNSKNTVYLQMNSLRAEDTAVYYCAR |
| 7G11 | EVQLVQSGAEVKKPGSSVKVSCKASGDTFT | NYAIS | WVRQAPGQGLEWMG | GFIPMFATANHAQKFQG | RLSITADKSISTAYMELSGLRSLRSDDTAVYYCAG |
| 2B23EK1 | EVQLLESGGGLVQPGGSLRLSCAASGFTFS | NYPMS | WVRQAPGKGLEWVS | SLTASGDNTFYADSVKG | RFTISRDNSKNTLYLQMHSLRAEDTAVYYCAK |
| 2B23EK4 | EVQLLESGGGLVQPGGSLRLSCAASGFTFS | NYPMS | WVRQAPGKGLEWVS | SLTASGDNTFYADSVKG | RFTISRDNSKNTLYLQMHSLRAEDTAVYYCAK |
| 2B23EK5 | EVQLLESGGGLVQPGGSLRLSCAASGFTFS | NYPMS | WVRQAPGKGLEWVS | SLTASGDNTFYADSVKG | RFTISRDNSKNTLYLQMHSLRAEDTAVYYCAK |
| 2B23EK6 | EVQLLESGGGLVQPGGSLRLSCAASGFTFS | NYPMS | WVRQAPGKGLEWVS | SLTASGDNTFYADSVKG | RFTISRDNSKNTLYLQMHSLRAEDTAVYYCAK |
| 2B23EK7 | EVQLLESGGGLVQPGGSLRLSCAASGFTFS | NYPMS | WVRQAPGKGLEWVS | SLTASGDNTFYADSVKG | RFTISRDNSKNTLYLQMHSLRAEDTAVYYCAK |
| 2B23EK10 | EVQLLESGGGLVQPGGSLRLSCAASGFTFS | NYPMS | WVRQAPGKGLEWVS | SLTASGDNTFYADSVKG | RFTISRDNSKNTLYLQMHSLRAEDTAVYYCAK |
| 2B23EK11 | EVQLLESGGGLVQPGGSLRLSCAASGFTFS | NYPMS | WVRQAPGKGLEWVS | SLTASGDNTFYADSVKG | RFTISRDNSKNTLYLQMHSLRAEDTAVYYCAK |
| 2B23EK12 | EVQLLESGGGLVQPGGSLRLSCAASGFTFS | NYPMS | WVRQAPGKGLEWVS | SLTASGDNTFYADSVKG | RFTISRDNSKNTLYLQMHSLRAEDTAVYYCAK |

FIG. 5A panel B

| VH/Clone | Framework1 | CDR1 | Framework2 | CDR2 | Framework3 |
|---|---|---|---|---|---|
| 8D2.2 | QVQLVQSGAEVKKPGESLKISCKGSGYSFT | SFWIG | WVRQMPGKGLEWMG | IIYPGDSDTRYSPSFQG | QVTISADKSISTAYLQWSSLKASDTAMYYCVS |
| 8D2.3 | QVQLVQSGAEVKKPGESLKISCKGSGYSFT | SYWIG | WVRQMPGKGLEWMG | IIYPGDSDTRYSPSFQG | QVTISADKSISTAYLQWSSLKASDTAMYYCVS |
| 8DC3.1 | QVQLVQSRGGLVKPGGSLRLSCAASGFTFS | SHSMN | WVRQAPGKGLEWVS | SISSSSYIYYADSVKG | RFTISRDNSKNSLYLQLNSLRAEDTAVYYCAR |
| 8DC8.3 | QVQLQQSGPGLVKPSETLSLTCTVSGGSIS | SAGYSWS | WIRQSPGKGLECIG | YIYQTGSTFYNLSLKG | RVTMSLDRSKNQISLRLTSVVAADTAVYYCAR |
| 8DC8.6 | QVQLQQSGPGLVKPSETLSLTCTVSGGSIS | SAGYSWS | WIRQSPGKGLECIG | YIYQTGSTFYNLSLKG | RVTMSLDRSKNQISLRLTSVVAADTAVYYCAR |
| B4 | QVQLVESGGGVVRPGGSLRLSCAASGFTFD | DYGMS | WVRQAPGKGLEWVS | AINWNGNTGYADSVKG | RFTISRDNAKNSLYLQMNSLRVEDIALYHCAR |
| A9 | QVQLVQSGGGVVQPGRSLRLSCAASGFTFS | SYGMH | WVRQAPGKGLEWVS | SISSSSYIYYADSVKG | RFTISRDNSKNTLYLQMNSLRAEDTAVYYCAR |
| A2S | QVQLQESGGGLVQPGGSLRLSCAASGFTFK | YDYMY | WFRQAPGKGLEWVA | TISDGGSYTYYSDSVEG | RFTTSRDNSKNTLYLQMNSLRAEDIAIYYCSR |

FIG. 5A (Cont.)

panel A

| VH/Clone | CDR3 | Framework4 | |
|---|---|---|---|
| 2B23K1 | ALVGRYDISTGYYRPVMDS | WGQGTLVTVSS | SEQ ID NO:286 |
| 2B23K2 | ALVGRYDISTGYYRPVMDS | WGQGTLVTVSS | SEQ ID NO:287 |
| 2B23K4 | ALVGRYDISTGYYRPVMDS | WGQGTLVTVSS | SEQ ID NO:288 |
| 2B23K7 | ALVGRYDISTGYYRPVMDS | WGQGTLVTVSS | SEQ ID NO:289 |
| 2B23K11 | ALVGRYDISTGYYRPVMDS | WGQGTLVTVSS | SEQ ID NO:290 |
| 6F5.1 | LQWGGYNGWLSP | WGQGTLVTVSS | SEQ ID NO:291 |
| 7G1.1 | GIHRSGWRKFFDF | WGQGTLVTVSS | SEQ ID NO:292 |
| 7G2.1 | LNNGEYDY | WGQGTLVTVSS | SEQ ID NO:293 |
| 7G3 | DGRWLALRRFDY | WGQGTLVTVSS | SEQ ID NO:294 |
| 7G4 | RPSMWYRHPFDF | WGQGTLVTVSS | SEQ ID NO:295 |
| 7G5 | DSPLLDYGDYRDY | WGQGTLVTVSS | SEQ ID NO:296 |
| 7G6 | SSSVDAFDI | WGQGTTVTVSS | SEQ ID NO:297 |
| 7G7 | KLGGSYNANDY | WGQGTTVTVSS | SEQ ID NO:298 |
| 7G8 | GRQLWPTAQYYLDY | WGPGTTVTVSS | SEQ ID NO:299 |
| 7G9 | VALGYCSSPTCAHFDY | WGQGTLVTVSS | SEQ ID NO:300 |
| 7G10 | DPGFTNGSHFYYYMDV | WGKGTLVTVSS | SEQ ID NO:301 |
| 7G11 | ARKIYHGSGSYPFNY | WGQGTLVTVSS | SEQ ID NO:302 |
| 2B23EK1 | ALVGRYDISTGYYRPVMDS | WGQGTLVTVSS | SEQ ID NO:303 |
| 2B23EK4 | ALVGRYDISTGYYRPVMDS | WGQGTLVTVSS | SEQ ID NO:304 |
| 2B23EK5 | ALVGRYDISTGYYRPVMDS | WGQGTLVTVSS | SEQ ID NO:305 |
| 2B23EK6 | ALVGRYDISTGYYRPVMDS | WGQGTLVTVSS | SEQ ID NO:306 |
| 2B23EK7 | ALVGRYDISTGYYRPVMDS | WGQGTLVTVSS | SEQ ID NO:307 |
| 2B23EK10 | ALVGRYDISTGYYRPVMDS | WGQGTLVTVSS | SEQ ID NO:308 |
| 2B23EK11 | ALVGRYDISTGYYRPVMDS | WGQGTLVTVSS | SEQ ID NO:309 |
| 2B23EK12 | ALVGRYDISTGYYRPVMDS | WGQGTLVTVSS | SEQ ID NO:310 |

FIG. 5B panel B

| VH/Clone | CDR3 | Framework4 | |
|---|---|---|---|
| 8D2.2 | YSSLDAFDI | WGQGTMVTVSS | SEQ ID NO:311 |
| 8D2.3 | YSSLDAFDI | WGQGTMVTVSS | SEQ ID NO:312 |
| 8DC3.1 | DQGGGSVVGTNWFDP | WGQGTLVTVSS | SEQ ID NO:313 |
| 8DC8.3 | VVGVYPGWFDS | WGQGTLVTVSS | SEQ ID NO:314 |
| 8DC8.6 | VVGVYPGWFDS | WGQGTLVTVSS | SEQ ID NO:315 |
| B4 | EGDYGGLYFDY | WGQGTMVTVSS | SEQ ID NO:501 |
| A9 | GAVAGGSYGMDV | WGQGTMVTVSS | SEQ ID NO:502 |
| A2S | YRYDDAMDY | WGQGTLVTVSS | SEQ ID NO:503 |

FIG. 5B (Cont.)

FIG. 5C panel A

| VL/Clone | Framework1 | CDR1 | Framework 2 | CDR2 | Framework3 |
|---|---|---|---|---|---|
| 2B23K1 | SYELTQPPSASGTPGQRVTISC | SGSSSNIGSNTVN | WYQQLPGTAPKLLIY | SNNQRPS | GVPDRFSGSKSGTSASLAIGEVQSEDEADYYC |
| 2B23K2 | DVVMTQSPATLSLSPGERATLSC | RASQNVNSHLA | WYQQKPGQAPRLLIY | DASSRAT | GIPARFSGSGSGTDFTLTISSLEPEDFAVYYC |
| 2B23K4 | EIVLTQSPSSLSASVGDRVTITC | RASQGISSYLA | WYQQKPGKAPKLLIY | AASTLQS | GVPSRFSGSGSGTEFTLTITISSLQPEDFAVYYC |
| 2B23K7 | ETTLTQSPATLSVSPGERATLSC | RASQSVSSHVA | WYQQKPGQAPRLLIY | DASNRAT | GVPARFSGSGSGTDFTLTISSLEPEDFAVYYC |
| 2B23K11 | EIVLTQSPGTLSLSPGERATLSC | RASQSISNNYLA | WYQQKPGQAPRLLIY | GASSRPT | GIPDRFSGSGSGTDFTLTISRLEPEDFAVYYC |
| 6F5.1 | DIVMTQSPPSLSASVGDRVSLTC | RASEYIGTSLN | WYQQKPGKAPKLLIY | AASALHS | GVPSRFSGSGSGTDFTLTIGLQPEDFATYYC |
| 7G1.1 | EIVLTQSPSSLSASVGDGVTITC | RASQSIGSYLN | WYQQKPGTAPKLLIY | AASSLQS | GVPSRFSGSGSGTDFTLTISSLQPEDFATYYC |
| 7G2.1 | EIVLTQSPSSLSASVGDRVTTTC | QASQDISNYLN | WYQQKPGKAPKLLIY | AASSLES | GVPSRFSGSGSGTDFTLTISSLQPEDVATYYC |
| 7G3 | DVVMTQSPPYLSASVGDRVTTTC | RASQAFTSALA | WYQQKAGEPPKLLIY | DASRLES | GVPSRFSGSGSGTDFTLSISLQPEDFATYFC |
| 7G4 | QPVLTQPPSASGTPGQRVTISC | SGSSSNIGNNPVN | WYQQLPGTAPKLLIY | SNNQRPS | GVPDRFSGSKSGTSASLAIGLQSEDEADYYC |
| 7G5 | DIQMTQSPLSLPVTPGEPASISC | RSGQSLMQSPGYDCLH | WYLQKPGRSPQLLIS | FGSSRAS | GVPDRFSASGSGTDFTLKISRVEADDVGIYYC |
| 7G6 | DIVMTQSPSTLSASVGDTVTIAC | RASRDIRNDLG | WYQQKPGRAPKLLIH | PASTLQT | GVPSRFSGSGSGTDFTLTITSLQPEDSATYYC |
| 7G7 | DIVMTQSPSSLSASVGDRVTITC | RASQGISGYLA | WYQQKPGKAPKLLIY | AASTLQS | GVPSRFSGSGSGTKFTFTISSLQPEDFATYYC |
| 7G8 | EIVLTQSPSSLSASMGDTVTITC | QASQGISSYLA | WYQQKPGKAPKLLIY | MASTLET | GVPSRFSGSRSGTEFTLTISSLQPEDFATYYC |
| 7G9 | SELTQDPAVSVALGQTVRITC | QGDSLRSYYAS | WYQQKPGQAPVIVIY | GKNNRPS | GIPDRFSGSSSGNTASLIITGAAEDEADYYC |
| 7G10 | HVILTQDPAVSVALGQTVRITC | QGDSLGTYYAN | WYQQKPGQAPILVMF | GKNNRPS | GIPDRFSGSSSGNTASLIITGAQAEDEADYYC |
| 7G11 | EIVLTQSPGTLSLSPGERATLSC | RASQVSSTYLA | WYQQKPDQAPRLLIY | GTSSRAT | GVTDRFTGSGSGTDFTLTISGLEPEDLAVYYC |
| 2B23EK1 | EIVLTQSPGTLSLSPGERATLSC | RASQSVSSNLA | WYQQKPGQAPRLLIY | SASTRAT | GVPARFSGSGSGTEFTLTISSLQSEDFAVYYC |
| 2B23EK4 | EIVLTQSPGTLSLSPGERATLSC | RASQSVSSSYLA | WYQQKPDQAPRLLIY | GTSSRAT | GVTDRFTGSGSGTDFTLTISRLEPEDFAVYYC |
| 2B23EK5 | DIVMTQTPATLSVSPGERATLSC | RASQSVRSNLA | WYQQKPGLAPRLLIY | GASTRAT | GIPARFSGSGFGKEFTLTISSLQSEDFAVYYC |
| 2B23EK6 | SYELTQPPSVSVALGQTARITC | GGNNIGSKNVH | WYQQKPGQAPVIVIY | RDSNRPS | GIPERFSGSNSGNTATLTISRAQAGDEADYYC |
| 2B23EK7 | ETTLTQSPATLSVSPGERATLSC | RASQSVSSNLA | WYQQKPGQAPRLLIY | GASTRAT | GIPARFSGSGSGTEFTLTISSLQSEDFAVYYC |
| 2B23EK10 | EIVLTQSPATLSLSPGERATLSC | RASQSISNNYLA | WYQQKPGQAPRLLIY | GASSRAT | GIPARFSGSGSGTDFTLTISGLEPEDVAVYYC |
| 2B23EK11 | EIVLTQSPATLSLSPGERATLSC | RASQSISNNYLA | WYQQKPGQAPRLLIY | GASSRAT | DIPARFSGSGSGSGTDFTLTISISSLEPEDFAVYYC |
| 2B23EK12 | DIQMTQSPSSVSASVGDTVSITC | RASQGIGNLLA | WYQQKPGKAPNLLIY | ASTLQS | GVPSRFSGSGSGTDFTLTISSLQSEDFATYFC | panel B

| VL/Clone | Framework1 | CDR1 | Framework 2 | CDR2 | Framework3 |
|---|---|---|---|---|---|
| 8D2.2 | DIVMTQSPSSLSASVGDRVTITC | QASQDISNYLN | WYQQKPGKAPKLLIY | DASNLET | GVPSRFSGSGSGTDFTFTISSLQPEDIATYYC |
| 8D2.3 | EIVLTQSPSSVSASVGDRVTITC | RASQSIGTYLS | WYQQKPGKAPKLLIY | DASKLEL | GVPSRFSGSGSGTDFTLTITDLQPDDLATYYC |
| 8DC3.1 | SALTQPASVSGSPGQSVTISC | TGTSSDVGGYNYVS | WYQQHPGKAPKLMIY | DVSKRPS | GVPDRFSGSKSGNTASLTISGLQAEDEADYYC |
| 8DC8.3 | DIVMTQSPSSLSASVGDRVTITC | RASQSVSRWLA | WYQQKPGKPPPKLLIY | EASSLES | GVPSRFSGSGSGTDFTLTITSLQPEDFATYYC |
| 8DC8.6 | DIQMTQSPSSLSASVGDRVTITC | RASQGVSTDLA | WYQQKPGRAPKLLIY | RASSLQS | GVPSRFSGSGSGTDFTLTISSLQPDDLATYYC |
| B4 | EIVLTQSPGTLSLSPGERATLSC | RASQSVSSSYLA | WYQQKPGQAPRLLIY | GASSRAT | GIPDRFSGSGSGTDFTLTISRLEPEDFAVYYC |
| A9 | DIQMTQSPDSLAVSLGERATINC | KSSQSVLYSSNNKNYLA | WYQQKPGQPPKLLIY | WASTRES | GVPDRFSGSGSGTDFTLTISSLQAEDVAVYYC |
| A2S | EIVLTQSPATLSLSPGERATISC | RASEKLNSWGHSFMQ | WYQQKPGQAPRLLIY | RASNLEP | GIPARFSGSGSGTDFTLTISSLEPEDFAVYYC |

FIG. 5C (Cont.)

panel A

| VL/Clone | CDR3 | Framework 4 | |
|---|---|---|---|
| 2B23K1 | AAWDNNVRGPV | FGGGTKLTIKP | SEQ ID NO:316 |
| 2B23K2 | QQRSNWPLT | FGGGTKVEIKR | SEQ ID NO:317 |
| 2B23K4 | QQLNSYPLT | FGQGTRLEINV | SEQ ID NO:318 |
| 2B23K7 | QQRSNWPLT | FGGGTKLEIKR | SEQ ID NO:319 |
| 2B23K11 | QQYRNLPLT | FGGGTKAEIKR | SEQ ID NO:320 |
| 6F5.1 | QQTNDLPLT | FGGGTKLEIKR | SEQ ID NO:321 |
| 7G1.1 | QQVNSFPLT | FGGGTKVEIKR | SEQ ID NO:322 |
| 7G2.1 | QQSYSTPRT | FGGGTKVEIKR | SEQ ID NO:323 |
| 7G3 | QQFNTYPLT | FGGGTKVEIKR | SEQ ID NO:324 |
| 7G4 | AAWDGSLNGHVV | FGGGTKVTVLG | SEQ ID NO:325 |
| 7G5 | MQTRETPWT | FGGGTKVEIKR | SEQ ID NO:326 |
| 7G6 | LQDYNSYT | FGPGTKVDIKR | SEQ ID NO:327 |
| 7G7 | QQLGSYPLT | FGQGTRLGIKR | SEQ ID NO:328 |
| 7G8 | QQSYTAPCT | FGQGTKVDIKR | SEQ ID NO:329 |
| 7G9 | NSRDSSGNHVV | FGGGTKLTVLG | SEQ ID NO:330 |
| 7G10 | NSRDSSSTHRGV | FGGGTKLTVLG | SEQ ID NO:331 |
| 7G11 | QQYDTSPWT | FGQGTKVEIKR | SEQ ID NO:332 |
| 2B23EK1 | QQYNNWPLT | FGQGTRLEINV | SEQ ID NO:333 |
| 2B23EK4 | QQYNNWPLT | FGGGTKAEIKR | SEQ ID NO:334 |
| 2B23EK5 | QQYNSYPLT | FGGGTKVEIKR | SEQ ID NO:335 |
| 2B23EK6 | QVWDSSTVV | FGGGTQLTLKR | SEQ ID NO:336 |
| 2B23EK7 | QQYNNWPLT | FGGGTKVEIKR | SEQ ID NO:337 |
| 2B23EK10 | QQYRNLPLT | FGGGTKVDIKR | SEQ ID NO:338 |
| 2B23EK11 | QQASSFPLT | FGGGTKLEIKR | SEQ ID NO:339 |
| 2B23EK12 | QQAKRLPLT | FGGGTKVDIKR | SEQ ID NO:340 |

FIG. 5D panel B

| VL/Clone | CDR3 | Framework 4 | |
|---|---|---|---|
| 8D2.2 | QQYDNLLRT | FGGGTKVDIKR | SEQ ID NO:341 |
| 8D2.3 | QQYLTYFRT | FGQGTKVDIKS | SEQ ID NO:342 |
| 8DC3.1 | CSYAGRYTYV | FGTGTKVTVLG | SEQ ID NO:343 |
| 8DC8.3 | QQYENLPPST | FGGGTKLEIKR | SEQ ID NO:344 |
| 8DC8.6 | QHYESYSPWT | FGQGTQGEIKR | SEQ ID NO:345 |
| B4 | QQYGSSPLT | FGGGTKVEIKR | SEQ ID NO:504 |
| A9 | QQYYSTPLT | FGGGTKLEIKR | SEQ ID NO:505 |
| A2S | QQGNEVPFT | FGQQGTKVEIKR | SEQ ID NO:506 |

|            | HT    | LC    | $H_N$ | $H_C$ |
|------------|-------|-------|-------|-------|
| BoNT F1 vs: |       |       |       |       |
| BoNT F2    | 83.4% | 81.8% | 86.3% | 82.3% |
| BoNT F3    | 83.9% | 82.9% | 85.0% | 83.7% |
| BoNT F4    | 92.2% | 96.4% | 90.9% | 89.1% |
| BoNT F5    | 69.8% | 46.8% | 80.4% | 83.2% |
| BoNT F6    | 87.4% | 94.3% | 87.0% | 80.9% |
| BoNT F7    | 73.7% | 63.3% | 79.2% | 78.9% |
|            |       |       |       |       |
| BoNT F2 vs: |       |       |       |       |
| BoNT F3    | 97.0% | 97.9% | 97.1% | 95.9% |
| BoNT F4    | 83.5% | 82.7% | 86.5% | 81.3% |
| BoNT F5    | 74.0% | 45.5% | 85.5% | 92.2% |
| BoNT F6    | 89.8% | 81.5% | 95.6% | 92.6% |
| BoNT F7    | 68.6% | 59.5% | 75.3% | 71.7% |
|            |       |       |       |       |
| BoNT F3 vs: |       |       |       |       |
| BoNT F4    | 83.8% | 83.8% | 85.5% | 82.0% |
| BoNT F5    | 74.0% | 45.9% | 83.8% | 93.3% |
| BoNT F6    | 89.8% | 82.9% | 93.9% | 92.8% |
| BoNT F7    |       |       |       |       |
|            |       |       |       |       |
| BoNT F4 vs: |       |       |       |       |
| BoNT F5    | 68.9% | 60.4% | 74.3% | 72.4% |
| BoNT F6    | 86.9% | 93.6% | 87.0% | 80.0% |
| BoNT F7    | 71.9% | 64.2% | 75.8% | 76.1% |
|            |       |       |       |       |
| BoNT 5 vs: |       |       |       |       |
| BoNT F6    | 73.6% | 47.3% | 85.0% | 89.4% |
| BoNT F7    | 63.7% | 46.5% | 72.2% | 73.0% |
|            |       |       |       |       |
| BoNT 6 vs: |       |       |       |       |
| BoNT F7    | 69.8% | 63.3% | 75.3% | 71.2% |

Figure 6B

|            | HT    | LC    | $H_N$ | $H_C$ |
|------------|-------|-------|-------|-------|
| BoNT C1 vs:|       |       |       |       |
| BoNT C/D   | 76.0% | 96.2% | 93.0% | 41.6% |
| BoNT D/C   | 64.7% | 47.1% | 67.7% | 75.8% |
| BoNT D     | 51.2% | 46.8% | 67.9% | 38.9% |
|            |       |       |       |       |
| BoNT C/D vs:|      |       |       |       |
| BoNT D/C   | 51.9% | 47.5% | 69.4% | 39.1% |
| BoNT D     | 68.7% | 47.3% | 69.2% | 89.8% |
|            |       |       |       |       |
| BoNT D/C vs:|      |       |       |       |
| BoNT D     | 76.5% | 98.2% | 95.8% | 40.9% |

SEQUENCE LISTING

<160> NUMBER OF SEQ ID NOS: 508

<210> SEQ ID NO 1
<211> LENGTH: 117
<212> TYPE: PRT
<213> ORGANISM: Artificial Sequence
<220> FEATURE:
<223> OTHER INFORMATION: Single chain antibody or single chain antibody domain

<400> SEQUENCE: 1

```
Leu Gln Leu Lys Gln Ser Gly Pro Gly Leu Val Lys Pro Ser Gln Ser
1               5                   10                  15

Leu Ser Leu Thr Cys Ser Val Thr Gly Tyr Ser Ile Thr Ser Gly Tyr
            20                  25                  30

Tyr Trp Tyr Trp Ile Arg Gln Phe Pro Gly Asn Lys Leu Glu Trp Met
        35                  40                  45

Gly Tyr Ile Ser Tyr Asp Gly Ser Asn Asn Tyr Asn Pro Ser Leu Lys
    50                  55                  60

Asn Arg Ile Ser Ile Thr Arg Asp Thr Ser Lys Asn Gln Phe Phe Leu
65                  70                  75                  80

Lys Leu Asn Ser Val Thr Thr Glu Asp Thr Ala Thr Tyr Tyr Cys Ala
                85                  90                  95

Arg Asn Leu Gly Leu Trp Tyr Phe Asp Val Trp Gly Thr Gly Thr Pro
            100                 105                 110

Leu Thr Val Ser Ser
            115
```

<210> SEQ ID NO 2
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 2

Glu Val Gln Leu Gln Gln Ser Gly Ala Glu Leu Val Arg Pro Gly Thr
1               5                   10                  15

Ser Val Lys Leu Ser Cys Lys Ser Gly Tyr Thr Phe Thr Ser Asp
        20                  25                  30

Trp Met His Trp Val Ile Gln Arg Pro Gly Gln Gly Leu Glu Trp Ile
            35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Arg Glu Gly His Tyr Tyr Gly Lys Ala Met Asp Tyr Trp Gly
            100                 105                 110

Gln Gly Thr Ser Val Thr Val Ser Ser
        115                 120

<210> SEQ ID NO 3
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 3

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
        20                  25                  30

Trp Met His Trp Ile Lys Gln Arg Pro Gly Gln Gly Leu Glu Trp Ile
            35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Gly Gly Asn Gly Phe Phe Asp Tyr Trp Gly Gln Gly Thr Thr
            100                 105                 110

Leu Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: Single chain antibody or single chain antibody domain

<400> SEQUENCE: 4

Glu Val Gln Leu Gln Gln Ser Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Ala Ser Glu Asp Ser Ala Val Tyr Tyr Cys
            85                  90                  95

Ala Arg Tyr Pro Gly Asn Arg Ala Met Asp Tyr Trp Gly Gln Gly Thr
            100                 105                 110

Ser Val Thr Val Ser Ser
            115

<210> SEQ ID NO 5
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 5

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Gly Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
            85                  90                  95

Ala Arg Asn Met Gly Leu Trp Tyr Phe Asp Val Trp Gly Thr Gly Thr
            100                 105                 110

Pro Val Thr Val Ser Ala
            115

<210> SEQ ID NO 6
<211> LENGTH: 116
<212> TYPE: PRT
<213> ORGANISM: Artificial Sequence
<220> FEATURE:
<223> OTHER INFORMATION: Single chain antibody or single chain antibody
      domain

<400> SEQUENCE: 6

Gln Val Gln Leu Lys Glu Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

```
Trp Ile Glu Trp Val Lys Gln Arg Pro Gly His Gly Leu Glu Trp Ile
            35                  40                  45

Gly Glu Ile Leu Pro Gly Ser Gly Ser Thr Asn Tyr Asn Glu Lys Phe
        50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Thr Glu Asp Ser Ala Ile Tyr Tyr Cys
                85                  90                  95

Ala Ser Ile Tyr Tyr Gly His Asp Tyr Trp Gly Gln Gly Thr Thr Leu
                100                 105                 110

Thr Val Ser Ser
        115
```

<210> SEQ ID NO 7
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 7

```
Glu Val Lys Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Asn Val
        50                  55                  60

Lys Gly Arg Phe Thr Ile Ser Arg Asp Asn Ala Lys Asn Asn Leu Phe
 65                  70                  75                  80

Leu Gln Met Ser His Leu Lys Ser Glu Asp Thr Ala Met Tyr Tyr Cys
                85                  90                  95

Ala Arg Asp Trp Asp Tyr Tyr Tyr Gly Ser Tyr Trp Tyr Phe Asp Val
                100                 105                 110

Trp Gly Thr Gly Thr Ser Val Thr Val Ser Ser
            115                 120
```

<210> SEQ ID NO 8
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 8

```
Gln Val Gln Leu Lys Glu Ser Gly Pro Gly Leu Val Lys Pro Ser Gln
 1               5                  10                  15

Thr Val Ser Leu Thr Cys Thr Val Thr Gly Tyr Ser Ile Thr Asn Gly
                20                  25                  30

Asn His Trp Trp Asn Trp Ile Arg Gln Val Ser Gly Ser Lys Leu Glu
            35                  40                  45

Trp Ile Gly Tyr Ile Ser Ser Ser Gly Tyr Thr Asp Ile Asn Pro Ser
        50                  55                  60

Leu Lys Ser Arg Ile Ser Ile Thr Arg Asp Thr Ser Lys Asn Gln Leu
 65                  70                  75                  80
```

```
Phe Leu Gln Leu Asn Ser Val Thr Thr Glu Asp Ile Ala Thr Tyr Tyr
                85                  90                  95

Cys Ala Arg Asp Asp Gly Tyr Tyr Glu Ala Leu Asp Tyr Trp Gly Gln
            100                 105                 110

Gly Thr Ser Val Thr Val Ser Ser
        115                 120

<210> SEQ ID NO 9
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 9

Gln Ile Gln Leu Leu Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Arg Ile Asp Pro Glu Asp Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Ser Ala Val Tyr Phe Cys
                85                  90                  95

Ala Arg Leu Asn Tyr Asp Tyr Pro Tyr Trp Tyr Phe Asp Val Trp Gly
            100                 105                 110

Thr Gly Thr Thr Leu Thr Val Ser Ser
        115                 120

<210> SEQ ID NO 10
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 10

Glu Val Gln Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Thr Ala Gly Phe Tyr Phe Asp Tyr Trp Gly Gln Gly Thr Thr
            100                 105                 110

Leu Thr Val Ser Ser
        115
```

```
<210> SEQ ID NO 11
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 11

Gln Ile Gln Leu Leu Gln Pro Gly Thr Glu Leu Val Arg Pro Gly Thr
 1               5                  10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Ala Arg Tyr Ser Gly Pro Tyr Ala Met Asp Tyr Trp Gly Gln Gly Thr
            100                 105                 110

Thr Leu Thr Val Ser Ala
        115

<210> SEQ ID NO 12
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 12

Glu Val Gln Leu Gln Glu Ser Gly Ala Glu Leu Val Arg Pro Gly Thr
 1               5                  10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Ser Ser Gly Tyr Val Asn Tyr Trp Gly Gln Gly Thr Thr
            100                 105                 110

Leu Thr Val Ser Ser
        115

<210> SEQ ID NO 13
<211> LENGTH: 117
<212> TYPE: PRT
<213> ORGANISM: Artificial Sequence
<220> FEATURE:
<223> OTHER INFORMATION: Single chain antibody or single chain antibody
      domain
```

<400> SEQUENCE: 13

```
Glu Val Gln Leu Gln Gln Ser Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Thr Gly Tyr Phe Asp Tyr Trp Gly Gln Gly Thr Thr
            100                 105                 110

Leu Thr Val Ser Ser
        115
```

<210> SEQ ID NO 14
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 14

```
Glu Val Gln Leu Gln Gln Ser Gly Ala Glu Leu Val Arg Pro Gly Thr
1               5                   10                  15

Ser Val Lys Leu Ser Cys Lys Ala Ser Asp Tyr Thr Phe Thr Asn Tyr
            20                  25                  30

Trp Thr His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Tyr Asp Thr Met Asp Tyr Trp Gly Gln Gly Thr Thr
            100                 105                 110

Val Thr Val Ser Ser
        115
```

<210> SEQ ID NO 15
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 15

```
Gln Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Glu Asp Asp
            20                  25                  30
```

```
Tyr Met His Trp Val Lys Gln Arg Pro Glu Gln Gly Leu Glu Trp Ile
            35                  40                  45

Gly Arg Ile Asp Pro Ala Asn Gly Asn Thr Glu Tyr Ala Pro Lys Phe
 50                  55                  60

Gln Asp Lys Ala Thr Ile Thr Ala Asp Thr Ser Ser Asn Thr Ala Tyr
65                  70                  75                  80

Leu Gln Leu Ser Arg Leu Thr Ser Glu Asp Thr Ala Val Tyr Tyr Cys
                85                  90                  95

Ala Arg Gly Gly Trp Leu Gly Asn Tyr Tyr Ala Met Asp Tyr Trp Gly
            100                 105                 110

Gln Gly Thr Ser Val Thr Val Ser Ser
            115                 120

<210> SEQ ID NO 16
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 16

Gln Val Gln Leu Gln Gln Ser Gly Ala Glu Leu Val Arg Pro Gly Thr
 1               5                  10                  15

Ser Val Lys Leu Ser Cys Lys Ala Ser Gly Tyr Thr Phe Thr Ser His
            20                  25                  30

Trp Met His Trp Val Lys Gln Arg Pro Gly Gln Gly Leu Glu Trp Ile
            35                  40                  45

Gly Val Ile Asp Pro Ser Asp Ser Tyr Thr Asn Tyr Asn Gln Lys Phe
 50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Arg Arg Asn Tyr Gly Met Asp Tyr Trp Gly Gln Gly Thr Ser
            100                 105                 110

Val Thr Val Ser Ser
            115

<210> SEQ ID NO 17
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 17

Gln Val Gln Leu Gln Gln Ser Gly Ala Glu Leu Val Arg Pro Gly Thr
 1               5                  10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Val Ile Asp Pro Ser Asp Ser Tyr Thr Asn Tyr Asn Gln Lys Phe
 50                  55                  60

Lys Gly Lys Ala Thr Leu Thr Val Asp Thr Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Arg Gly Gly Gly Arg Ser Ser Leu Asp Tyr Trp Gly Gln Gly Thr
            100                 105                 110

Ser Val Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 18

Glu Val Gln Leu Gln Gln Ser Gly Pro Glu Leu Val Lys Pro Gly Ala
 1               5                  10                  15

Ser Val Lys Ile Thr Cys Lys Ala Ser Gly Tyr Thr Phe Thr Asp Asn
            20                  25                  30

Asn Met Asp Trp Val Lys Gln Ser His Gly Lys Ser Leu Glu Trp Ile
        35                  40                  45

Gly Asp Ile Asn Pro Asn Asn Gly Gly Ser Ile Tyr Asn Gln Lys Phe
    50                  55                  60

Lys Gly Lys Ala Ser Leu Thr Leu Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Trp Gly Tyr Tyr Gly Ser Leu Ala Tyr Trp Gly Gln Gly Thr
            100                 105                 110

Leu Val Thr Val Ser Ser
        115

<210> SEQ ID NO 19
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 19

Glu Val Lys Leu Val Glu Ser Gly Ala Glu Leu Val Arg Pro Gly Ala
 1               5                  10                  15

Ser Val Lys Leu Ser Cys Thr Pro Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Arg Tyr Ala Pro Lys Phe
    50                  55                  60

Gln Asp Lys Ala Thr Leu Thr Ala Asp Thr Ser Ser Asn Thr Ala Tyr
65                  70                  75                  80

Leu His Leu Thr Ser Leu Thr Ser Glu Asp Thr Ala Val Tyr Tyr Cys
                85                  90                  95

Ala Arg Ser Tyr Tyr Arg Ala Trp Phe Asp Tyr Trp Gly Gln Gly Thr
            100                 105                 110

Leu Val Thr Val Ser Ser
        115
```

<210> SEQ ID NO 20
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 20

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Asp Asn
            20                  25                  30

Tyr Ile Asn Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
 50                  55                  60

Lys Gly Lys Ala Thr Leu Thr Val Asp Thr Ser Ser Asn Thr Ala Tyr
 65                  70                  75                  80

Met Gln Leu Thr Gly Leu Ala Ser Asp Asp Ser Ala Val Tyr Phe Cys
                85                  90                  95

Ala Arg Val Asn Phe Tyr Val Ser Trp Asp Tyr Trp Gly Gln Gly Thr
            100                 105                 110

Ser Val Thr Val Ser Ser
        115

<210> SEQ ID NO 21
<211> LENGTH: 116
<212> TYPE: PRT
<213> ORGANISM: Artificial Sequence
<220> FEATURE:
<223> OTHER INFORMATION: Single chain antibody or single chain antibody
      domain

<400> SEQUENCE: 21

Asp Val Gln Leu Gln Gln Ser Gly Ile Glu Val Met Lys Pro Gly Ala
 1               5                  10                  15

Ser Val Lys Leu Ser Cys Lys Ala Ser Gly Tyr Pro Phe Thr Ala Tyr
            20                  25                  30

Trp Ile Glu Trp Val Lys Gln Arg Pro Gly His Gly Leu Glu Trp Ile
        35                  40                  45

Gly Glu Phe Leu Pro Gly Gly Ile Ser Thr Asn Phe Asn Glu Lys Phe
 50                  55                  60

Lys Gly Lys Ala Thr Phe Ser Ala Asp Thr Ser Ser Asn Ser Ala Tyr
 65                  70                  75                  80

Ile Gln Leu Asn Ser Leu Thr Thr Glu Asp Ser Ala Ile Tyr Tyr Cys
                85                  90                  95

Val Leu Thr Gly Thr Gly Phe Asp Tyr Trp Gly Gln Gly Thr Thr Leu
            100                 105                 110

Thr Val Ser Ser
        115

<210> SEQ ID NO 22
<211> LENGTH: 116
<212> TYPE: PRT
<213> ORGANISM: Artificial Sequence
<220> FEATURE:
<223> OTHER INFORMATION: Single chain antibody or single chain antibody
      domain

```
<400> SEQUENCE: 22

Gln Val Gln Leu Lys Gln Ser Gly Ile Glu Val Met Lys Pro Gly Ala
1               5                   10                  15

Ser Val Lys Leu Ser Cys Lys Ala Ser Gly Tyr Pro Phe Thr Ala Tyr
            20                  25                  30

Trp Ile Glu Trp Val Lys Gln Arg Pro Gly His Gly Leu Glu Trp Ile
        35                  40                  45

Gly Glu Phe Leu Pro Gly Gly Ile Ser Thr Asn Phe Asn Glu Lys Phe
    50                  55                  60

Lys Gly Lys Ala Thr Phe Ser Ala Asp Thr Ser Asn Ser Ala Tyr
65                  70                  75                  80

Ile Gln Leu Asn Ser Leu Thr Thr Glu Asp Ser Ala Ile Tyr Tyr Cys
                85                  90                  95

Val Leu Thr Gly Thr Gly Phe Asp Tyr Trp Gly Gln Gly Thr Ser Val
            100                 105                 110

Thr Val Ser Ser
            115

<210> SEQ ID NO 23
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 23

Glu Val Gln Leu Gln Glu Ser Gly Pro Glu Leu Val Lys Pro Gly Ala
1               5                   10                  15

Ser Val Lys Ile Ser Cys Lys Ala Ser Gly Tyr Thr Phe Thr Asp His
            20                  25                  30

Asn Met Asp Trp Val Lys Gln Ser Leu Gly Lys Ser Leu Glu Trp Ile
        35                  40                  45

Gly Asp Ile Asn Pro Asn Asn Gly Gly Ala Val Tyr Asn Gln Asn Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Tyr Gly Tyr Tyr Gly Tyr Phe Asp Tyr Trp Gly Gln Gly Thr
            100                 105                 110

Thr Leu Thr Val Ser Ser
            115

<210> SEQ ID NO 24
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 24

Glu Val Gln Leu Gln Gln Ser Gly Pro Glu Leu Met Lys Pro Gly Ala
1               5                   10                  15

Ser Val Lys Ile Ser Cys Lys Ala Ser Gly Tyr Ala Phe Ser Arg Ser
            20                  25                  30

Trp Met Asn Trp Val Lys Gln Arg Pro Gly Lys Gly Leu Glu Trp Ile
```

```
              35                  40                  45

Gly Arg Ile Tyr Pro Gly Asp Gly Asp Thr Asn Tyr Asn Gly Lys Phe
     50                  55                  60

Lys Asp Lys Ala Ser Leu Thr Ala Asp Thr Ser Ser Thr Ala Tyr
 65                  70                  75                  80

Met Gln Leu Ser Ser Leu Thr Ser Glu Asp Ser Ala Val Tyr Phe Cys
              85                  90                  95

Thr Lys Ser Glu Gly Tyr Tyr His Asn Leu Gly Ala Tyr Trp Gly Gln
             100                 105                 110

Gly Thr Thr Val Thr Val Ser Ser
         115                 120

<210> SEQ ID NO 25
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 25

Glu Val Gln Leu Gln Gln Pro Gly Ser Glu Leu Ala Arg Pro Gly Ala
  1               5                  10                  15

Ser Val Lys Leu Ser Cys Lys Ala Ser Gly Tyr Thr Phe Thr Ser Tyr
             20                  25                  30

Pro Ile Thr Trp Val Lys Gln Thr Gly Gln Gly Leu Glu Trp Ile
         35                  40                  45

Gly Glu Ile Tyr Pro Arg Ser Gly Asn Thr Tyr Tyr Asn Glu Lys Phe
     50                  55                  60

Lys Gly Lys Ala Thr Leu Thr Ala Asp Lys Ser Ser Ser Thr Ala Tyr
 65                  70                  75                  80

Met Glu Leu Arg Ser Leu Thr Ser Glu Asp Ser Ala Val Tyr Phe Cys
              85                  90                  95

Ala Arg Asp Tyr Tyr Asp Tyr Ala Gly Gly Arg Gly Tyr Trp Gly
             100                 105                 110

Gln Gly Thr Thr Leu Thr Val Ser Ser
         115                 120

<210> SEQ ID NO 26
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 26

Gln Val Gln Leu Gln Gln Ser Gly Ala Glu Leu Val Lys Pro Gly Ala
  1               5                  10                  15

Ser Val Lys Ile Ser Cys Lys Ala Ser Gly Tyr Thr Phe Thr Asp Asn
             20                  25                  30

Tyr Ile Asn Trp Val Lys Gln Arg Pro Gly Gln Gly Leu Glu Trp Ile
         35                  40                  45

Gly Trp Ile His Pro Gly Ser Gly Asn Ala Lys Tyr Asn Glu Lys Phe
     50                  55                  60

Arg Ala Lys Ala Thr Leu Thr Val Asp Thr Ser Ser Asn Thr Ala Tyr
 65                  70                  75                  80

Met Gln Leu Ser Ser Leu Thr Ser Glu Asp Ser Ala Val Tyr Phe Cys
```

```
                    85                  90                  95

Ala Arg Val Gly Phe Arg Val Asn Phe Asp Tyr Trp Gly Gln Gly Thr
                100                 105                 110

Thr Leu Thr Val Ser Ser
        115

<210> SEQ ID NO 27
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 27

Glu Val Gln Leu Gln Gln Ser Gly Gly Glu Leu Ala Arg Pro Gly Ser
 1               5                  10                  15

Ser Val Lys Leu Ser Cys Lys Ala Ser Gly Tyr Ser Phe Thr Gly Tyr
                20                  25                  30

Ser Leu Thr Trp Val Lys Gln Thr Pro Gly Gln Gly Leu Glu Trp Ile
        35                  40                  45

Gly Glu Ile Tyr Pro Arg Ser Gly Asn Thr Tyr Tyr Asn Glu Asn Phe
 50                  55                  60

Gln Gly Lys Ala Thr Leu Thr Ala Asp Glu Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Phe Tyr Asp Tyr Asp Gly Gly Arg Gly Tyr Trp Gly
                100                 105                 110

Gln Gly Thr Thr Leu Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 28

Gln Ile Gln Leu Leu Gln Ser Gly Ala Glu Leu Val Arg Pro Gly Thr
 1               5                  10                  15

Ser Val Lys Met Ser Cys Lys Ala Ala Gly Tyr Pro Phe Thr Ser Tyr
                20                  25                  30

Trp Met Gly Trp Val Lys Gln Arg Pro Gly His Gly Leu Glu Trp Ile
        35                  40                  45

Gly Asp Ile Tyr Pro Gly Gly Pro Tyr Thr Asn Tyr Asn Glu Lys Phe
 50                  55                  60

Lys Gly Lys Ala Thr Leu Thr Ala Asp Thr Ser Ser Ser Thr Ala Tyr
65                  70                  75                  80

Met Gln Phe Ser Ser Leu Thr Ser Glu Asp Ser Ala Ile Tyr Tyr Cys
                85                  90                  95

Ala Leu Tyr Gly Gln Val Gly Ser Tyr Ala Met Asp Tyr Trp Gly Gln
                100                 105                 110

Gly Thr Ser Val Thr Val Ser Ser
        115                 120
```

```
<210> SEQ ID NO 29
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 29

Gln Ile Gln Leu Leu Gln Ser Gly Ala Glu Leu Val Arg Pro Gly Thr
 1               5                  10                  15

Ser Val Lys Met Ser Cys Lys Ala Ala Gly Tyr Pro Phe Thr Ser Tyr
                20                  25                  30

Trp Met Gly Trp Val Lys Gln Arg Pro Gly His Gly Leu Glu Trp Ile
            35                  40                  45

Gly Asp Ile Tyr Pro Gly Gly Pro Tyr Thr Asn Tyr Asn Glu Lys Phe
        50                  55                  60

Lys Gly Lys Ala Thr Leu Thr Ala Asp Thr Ser Ser Thr Ala Tyr
65                  70                  75                  80

Met Gln Phe Ser Ser Leu Thr Ser Glu Asp Ser Ala Ile Tyr Tyr Cys
                85                  90                  95

Ala Leu Tyr Gly Gln Val Gly Ser Tyr Ala Met Asp Tyr Trp Gly Gln
                100                 105                 110

Gly Thr Ser Val Thr Val Ser Ser
        115                 120

<210> SEQ ID NO 30
<211> LENGTH: 116
<212> TYPE: PRT
<213> ORGANISM: Artificial Sequence
<220> FEATURE:
<223> OTHER INFORMATION: Single chain antibody or single chain antibody
      domain

<400> SEQUENCE: 30

Gln Val Gln Leu Gln Gln Ser Gly Ala Glu Leu Val Lys Pro Gly Ala
 1               5                  10                  15

Ser Val Lys Met Ser Cys Lys Ala Ser Gly Tyr Pro Phe Thr Ile Tyr
                20                  25                  30

Trp Ile Thr Trp Val Lys Gln Arg Pro Gly Gln Gly Leu Glu Trp Ile
            35                  40                  45

Gly Glu Ile Tyr Pro Gly Ser Gly Phe Thr Lys Tyr Asn Glu Lys Phe
        50                  55                  60

Arg Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Leu Tyr Gly Ser Asn Phe Asp Tyr Trp Gly Gln Gly Thr Thr Leu
                100                 105                 110

Thr Val Ser Ser
        115

<210> SEQ ID NO 31
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 31
```

-continued

```
Asp Val Gln Leu Gln Glu Ser Gly Pro Glu Leu Val Lys Pro Gly Ala
 1               5                  10                  15

Ser Val Lys Ile Ser Cys Lys Ala Ser Gly Tyr Ser Phe Thr Asp Tyr
             20                  25                  30

Asn Met Asn Trp Val Lys Gln Ser Asn Gly Lys Ser Leu Glu Trp Ile
         35                  40                  45

Gly Val Ile Asn Pro Asn Tyr Gly Thr Thr Ser Tyr Asn Gln Lys Phe
     50                  55                  60

Lys Gly Lys Ala Thr Leu Thr Val Asp Gln Ser Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Ser Gly Gly Thr Gly Tyr Tyr Phe Asp Tyr Trp Gly Gln Gly
             100                 105                 110

Thr Thr Leu Thr Val Ser Ser
         115
```

<210> SEQ ID NO 32
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 32

```
Asp Val Gln Leu Gln Glu Ser Gly Pro Glu Leu Val Lys Pro Gly Ala
 1               5                  10                  15

Ser Val Lys Ile Ser Cys Lys Ala Ser Gly Tyr Ser Phe Thr Asp Tyr
             20                  25                  30

Asn Met Asn Trp Val Lys Gln Ser Asn Gly Lys Ser Leu Glu Trp Ile
         35                  40                  45

Gly Val Ile Asn Pro Asn Tyr Gly Thr Thr Ser Tyr Asn Gln Lys Phe
     50                  55                  60

Lys Gly Lys Ala Thr Leu Thr Val Asp Gln Ser Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Ser Gly Gly Thr Gly Tyr Tyr Phe Asp Tyr Trp Gly Gln Gly
             100                 105                 110

Thr Thr Leu Thr Val Ser Ser
         115
```

<210> SEQ ID NO 33
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 33

```
Glu Val Lys Leu Val Glu Thr Gly Pro Glu Leu Lys Lys Pro Gly Glu
 1               5                  10                  15

Thr Val Lys Ile Ser Cys Lys Ala Ser Gly Tyr Thr Phe Thr Asn Tyr
             20                  25                  30

Gly Met Asn Trp Val Lys Gln Ala Pro Gly Lys Gly Leu Lys Trp Met
         35                  40                  45
```

Gly Trp Ile Asn Thr Asn Thr Gly Glu Pro Tyr Ala Glu Glu Phe
            50                  55                  60

Lys Gly Arg Phe Ala Phe Ser Leu Glu Thr Ser Ala Ser Thr Ala Phe
 65                  70                  75                  80

Leu Gln Ile Asn Asn Leu Lys Asn Glu Asp Thr Ala Thr Tyr Phe Cys
                85                  90                  95

Ala Arg Gly Pro Ile Tyr Tyr Gly Thr Ser Tyr Arg Phe Phe Asp Val
                100                 105                 110

Trp Gly Thr Gly Thr Ser Val Thr Val Ser Ser
            115                 120

<210> SEQ ID NO 34
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 34

Glu Val Lys Leu Val Glu Thr Gly Pro Glu Leu Lys Lys Pro Gly Glu
  1               5                  10                  15

Thr Val Lys Ile Ser Cys Lys Ala Ser Gly Tyr Thr Phe Thr Asn Tyr
                 20                  25                  30

Gly Met Asn Trp Val Lys Gln Ala Pro Gly Lys Gly Leu Lys Trp Met
             35                  40                  45

Gly Trp Ile Asn Thr Asn Thr Gly Glu Pro Tyr Ala Glu Glu Phe
         50                  55                  60

Lys Gly Arg Phe Ala Phe Ser Leu Glu Thr Ser Ala Ser Thr Ala Phe
 65                  70                  75                  80

Leu Gln Ile Asn Asn Leu Lys Asn Glu Asp Thr Ala Thr Tyr Phe Cys
                85                  90                  95

Ala Arg Gly Pro Ile Tyr Tyr Gly Thr Ser Tyr Arg Phe Phe Asp Val
                100                 105                 110

Trp Gly Thr Gly Thr Ser Val Thr Val Ser Ala
            115                 120

<210> SEQ ID NO 35
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 35

Glu Val Lys Leu Val Glu Thr Gly Pro Glu Leu Lys Lys Pro Gly Glu
  1               5                  10                  15

Thr Val Lys Ile Ser Cys Lys Ala Ser Gly Tyr Thr Phe Thr Asn Tyr
                 20                  25                  30

Gly Met Asn Trp Val Lys Gln Ala Pro Gly Lys Gly Leu Lys Trp Met
             35                  40                  45

Gly Trp Ile Asn Thr Asn Thr Gly Glu Pro Thr Tyr Ala Glu Glu Phe
         50                  55                  60

Lys Gly Arg Phe Ala Phe Ser Leu Glu Thr Ser Ala Ser Thr Ala Phe
 65                  70                  75                  80

Leu Gln Ile Asn Asn Leu Lys Asn Glu Asp Thr Ala Thr Tyr Phe Cys
                85                  90                  95

```
Ala Arg Gly Pro Ile Tyr Tyr Gly Thr Ser Tyr Arg Phe Phe Asp Val
            100                 105                 110

Trp Gly Thr Gly Thr Ser Val Thr Val Ser Ala
        115                 120
```

<210> SEQ ID NO 36
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 36

```
Glu Val Lys Leu Val Glu Ser Gly Ala Glu Leu Val Arg Pro Gly Ala
 1               5                  10                  15

Ser Val Lys Leu Ser Cys Thr Ala Ser Gly Phe Asn Ile Lys Asp Asp
            20                  25                  30

Tyr Val His Trp Val Lys Gln Arg Pro Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Trp Ser Asn Trp Tyr Phe Asp Val Trp Gly Ala Gly Thr Thr
            100                 105                 110

Val Thr Val Ser Ser
        115
```

<210> SEQ ID NO 37
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 37

```
Glu Val Lys Leu Val Glu Ser Gly Ala Glu Leu Val Arg Pro Gly Ala
 1               5                  10                  15

Ser Val Lys Leu Ser Cys Thr Ala Ser Gly Phe Asn Ile Lys Asp Asp
            20                  25                  30

Tyr Val His Trp Val Lys Gln Arg Pro Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Trp Ser Asn Trp Tyr Phe Asp Val Trp Gly Ala Gly Thr Thr
            100                 105                 110

Val Thr Val Ser Ala
        115
```

<210> SEQ ID NO 38

```
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 38

Gln Val Gln Leu Gln Gln Ser Gly Ala Glu Leu Val Lys Pro Gly Ala
  1               5                  10                  15

Ser Val Lys Leu Ser Cys Thr Ala Ser Gly Phe Asn Ile Lys Asp Thr
             20                  25                  30

Tyr Met His Trp Val Lys Gln Arg Pro Glu Gln Gly Leu Glu Trp Ile
         35                  40                  45

Gly Arg Ile Asp Pro Glu Asp Gly Glu Thr Lys Tyr Ala Pro Lys Phe
 50                  55                  60

Gln Gly Lys Ala Thr Ile Thr Ala Asp Thr Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ala Arg Trp Leu Leu Tyr Tyr Tyr Ala Met Asp Tyr Trp Gly Gln Gly
                100                 105                 110

Thr Ser Val Thr Val Ser Ala
            115

<210> SEQ ID NO 39
<211> LENGTH: 116
<212> TYPE: PRT
<213> ORGANISM: Artificial Sequence
<220> FEATURE:
<223> OTHER INFORMATION: Single chain antibody or single chain antibody
      domain

<400> SEQUENCE: 39

Glu Val Gln Leu Gln Gln Ser Gly Ala Glu Leu Val Arg Pro Gly Ala
  1               5                  10                  15

Ser Val Lys Met Ser Cys Lys Ala Ser Gly Tyr Pro Phe Thr Ile Tyr
             20                  25                  30

Trp Ile Thr Trp Val Lys Gln Arg Pro Gly Gln Gly Leu Glu Trp Ile
         35                  40                  45

Gly Glu Ile Tyr Pro Gly Ser Gly Phe Thr Lys Tyr Asn Glu Lys Phe
 50                  55                  60

Arg Ser Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Leu Tyr Gly Ser Asn Phe Asp Tyr Trp Gly Gln Gly Thr Thr Leu
                100                 105                 110

Thr Val Ser Ser
            115

<210> SEQ ID NO 40
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 40
```

Gln Val Gln Leu Val Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Val Tyr Tyr Asp Tyr Asp Gly Asp Tyr Phe Asp Tyr Trp Gly Gln
            100                 105                 110

Gly Thr Thr Leu Thr Val Ser Ser
            115                 120

<210> SEQ ID NO 41
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 41

Gln Val Gln Leu Val Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Val Tyr Tyr Asp Tyr Asp Gly Asp Tyr Phe Asp Tyr Trp Gly Gln
            100                 105                 110

Gly Thr Thr Leu Thr Val Ser Ser
            115                 120

<210> SEQ ID NO 42
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 42

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Ala Phe Thr Gly Pro
            20                  25                  30

Phe Met Asn Trp Val Lys Gln Ser His Gly Lys Ser Leu Glu Trp Ile
        35                  40                  45

```
Gly Arg Ile Asn Pro Tyr Asn Gly Asp Ala Phe Tyr Asn Gln Lys Phe
        50                  55                  60

Lys Asp Lys Ala Thr Leu Thr Val Asp Lys Ser Ser Thr Thr Ala His
 65                  70                  75                  80

Met Glu Leu Arg Ser Leu Thr Ser Asp Ser Ala Val Tyr Tyr Cys
                 85                  90                  95

Ala Arg Glu Tyr Asp Gly Ser Tyr Pro Tyr Tyr Asp Thr Leu Asp Tyr
            100                 105                 110

Trp Gly Gln Gly Thr Ser Val Thr Val Ser Ser
            115                 120

<210> SEQ ID NO 43
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 43

Asp Val Gln Leu Gln Glu Ser Gly Pro Glu Leu Val Lys Pro Gly Ala
 1               5                  10                  15

Ser Val Lys Ile Ser Cys Lys Ala Ser Gly Tyr Thr Phe Ala Asp Tyr
                20                  25                  30

Tyr Ile Asn Trp Val Lys Gln Ser His Gly Lys Ser Leu Glu Trp Ile
            35                  40                  45

Gly Asp Phe Asn Pro Asn Asn Gly Asp His Ser Tyr Asn Gln Lys Phe
        50                  55                  60

Lys Asp Lys Ala Thr Leu Thr Val Asp Glu Ser Ser Asn Thr Ala Tyr
 65                  70                  75                  80

Met Glu Leu Arg Ser Leu Thr Ser Glu Asp Ser Ala Val Tyr Tyr Cys
                 85                  90                  95

Thr Arg Glu Phe Tyr Tyr Tyr Phe Asp Val Trp Gly Thr Gly Thr Ser
            100                 105                 110

Val Thr Val Ser Ser
            115

<210> SEQ ID NO 44
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 44

Gln Val Gln Leu Lys Gln Ser Gly Pro Glu Leu Val Lys Pro Gly Ala
 1               5                  10                  15

Ser Val Lys Leu Ser Cys Lys Ala Ser Gly Tyr Thr Phe Thr Ser Tyr
                20                  25                  30

Asp Ile Asn Trp Val Lys Gln Arg Pro Gly Gln Gly Leu Glu Trp Ile
            35                  40                  45

Gly Trp Ile Tyr Pro Arg Asp Asp Ile Thr Lys Tyr Asn Glu Lys Phe
        50                  55                  60

Lys Asp Lys Ala Thr Leu Thr Val Asp Thr Ser Ser Ser Thr Ala Tyr
 65                  70                  75                  80

Met Glu Leu His Ser Leu Thr Ser Glu Asp Ser Ala Val Tyr Phe Cys
                 85                  90                  95
```

```
Ala Arg Gly Asp Tyr Tyr Gly Ser Leu Asp Tyr Trp Gly Gln Gly Thr
            100                 105                 110

Thr Leu Thr Val Ser Ser
        115

<210> SEQ ID NO 45
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 45

Glu Leu Lys Leu Val Glu Ser Gly Gly Gly Leu Val Gln Pro Gly Gly
  1               5                  10                  15

Ser Leu Glu Leu Ser Cys Ala Ala Ser Gly Phe Thr Phe Ser Asn Tyr
             20                  25                  30

Gly Met Ser Trp Ile Arg Gln Thr Pro Asp Lys Arg Leu Glu Leu Val
         35                  40                  45

Ala Thr Ile Asn Ser Asn Gly Gly Thr Tyr Tyr Pro Asp Arg Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Phe Glu Asp Thr Ala Met Phe Tyr Cys
                 85                  90                  95

Ala Arg Asp Gly Tyr Tyr Val Tyr Asp Tyr Trp Gly Gln Gly Thr Thr
            100                 105                 110

Leu Thr Val Ser Ser
        115

<210> SEQ ID NO 46
<211> LENGTH: 116
<212> TYPE: PRT
<213> ORGANISM: Artificial Sequence
<220> FEATURE:
<223> OTHER INFORMATION: Single chain antibody or single chain antibody
      domain

<400> SEQUENCE: 46

Glu Val Gln Leu Lys Gln Ser Gly Ala Glu Leu Val Lys Pro Gly Ala
  1               5                  10                  15

Ser Val Lys Leu Ser Cys Thr Ala Ser Gly Phe Asn Ile Lys Asp Tyr
             20                  25                  30

Tyr Met His Trp Val Lys Gln Arg Thr Glu Gln Gly Leu Glu Trp Ile
         35                  40                  45

Gly Arg Ile Asp Pro Glu Asp Gly Glu Thr Lys Tyr Ala Pro Lys Phe
     50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Ala Thr Ala Val Tyr Tyr Cys
                 85                  90                  95

Val Thr Ser Arg Ala Gly Ala Val Tyr Trp Gly Gln Gly Thr Thr Leu
            100                 105                 110

Thr Val Ser Ser
        115

<210> SEQ ID NO 47
<211> LENGTH: 121
```

```
<212> TYPE: PRT
<213> ORGANISM: Artificial Sequence
<220> FEATURE:
<223> OTHER INFORMATION: Single chain antibody or single chain antibody
      domain

<400> SEQUENCE: 47

Asp Val Gln Leu Gln Glu Ser Gly Ala Glu Leu Val Lys Pro Gly Ala
  1               5                  10                  15

Ser Val Lys Leu Ser Cys Lys Ala Ser Gly Phe Thr Phe Thr Asp Tyr
             20                  25                  30

Trp Met His Trp Val Lys Gln Arg Pro Gly Gln Gly Leu Glu Trp Ile
         35                  40                  45

Gly Met Ile His Pro Tyr Asn Gly Asp Asn Asn Tyr His Glu Lys Phe
     50                  55                  60

Lys Ser Lys Ala Thr Leu Thr Val Asp Lys Ser Ser Thr Ala Tyr
 65                  70                  75                  80

Met Gln Leu Ser Ser Leu Thr Thr Glu Asp Ser Ala Val Tyr Tyr Cys
                 85                  90                  95

Val Arg Asn Asp Tyr Asp Pro Tyr Tyr Tyr Ala Leu Asp Tyr Trp Gly
            100                 105                 110

Gln Gly Thr Ser Leu Thr Val Ser Ala
            115                 120

<210> SEQ ID NO 48
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 48

Glu Val Gln Leu Gln Glu Ser Gly Pro Gly Leu Val Gln Pro Ser Gln
  1               5                  10                  15

Ser Leu Ser Ile Thr Cys Thr Val Ser Gly Phe Ser Leu Thr Asn His
             20                  25                  30

Gly Val His Trp Ile Arg Gln Ser Pro Gly Lys Gly Leu Glu Trp Leu
         35                  40                  45

Gly Val Ile Trp Arg Ser Gly Ser Arg Asp Tyr Asn Val Thr Phe Lys
     50                  55                  60

Ser Arg Leu Ser Ile Thr Lys Asp Asn Ser Lys Ser Gln Val Phe Phe
 65                  70                  75                  80

Lys Leu Asn Ser Leu Gln Ala Asp Asp Thr Ala Ile Tyr Tyr Cys Ala
                 85                  90                  95

Lys Ile Gly Pro Arg Leu Gly Tyr Phe Asp Val Trp Gly Ala Gly Thr
            100                 105                 110

Ser Val Thr Val Ser Ser
            115

<210> SEQ ID NO 49
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 49

Glu Val Gln Leu Gln Gln Ser Gly Pro Glu Leu Val Lys Pro Gly Ala
```

```
                1               5                  10                 15
Ser Val Lys Ile Ser Cys Met Ala Ser Gly Tyr Pro Phe Thr Gly Pro
                20                 25                 30

Phe Met Asn Trp Val Lys Gln Ser His Gly Lys Ser Leu Glu Trp Ile
            35                 40                 45

Gly Arg Ile Asn Pro Tyr Asn Gly Asp Ala Phe Tyr Asn Pro Lys Phe
        50                 55                 60

Asn Gly Lys Ala Thr Leu Thr Val Asp Lys Ser Ser Thr Ala His
65                 70                 75                 80

Met Glu Leu Arg Ser Leu Thr Ser Gly Asp Ser Ala Val Tyr Tyr Cys
                85                 90                 95

Ala Arg Glu Tyr Asp Gly Arg Tyr Pro Tyr Tyr Ser Thr Leu Asp Tyr
                100                105                110

Trp Gly Gln Gly Thr Ser Val Thr Val Ser Ser
            115                120
```

<210> SEQ ID NO 50
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 50

```
Gln Val Gln Leu Gln Gln Ser Gly Ala Glu Leu Val Arg Pro Gly Ala
1               5                  10                 15

Ser Val Lys Leu Ser Cys Thr Ala Ser Gly Phe Asn Ile Lys Asp Asp
                20                 25                 30

Tyr Met His Trp Val Lys Gln Arg Pro Glu Gln Gly Leu Glu Trp Ile
            35                 40                 45

Gly Arg Ile Asp Pro Ala Asn Gly Asn Thr Lys Tyr Ala Pro Lys Phe
        50                 55                 60

Gln Asp Lys Ala Thr Ile Thr Ala Asp Thr Ser Ser Asn Thr Ala Tyr
65                 70                 75                 80

Leu Gln Leu Ser Ser Leu Thr Ser Glu Asp Thr Ala Val Tyr Tyr Cys
                85                 90                 95

Ala Arg Glu Gly Val Tyr Tyr Tyr Asp Gly Ser Tyr Met Arg Ala Met
                100                105                110

Asp Tyr Trp Gly Gln Gly Thr Ser Val Thr Val Ser Ser
            115                120                125
```

<210> SEQ ID NO 51
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 51

```
Gln Val Gln Leu Gln Gln Ser Gly Ala Glu Leu Val Lys Pro Gly Ala
1               5                  10                 15

Ser Val Lys Leu Ser Cys Lys Ala Ser Gly Tyr Thr Phe Thr Thr Tyr
                20                 25                 30

Trp Met His Trp Val Lys Gln Arg Pro Gly Gln Gly Leu Glu Trp Ile
            35                 40                 45

Gly Met Ile His Pro Asn Thr Gly Gly Ile Asn Tyr Asn Glu Lys Phe
```

```
                50                  55                  60
Lys Ser Lys Ala Thr Leu Thr Val Asp Lys Ser Ser Thr Ala Tyr
 65                  70                  75                  80

Met Gln Leu Ser Gly Leu Thr Ser Glu Asp Ser Ala Val Phe Tyr Cys
                 85                  90                  95

Ala Ile Leu Arg Val Val Pro Glu Ala Tyr Trp Gly Gln Gly Thr Leu
                100                 105                 110

Val Thr Val Ser Ala
        115

<210> SEQ ID NO 52
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 52

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Ala Asp Tyr
                20                  25                  30

Tyr Ile Asn Trp Val Lys Gln Ser His Gly Lys Ser Leu Glu Trp Ile
                35                  40                  45

Gly Asp Phe Asn Pro Asn Asn Gly Asp His Ser Tyr Asn Gln Lys Phe
            50                  55                  60

Lys Asp Lys Ala Thr Leu Thr Val Asp Glu Ser Ser Asn Thr Ala Tyr
 65                  70                  75                  80

Met Glu Leu Arg Ser Leu Thr Ser Glu Asp Ser Ala Val Tyr Tyr Cys
                 85                  90                  95

Thr Arg Glu Phe Tyr Tyr Tyr Phe Asp Val Trp Gly Thr Gly Thr Thr
                100                 105                 110

Val Thr Val Ser Ser
        115

<210> SEQ ID NO 53
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 53

Glu Val Gln Leu Gln Glu Ser Gly Pro Gly Leu Ala Lys Pro Ser Gln
 1               5                  10                  15

Thr Leu Ser Leu Thr Cys Ser Val Thr Gly Tyr Ser Ile Thr Ser Asp
                20                  25                  30

Tyr Trp Asn Trp Ile Arg Lys Phe Pro Gly Asn Lys Leu Glu Tyr Met
                35                  40                  45

Gly Tyr Ile Ser Tyr Ser Gly Ser Thr Tyr Tyr Asn Pro Ser Leu Lys
            50                  55                  60

Ser Arg Ile Ser Ile Thr Arg Asp Thr Ser Lys Asn Gln Tyr Tyr Leu
 65                  70                  75                  80

Gln Leu Asn Ser Val Thr Thr Glu Asp Thr Ala Thr Tyr Tyr Cys Ala
                 85                  90                  95

Arg Ser Phe Tyr Asp Gly Tyr Leu Tyr Phe Asp Tyr Trp Gly Gln Gly
```

```
                100                 105                 110
Thr Thr Val Thr Val Ser Ser
        115

<210> SEQ ID NO 54
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 54

Glu Val Gln Leu Gln Gln Ser Gly Ala Glu Leu Val Lys Pro Gly Ala
 1               5                  10                  15

Ser Val Lys Ile Ser Cys Lys Ala Ser Gly Tyr Ala Phe Thr Gly Tyr
                20                  25                  30

Asn Ile Asn Trp Val Lys Gln Ser His Gly Lys Ser Leu Glu Trp Ile
            35                  40                  45

Gly Leu Val Asn Pro Tyr Tyr Gly Ser Ser Thr Tyr Asn Gln Met Phe
        50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Lys Asp Tyr Gly Asn Ser Tyr Pro Tyr Tyr Phe Asp Phe Trp Gly
                100                 105                 110

Gln Gly Thr Thr Leu Thr Val Ser Ser
            115                 120

<210> SEQ ID NO 55
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 55

Glu Val Gln Leu Leu Glu Ser Gly Pro Glu Leu Val Lys Pro Gly Ala
 1               5                  10                  15

Ser Val Lys Ile Ser Cys Lys Ala Ser Gly Tyr Ala Phe Thr Gly Pro
                20                  25                  30

Phe Met Asn Trp Val Lys Gln Ser His Gly Glu Ser Leu Glu Trp Ile
            35                  40                  45

Gly Arg Ile Asn Pro Tyr Asn Gly Asp Ser Phe Tyr Asn Gln Lys Phe
        50                  55                  60

Lys Gly Lys Ala Thr Leu Thr Val Asp Lys Ser Ser Thr Ala His
65                  70                  75                  80

Met Glu Leu Arg Ser Leu Thr Ser Asp Asp Ser Ala Val Tyr Tyr Cys
                85                  90                  95

Ala Arg Glu Tyr Gly Gly Ser Tyr Pro Tyr Tyr Ser Thr Leu Asp Tyr
                100                 105                 110

Trp Gly Gln Gly Thr Ser Val Thr Val Ser Ser
            115                 120

<210> SEQ ID NO 56
<211> LENGTH: 123
<212> TYPE: PRT
```

<213> ORGANISM: Artificial Sequence
<220> FEATURE:
<223> OTHER INFORMATION: Single chain antibody or single chain antibody domain

<400> SEQUENCE: 56

Gln Val Asn Leu Arg Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Leu His Trp Val Arg Gln Thr Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser His Tyr Gly Asp Tyr Val Gly Tyr Leu Asp Tyr
            100                 105                 110

Trp Gly Gln Gly Thr Leu Val Thr Val Ser Ser
        115                 120

<210> SEQ ID NO 57
<211> LENGTH: 123
<212> TYPE: PRT
<213> ORGANISM: Artificial Sequence
<220> FEATURE:
<223> OTHER INFORMATION: Single chain antibody or single chain antibody domain

<400> SEQUENCE: 57

Gln Val Asn Leu Arg Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Leu His Trp Val Arg Gln Thr Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser His Tyr Gly Asp Tyr Val Gly Tyr Leu Asp Tyr
            100                 105                 110

Trp Gly Gln Gly Thr Leu Val Thr Val Ser Ser
        115                 120

<210> SEQ ID NO 58
<211> LENGTH: 122
<212> TYPE: PRT
<213> ORGANISM: Artificial Sequence
<220> FEATURE:
<223> OTHER INFORMATION: Single chain antibody or single chain antibody domain

<400> SEQUENCE: 58

Gln Val Gln Leu Gln Glu Ser Gly Ser Gly Leu Val Lys Pro Ser Gln
1               5                   10                  15

```
Ser Leu Ser Leu Thr Cys Ala Val Ser Gly Gly Ser Ile Ser Ser Gly
            20                  25                  30

Asp Tyr Ser Trp Ser Trp Ile Arg Gln Pro Pro Gly Glu Gly Leu Glu
        35                  40                  45

Trp Ile Gly Tyr Ile Phe Pro Arg Gly Ser Thr Tyr Tyr Asn Pro Ser
 50                  55                  60

Leu Arg Ser Arg Val Thr Met Ser Val Asp Arg Ser Lys Asn Gln Phe
65                  70                  75                  80

Ser Leu Ser Leu Asn Ser Val Thr Ala Ala Asp Thr Ala Val Tyr Tyr
            85                  90                  95

Cys Ala Arg Thr Lys Met Gly Ala Ala Glu Gly Val Phe Asp Tyr Trp
            100                 105                 110

Gly Gln Gly Thr Leu Val Thr Val Ser Ser
            115                 120
```

<210> SEQ ID NO 59
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 59

```
Gln Val Gln Leu Gln Glu Ser Gly Ser Gly Leu Val Lys Pro Ser Gln
 1               5                   10                  15

Ser Leu Ser Leu Thr Cys Ala Val Ser Gly Gly Ser Ile Ser Ser Gly
            20                  25                  30

Asp Tyr Ser Trp Ser Trp Ile Arg Gln Pro Pro Gly Glu Gly Leu Glu
        35                  40                  45

Trp Ile Gly Tyr Ile Phe Pro Arg Gly Ser Thr Tyr Tyr Asn Pro Ser
 50                  55                  60

Leu Arg Ser Arg Val Thr Met Ser Val Asp Arg Ser Lys Asn Gln Phe
65                  70                  75                  80

Ser Leu Ser Leu Asn Ser Val Thr Ala Ala Asp Thr Ala Val Tyr Tyr
            85                  90                  95

Cys Ala Arg Thr Lys Met Gly Ala Ala Glu Gly Val Phe Asp Tyr Trp
            100                 105                 110

Gly Gln Gly Thr Leu Val Thr Val Ser Ser
            115                 120
```

<210> SEQ ID NO 60
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 60

```
Gln Val Gln Leu Gln Gln Ser Gly Ala Glu Val Arg Lys Ser Gly Ala
 1               5                   10                  15

Ser Val Lys Val Ser Cys Lys Thr Ser Gly Tyr Thr Phe Thr Thr Tyr
            20                  25                  30

Tyr Ile His Trp Val Arg Gln Ala Pro Gly Gln Gly Leu Glu Trp Met
        35                  40                  45

Gly Met Ile Asp Pro Arg Gly Gly Ser Ala Ser Tyr Ala Gln Arg Phe
 50                  55                  60
```

```
Gln Gly Arg Val Thr Met Thr Arg Asp Thr Ser Thr Thr Thr Val Phe
 65                  70                  75                  80

Leu Ala Leu Asn Ser Leu Glu Ser Asn Asp Thr Ala Val Tyr Tyr Cys
                 85                  90                  95

Ala Arg Gly Gly Leu Pro Tyr Gln Gln Leu Pro Leu Trp Gly Gln Gly
            100                 105                 110

Thr Leu Val Thr Val Ser Ser
            115

<210> SEQ ID NO 61
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 61

Gln Val Gln Leu Gln Gln Ser Gly Ala Glu Val Arg Lys Pro Gly Ala
 1               5                  10                  15

Ser Val Lys Val Ser Cys Lys Thr Ser Gly Tyr Thr Phe Thr Thr Tyr
             20                  25                  30

Tyr Ile His Trp Val Arg Gln Ala Pro Gly Gln Gly Leu Glu Trp Met
         35                  40                  45

Gly Met Ile Asp Pro Arg Gly Gly Ser Ala Ser Tyr Ala Gln Arg Phe
     50                  55                  60

Gln Gly Arg Val Thr Met Thr Arg Asp Thr Ser Thr Thr Thr Val Phe
 65                  70                  75                  80

Leu Ala Leu Asn Ser Leu Glu Ser Asn Asp Thr Ala Val Tyr Tyr Cys
                 85                  90                  95

Ala Arg Gly Gly Leu Pro Tyr Gln Gln Leu Pro Leu Trp Gly Gln Gly
            100                 105                 110

Thr Leu Val Thr Val Ser Ser
            115

<210> SEQ ID NO 62
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 62

Gln Val Gln Leu Gln Gln Ser Gly Ala Glu Val Arg Lys Pro Gly Ala
 1               5                  10                  15

Ser Val Lys Val Ser Cys Lys Thr Ser Gly Tyr Thr Phe Thr Thr Tyr
             20                  25                  30

Tyr Ile His Trp Val Arg Gln Ala Pro Gly Gln Gly Leu Glu Trp Met
         35                  40                  45

Gly Met Ile Asp Pro Arg Gly Gly Ser Ala Ser Tyr Ala Gln Arg Phe
     50                  55                  60

Gln Gly Arg Val Thr Met Thr Arg Asp Thr Ser Thr Thr Thr Ala Phe
 65                  70                  75                  80

Leu Ala Leu Asn Ser Leu Glu Ser Asn Asp Thr Ala Val Tyr Tyr Cys
                 85                  90                  95

Ala Arg Gly Gly Leu Pro Tyr Gln Gln Leu Pro Leu Trp Gly Gln Gly
            100                 105                 110
```

Thr Leu Val Thr Val Ser Ser
115

<210> SEQ ID NO 63
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 63

Gln Val Gln Leu Gln Gln Ser Gly Ala Glu Val Lys Lys Pro Gly Ala
1               5                   10                  15

Ser Val Lys Val Ser Cys Lys Ala Ser Ala Phe Thr Phe Asn Ser Asn
            20                  25                  30

Tyr Ile His Trp Val Arg Leu Ala Pro Gly Gln Gly Pro Glu Trp Met
        35                  40                  45

Gly Ile Ile Asn Pro Asp Gly Gly Arg Thr Thr Tyr Ala Gln Lys Phe
    50                  55                  60

Gln Gly Arg Ile Thr Met Thr Thr Asp Thr Ser Thr Tyr Ala Val Tyr
65                  70                  75                  80

Met Glu Leu Ser Ser Leu Arg Ser Glu Asp Thr Ala Val Tyr Tyr Cys
                85                  90                  95

Ala Arg Gly Ala Thr Asn Ile Pro Tyr Gly Met Ser Val Trp Gly Gln
            100                 105                 110

Gly Thr Thr Val Thr Val Ser Ser
        115                 120

<210> SEQ ID NO 64
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 64

Gln Val Gln Leu Gln Gln Ser Gly Gly Gly Val Val Gln Pro Gly Arg
1               5                   10                  15

Ser Leu Arg Leu Ser Cys Ala Gly Ser Gly Phe Thr Leu Ser Thr Tyr
            20                  25                  30

Gly Met His Trp Val Arg Gln Ala Pro Gly Lys Gly Leu Glu Trp Val
        35                  40                  45

Ala Val Ile Ser Asn Asp Gly Ser Lys Glu Tyr Tyr Ala Asp Ser Val
    50                  55                  60

Lys Gly Arg Phe Ala Ile Ser Arg Asp Asn Ser Lys Asn Thr Leu Ser
65                  70                  75                  80

Leu Gln Met Asn Gly Leu Arg Ala Glu Asp Thr Ala Ile Tyr Tyr Cys
                85                  90                  95

Ala Lys Ala Ile Lys Ser Tyr Ser Thr Ile Gly Gly Ala Cys Asn Leu
            100                 105                 110

Trp Gly Gln Gly Thr Met Val Thr Val Ser Ser
        115                 120

<210> SEQ ID NO 65
<211> LENGTH: 120
<212> TYPE: PRT
<213> ORGANISM: Artificial Sequence

```
<220> FEATURE:
<223> OTHER INFORMATION: Single chain antibody or single chain antibody
      domain
<220> FEATURE:
<221> NAME/KEY: VARIANT
<222> LOCATION: 18
<223> OTHER INFORMATION: Xaa = any amino acid

<400> SEQUENCE: 65

Gln Val Gln Leu Val Glu Ser Gly Gly Val Val Gln Thr Gly Arg
 1               5                  10                  15

Ser Xaa Arg Leu Ser Cys Glu Ala Ser Gly Phe Thr Phe Ser Thr Tyr
                20                  25                  30

Gly Met His Trp Val Arg Gln Pro Pro Gly Lys Gly Leu Glu Trp Val
             35                  40                  45

Ala Ala Val Ser Asn Asp Gly Ser Asp Lys Tyr Tyr Thr Asp Ser Val
         50                  55                  60

Arg Gly Arg Phe Thr Ile Ser Arg Asp Asn Ser Lys Asn Ala Gly Tyr
 65                  70                  75                  80

Leu Gln Met Asn Ser Leu Arg Ala Glu Asp Thr Ala Met Tyr Tyr Cys
                 85                  90                  95

Ala Lys Thr Leu Lys Phe Gly Leu Asn Tyr Met Asp Val Trp Gly Lys
            100                 105                 110

Gly Thr Thr Val Thr Val Ser Ser
        115                 120

<210> SEQ ID NO 66
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 66

Gln Val Gln Leu Gln Glu Ser Gly Gly Val Val Gln Pro Gly Lys
 1               5                  10                  15

Ser Leu Arg Leu Ser Cys Val Thr Ser Thr Phe Thr Leu Gly Thr Tyr
                20                  25                  30

Ala Met His Trp Val Arg Gln Ala Pro Gly Lys Gly Leu Gln Trp Val
             35                  40                  45

Ala Val Ile Ser Tyr Asp Gly Arg Tyr Ala Asp Tyr Ala Asp Ser Val
         50                  55                  60

Lys Gly Arg Phe Asn Ile Ser Arg Asp Asn Ser Lys Asn Thr Leu Tyr
 65                  70                  75                  80

Leu Gln Met His Ser Leu Thr Thr Glu Asp Thr Ala Leu Tyr Tyr Cys
                 85                  90                  95

Ala Lys Ala Ile Lys Ala Phe Arg Pro Val Pro Pro Ser Phe His Met
            100                 105                 110

Asp Val Trp Gly Ile Gly Thr Thr Val Thr Val Ser Ser
            115                 120                 125

<210> SEQ ID NO 67
<211> LENGTH: 127
<212> TYPE: PRT
<213> ORGANISM: Artificial Sequence
<220> FEATURE:
<223> OTHER INFORMATION: Single chain antibody or single chain antibody
      domain

<400> SEQUENCE: 67
```

Gln Val Gln Leu Gln Glu Ser Gly Pro Gly Leu Val Lys Pro Ser Gln
 1               5                  10                  15

Thr Leu Ser Leu Thr Cys Ala Val Ser Gly Gly Ser Ile Asn Ser Gly
             20                  25                  30

Asp Tyr Tyr Trp Thr Trp Ile Arg Gln His Pro Gly Lys Gly Leu Glu
         35                  40                  45

Trp Ile Gly Asn Ile Tyr Tyr Thr Gly Arg Thr Tyr Tyr Asn Pro Ser
 50                  55                  60

Leu Gln Ser Arg Leu Thr Met Ser Val Asp Thr Ser Arg Thr His Phe
65                  70                  75                  80

Ser Leu Lys Leu Ser Ala Val Thr Ala Ala Asp Thr Ala Val Tyr Tyr
                 85                  90                  95

Cys Ala Arg Gly Gln Asp Thr Ser Met Val Thr Arg Asn Phe Tyr Tyr
                 100                 105                 110

Gly Leu Asp Val Trp Gly Gln Gly Thr Thr Val Thr Val Ser Ser
             115                 120                 125

<210> SEQ ID NO 68
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 68

Glu Val Gln Leu Val Gln Ser Gly Gly Asn Leu Val Gln Pro Gly Gly
 1               5                  10                  15

Ser Leu Arg Leu Ser Cys Thr Ala Ser Gly Phe Ile Phe Ser Asn His
             20                  25                  30

Trp Met Gln Trp Val Arg Gln Ile Pro Gly Lys Gly Leu Met Trp Val
         35                  40                  45

Ser Arg Ile Asn Asp Ser Gly Arg Ser Thr Ser Tyr Ala Gly Phe Val
 50                  55                  60

Lys Gly Arg Phe Thr Met Ser Arg Asp Asn Ala Lys Asn Thr Leu Phe
65                  70                  75                  80

Leu Gln Met Asn Ser Leu Thr Ala Glu Asp Thr Gly Val Tyr Tyr Cys
                 85                  90                  95

Val Arg Glu Thr Trp Glu Val Leu Gly His Leu Gly Tyr Glu Val Leu
                 100                 105                 110

Asp His Trp Gly Leu Gly Thr Leu Val Thr Val Ser Ser
             115                 120                 125

<210> SEQ ID NO 69
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 69

Glu Val Gln Leu Val Gln Ser Gly Ala Glu Val Lys Lys Pro Gly Ser
 1               5                  10                  15

Ser Val Lys Val Ser Cys Lys Ala Ser Gly Asn Ser Leu Asn Asn Tyr
             20                  25                  30

Ala Ile Thr Trp Val Arg Gln Ala Pro Gly Gln Gly Leu Glu Trp Met
         35                  40                  45

Gly Gly Ile Asn Pro Leu Phe Gly Thr Ala Asn Tyr Ala Gln Lys Phe
        50                  55                  60

Gln Asp Arg Val Thr Met Thr Ala Asp Glu Ser Thr Asn Ile Ala Tyr
 65                  70                  75                  80

Leu Asp Leu Ser Ser Leu Thr Thr Ala Asp Thr Ala Val Tyr Phe Cys
                    85                  90                  95

Ala Val Gly Ala Phe Thr Asn Tyr Pro Phe Trp Gly Gln Gly Thr Thr
               100                 105                 110

Val Thr Val Ser Ser
         115

<210> SEQ ID NO 70
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 70

Gln Val Gln Leu Val Glu Ser Gly Pro Gly Leu Val Lys Pro Ser Gln
  1               5                  10                  15

Thr Leu Ser Leu Thr Cys Ser Val Ser Gly Ala Ser Ile Asn Asn Ser
                20                  25                  30

Pro Tyr Phe Trp Asn Trp Phe Arg Gln Phe Pro Gly Lys Gly Leu Glu
            35                  40                  45

Trp Ile Gly Tyr Ile Tyr Trp Ser Gly Ser Thr Asn Tyr Asn Pro Ser
 50                  55                  60

Leu Lys Ser Arg Leu Ala Met Ser Val Asp Thr Ser Lys Asn Gln Phe
 65                  70                  75                  80

Ser Leu Lys Leu Thr Ser Ala Thr Ala Ala Asp Thr Ala Val Tyr Tyr
                85                  90                  95

Cys Ala Arg Asp Gln Gly Gly Gly Thr Val Val Lys Glu Asn Trp Phe
               100                 105                 110

Asp Pro Trp Gly Gln Gly Thr Leu Val Thr Val Ser Ser
           115                 120                 125

<210> SEQ ID NO 71
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 71

Gln Val Gln Leu Val Glu Ser Gly Pro Gly Leu Val Lys Pro Ser Gln
  1               5                  10                  15

Thr Leu Ser Leu Thr Cys Ser Val Ser Gly Ala Ser Ile Asn Asn Ser
                20                  25                  30

Pro Tyr Phe Trp Asn Trp Phe Arg Gln Phe Pro Gly Lys Gly Leu Glu
            35                  40                  45

Trp Ile Gly Tyr Ile Tyr Trp Ser Gly Ser Thr Asn Tyr Asn Pro Ser
 50                  55                  60

Leu Lys Ser Arg Leu Ala Met Ser Val Asp Thr Ser Lys Asn Gln Phe
 65                  70                  75                  80

Ser Leu Lys Leu Thr Ser Ala Thr Ala Ala Asp Thr Ala Val Tyr Tyr
                85                  90                  95

```
Cys Ala Arg Asp Gln Gly Gly Thr Val Val Lys Glu Asn Trp Phe
            100                 105                 110

Asp Pro Trp Gly Gln Gly Thr Leu Val Thr Val Ser Ser
            115                 120                 125

<210> SEQ ID NO 72
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 72

Gln Val Gln Leu Val Glu Ser Gly Pro Gly Leu Val Lys Pro Ser Gln
1               5                   10                  15

Thr Leu Ser Leu Thr Cys Ser Val Ser Gly Ala Ser Ile Asn Asn Ser
            20                  25                  30

Pro Tyr Phe Trp Asn Trp Phe Arg Gln Phe Pro Gly Lys Gly Leu Glu
        35                  40                  45

Trp Ile Gly Tyr Ile Tyr Trp Ser Gly Ser Thr Asn Tyr Asn Pro Ser
    50                  55                  60

Leu Lys Ser Arg Leu Ala Met Ser Val Asp Thr Ser Lys Asn Gln Phe
65                  70                  75                  80

Ser Leu Lys Leu Thr Ser Ala Thr Ala Ala Asp Thr Ala Val Tyr Tyr
                85                  90                  95

Cys Ala Arg Asp Gln Gly Gly Thr Val Val Lys Glu Asn Trp Phe
            100                 105                 110

Asp Pro Trp Gly Gln Gly Thr Leu Val Thr Val Ser Ser
            115                 120                 125

<210> SEQ ID NO 73
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 73

Gln Val Gln Leu Val Gln Ser Gly Ala Asp Val Lys Lys Pro Gly Ala
1               5                   10                  15

Ser Val Arg Val Ser Cys Lys Ala Ser Gly Tyr Thr Ile Ser Thr Tyr
            20                  25                  30

Ala Met Ser Trp Val Arg Gln Ala Pro Gly Gln Gly Leu Glu Trp Met
        35                  40                  45

Gly Trp Ile Ser Gly Tyr Asn Gly Asn Thr Asn Tyr Ala Gln Glu Phe
    50                  55                  60

Gln Gly Arg Val Thr Met Thr Arg Asp Thr Ser Thr Asn Thr Ala Tyr
65                  70                  75                  80

Met Glu Leu Arg Ser Leu Arg Ser Asp Asp Thr Ala Phe Tyr Tyr Cys
                85                  90                  95

Ala Arg Val Lys Leu Thr Thr Met Val Arg Gly Pro Phe Asp Tyr
            100                 105                 110

Trp Gly Gln Gly Thr Leu Val Thr Val Ser Ser
        115                 120

<210> SEQ ID NO 74
```

-continued

```
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 74

Gln Val Gln Leu Val Gln Ser Gly Ala Asp Val Lys Pro Gly Ala
  1               5                  10                  15

Ser Val Arg Val Ser Cys Lys Ala Ser Gly Tyr Thr Ile Ser Ser Phe
             20                  25                  30

Ala Leu Ser Trp Val Arg Gln Ala Pro Gly Arg Gly Leu Glu Trp Met
         35                  40                  45

Gly Trp Ile Ser Gly Tyr Asn Gly Asn Thr Asn Tyr Ala Gln Asp Phe
     50                  55                  60

Gln Gly Arg Val Thr Met Thr Arg Asp Thr Ser Thr Asn Thr Ala Tyr
 65                  70                  75                  80

Leu Glu Leu Arg Ser Leu Thr Ser Asp Asp Met Ala Leu Tyr Tyr Cys
                 85                  90                  95

Ala Arg Val Lys Leu Ser Thr Met Val Arg Gly Gly Pro Phe Asp Tyr
            100                 105                 110

Trp Gly Gln Gly Thr Leu Val Thr Val Ser Ser
        115                 120

<210> SEQ ID NO 75
<211> LENGTH: 124
<212> TYPE: PRT
<213> ORGANISM: Artificial Sequence
<220> FEATURE:
<223> OTHER INFORMATION: Single chain antibody or single chain antibody
      domain

<400> SEQUENCE: 75

Gln Val Gln Val Val Gln Ser Gly Gly Gly Leu Val Gln Pro Gly Arg
  1               5                  10                  15

Ser Leu Arg Leu Ser Cys Ala Gly Ser Gly Phe Thr Phe Ser Thr Tyr
             20                  25                  30

Ala Met Ser Trp Val Arg Gln Ala Pro Gly Lys Gly Leu Glu Leu Val
         35                  40                  45

Ser Gly Ile Ser Phe Gly Gly Asp Asn Thr His Gln Ala Asp Ser Val
     50                  55                  60

Lys Gly Arg Phe Thr Ile Ser Arg Val Asp Ser Lys Ser Thr Leu Tyr
 65                  70                  75                  80

Leu Gln Met Asn Arg Met Arg Thr Glu Asp Thr Val Val Tyr Tyr Cys
                 85                  90                  95

Glu Lys Ala Ile Lys Gly Tyr Ser Ser Arg Pro Val Arg Ala Tyr Glu
            100                 105                 110

Met Trp Gly Leu Gly Thr Met Val Thr Val Ser Ser
        115                 120

<210> SEQ ID NO 76
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 76
```

```
Gln Val Gln Leu Val Glu Ser Gly Gly Leu Val Gln Pro Gly Arg
1               5                   10                  15

Ser Leu Arg Leu Ser Cys Ala Ala Ser Gly Leu Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile His Gln Asp Gly Val Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Gly Gly Lys Tyr Ser Asn Ser Ser Ala Met Tyr Gln Trp Gly
            100                 105                 110

Gln Gly Thr Leu Val Thr Val Ser Ser
            115                 120

<210> SEQ ID NO 77
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 77

Gln Val Gln Leu Val Glu Ser Gly Ala Glu Val Lys Lys Pro Gly Ala
1               5                   10                  15

Ser Val Lys Val Ser Cys Thr Ala Ser Gly Tyr Thr Phe Ala Gly Tyr
            20                  25                  30

Tyr Met Asp Trp Val Arg Gln Ala Pro Gly Gln Gly Leu Glu Trp Met
        35                  40                  45

Gly Arg Ile Asn Pro Lys Ser Gly Asp Pro Asn Tyr Glu Gln Lys Phe
    50                  55                  60

Gln Gly Arg Val Thr Leu Thr Arg Asp Lys Ser Ile Asn Thr Val Tyr
65                  70                  75                  80

Met Glu Leu Ser Arg Leu Lys Ser Asp Asp Thr Ala Ile Tyr Tyr Cys
                85                  90                  95

Ala Arg Ser Val Ser Gly Gly Ala Phe Asp Leu Trp Gly Arg Gly Thr
            100                 105                 110

Leu Val Thr Val Ser Ser
        115

<210> SEQ ID NO 78
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 78

Gln Val Gln Leu Val Glu Ser Gly Gly Gly Ala Val Gln Pro Gly Glu
1               5                   10                  15

Ser Leu Arg Leu Ser Cys Ala Ala Ser Gly Phe Thr Phe Ser Gly Phe
            20                  25                  30

Asp Met His Trp Val Arg Gln Ser Pro Gly Arg Gly Leu Glu Trp Val
        35                  40                  45
```

```
Ala Arg Ile Ser His Asp Gly Ser Met Ala Asp Tyr Ala Asp Ser Leu
 50                  55                  60

Arg Gly Arg Phe Thr Ile Ser Arg Asp Asn Pro Lys Asn Thr Leu Tyr
 65                  70                  75                  80

Leu His Met Asn Ser Leu Arg Val Glu Asp Thr Ala Leu Tyr Tyr Cys
                 85                  90                  95

Ala Lys Asp Arg Trp Arg Ser Gly Ser Tyr Pro Ala Phe Glu Lys Trp
                100                 105                 110

Gly Gln Gly Thr Met Val Thr Val Ser Ser
        115                 120
```

<210> SEQ ID NO 79
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 79

```
Gln Val Gln Leu Val Gln Ser Gly Gly Val Val Gln Pro Gly Arg
 1               5                   10                  15

Ser Leu Arg Leu Ser Cys Gly Ala Ser Arg Phe Thr Phe Ser Gly Phe
                 20                  25                  30

Asp Met His Trp Val Arg Gln Ala Pro Gly Lys Gly Leu Glu Trp Val
             35                  40                  45

Ala Arg Ile Ser His Asp Gly Ser Met Ala Asp Tyr Ala Asp Ser Leu
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Leu Tyr Tyr Cys
                 85                  90                  95

Ala Lys Asp Arg Trp Arg Ser Gly Ser Tyr Pro Ala Phe Glu Ile Trp
                100                 105                 110

Gly Gln Gly Thr Met Val Thr Val Ser Ser
        115                 120
```

<210> SEQ ID NO 80
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 80

```
Gln Val Gln Leu Val Glu Ser Gly Gly Ala Val Gln Pro Gly Glu
 1               5                   10                  15

Ser Leu Arg Leu Ser Cys Ala Ala Ser Gly Phe Thr Phe Ser Gly Phe
                 20                  25                  30

Asp Met His Trp Val Arg Gln Ser Pro Gly Arg Gly Leu Glu Trp Val
             35                  40                  45

Ala Arg Ile Ser His Asp Gly Ser Met Ala Asp Tyr Ala Asp Ser Leu
 50                  55                  60

Arg Gly Arg Phe Thr Ile Ser Arg Asp Asn Pro Lys Asn Thr Leu Tyr
 65                  70                  75                  80

Leu His Met Asn Ser Leu Arg Val Glu Asp Thr Ala Leu Tyr Tyr Cys
                 85                  90                  95
```

```
Ala Lys Asp Arg Trp Arg Ser Gly Ser Tyr Pro Ala Phe Glu Lys Trp
            100                 105                 110

Gly Gln Gly Thr Met Val Thr Val Ser Ser
        115                 120
```

<210> SEQ ID NO 81
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 81

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ile Thr Leu Ser Ser Tyr
            20                  25                  30

Trp Met Asn Trp Val Arg Gln Val Pro Gly Lys Gly Leu Glu Trp Leu
        35                  40                  45

Ala Asn Ile Asn Gln Asp Ala Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Asn Leu Arg Val Glu Asp Thr Ala Ile Tyr Tyr Cys
                85                  90                  95

Ala Arg Gly Gly Lys Phe Ser Lys Ser Ser Pro Gln Trp Ala Trp Gly
            100                 105                 110

Gln Gly Thr Leu Val Thr Val Ser Ser
        115                 120
```

<210> SEQ ID NO 82
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 82

```
Gln Val Asn Leu Arg Glu Ser Gly Pro Gly Leu Val Lys Pro Ser Gln
1               5                   10                  15

Thr Leu Ser Leu Thr Cys Thr Val Ser Gly Gly Ser Ile Asn Thr Gly
            20                  25                  30

Glu Phe Tyr Trp Gly Trp Ile Arg Gln Leu Pro Gly Lys Gly Leu Glu
        35                  40                  45

Trp Ile Gly Tyr Thr His His Thr Gly Ser Pro Tyr Tyr Lys Ser Ser
    50                  55                  60

Leu Lys Ser Arg Val Ser Ile Ser Ile Asp Arg Ser Lys Asn Gln Phe
65                  70                  75                  80

Ser Leu Glu Leu Arg Ser Val Thr Ala Ala Asp Thr Ala Val Tyr Tyr
                85                  90                  95

Cys Val Arg Asp Arg Asp Gly Ser Gly Phe Phe Asp Asn Trp Gly Arg
            100                 105                 110

Gly Thr Leu Val Thr Val Ser Ser
        115                 120
```

<210> SEQ ID NO 83
<211> LENGTH: 125

```
<212> TYPE: PRT
<213> ORGANISM: Artificial Sequence
<220> FEATURE:
<223> OTHER INFORMATION: Single chain antibody or single chain antibody
      domain

<400> SEQUENCE: 83

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Pro Ile Asn Asn Ser
            20                  25                  30

Pro Tyr Phe Trp Asn Trp Phe Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ser Met Ala Val Asp Thr Ser Lys Asn Gln Phe
65                  70                  75                  80

Thr Leu Arg Leu Ser Ser Val Thr Ala Ala Asp Thr Ala Met Tyr Phe
                85                  90                  95

Cys Ala Arg Asp Gln Gly Gly Ser Val Val Gly Thr Asn Trp Phe
            100                 105                 110

Asp Pro Trp Gly Gln Gly Thr Leu Val Thr Val Ser Ser
        115                 120                 125

<210> SEQ ID NO 84
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 84

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Val Ser Arg Asp Asn Gly Lys Asn Ser Leu Tyr
65                  70                  75                  80

Leu Gln Met Asn Ser Leu Arg Ala Glu Asp Thr Ala Leu Tyr Phe Cys
                85                  90                  95

Ala Lys Asp Gly Gly Pro Glu Trp Glu Leu Arg Gly Ala Phe Asp Ile
            100                 105                 110

Trp Gly Gln Gly Thr Leu Val Thr Val Ser Ser
        115                 120

<210> SEQ ID NO 85
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 85

Glu Val Gln Leu Val Gln Ser Gly Ala Glu Val Lys Lys Pro Gly Ala
```

```
                1               5                  10                 15
Ser Val Lys Val Ser Cys Lys Ala Phe Gly Tyr Thr Leu Thr Asn Tyr
                20                  25                 30

Ala Met His Trp Val Arg Gln Ala Pro Gly Gln Arg Leu Glu Trp Met
                35                  40                 45

Gly Leu Ile Lys Ala Gly Asn Gly Asn Thr Lys Tyr Ser Gln Lys Phe
                50                  55                 60

Gln Gly Arg Val Thr Ile Thr Arg Asp Pro Ser Ala Ser Thr Ala Tyr
 65             70                  75                         80

Met Glu Leu Ser Ser Leu Arg Ser Glu Asp Thr Ala Val Tyr Tyr Cys
                    85                  90                 95

Ala Arg Val Arg Asp Lys Arg Thr Thr Thr Asp Val Ser Asn Tyr Tyr
                   100                 105                110

Tyr Gly Met Asp Val Trp Gly Gln Gly Thr Thr Val Thr Val Ser Ser
                   115                 120                125

<210> SEQ ID NO 86
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 86

Gln Val Gln Leu Gln Glu Ser Gly Gly Gly Leu Val Gln Pro Gly Gly
 1               5                  10                 15

Ser Leu Arg Leu Ser Cys Ala Ala Ser Gly Phe Ser Phe Arg Ser Tyr
                20                  25                 30

Asp Met Thr Trp Val Arg Gln Ala Pro Gly Arg Gly Leu Val Trp Val
                35                  40                 45

Ser Ser Ile Thr Ser Thr Gly Ser Ser Thr Tyr Tyr Ala Asp Ser Val
                50                  55                 60

Lys Gly Arg Phe Thr Ile Ser Arg Asp Asn Ser Lys Asn Thr Val Tyr
 65             70                  75                         80

Leu Gln Met Asn Ser Leu Arg Ala Glu Asp Thr Ala Val Tyr Tyr Cys
                    85                  90                 95

Ala Lys Val Leu Gln Pro Lys Trp Glu Leu Pro His Trp Gly Gln Gly
                   100                 105                110

Thr Leu Val Thr Val Ser Ser
        115

<210> SEQ ID NO 87
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 87

Gln Val Gln Leu Val Glu Ser Gly Ala Glu Val Arg Lys Pro Gly Ala
 1               5                  10                 15

Ser Val Lys Val Ser Cys Trp Thr Ser Gly Tyr Pro Phe Thr Asp Phe
                20                  25                 30

Tyr Ile His Trp Val Arg Gln Ala Pro Gly Gln Gly Leu Glu Trp Met
                35                  40                 45

Gly Val Ile Asn Pro Thr Val Gly Asn Thr Ala Tyr Ala Glu Arg Phe
```

```
                    50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Arg Gly Gly Arg Arg Asp Ala Phe Asp Ile Trp Gly Gln
                100                 105                 110

Gly Thr Met Val Thr Val Ser Ser
            115                 120

<210> SEQ ID NO 88
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 88

Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Val Ser Tyr Ser Ser Leu Asp Ala Phe Asp Ile Trp Gly Gln Gly Thr
                100                 105                 110

Met Val Thr Val Ser Ser
            115

<210> SEQ ID NO 89
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 89

Gln Val Thr Leu Lys Glu Ser Gly Gly Gly Leu Val Gln Pro Gly Arg
  1               5                  10                  15

Ser Leu Thr Leu Ser Cys Pro Leu Ser Gly Phe Thr Ser Ser Asp Tyr
                 20                  25                  30

Val Leu His Trp Val Arg Gln Ala Pro Gly Thr Gly Leu Asp Trp Val
             35                  40                  45

Ala Val Ile Ser Ser Asp Gly Thr Lys Ala Tyr Tyr Gly Asp Ser Val
         50                  55                  60

Lys Gly Arg Phe Thr Ile Ser Arg Asp Thr Ser Lys Asn Thr Leu Leu
 65                  70                  75                  80

Leu Gln Met Asn Ser Pro Arg Ala Glu Asp Thr Ala Ile Tyr Tyr Cys
                 85                  90                  95

Ala Ile Ser Thr Arg Gly Pro Phe Asp Ile Trp Gly Gln Gly Thr Met
```

```
                    100                 105                 110

Val Thr Val Ser Ser
        115

<210> SEQ ID NO 90
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 90

Gln Val Thr Leu Lys Glu Ser Gly Gly Gly Leu Val Gln Pro Gly Arg
 1               5                  10                  15

Ser Leu Thr Leu Ser Cys Pro Leu Ser Gly Phe Thr Ser Ser Asp Tyr
                20                  25                  30

Val Leu His Trp Val Arg Gln Ala Pro Gly Thr Gly Leu Asp Trp Val
            35                  40                  45

Ala Val Ile Ser Ser Asp Gly Thr Lys Ala Tyr Tyr Gly Asp Ser Val
        50                  55                  60

Lys Gly Arg Phe Thr Ile Ser Arg Asp Thr Ser Lys Asn Thr Leu Leu
65                  70                  75                  80

Leu Gln Met Asn Ser Pro Arg Ala Glu Asp Thr Ala Ile Tyr Tyr Cys
                85                  90                  95

Ala Ile Ser Thr Arg Gly Pro Phe Asp Ile Trp Gly His Gly Thr Met
            100                 105                 110

Val Thr Val Ser Ser
        115

<210> SEQ ID NO 91
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 91

Gln Val Gln Leu Val Gln Ser Gly Ala Glu Val Lys Lys Pro Gly Ser
 1               5                  10                  15

Ser Val Lys Val Ser Cys Lys Thr Ser Gly Gly Thr Phe Arg Asn Phe
                20                  25                  30

Ala Ile Ser Trp Val Arg Gln Ala Pro Gly Gln Gly Leu Glu Trp Met
            35                  40                  45

Gly Gly Ile Ile Pro Met Phe Gly Lys Gly His Tyr Ala Gln Asn Phe
        50                  55                  60

Gln Gly Arg Val Thr Ile Thr Ala Asp Asp Ser Thr Thr Thr Ala Tyr
65                  70                  75                  80

Met Glu Leu Ser Ser Leu Arg Tyr Glu Asp Thr Ala Val Tyr Tyr Cys
                85                  90                  95

Ala Arg Gly Thr Arg Asn Gly Ser Leu Arg Asp Ala Phe Asp Ile Trp
            100                 105                 110

Gly Gln Gly Thr Thr Val Thr Val Ser Ser
        115                 120

<210> SEQ ID NO 92
<211> LENGTH: 123
<212> TYPE: PRT
```

<213> ORGANISM: Artificial Sequence
<220> FEATURE:
<223> OTHER INFORMATION: Single chain antibody or single chain antibody
      domain

<400> SEQUENCE: 92

```
Gln Val Gln Leu Val Gln Ser Gly Gly Gly Leu Val Lys Pro Gly Gly
 1               5                  10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Ser Leu Tyr
 65                  70                  75                  80

Leu Gln Leu Asn Ser Leu Arg Ala Glu Asp Thr Ala Val Tyr Tyr Cys
                85                  90                  95

Ala Arg Gly Asp His Asp Phe Arg Ser Gly Tyr Tyr Gly Met Asp Val
            100                 105                 110

Trp Gly Gln Gly Thr Met Val Thr Val Ser Ser
        115                 120
```

<210> SEQ ID NO 93
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 93

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Asp
            20                  25                  30

Asn Tyr Phe Trp Thr Trp Ile Arg Gln Ser Pro Gly Lys Gly Leu Glu
        35                  40                  45

Trp Leu Gly His Ile Ser Tyr Ser Gly Arg Ser Tyr Ser Asn Leu Ser
    50                  55                  60

Leu Lys Arg Arg Leu Thr Ile Ser Val Asp Thr Ser Lys Asn Gln Phe
 65                  70                  75                  80

Ser Leu Asn Leu Ser Ser Val Thr Ala Ala Asp Thr Ala Val Tyr Tyr
                85                  90                  95

Cys Ala Arg Glu Arg Leu Pro Pro Gly Arg Gly Tyr Asp Met Asp Val
            100                 105                 110

Trp Gly Gln Gly Thr Thr Val Thr Val Ser Ser
        115                 120
```

<210> SEQ ID NO 94
<211> LENGTH: 123
<212> TYPE: PRT
<213> ORGANISM: Artificial Sequence
<220> FEATURE:
<223> OTHER INFORMATION: Single chain antibody or single chain antibody
      domain

<400> SEQUENCE: 94

```
Gln Val Gln Leu Gln Glu Ser Gly Pro Gly Leu Val Lys Pro Ser Gln
 1               5                  10                  15
```

```
Thr Leu Ser Leu Thr Cys Thr Val Ser Gly Gly Ser Ile Ser Ser Asp
            20                  25                  30

Asn Tyr Phe Trp Thr Trp Ile Arg Gln Ser Pro Gly Lys Gly Leu Glu
            35                  40                  45

Trp Leu Gly His Ile Ser Tyr Ser Gly Arg Ser Tyr Thr Asn Leu Ser
    50                  55                  60

Leu Lys Arg Arg Leu Thr Ile Ser Val Asp Thr Ser Lys Asn Gln Phe
65                  70                  75                  80

Ser Leu Asn Leu Asn Ser Val Thr Ala Ala Asp Thr Ala Val Tyr Tyr
                85                  90                  95

Cys Ala Arg Glu Arg Leu Pro Pro Gly Arg Gly Tyr Asp Met Asp Val
                100                 105                 110

Trp Gly Gln Gly Thr Thr Val Thr Val Ser Ser
            115                 120
```

<210> SEQ ID NO 95
<211> LENGTH: 122
<212> TYPE: PRT
<213> ORGANISM: Artificial Sequence
<220> FEATURE:
<223> OTHER INFORMATION: Single chain antibody or single chain antibody
    domain

<400> SEQUENCE: 95

```
Gln Leu Gln Leu Val Glu Ser Gly Gly Gly Leu Val Gln Pro Gly Gly
1               5                   10                  15

Ser Leu Arg Leu Ser Cys Glu Ala Ser Gly Phe Asn Phe Arg Thr Tyr
            20                  25                  30

Gly Met His Trp Val Arg Gln Ala Pro Gly Lys Gly Leu Glu Trp Val
            35                  40                  45

Ala Val Ile Trp Phe Asp Gly Ser Lys Ile Tyr Tyr Ala Asp Pro Val
    50                  55                  60

Lys Gly Arg Phe Thr Ile Ser Lys Asp Asn Ser Lys Asn Thr Leu Tyr
65                  70                  75                  80

Leu Gln Met Ser Ser Leu Arg Gly Glu Asp Thr Ala Val Tyr Tyr Cys
                85                  90                  95

Ala Arg Gly Gly Trp Phe Gly Thr Trp Arg Asp Asn Met Asp Val Trp
                100                 105                 110

Gly Gln Gly Thr Leu Val Thr Val Ser Ser
            115                 120
```

<210> SEQ ID NO 96
<211> LENGTH: 121
<212> TYPE: PRT
<213> ORGANISM: Artificial Sequence
<220> FEATURE:
<223> OTHER INFORMATION: Single chain antibody or single chain antibody
    domain

<400> SEQUENCE: 96

```
Glu Val Gln Met Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Ala Met His Trp Val Arg Gln Ala Pro Gly Lys Gly Leu Glu Trp Val
            35                  40                  45

Ala Met Ile Ser Asn Asp Glu Ser Asn Thr Lys Tyr Ala Asp Ser Val
    50                  55                  60
```

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Met Tyr Ser Cys
                85                  90                  95

Ala Arg Gly Gly Tyr Tyr Thr Arg Pro Leu Ala Phe Asp Thr Trp Gly
            100                 105                 110

Pro Gly Thr Thr Val Thr Val Ser Ser
        115                 120

<210> SEQ ID NO 97
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 97

Gln Val Gln Leu Val Gln Ser Gly Gly Arg Leu Val Arg Pro Gly Gly
1               5                   10                  15

Ser Leu Arg Leu Ser Cys Ala Ala Ser Gly Phe Val Phe Ser Asn Tyr
            20                  25                  30

Gly Met His Trp Val Arg Gln Ala Pro Gly Lys Gly Leu Glu Trp Val
        35                  40                  45

Ala Phe Leu Thr His Gly Gly Thr Asn Lys Tyr Tyr Ser Asp Ser Val
    50                  55                  60

Lys Gly Arg Leu Thr Ile Ser Arg Asp Asn Ala Lys Ser Thr Leu Phe
65                  70                  75                  80

Leu Glu Val Asn Ser Leu Arg Val Glu Asp Thr Ala Ile Tyr Tyr Cys
                85                  90                  95

Val Lys Glu Gly Gln Leu Asp Ser Lys Tyr Tyr Phe Asp Ser Trp Gly
            100                 105                 110

Gln Gly Thr Leu Val Thr Val Ser Ser
        115                 120

<210> SEQ ID NO 98
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 98

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Ser Ile Ser Ser Ala
            20                  25                  30

Gly Tyr Ser Trp Ser Trp Ile Arg Gln Ser Pro Gly Lys Gly Leu Glu
        35                  40                  45

Cys Leu Gly Tyr Ile Tyr Gln Thr Gly Ser Thr Phe Tyr Asn Leu Ser
    50                  55                  60

Leu Lys Gly Arg Val Thr Met Ser Leu Asp Arg Ser Lys Asn Gln Ile
65                  70                  75                  80

Ser Leu Arg Leu Thr Ser Val Val Ala Ala Asp Thr Ala Val Tyr Tyr
                85                  90                  95

Cys Ala Arg Val Val Gly Val Tyr Pro Gly Trp Phe Asp Ser Trp Gly
            100                 105                 110

Gln Gly Thr Leu Val Thr Val Ser Ser
         115                 120

<210> SEQ ID NO 99
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 99

Gln Val Gln Leu Val Gln Ser Gly Ala Glu Ala Lys Lys Pro Gly Ala
1               5                   10                  15

Ser Val Lys Leu Ser Cys Gln Ala Ser Gly Tyr Thr Phe Thr Gly Tyr
            20                  25                  30

Ala Ile His Trp Val Arg Gln Ala Pro Gly Gln Arg Leu Glu Trp Leu
        35                  40                  45

Gly Trp Ile Asn Cys Val Asn Gly Asn Thr Lys Tyr Ser Pro Lys Leu
    50                  55                  60

Pro Gly Arg Val Thr Ile Thr Arg Asp Thr Ser Ala Thr Thr Ala Tyr
65                  70                  75                  80

Leu Glu Leu Asn Ser Leu Thr Ser Glu Asp Thr Ala Val Tyr Tyr Cys
                85                  90                  95

Ala Arg Ser Met Leu Val Ala Ala Arg Val Tyr Tyr Tyr Gly Met
            100                 105                 110

Asp Val Trp Gly Gln Gly Thr Met Val Thr Val Ser Ser
        115                 120                 125

<210> SEQ ID NO 100
<211> LENGTH: 126
<212> TYPE: PRT
<213> ORGANISM: Artificial Sequence
<220> FEATURE:
<223> OTHER INFORMATION: Single chain antibody or single chain antibody
      domain

<400> SEQUENCE: 100

Gln Val Gln Leu Val Glu Ser Gly Pro Gly Leu Val Lys Pro Ser Gln
1               5                   10                  15

Thr Leu Ser Leu Ser Cys Thr Val Ser Gly Gly Ser Val Asn His Tyr
            20                  25                  30

Tyr Trp Asn Trp Ile Arg Gln Pro Pro Gly Lys Gly Leu Glu Trp Ile
        35                  40                  45

Gly Tyr Ile Phe Tyr Asn Gly Arg Thr Asn Tyr Asn Pro Ser Leu Lys
    50                  55                  60

Ser Arg Val Thr Met Ser Val Asp Thr Ser Lys Asn Gln Ile Ser Leu
65                  70                  75                  80

Lys Leu Arg Ser Val Thr Ala Ala Asp Thr Ala Val Tyr Tyr Cys Ala
                85                  90                  95

Arg Glu Gly Ala Arg Gly Tyr Cys Ser Ser Thr Ser Cys His Asp Ala
            100                 105                 110

Phe Asp Ile Trp Gly Arg Gly Thr Leu Val Thr Val Ser Ser
        115                 120                 125

<210> SEQ ID NO 101
<211> LENGTH: 121
<212> TYPE: PRT
<213> ORGANISM: Artificial Sequence

```
<220> FEATURE:
<223> OTHER INFORMATION: Single chain antibody or single chain antibody
      domain

<400> SEQUENCE: 101

Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Ala Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu His Phe Val Val Thr Ala Phe Ala Thr Trp Gly
            100                 105                 110

Gln Gly Thr Leu Val Thr Val Ser Ser
            115                 120

<210> SEQ ID NO 102
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 102

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Ile His Trp Val Arg Gln Ala Pro Gly Gln Gly Leu Glu Trp Met
             35                  40                  45

Gly Arg Ile Asn Pro Asn Ser Gly Gly Ala Asn Tyr Ala His Lys Phe
 50                  55                  60

Gln Gly Arg Val Thr Met Thr Arg Asp Thr Ser Ser Asn Thr Ala Tyr
 65                  70                  75                  80

Met Glu Val Ser Arg Leu Lys Ser Asp Asp Thr Ala Val Tyr Tyr Cys
                 85                  90                  95

Ala Arg Arg Arg Ala Val Ala Asn Leu Asp Tyr His Tyr Tyr Gly Met
            100                 105                 110

Asp Val Trp Gly Gln Gly Thr Thr Val Thr Val Ser Ser
            115                 120                 125

<210> SEQ ID NO 103
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 103

Gln Val Gln Leu Val Gln Ser Gly Gly Gly Val Val Gln Pro Gly Arg
  1               5                  10                  15
```

```
Ser Leu Arg Leu Ser Cys Val Ala Ser Gly Phe Thr Phe Ser Ser Tyr
            20                  25                  30

Thr Met His Trp Val Arg Gln Ala Pro Gly Glu Gly Leu Glu Trp Val
        35                  40                  45

Ala Gly Ile Ser Asn Asp Gly Arg Asn Gln Tyr Tyr Ser Asp Ser Val
 50                  55                  60

Lys Gly Arg Ala Thr Ile Ser Arg Asp Asn Ser Lys Asp Thr Leu Tyr
 65                  70                  75                  80

Leu Gln Met His Ser Leu Arg Ala Glu Asp Thr Ala Val Tyr Tyr Cys
                 85                  90                  95

Ala Lys Ala Asn Tyr His Phe Ile Leu Ala Thr Thr Phe His Ser Trp
            100                 105                 110

Gly Gln Gly Thr Leu Val Thr Val Ser Ser
            115                 120

<210> SEQ ID NO 104
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 104

Gln Val Gln Leu Gln Glu Ser Gly Pro Gly Leu Leu Lys Pro Ser Gln
 1               5                  10                  15

Thr Leu Ser Leu Thr Cys Ser Val Ser Gly Gly Ser Met Ile Thr Gly
            20                  25                  30

Gly Tyr Tyr Trp Thr Trp Val Arg Gln Leu Pro Gly Lys Gly Leu Glu
        35                  40                  45

Trp Ile Gly His Val Tyr Tyr Thr Gly Lys Thr Tyr Tyr Asn Pro Ser
 50                  55                  60

Leu Asn Gly Arg Phe Thr Ile Ala Ile Asp Thr Ser Lys Asn Gln Phe
 65                  70                  75                  80

Ser Leu Asn Leu Asn Ser Val Thr Ala Thr Asp Thr Ala Val Phe Tyr
                 85                  90                  95

Cys Ala Arg Ala Ile Trp Gly Gly Trp Tyr Phe Asp Leu Trp Gly Gln
            100                 105                 110

Gly Thr Leu Val Thr Val Ser Ser
            115                 120

<210> SEQ ID NO 105
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 105

Gln Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Phe Ser Ser Tyr
            20                  25                  30

Ala Met Arg Trp Val Arg Gln Ala Pro Gly Lys Gly Leu Glu Trp Val
        35                  40                  45

Ser Gly Ile Ser Gly Ser Gly Gly Arg Lys Tyr Tyr Ala Asp Ser Val
 50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Lys Asp Arg Trp Tyr Ser Gly Tyr Asp Phe Asp Tyr Trp Gly Gln
            100                 105                 110

Gly Thr Leu Val Thr Val Ser Ser
        115                 120

<210> SEQ ID NO 106
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 106

Gln Val Gln Leu Gln Gln Ser Gly Pro Glu Val Val Lys Pro Gly Ala
  1               5                  10                  15

Ser Val Lys Ile Ser Cys Lys Ala Ser Gly Tyr Thr Phe Ala Asp Tyr
                 20                  25                  30

Trp Ile Gly Trp Thr Lys Gln Gly Pro Gly His Gly Leu Glu Trp Ile
             35                  40                  45

Gly His Ile Tyr Pro Gly Gly Gly Tyr Ile Asn Tyr Asn Glu Lys Phe
         50                  55                  60

Lys Gly Lys Ala Thr Leu Thr Ala Asp Met Ser Ser Ser Thr Ala Tyr
 65                  70                  75                  80

Met Gln Phe Ser Ser Leu Thr Ser Glu Asp Ser Ala Ile Tyr Tyr Cys
                 85                  90                  95

Ala Arg Val Thr Met Val Glu Ser Gly Asp Trp Tyr Phe Asp Val Trp
            100                 105                 110

Gly Thr Gly Thr Thr Val Thr Val Ser Ser
        115                 120

<210> SEQ ID NO 107
<211> LENGTH: 116
<212> TYPE: PRT
<213> ORGANISM: Artificial Sequence
<220> FEATURE:
<223> OTHER INFORMATION: Single chain antibody or single chain antibody
      domain

<400> SEQUENCE: 107

Glu Val Gln Leu Gln Glu Ser Gly Pro Glu Leu Val Lys Pro Gly Ala
  1               5                  10                  15

Ser Val Lys Ile Ser Cys Lys Thr Ser Gly Tyr Thr Phe Thr Asp Tyr
                 20                  25                  30

Tyr Met Asn Trp Val Lys Gln Ser His Gly Lys Ser Leu Glu Trp Ile
             35                  40                  45

Gly Asp Ile Asn Pro Asn Gly Gly Ala Thr Tyr Asn Gln Lys Phe
         50                  55                  60

Lys Gly Lys Ala Thr Leu Thr Val Asp Lys Ser Ser Arg Thr Leu Tyr
 65                  70                  75                  80

Met Glu Leu Arg Ser Leu Thr Ser Glu Asp Ser Ala Val Tyr His Cys
                 85                  90                  95

Ala Cys Gly Pro Tyr Phe Phe Asp Phe Trp Gly Gln Gly Thr Thr Leu
            100                 105                 110
```

-continued

Thr Val Ser Ser
        115

<210> SEQ ID NO 108
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 108

Glu Val Gln Leu Val Gln Ser Gly Gly Asn Leu Val Gln Pro Gly Gly
 1               5                  10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 109
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 109

Glu Val Gln Gln Val Gln Ser Gly Gly Asn Leu Val Gln Pro Gly Gly
 1               5                  10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 110
<211> LENGTH: 120
<212> TYPE: PRT
<213> ORGANISM: Artificial Sequence
<220> FEATURE:

<223> OTHER INFORMATION: Single chain antibody or single chain antibody
     domain

<400> SEQUENCE: 110

Glu Val Gln Gln Val Gln Ser Gly Gly Asn Leu Val Gln Pro Gly Gly
 1               5                  10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 111
<211> LENGTH: 120
<212> TYPE: PRT
<213> ORGANISM: Artificial Sequence
<220> FEATURE:
<223> OTHER INFORMATION: Single chain antibody or single chain antibody
     domain

<400> SEQUENCE: 111

Glu Val Gln Gln Val Gln Ser Gly Gly Asn Leu Val Gln Pro Gly Gly
 1               5                  10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 112
<211> LENGTH: 120
<212> TYPE: PRT
<213> ORGANISM: Artificial Sequence
<220> FEATURE:
<223> OTHER INFORMATION: Single chain antibody or single chain antibody
     domain

<400> SEQUENCE: 112

Glu Val Gln Leu Val Pro Ser Gly Gly Asn Leu Val Gln Pro Gly Gly
 1               5                  10                  15

Ser Leu Arg Leu Ser Cys Ala Ala Thr Gly Pro Ile Gly Ser His Trp

```
                20                  25                  30

Met Thr Trp Val Arg Gln Ala Pro Gly Gln Gly Leu Glu Trp Val Ala
            35                  40                  45

Asn Ile Asn Leu Asp Gly Thr Glu Lys Phe Tyr Val Asp Ser Val Lys
        50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 113
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 113

Glu Val Gln Leu Val Pro Ser Gly Gly Asn Leu Val Gln Pro Gly Gly
1               5                   10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
            35                  40                  45

Asn Ile Asn Leu Asp Gly Thr Glu Lys Phe Tyr Val Asp Ser Val Lys
        50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 114
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 114

Glu Val Gln Leu Val Pro Ser Gly Gly Asn Leu Val Gln Pro Gly Gly
1               5                   10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
            35                  40                  45

Asn Ile Asn Leu Asp Gly Thr Glu Lys Phe Tyr Val Asp Ser Val Lys
        50                  55                  60

Gly Arg Phe Thr Val Ser Arg Asp Asn Arg Lys Ser Ser Val Phe Leu
```

```
                65                  70                  75                  80
Gln Met Asn Asn Leu Arg Val Asp Asp Thr Ala Val Tyr Tyr Cys Ala
                    85                  90                  95

Arg Leu Gln Trp Gly Gly Tyr Asn Gly Trp Leu Ser Pro Trp Gly Gln
                100                 105                 110

Gly Thr Leu Val Thr Val Ser Ser
            115                 120

<210> SEQ ID NO 115
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 115

Glu Val Gln Leu Val Pro Ser Gly Gly Asn Leu Val Gln Pro Gly Gly
1               5                   10                  15

Ser Leu Arg Leu Ser Cys Ala Ala Thr Gly Pro Ile Gly Ser His Trp
                20                  25                  30

Met Thr Trp Val Arg Gln Ala Pro Gly Gln Gly Leu Glu Trp Val Ala
            35                  40                  45

Asn Ile Asn Leu Asp Gly Thr Glu Lys Phe Tyr Val Asp Ser Val Lys
        50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                    85                  90                  95

Arg Leu Gln Trp Gly Gly Tyr Asn Gly Trp Leu Ser Pro Trp Gly Gln
                100                 105                 110

Gly Thr Leu Val Thr Val Ser Ser
            115                 120

<210> SEQ ID NO 116
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 116

Glu Val Gln Leu Val Gln Ser Gly Gly Asn Leu Val Gln Pro Gly Gly
1               5                   10                  15

Ser Leu Arg Leu Ser Cys Ala Ala Thr Gly Pro Ile Gly Ser His Trp
                20                  25                  30

Met Thr Trp Val Arg Gln Ala Pro Gly Gln Gly Leu Glu Trp Val Ala
            35                  40                  45

Asn Ile Asn Leu Asp Gly Thr Glu Lys Phe Tyr Val Asp Ser Val Lys
        50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                    85                  90                  95

Arg Leu Gln Trp Gly Gly Tyr Asp Gly Trp Leu Ser Pro Trp Gly Gln
                100                 105                 110

Gly Thr Leu Val Thr Val Ser Ser
```

<210> SEQ ID NO 117
<211> LENGTH: 120
<212> TYPE: PRT
<213> ORGANISM: Artificial Sequence
<220> FEATURE:
<223> OTHER INFORMATION: Single chain antibody or single chain antibody
     domain

<400> SEQUENCE: 117

Glu Val Gln Leu Val Gln Ser Gly Gly Asn Leu Val Gln Pro Gly Gly
1               5                   10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asp Gly Trp Leu Ser Pro Trp Gly Gln
            100                 105                 110

Gly Thr Leu Val Thr Val Ser Ser
        115                 120

<210> SEQ ID NO 118
<211> LENGTH: 120
<212> TYPE: PRT
<213> ORGANISM: Artificial Sequence
<220> FEATURE:
<223> OTHER INFORMATION: Single chain antibody or single chain antibody
     domain

<400> SEQUENCE: 118

Glu Val Gln Leu Val Gln Ser Gly Gly Asn Leu Val Gln Pro Gly Gly
1               5                   10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asp Gly Trp Leu Ser Pro Trp Gly Gln
            100                 105                 110

Gly Thr Leu Val Thr Val Ser Ser
        115                 120

<210> SEQ ID NO 119
<211> LENGTH: 120
<212> TYPE: PRT
<213> ORGANISM: Artificial Sequence
<220> FEATURE:
<223> OTHER INFORMATION: Single chain antibody or single chain antibody

<400> SEQUENCE: 119

Glu Val Gln Leu Val Gln Ser Gly Gly Asn Leu Val Gln Pro Gly Gly
1               5                   10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Ser Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 120
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 120

Glu Val Gln Leu Val Gln Ser Gly Gly Asn Leu Val Gln Pro Gly Gly
1               5                   10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Ser Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Tyr Asn Gly Trp Leu Ser Pro Trp Gly Gln
            100                 105                 110

Gly Thr Leu Val Thr Val Ser Ser
        115                 120

<210> SEQ ID NO 121
<211> LENGTH: 116
<212> TYPE: PRT
<213> ORGANISM: Artificial Sequence
<220> FEATURE:
<223> OTHER INFORMATION: Single chain antibody or single chain antibody
      domain

<400> SEQUENCE: 121

Glu Val Gln Leu Leu Glu Ser Gly Gly Gly Leu Val Lys Pro Gly Gly
1               5                   10                  15

Ser Arg Lys Leu Ser Cys Glu Ala Ser Gly Phe Thr Phe Ser Asp Tyr
            20                  25                  30

```
Gly Met His Trp Val Arg Gln Ala Pro Glu Lys Gly Leu Glu Trp Val
        35                  40                  45

Gly Tyr Ile Ser Ser Gly Ser Arg Ile Ile Tyr Tyr Ala Asp Thr Val
 50                  55                  60

Lys Gly Arg Ile Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                 85                  90                  95

Val Arg Gly Thr Trp Val Phe Asp Tyr Trp Gly Gln Gly Thr Thr Leu
            100                 105                 110

Thr Val Ser Ser
        115

<210> SEQ ID NO 122
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 122

Gln Val Gln Leu Gln Glu Ser Gly Pro Gly Leu Val Lys Pro Ser Gln
 1               5                  10                  15

Thr Val Ser Leu Thr Cys Thr Val Ala Gly Tyr Ser Ile Thr Asn Gly
             20                  25                  30

Asn His Trp Trp Asn Trp Ile Arg Gln Val Ser Gly Ser Lys Leu Glu
         35                  40                  45

Trp Ile Gly Tyr Ile Thr Ser Ser Gly Ser Thr Asp Ser Asn Pro Ser
     50                  55                  60

Leu Lys Ser Arg Ile Ser Ile Thr Arg Asp Thr Ser Lys Asn Gln Leu
 65                  70                  75                  80

Phe Leu Gln Leu Asn Ser Val Thr Thr Glu Asp Ile Ala Thr Tyr Tyr
                 85                  90                  95

Cys Ala Arg Ser Ser Asn Tyr Phe Phe His Val Leu Asp Tyr Trp Gly
            100                 105                 110

Gln Gly Thr Ser Val Thr Val Ser Ser
        115                 120

<210> SEQ ID NO 123
<211> LENGTH: 114
<212> TYPE: PRT
<213> ORGANISM: Artificial Sequence
<220> FEATURE:
<223> OTHER INFORMATION: Single chain antibody or single chain antibody
      domain

<400> SEQUENCE: 123

Gln Val Gln Leu Lys Gln Ser Gly Ala Glu Leu Val Lys Ser Gly Ala
 1               5                  10                  15

Ser Val Lys Leu Ser Cys Thr Ala Ser Gly Phe Asn Ile Lys Asp Phe
             20                  25                  30

Tyr Met His Trp Val Lys Gln Arg Thr Glu Gln Gly Leu Glu Trp Ile
         35                  40                  45

Gly Arg Ile Asp Pro Glu Asp Gly Glu Thr Lys Tyr Ala Pro Lys Phe
     50                  55                  60

Gln Gly Lys Ala Thr Ile Thr Ala Asp Thr Ser Ser Asn Thr Ala Tyr
 65                  70                  75                  80
```

Leu Gln Leu Ser Ser Leu Thr Ser Glu Asp Thr Ala Val Tyr Tyr Cys
                85                  90                  95

Val Arg Asp Arg Asp Tyr Asp Trp Gly Gln Gly Thr Thr Leu Thr Val
            100                 105                 110

Ser Ser

<210> SEQ ID NO 124
<211> LENGTH: 114
<212> TYPE: PRT
<213> ORGANISM: Artificial Sequence
<220> FEATURE:
<223> OTHER INFORMATION: Single chain antibody or single chain antibody
      domain

<400> SEQUENCE: 124

Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asn Ile Lys Asp Phe
            20                  25                  30

Tyr Met His Trp Val Arg Gln Ala Pro Gly Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Arg Ala Thr Ile Thr Ala Asp Thr Ser Thr Asn Thr Ala Tyr
65                  70                  75                  80

Leu Glu Leu Arg Ser Leu Arg Ser Asp Thr Ala Val Tyr Tyr Cys
                85                  90                  95

Val Arg Asp Arg Asp Tyr Asp Trp Gly Gln Gly Thr Thr Leu Thr Val
            100                 105                 110

Ser Ser

<210> SEQ ID NO 125
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 125

Gln Val Gln Leu Gln Gln Pro Gly Ala Glu Leu Val Lys Pro Gly Ala
1               5                   10                  15

Ser Val Lys Leu Ser Cys Lys Ala Ser Gly Asn Ser Phe Ala Ser Ser
            20                  25                  30

Trp Met His Trp Val Lys Gln Arg Pro Gly Gln Gly Leu Glu Trp Ile
        35                  40                  45

Gly Met Ile His Pro Tyr Ser Gly Ser Thr Asn Phe Asn Glu Lys Phe
    50                  55                  60

Lys Ser Lys Ala Thr Leu Ser Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Met Asn Trp Asp Trp Tyr Phe Asp Val Trp Gly Thr Gly Thr Thr
            100                 105                 110

Val Thr Val Ser Ala
        115

<210> SEQ ID NO 126
<211> LENGTH: 117
<212> TYPE: PRT
<213> ORGANISM: Artificial Sequence
<220> FEATURE:
<223> OTHER INFORMATION: Single chain antibody or single chain antibody domain

<400> SEQUENCE: 126

```
Gln Val Gln Leu Val Gln Ser Gly Ala Glu Val Lys Lys Pro Gly Ala
 1               5                  10                  15

Ser Val Lys Leu Ser Cys Lys Ala Ser Gly Asn Ser Phe Ala Ser Ser
            20                  25                  30

Trp Met His Trp Val Arg Gln Ala Pro Gly Gln Gly Leu Glu Trp Ile
        35                  40                  45

Gly Met Ile His Pro Tyr Ser Gly Ser Thr Asn Phe Asn Glu Lys Phe
    50                  55                  60

Lys Ser Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Met Asn Trp Asp Trp Tyr Phe Asp Val Trp Gly Gln Gly Thr Thr
            100                 105                 110

Val Thr Val Ser Ser
        115
```

<210> SEQ ID NO 127
<211> LENGTH: 122
<212> TYPE: PRT
<213> ORGANISM: Artificial Sequence
<220> FEATURE:
<223> OTHER INFORMATION: Single chain antibody or single chain antibody domain

<400> SEQUENCE: 127

```
Glu Val Gln Leu Gln Glu Ser Gly Gly Asp Leu Val Lys Pro Gly Gly
 1               5                  10                  15

Ser Leu Lys Leu Ser Cys Ala Ala Ser Gly Phe Thr Phe Ser Tyr Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Ser Ser Glu Asp Thr Ala Met Tyr Tyr Cys
                85                  90                  95

Ala Arg Arg Arg Ser Tyr Asp Ser Val Tyr Trp Tyr Phe Asp Val Trp
            100                 105                 110

Gly Ala Gly Thr Ser Val Thr Val Ser Ser
        115                 120
```

<210> SEQ ID NO 128
<211> LENGTH: 122
<212> TYPE: PRT
<213> ORGANISM: Artificial Sequence
<220> FEATURE:
<223> OTHER INFORMATION: Single chain antibody or single chain antibody domain

<400> SEQUENCE: 128

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Tyr Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg Arg Arg Ser Tyr Asp Ser Val Tyr Trp Tyr Phe Asp Val Trp
            100                 105                 110

Gly Arg Gly Thr Leu Val Thr Val Ser Ser
        115                 120
```

<210> SEQ ID NO 129
<211> LENGTH: 115
<212> TYPE: PRT
<213> ORGANISM: Artificial Sequence
<220> FEATURE:
<223> OTHER INFORMATION: Single chain antibody or single chain antibody
      domain

<400> SEQUENCE: 129

```
Glu Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Ser Arg Ser
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Asp Ser Tyr Asp Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Ser Ser Val Thr Thr Glu Asp Thr Ala Thr Tyr Tyr Cys
                85                  90                  95

Ala Arg Ala Ser Asp Phe Asp Val Trp Gly Thr Gly Thr Thr Val Thr
            100                 105                 110

Val Ser Ser
    115
```

<210> SEQ ID NO 130
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 130

```
Glu Val Gln Leu Gln Gln Ser Gly Ala Glu Leu Ala Lys Pro Gly Ala
 1               5                  10                  15

Ser Val Lys Leu Ser Cys Lys Ala Ser Gly Tyr Thr Phe Thr Ser Tyr
            20                  25                  30

Trp Met His Trp Val Lys Gln Gly Pro Gly Gln Gly Leu Glu Trp Ile
        35                  40                  45
```

```
Gly Ala Ile Tyr Pro Gly Asn Ser Asp Thr Gly Tyr Asn Gln Lys Phe
        50                  55                  60

Lys Gly Lys Ala Lys Leu Thr Ala Val Thr Ser Ala Ser Thr Ala Tyr
 65                  70                  75                  80

Met Glu Leu Ser Ser Leu Thr Asn Glu Asp Ser Ala Val Tyr Tyr Cys
                 85                  90                  95

Thr Arg His Gly Tyr Tyr Ile Tyr Ala Leu Asp Tyr Trp Gly Gln Gly
                100                 105                 110

Thr Ser Val Thr Val Ser Ser
            115
```

<210> SEQ ID NO 131
<211> LENGTH: 121
<212> TYPE: PRT
<213> ORGANISM: Artificial Sequence
<220> FEATURE:
<223> OTHER INFORMATION: Single chain antibody or single chain antibody domain

<400> SEQUENCE: 131

```
Glu Val Gln Leu Leu Glu Thr Gly Gly Asp Leu Val Lys Pro Gly Gly
 1               5                  10                  15

Ser Leu Lys Leu Ser Cys Ala Ala Ser Gly Phe Thr Phe Ser Tyr Tyr
                20                  25                  30

Gly Met Ser Trp Val Arg Gln Thr Pro Asp Lys Arg Leu Glu Trp Val
             35                  40                  45

Ala Thr Ile Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                85                  90                  95

Ala Arg Arg Val Tyr Tyr Gly Ser Ser Tyr Glu Asp Tyr Trp Gly
                100                 105                 110

Gln Gly Thr Thr Leu Thr Val Ser Ser
        115                 120
```

<210> SEQ ID NO 132
<211> LENGTH: 120
<212> TYPE: PRT
<213> ORGANISM: Artificial Sequence
<220> FEATURE:
<223> OTHER INFORMATION: Single chain antibody or single chain antibody domain

<400> SEQUENCE: 132

```
Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Tyr
                20                  25                  30

Tyr Met His Trp Val Lys Gln Arg Thr Glu Gln Gly Leu Glu Trp Ile
             35                  40                  45

Gly Arg Ile Asp Pro Glu Asp Gly Glu Thr Lys Tyr Ala Pro Lys Phe
        50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                85                  90                  95
```

```
Val Ser Leu Leu Arg Ser Arg Thr Gly Tyr Phe Asp Tyr Trp Gly Gln
            100                 105                 110

Gly Thr Thr Leu Thr Val Ser Ser
            115                 120

<210> SEQ ID NO 133
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 133

Glu Val Gln Leu Lys Gln Ser Gly Thr Glu Leu Val Lys Pro Arg Ser
1               5                   10                  15

Ser Val Lys Met Ser Cys Lys Ala Ser Gly Tyr Thr Phe Thr Asp Tyr
            20                  25                  30

Trp Ile Gly Trp Thr Lys Gln Arg Pro Gly His Gly Leu Glu Trp Ile
        35                  40                  45

Gly His Ile Tyr Pro Gly Gly Gly Tyr Thr Asn Tyr Asn Glu Lys Phe
    50                  55                  60

Lys Gly Lys Ala Thr Leu Thr Ala Asp Ile Ser Ser Ser Ala Ala Tyr
65                  70                  75                  80

Met Gln Phe Ser Ser Pro Thr Ser Glu Asp Ser Ala Ile Tyr Tyr Cys
                85                  90                  95

Ala Arg Ile Ile Met Val Glu Ser Gly Asp Trp Tyr Phe Asp Val Trp
            100                 105                 110

Gly Thr Gly Thr Thr Leu Thr Val Ser Ser
            115                 120

<210> SEQ ID NO 134
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 134

Gln Val Gln Leu Lys Gln Ser Gly Gly Gly Leu Val Arg Pro Gly Gly
1               5                   10                  15

Ser Met Lys Leu Ser Cys Val Ala Ser Gly Phe Thr Phe Ser Asn Ser
            20                  25                  30

Trp Met Asn Trp Val Arg Gln Ser Pro Glu Lys Gly Leu Glu Trp Val
        35                  40                  45

Ala Gln Ile Arg Ser Asn Ser Asp Asn Tyr Ala Thr His Tyr Met Glu
    50                  55                  60

Ser Val Lys Gly Arg Phe Thr Ile Ser Arg Asp Asp Ser Lys Ser Cys
65                  70                  75                  80

Val Tyr Leu Gln Met Asn Asn Leu Trp Ala Glu Asp Thr Gly Ile Tyr
                85                  90                  95

Tyr Cys Thr Ser Tyr Ser Asp Leu Ala Tyr Trp Gly Gln Gly Thr Leu
            100                 105                 110

Val Thr Val Ser Ala
        115

<210> SEQ ID NO 135
```

```
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 135

Gln Val Gln Leu Val Gln Ser Gly Ala Glu Val Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Glu Asp Tyr Tyr Asp Ser Ser Gly Tyr Tyr Asp Tyr Trp
            100                 105                 110

Gly Gln Gly Thr Leu Val Thr Val Ser Ser
        115                 120

<210> SEQ ID NO 136
<211> LENGTH: 124
<212> TYPE: PRT
<213> ORGANISM: Artificial Sequence
<220> FEATURE:
<223> OTHER INFORMATION: Single chain antibody or single chain antibody
      domain

<400> SEQUENCE: 136

Gln Val Gln Leu Gln Glu Ser Gly Gly Gly Leu Val Gln Pro Gly Arg
 1               5                  10                  15

Ser Leu Arg Leu Ser Cys Glu Thr Ser Gly Phe Pro Phe Gly Asp Tyr
            20                  25                  30

Thr Met Ser Trp Phe Arg Gln Thr Pro Gly Met Arg Pro Glu Trp Val
        35                  40                  45

Gly Phe Ile Lys Asn Lys Asp Tyr Gly Asp Val Thr Gln Tyr Ala Ala
    50                  55                  60

Ser Val Arg Gly Arg Phe Ile Ile Ser Arg Asp Asp Ser Asn Ser Val
65                  70                  75                  80

Thr Tyr Leu Gln Met Asn Ser Leu Lys Val Asp Asp Ser Ala Leu Tyr
                85                  90                  95

Tyr Cys Val Arg Gly Gly Gly Gln Trp Trp Gln Asn Asp Ala Phe Asp
            100                 105                 110

Val Trp Gly Arg Gly Thr Met Val Thr Val Ser Ser
        115                 120

<210> SEQ ID NO 137
<211> LENGTH: 119
<212> TYPE: PRT
<213> ORGANISM: Artificial Sequence
<220> FEATURE:
<223> OTHER INFORMATION: Single chain antibody or single chain antibody
      domain

<400> SEQUENCE: 137
```

```
Glu Val Gln Leu Val Gln Ser Gly Gly Gly Leu Val Gln Pro Gly
 1               5                  10                  15

Ser Leu Arg Leu Ser Cys Ala Ala Ser Gly Phe Thr Phe Ser Ser Cys
             20                  25                  30

Trp Met Ser Trp Val Arg Gln Ala Pro Gly Lys Gly Leu Glu Trp Val
         35                  40                  45

Ala Asn Ile Lys Gln Asp Gly Ser Val Glu Gln Tyr Val Asn Ser Val
     50                  55                  60

Lys Gly Arg Phe Thr Ile Ser Arg Asp Asn Ala Asn Asn Ser Leu Tyr
 65                  70                  75                  80

Leu Gln Met Asn Ser Leu Arg Ala Glu Asp Thr Ala Val Tyr Tyr Cys
             85                  90                  95

Ala Ile Pro His Arg Ser Asp Tyr Gly Leu Gly Val Trp Gly Gln Gly
            100                 105                 110

Thr Thr Val Thr Val Ser Ser
            115
```

```
<210> SEQ ID NO 138
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 138

Gln Val Gln Leu Val Gln Ser Gly Gly Gly Val Val Gln Pro Gly Arg
 1               5                  10                  15

Ser Leu Arg Leu Ser Cys Glu Ala Ser Gly Phe Ser Phe Ser Asn His
             20                  25                  30

Gly Met His Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Pro Asn Pro Gly Lys Lys Trp Gly Ala Glu Trp Gly Ala Ser
            100                 105                 110

Gly Asn Trp Gly Gln Gly Thr Leu Val Thr Val Ser Ser
        115                 120                 125
```

```
<210> SEQ ID NO 139
<211> LENGTH: 124
<212> TYPE: PRT
<213> ORGANISM: Artificial Sequence
<220> FEATURE:
<223> OTHER INFORMATION: Single chain antibody or single chain antibody
      domain

<400> SEQUENCE: 139

Gln Val Gln Leu Gln Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45
```

-continued

```
Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Lys Gly Trp Glu Leu Met Thr Asn Thr Asp Ala Phe Asp
            100                 105                 110

Ile Trp Gly Gln Gly Thr Leu Val Thr Val Ser Ser
        115                 120
```

<210> SEQ ID NO 140
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 140

```
Glu Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Ala Gly Thr Ser Arg Ser Ala Phe Asp Ile Trp Gly Gln
            100                 105                 110

Gly Thr Met Val Thr Val Ser Ser
        115                 120
```

<210> SEQ ID NO 141
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 141

```
Glu Ile Val Leu Thr Gln Ser Pro Ala Ile Leu Ser Ala Ser Pro Gly
  1               5                  10                  15

Glu Lys Val Thr Met Thr Cys Arg Ala Ser Ser Ser Val Arg Tyr Met
                 20                  25                  30

His Trp Tyr Gln Gln Lys Pro Gly Ser Ser Pro Lys Pro Trp Ile Tyr
             35                  40                  45

Ala Thr Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Gly Asn Ala Pro Thr
                 85                  90                  95
```

```
Phe Gly Gly Gly Thr Lys Leu Glu Ile Lys Arg
            100                 105

<210> SEQ ID NO 142
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 142

Asp Ile Val Met Ser Gln Ser Pro Ala Ser Leu Ala Val Ser Leu Gly
  1               5                  10                  15

Gln Arg Ala Thr Ile Ser Cys Arg Ala Ser Glu Ser Val Asp Tyr Asp
             20                  25                  30

Gly Asp Ser Tyr Met Asn Trp Tyr Gln Gln Lys Pro Gly Gln Pro Pro
         35                  40                  45

Lys Leu Leu Ile Tyr Ala Ala Ser Asn Leu Glu Ser Gly Ile Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Leu Gln Ser Asn
                 85                  90                  95

Glu Ala Pro Trp Thr Phe Gly Gly Gly Thr Lys Leu Glu Ile Lys Arg
            100                 105                 110

<210> SEQ ID NO 143
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 143

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Tyr Asp
             20                  25                  30

Gly Asp Ser Tyr Met Asn Trp Tyr Gln Gln Lys Pro Gly Gln Pro Pro
         35                  40                  45

Lys Leu Leu Ile Tyr Ala Ala Ser Asn Leu Glu Ser Gly Ile Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Leu Gln Ser Asn
                 85                  90                  95

Glu Ala Pro Trp Thr Phe Gly Gly Gly Thr Lys Leu Glu Leu Lys Arg
            100                 105                 110

<210> SEQ ID NO 144
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 144

Asp Ile Val Leu Thr Gln Ser Pro Ala Ser Leu Ala Val Ser Leu Gly
```

```
                1               5                  10                 15
        Gln Arg Ala Thr Ile Ser Cys Arg Ala Ser Glu Ser Val Asp Tyr Asp
                            20                  25                 30

Gly Asp Ser Tyr Met Asn Trp Tyr Gln Gln Lys Pro Gly Gln Pro Pro
                        35                  40                  45

Lys Leu Leu Ile Tyr Ala Ala Ser Asn Leu Glu Ser Gly Ile Pro Ala
                    50                  55                  60

Arg Phe Ser Gly Ser Gly Ser Gly Thr Asp Phe Thr Leu Asn Ile His
        65                  70                  75                  80

Pro Val Glu Glu Glu Asp Ala Ala Thr Tyr Tyr Cys Leu Gln Ser Asn
                            85                  90                  95

Glu Ala Pro Trp Thr Phe Gly Gly Gly Thr Lys Leu Glu Ile Lys Arg
                        100                 105                 110
```

<210> SEQ ID NO 145
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 145

```
        Gln Ile Val Leu Thr Gln Ser Pro Ala Asn Leu Ser Ala Ser Pro Gly
        1               5                   10                  15

Glu Lys Val Thr Met Thr Cys Ser Ala Ser Ser Ser Val Ser Tyr Met
                            20                  25                  30

His Trp Tyr Gln Gln Lys Pro Gly Ser Ser Pro Lys Pro Trp Ile Tyr
                        35                  40                  45

Ala Thr Ser Asn Leu Ala Ser Gly Val Pro Ala Arg Phe Ser Gly Ser
                    50                  55                  60

Gly Ser Gly Thr Ser Tyr Ser Leu Thr Ile Ser Arg Met Glu Ala Glu
        65                  70                  75                  80

Asp Ala Ala Thr Tyr Tyr Cys Gln Gln Trp Ser Ser Tyr Pro Pro Met
                            85                  90                  95

Tyr Thr Phe Gly Gly Gly Thr Lys Leu Glu Leu Lys Arg
                        100                 105
```

<210> SEQ ID NO 146
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 146

```
        Asp Ile Val Met Thr Gln Ser Pro Lys Phe Met Ser Thr Ser Val Gly
        1               5                   10                  15

Asp Arg Val Ser Val Thr Cys Lys Ala Ser Gln Asn Val Gly Thr Asn
                            20                  25                  30

Val Ala Trp Tyr Gln Gln Lys Pro Gly Gln Ser Pro Lys Ala Leu Ile
                        35                  40                  45

Tyr Ser Ala Ser Tyr Arg Tyr Ser Gly Val Pro Asp Arg Phe Thr Gly
                    50                  55                  60

Ser Gly Ser Gly Thr Asp Phe Thr Leu Thr Ile Ser Asn Val Gln Ser
        65                  70                  75                  80

Glu Asp Leu Ala Glu Tyr Phe Cys Gln Gln Tyr Asn Ser Tyr Pro Tyr
```

```
                85                  90                  95
Thr Phe Gly Gly Gly Thr Lys Leu Glu Ile Lys Arg
            100                 105

<210> SEQ ID NO 147
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 147

Glu Asn Val Leu Thr Gln Ser Pro Ala Ile Leu Ser Ala Ser Pro Gly
 1               5                  10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Tyr Thr
                85                  90                  95

Phe Gly Gly Gly Thr Lys Leu Glu Ile Lys Arg
            100                 105

<210> SEQ ID NO 148
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 148

Asp Ile Val Met Ser Gln Ser Pro Ala Ile Met Ser Ala Ser Pro Gly
 1               5                  10                  15

Glu Lys Val Thr Leu Thr Cys Ser Ala Ser Ser Ser Val Ser Ser Asn
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Arg Val Glu
65                  70                  75                  80

Ala Glu Asp Ala Ala Thr Tyr Tyr Cys Gln Gln Trp Ser Ser Asn Pro
                85                  90                  95

Pro Thr Phe Gly Gly Gly Thr Lys Leu Glu Ile Lys Arg
            100                 105

<210> SEQ ID NO 149
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 149
```

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Tyr Pro Leu Thr
                85                  90                  95

Phe Gly Ala Gly Thr Arg Leu Glu Leu Lys Arg
            100                 105

<210> SEQ ID NO 150
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 150

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys Ala
            100                 105

<210> SEQ ID NO 151
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 151

Glu Ile Val Leu Thr Gln Ser Pro Ala Ser Leu Ala Val Ser Leu Gly
1               5                   10                  15

Gln Arg Ala Thr Ile Ser Cys Arg Ala Cys Glu Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Leu Gln Ser Asn
            85                  90                  95

Glu Ala Pro Trp Thr Phe Gly Gly Gly Thr Lys Leu Glu Ile Lys Ala
        100                 105                 110

<210> SEQ ID NO 152
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 152

Asp Ile Val Met Ser Gln Ser Pro Ala Ser Leu Ala Val Ser Leu Gly
1               5                   10                  15

Gln Arg Ala Thr Ile Ser Cys Arg Ala Ser Glu Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Leu Gln Ser Asn
            85                  90                  95

Glu Ala Pro Trp Thr Phe Gly Gly Gly Thr Lys Leu Glu Ile Lys Ala
        100                 105                 110

<210> SEQ ID NO 153
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 153

Asp Ile Val Met Thr Gln Thr Pro Ala Ser Leu Ala Val Ser Leu Gly
1               5                   10                  15

Gln Arg Ala Thr Ile Ser Cys Arg Ala Ser Glu Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Ser Val Glu Glu Glu Asp Ala Ala Thr Tyr Tyr Cys Leu Gln Ser Asn
            85                  90                  95

Glu Ala Pro Trp Thr Phe Gly Gly Gly Thr Lys Leu Glu Ile Lys Ala
        100                 105                 110

<210> SEQ ID NO 154
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 154

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Leu Gln Ser Asn
                85                  90                  95

Glu Ala Pro Trp Thr Phe Gly Gly Gly Thr Lys Leu Glu Ile Lys Ala
            100                 105                 110

<210> SEQ ID NO 155
<211> LENGTH: 113
<212> TYPE: PRT
<213> ORGANISM: Artificial Sequence
<220> FEATURE:
<223> OTHER INFORMATION: Single chain antibody or single chain antibody
      domain

<400> SEQUENCE: 155

Asp Ile Val Met Thr Gln Thr Pro Leu Thr Leu Ser Val Thr Ile Gly
1               5                   10                  15

Gln Pro Ala Ser Ile Ser Cys Arg Ser Ser Gln Ser Leu Leu His Asn
                20                  25                  30

Tyr Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Trp Thr Phe Gly Gly Gly Thr Lys Leu Glu Ile Lys
            100                 105                 110

Ala

<210> SEQ ID NO 156
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 156

Asp Ile Val Met Thr Gln Ser Pro Thr Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Phe Met Asn Trp Tyr Gln Gln Lys Pro Gly Gln Pro Pro
            35                  40                  45

Lys Leu Leu Ile Tyr Gly Ala Ser Asn Leu Glu Ser Gly Ile Pro Ala

```
            50                  55                  60
Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Leu Thr Phe Gly Ala Gly Thr Lys Leu Glu Leu Lys Ala
            100                 105                 110

<210> SEQ ID NO 157
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 157

Asp Val Val Met Thr Gln Thr Pro Ala Ser Leu Ala Val Ser Leu Gly
  1               5                  10                  15

Gln Arg Ala Thr Ile Ser Cys Lys Ala Ser Gln Ser Val Asp Tyr Asp
                 20                  25                  30

Gly Asp Ser Tyr Met Asn Trp Tyr Gln Gln Lys Pro Gly Gln Pro Pro
             35                  40                  45

Lys Leu Leu Ile Tyr Ala Ala Ser Ser Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                 85                  90                  95

Glu Asp Pro Tyr Thr Phe Gly Gly Gly Thr Lys Leu Glu Ile Lys Ala
            100                 105                 110

<210> SEQ ID NO 158
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 158

Gln Asn Val Leu Thr Gln Ser Pro Ala Ile Met Ser Ala Ser Pro Gly
  1               5                  10                  15

Glu Lys Val Thr Met Thr Cys Ser Ala Ser Ser Val Ser Ser Arg
                 20                  25                  30

Tyr Leu His Trp Tyr Gln Gln Lys Ser Gly Ala Ser Pro Lys Leu Trp
             35                  40                  45

Ile Tyr Gly Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr His Ser Asp Pro
                 85                  90                  95

Leu Thr Phe Gly Gly Gly Thr Lys Leu Glu Ile Lys Ala
            100                 105

<210> SEQ ID NO 159
<211> LENGTH: 108
<212> TYPE: PRT
```

```
<213> ORGANISM: Artificial Sequence
<220> FEATURE:
<223> OTHER INFORMATION: Single chain antibody or single chain antibody
      domain

<400> SEQUENCE: 159

Gln Ile Val Leu Thr Gln Ser Pro Ala Thr Leu Ser Val Thr Pro Gly
  1               5                  10                  15

Asp Ser Val Ser Leu Ser Cys Arg Ala Ser Gln Ser Ile Ser Asn Asn
             20                  25                  30

Leu His Trp Tyr Gln Gln Lys Ser His Glu Ser Pro Arg Leu Leu Ile
         35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Leu
             85                  90                  95

Thr Phe Gly Ala Gly Thr Arg Leu Glu Ile Lys Ala
            100                 105

<210> SEQ ID NO 160
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 160

Glu Ile Val Leu Thr Gln Ser Pro Ala Ile Met Ser Ala Ser Pro Gly
  1               5                  10                  15

Glu Lys Val Thr Met Thr Cys Ser Ala Ser Ser Ser Ile Ser Tyr Met
             20                  25                  30

His Trp Phe Gln Gln Lys Pro Gly Met Ser Pro Lys Arg Arg Ile Phe
         35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Gly Thr Tyr Tyr Cys His Gln Arg Ser Ser Tyr Pro Phe Thr
             85                  90                  95

Phe Gly Gly Gly Thr Lys Leu Glu Leu Lys Ala
            100                 105

<210> SEQ ID NO 161
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 161

Gln Ile Val Leu Thr Gln Ser Pro Ala Ile Met Ser Ala Ser Pro Gly
  1               5                  10                  15

Glu Lys Val Thr Ile Thr Cys Ser Ala Ser Ser Ser Val Ser Tyr Met
             20                  25                  30

His Trp Phe Gln Gln Lys Pro Gly Thr Ser Pro Lys Leu Trp Ile Tyr
         35                  40                  45
```

```
Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Val Ala Thr Tyr Tyr Cys Gln Gln Trp Ser Ser Asn Pro Leu Thr
                85                  90                  95

Phe Gly Gly Gly Thr Lys Leu Glu Ile Lys Ala
                100                 105
```

<210> SEQ ID NO 162
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 162

```
Glu Asn Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Ala
                100                 105
```

<210> SEQ ID NO 163
<211> LENGTH: 109
<212> TYPE: PRT
<213> ORGANISM: Artificial Sequence
<220> FEATURE:
<223> OTHER INFORMATION: Single chain antibody or single chain antibody domain

<400> SEQUENCE: 163

```
Gln Ile Val Leu Thr Gln Ser Pro Ala Ile Met Ser Ala Ser Pro Gly
1               5                   10                  15

Glu Lys Val Thr Met Thr Cys Arg Ala Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asp Ser Ser Pro
                85                  90                  95

Ser Thr Phe Gly Ala Gly Thr Lys Leu Glu Ile Lys Ala
                100                 105
```

<210> SEQ ID NO 164

<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 164

```
Glu Ile Val Leu Thr Gln Ser Pro Ala Ile Met Ser Ala Ser Pro Gly
 1               5                  10                  15
Gln Lys Val Thr Ile Thr Cys Ser Ala Ser Ser Val Ser Tyr Met
                20                  25                  30
His Trp Tyr Gln Gln Lys Ser Gly Thr Ser Pro Lys Arg Trp Ile Tyr
            35                  40                  45
Asp Thr Ser Lys Leu Ala Ser Gly Val Pro Ala Arg Phe Ser Gly Ser
        50                  55                  60
Gly Ser Gly Thr Ser Tyr Ser Leu Ile Ile Ser Ser Met Glu Ala Glu
65                  70                  75                  80
Asp Ala Ala Thr Tyr Tyr Cys Gln Gln Trp Arg Ser Asn Pro Pro Thr
                85                  90                  95
Phe Gly Gly Gly Thr Arg Leu Glu Ile Lys Ala
               100                 105
```

<210> SEQ ID NO 165
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 165

```
Asp Ile Val Leu Thr Gln Ser Pro Ala Ile Met Ser Ala Ser Pro Gly
 1               5                  10                  15
Gly Lys Ile Thr Ile Thr Cys Ser Ala Ser Ser Ser Val Ser Tyr Met
                20                  25                  30
His Trp Phe Gln Gln Lys Pro Gly Thr Ser Pro Lys Leu Trp Ile Tyr
            35                  40                  45
Ser Thr Ser Asn Leu Ala Ser Gly Val Pro Ala Arg Phe Ser Gly Ser
        50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Arg Ser Ser Tyr Pro Tyr Thr
                85                  90                  95
Phe Gly Gly Gly Thr Lys Leu Glu Ile Lys Ala
               100                 105
```

<210> SEQ ID NO 166
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 166

```
Gln Ile Val Leu Thr Gln Ser Pro Ala Ile Met Ser Ala Ser Pro Gly
 1               5                  10                  15
Glu Lys Val Thr Met Thr Cys Ser Ala Ser Ser Ser Leu Ser Tyr Val
                20                  25                  30
```

His Trp Tyr Gln Gln Lys Pro Gly Ser Ser Pro Lys Pro Trp Ile Tyr
          35                  40                  45

Ala Thr Ser Asn Leu Val Ser Gly Val Pro Ala Arg Phe Ser Gly Ser
 50                  55                  60

Arg Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Tyr Pro Pro Thr
                 85                  90                  95

Phe Gly Ala Gly Thr Lys Leu Glu Ile Lys Ala
                100                 105

<210> SEQ ID NO 167
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 167

Asp Ile Val Met Thr Gln Thr Pro Ala Ile Met Ser Ala Ser Pro Gly
 1                5                  10                  15

Glu Lys Val Thr Ile Thr Cys Ser Ala Ser Ser Ser Val Ser Tyr Met
                 20                  25                  30

His Trp Tyr Gln Gln Lys Pro Gly Thr Ser Pro Lys Leu Trp Ile Tyr
          35                  40                  45

Ser Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Tyr Thr
                 85                  90                  95

Phe Gly Gly Gly Thr Lys Leu Glu Ile Lys Ala
                100                 105

<210> SEQ ID NO 168
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 168

Gln Ile Val Leu Thr Gln Ser Pro Ala Ile Met Ser Ala Ser Pro Gly
 1                5                  10                  15

Glu Lys Val Thr Met Thr Cys Ser Ala Ser Ser Ser Val Ser Tyr Met
                 20                  25                  30

Tyr Trp Tyr Gln Gln Lys Pro Gly Ser Ser Pro Arg Leu Leu Ile Tyr
          35                  40                  45

Asp Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Ser Ser Tyr Pro Pro Ile
                 85                  90                  95

Thr Phe Gly Ala Gly Thr Lys Leu Glu Ile Lys Ala
                100                 105

<210> SEQ ID NO 169
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 169

```
Glu Asn Val Leu Thr Gln Ser Pro Ala Ile Met Ser Ala Ser Pro Gly
 1               5                  10                  15

Glu Lys Val Thr Met Thr Cys Ser Ala Ser Ser Ser Val Asn Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Lys Ala Glu
65                  70                  75                  80

Asp Ala Ala Thr Tyr Phe Cys Gln Gln Trp Ser Ser Phe Pro Pro Thr
                85                  90                  95

Phe Gly Gly Gly Thr Arg Leu Glu Ile Lys Ala
            100                 105
```

<210> SEQ ID NO 170
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 170

```
Gln Ile Val Leu Thr Gln Ser Pro Ala Ile Leu Ser Ala Ser Pro Gly
 1               5                  10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Ala Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Tyr Pro Pro Thr
                85                  90                  95

Phe Gly Ser Gly Thr Lys Leu Glu Ile Lys Ala
            100                 105
```

<210> SEQ ID NO 171
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 171

```
Gln Ile Val Leu Thr Gln Ser Pro Ala Ile Leu Ser Ala Ser Pro Gly
 1               5                  10                  15

Glu Lys Val Ala Met Thr Cys Arg Ala Ser Ser Ser Val Ser Tyr Met
```

```
                20                  25                  30
His Trp Tyr Gln Gln Lys Pro Gly Ser Ser Pro Lys Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
 65                 70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Ile Lys Ala
            100                 105

<210> SEQ ID NO 172
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 172

Gln Ile Val Leu Thr Gln Ser Pro Ala Ile Met Ser Ala Ser Pro Gly
 1               5                  10                  15

Glu Lys Val Thr Met Thr Cys Arg Ala Ser Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Ile Ser Arg Met Glu
 65                 70                  75                  80

Ala Glu Asp Ala Ala Thr Tyr Phe Cys Gln Gln Trp Ser Ser Phe Pro
                85                  90                  95

Pro Thr Phe Gly Gly Gly Thr Lys Leu Glu Leu Lys Ala
            100                 105

<210> SEQ ID NO 173
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 173

Asp Ile Val Met Thr Gln Ser Pro Val Ser Ile Thr Ala Ser Arg Gly
 1               5                  10                  15

Glu Lys Val Thr Ile Thr Cys Arg Ala Ser Ser Ser Ile Ser Ser Asn
                20                  25                  30

Tyr Leu His Trp Tyr Gln Gln Lys Pro Gly Ser Ser Pro Lys Leu Leu
            35                  40                  45

Ile Tyr Arg Thr Ser Asn Leu Ala Ser Gly Val Pro Ala Arg Phe Ser
        50                  55                  60

Gly Ser Gly Ser Gly Asn Ser Tyr Ser Leu Thr Ile Ser Met Glu
 65                 70                  75                  80

Ala Glu Asp Ala Ala Ser Tyr Phe Cys His Gln Trp Ser Ser Tyr Pro
                85                  90                  95

Pro Thr Phe Gly Gly Gly Thr Lys Leu Glu Ile Lys Arg
```

```
                100             105

<210> SEQ ID NO 174
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 174

Asp Ile Val Met Thr Gln Ser Pro Val Ser Ile Thr Ala Ser Arg Gly
1               5                   10                  15

Glu Lys Val Thr Ile Thr Cys Arg Ala Ser Ser Ser Ile Ser Ser Asn
            20                  25                  30

Tyr Leu His Trp Tyr Gln Gln Lys Pro Gly Ser Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Asn Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Pro Thr Phe Gly Gly Gly Thr Lys Leu Glu Ile Lys Ala
            100                 105

<210> SEQ ID NO 175
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 175

Glu Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ala
            100                 105

<210> SEQ ID NO 176
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 176

Glu Ile Val Leu Thr Gln Ser Pro Glu Ile Leu Ser Ala Ser Pro Gly
1               5                   10                  15
```

```
Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Phe His Asn Tyr Pro Pro Thr
                85                  90                  95

Phe Gly Ala Gly Thr Lys Leu Glu Leu Lys Ala
            100                 105
```

<210> SEQ ID NO 177
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 177

```
Gln Ile Val Leu Thr Gln Ser Pro Ala Leu Met Ala Ala Ser Pro Gly
 1               5                  10                  15

Glu Lys Val Thr Ile Thr Cys Ser Val Ser Ser Ser Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Ala Arg Phe Ser
 50                  55                  60

Gly Ser Gly Ser Gly Thr Ser Tyr Ser Leu Thr Ile Ser Arg Val Glu
 65                  70                  75                  80

Ala Glu Asp Ala Ala Thr Tyr Tyr Cys His Gln Arg Ser Ser Tyr Pro
                85                  90                  95

Leu Thr Phe Gly Ala Gly Thr Lys Leu Glu Ile Lys Ala
            100                 105
```

<210> SEQ ID NO 178
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 178

```
Asp Ile Val Met Thr Gln Ser Pro Ala Ile Met Ser Ala Ser Pro Gly
 1               5                  10                  15

Glu Lys Val Thr Met Pro Cys Ser Ala Ser Ser Ser Val Ser Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Ser His Pro Pro Thr
                85                  90                  95
```

```
Phe Gly Ala Gly Thr Arg Leu Glu Ile Lys Ala
            100                 105
```

<210> SEQ ID NO 179
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 179

```
Asp Val Val Met Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
            20                  25                  30

Tyr Trp Phe Gln Gln Lys Pro Gly Ser Ser Pro Lys Pro Trp Ile Tyr
        35                  40                  45

Arg Thr Ser Asn Leu Ala Pro Gly Val Pro Ala Arg Phe Ser Gly Ser
50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Trp
                85                  90                  95

Thr Phe Gly Gly Gly Thr Lys Leu Glu Ile Lys Ala
            100                 105
```

<210> SEQ ID NO 180
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 180

```
Glu Asn Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asp Ser Ser Pro
                85                  90                  95

Leu Thr Phe Gly Ala Gly Thr Lys Leu Glu Ile Lys Ala
            100                 105
```

<210> SEQ ID NO 181
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 181

Asp Ile Glu Met Thr Gln Thr Pro Ala Ile Met Ser Ala Ser Pro Gly
1               5                   10                  15

Glu Lys Val Thr Met Thr Cys Ser Ala Ser Ser Val Ser Ser Arg
            20                  25                  30

Tyr Leu His Trp Tyr Gln Gln Lys Ser Gly Ala Ser Pro Lys Leu Trp
            35                  40                  45

Ile Tyr Gly Thr Ser Asn Leu Ala Ser Gly Val Pro Ala Arg Phe Ser
        50                  55                  60

Gly Ser Gly Ser Gly Thr Ser Tyr Ser Leu Thr Ile Ser Asn Val Glu
65                  70                  75                  80

Ala Glu Asp Ala Ala Thr Tyr Tyr Cys Gln Gln Tyr His Ser Asp Pro
                85                  90                  95

Leu Thr Phe Gly Ala Gly Thr Lys Leu Glu Ile Lys Ala
            100                 105

<210> SEQ ID NO 182
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 182

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ala Gly Thr Lys Leu Glu Ile Lys Ala
            100                 105

<210> SEQ ID NO 183
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 183

Asp Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Pro Thr
                85                  90                  95

Phe Gly Gly Gly Thr Lys Leu Glu Ile Lys Ala
            100                 105

<210> SEQ ID NO 184
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 184

Asp Ile Val Ile Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Tyr Thr Phe Gly Gly Gly Thr Arg Leu Glu Ile Lys Ala
            100                 105                 110

<210> SEQ ID NO 185
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 185

Gln Ile Val Leu Thr Gln Ser Pro Ala Ile Met Ser Ala Ser Pro Gly
1               5                   10                  15

Glu Lys Val Thr Met Ser Cys Arg Ala Ser Ser Ser Val Ser Tyr Val
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Ile Lys Ala
            100                 105

<210> SEQ ID NO 186
<211> LENGTH: 111
<212> TYPE: PRT
<213> ORGANISM: Artificial Sequence
<220> FEATURE:
<223> OTHER INFORMATION: Single chain antibody or single chain antibody
      domain

<400> SEQUENCE: 186

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Tyr Thr Phe Gly Gly Gly Thr Lys Leu Glu Ile Lys Ala
            100                 105                 110

<210> SEQ ID NO 187
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 187

Asp Ile Val Met Thr Gln Ser Pro Ala Ile Met Ala Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser His Leu Ala Ser Gly Val Pro Ala Arg Phe Ser
    50                  55                  60

Gly Ser Gly Ser Gly Thr Ser Phe Ser Leu Thr Ile Ser Ser Met Glu
65                  70                  75                  80

Ala Glu Asp Ala Ala Thr Tyr Tyr Cys Gln Gln Trp Ser Ser Asp Leu
                85                  90                  95

Val Thr Phe Gly Ala Gly Thr Arg Leu Glu Ile Lys Ala
            100                 105

<210> SEQ ID NO 188
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 188

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu

```
                65                  70                  75                  80
Asp Ala Ala Thr Tyr Tyr Cys Gln Gln Trp Ser Ser Asn Pro Pro Phe
                    85                  90                  95
Thr Phe Gly Ala Gly Thr Lys Leu Glu Leu Lys Ala
                100                 105

<210> SEQ ID NO 189
<211> LENGTH: 113
<212> TYPE: PRT
<213> ORGANISM: Artificial Sequence
<220> FEATURE:
<223> OTHER INFORMATION: Single chain antibody or single chain antibody
      domain

<400> SEQUENCE: 189

Asp Ile Val Met Ser Gln Ser Pro Leu Ser Leu Pro Val Ser Leu Gly
 1               5                  10                  15
Asp Gln Ala Phe Ile Ser Cys Arg Phe Ser Gln Ser Ile Val His Ser
                20                  25                  30
Asn Gly Asn Thr Tyr Leu Glu Trp Tyr Leu Gln Lys Pro Gly Gln Ser
                35                  40                  45
Pro Lys Leu Leu Ile Tyr Lys Val Ser Asn Arg Phe Ser Gly Val Pro
            50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                    85                  90                  95
Ser His Val Pro Tyr Thr Phe Gly Gly Gly Thr Lys Leu Glu Ile Lys
                100                 105                 110
Ala

<210> SEQ ID NO 190
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 190

Glu Ile Val Leu Thr Gln Ser Pro Ala Ile Leu Ser Ala Ser Pro Gly
 1               5                  10                  15
Glu Lys Val Thr Met Thr Cys Ser Ala Ser Ser Ser Val Ser Tyr Met
                20                  25                  30
Tyr Trp Tyr Gln Gln Lys Pro Gly Ser Ser Pro Arg Leu Leu Ile Tyr
                35                  40                  45
Asp Thr Ser Asn Leu Ala Ser Gly Val Pro Ala Arg Phe Ser Gly Ser
            50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Ser Ser Tyr Pro Pro Thr
                    85                  90                  95
Phe Gly Asp Gly Thr Arg Leu Glu Ile Lys Ala
                100                 105

<210> SEQ ID NO 191
<211> LENGTH: 107
<212> TYPE: PRT
<213> ORGANISM: Artificial Sequence
```

```
<220> FEATURE:
<223> OTHER INFORMATION: Single chain antibody or single chain antibody
      domain

<400> SEQUENCE: 191

Glu Ile Val Leu Thr Gln Ser Pro Ala Ile Leu Ser Ala Ser Pro Gly
 1               5                  10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Ser Met Glu Ala Glu
 65                 70                  75                  80

Asp Ala Ala Thr Tyr Tyr Cys His Gln Arg Ser Ser Asn Pro Pro Thr
                85                  90                  95

Phe Gly Asp Gly Thr Arg Leu Glu Ile Lys Ala
            100                 105

<210> SEQ ID NO 192
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 192

Gln Ile Val Leu Thr Gln Ser Pro Ala Ile Met Ser Ala Ser Leu Gly
 1               5                  10                  15

Glu Arg Val Thr Met Thr Cys Thr Ala Ser Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Met Glu
 65                 70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Leu Glu Ile Lys Ala
            100                 105

<210> SEQ ID NO 193
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 193

Asp Ile Val Met Thr Gln Ser Pro Ser Thr Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45
```

```
Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn His Pro Tyr Pro Arg
                85                  90                  95

Ala Phe Gly Gln Gly Thr Lys Leu Glu Ile Lys Arg
                100                 105
```

<210> SEQ ID NO 194
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 194

```
Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Lys Pro Trp Gly Lys Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn His Pro Tyr Pro Arg
                85                  90                  95

Ala Phe Gly Gln Gly Thr Lys Leu Glu Ile Lys Arg
                100                 105
```

<210> SEQ ID NO 195
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 195

```
Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Val Ser Thr Trp
                20                  25                  30

Leu Ala Trp Tyr Gln Gln Lys Pro Gly Lys Ala Pro Asn Leu Leu Ile
            35                  40                  45

Ser Glu Ala Ser Asn Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Ile Tyr Tyr Cys Gln Gln Tyr Asn Ser Tyr Val Trp
                85                  90                  95

Thr Phe Gly Gln Gly Thr Lys Leu Glu Ile Lys Arg
                100                 105
```

<210> SEQ ID NO 196
<211> LENGTH: 108

```
<212> TYPE: PRT
<213> ORGANISM: Artificial Sequence
<220> FEATURE:
<223> OTHER INFORMATION: Single chain antibody or single chain antibody
      domain

<400> SEQUENCE: 196

Glu Ile Val Leu Thr Gln Ser Pro Ser Ser Leu Pro Ala Ser Val Gly
1               5                   10                  15

Asp Arg Val Thr Ile Thr Cys Arg Ala Ser Gln Ser Ile Gly Thr Tyr
            20                  25                  30

Leu Asn Trp Tyr Gln His Lys Pro Gly Ser Ala Pro Lys Leu Leu Ile
        35                  40                  45

Asn Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asn Ser Tyr Thr Trp
                85                  90                  95

Thr Phe Gly Gln Gly Thr Lys Val Gly Ile Lys Arg
            100                 105

<210> SEQ ID NO 197
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 197

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg
            100                 105

<210> SEQ ID NO 198
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 198

Asp Ile Gln Met Thr Gln Ser Pro Ser Thr Leu Ser Ala Ser Ile Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
```

```
            35                  40                  45
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Leu Ala Thr Tyr Tyr Cys Gln Gln Ser Tyr Ser Thr Pro Leu
                 85                  90                  95

Phe Phe Gly Gly Gly Thr Lys Val Glu Ile Lys Arg
             100                 105

<210> SEQ ID NO 199
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 199

Asp Ile Val Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                 85                  90                  95

Thr Phe Gly Gln Gly Thr Lys Leu Glu Ile Lys Arg
             100                 105

<210> SEQ ID NO 200
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 200

Asp Ile Val Met Thr Gln Ser Pro Ser Ser Leu Ser Ala Ser Val Gly
  1               5                  10                  15

Asp Arg Val Thr Ile Thr Cys Arg Ala Ser Gln Ala Ile Arg Asn Asp
                 20                  25                  30

Leu Gly Trp Tyr Gln Gln Glu Pro Gly Lys Ala Pro Lys Leu Leu Ile
             35                  40                  45

Tyr Ala Ala Ser Thr Leu Gln Ser Gly Val Pro Ser Arg Phe Ser Gly
         50                  55                  60

Arg Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Asp Ile Lys Arg
             100                 105
```

<210> SEQ ID NO 201
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 201

Asp Ile Val Met Thr Gln Ser Pro Ser Phe Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Tyr Phe Thr Leu Thr Ile Ser Ser Leu Gln Pro
65                  70                  75                  80

Glu Asp Phe Ala Thr Tyr Tyr Cys Gln Gln Ser Tyr Ile Thr Trp Thr
                85                  90                  95

Phe Gly Gln Gly Thr Arg Leu Glu Ile Lys His
            100                 105

<210> SEQ ID NO 202
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 202

Glu Thr Thr Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Arg Leu
                85                  90                  95

Trp Thr Phe Gly Gln Gly Thr Lys Leu Glu Ile Lys Arg
            100                 105

<210> SEQ ID NO 203
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 203

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

```
Leu Ala Trp Tyr Gln Gln Lys Pro Gly Lys Ala Pro Gln Leu Leu Ile
            35                  40                  45

Tyr Lys Ala Ser Ile Leu Lys Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Phe Cys Gln Gln Thr Phe Asp Thr Pro Leu
                 85                  90                  95

Thr Phe Gly Gln Gly Thr Lys Val Glu Ile Lys Arg
            100                 105
```

<210> SEQ ID NO 204
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 204

```
Asp Ile Val Met Thr Gln Ser Pro Ser Phe Val Ser Ala Ser Val Gly
 1               5                  10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Glu Leu Ser Ser Tyr Pro Leu
                 85                  90                  95

Thr Phe Gly Gly Gly Thr Lys Leu Glu Ile Lys Arg
            100                 105
```

<210> SEQ ID NO 205
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 205

```
Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Arg
                 85                  90                  95

Thr Phe Gly Gln Gly Thr Lys Val Asp Ile Lys Arg
            100                 105
```

<210> SEQ ID NO 206
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 206

Ser Gly Leu Thr Gln Asp Pro Ala Val Ser Glu Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Leu Leu Val Ile Tyr Ala
        35                  40                  45

Gly Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Arg Ala Glu Asp
65                  70                  75                  80

Glu Ala Asp Tyr Tyr Cys Asn Ser Arg Asp Ser Ser Gly Asn Tyr Leu
                85                  90                  95

Phe Gly Ala Gly Thr Lys Leu Thr Val Leu Gly
            100                 105

<210> SEQ ID NO 207
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 207

Glu Thr Thr Leu Thr Gln Ser Pro Ser Ser Leu Ser Ala Ser Val Gly
1               5                   10                  15

Asp Arg Val Ser Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asp Pro Pro
                85                  90                  95

Thr Phe Gly Gln Gly Thr Lys Val Glu Ile Lys Arg
            100                 105

<210> SEQ ID NO 208
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 208

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Thr Tyr
            20                  25                  30

Leu Asn Trp Tyr Gln Gln Lys Pro Gly Arg Ala Pro Thr Leu Leu Val
        35                  40                  45

Ser Arg Thr Ser Asn Leu His Thr Gly Val Pro Ser Arg Phe Ser Gly
50                  55                  60

Asp Gly Ser Gly Ser His Phe Ser Leu Thr Ile Asp Ser Leu Gln Pro
65                  70                  75                  80

Glu Asp Phe Ala Thr Tyr Tyr Cys Gln Gln Ser His Thr Ser Pro Val
                85                  90                  95

Thr Phe Gly Gln Gly Thr Lys Val Glu Ile Lys Arg
            100                 105

<210> SEQ ID NO 209
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 209

Asp Ile Val Met Thr Gln Ser Pro Ser Ser Leu Ser Ala Ser Val Gly
1               5                   10                  15

Asp Arg Leu Thr Met Thr Cys Gln Ala Ser Gln Asp Ile Gly Lys His
            20                  25                  30

Leu Asn Trp Tyr Gln Gln Lys Ala Gly Lys Pro Pro Lys Leu Leu Ile
        35                  40                  45

Tyr Gly Ala Ser Asn Leu Lys Thr Gly Val Pro Ser Arg Phe Ser Ala
50                  55                  60

Gly Val Ser Trp Thr Asp Phe Thr Phe Thr Ile Ser Asn Val Gln Pro
65                  70                  75                  80

Glu Asp Val Ala Thr Tyr Tyr Cys Gln Gln Ser Tyr Ser Thr Pro Pro
                85                  90                  95

Thr Phe Gly Gln Gly Thr Lys Val Glu Ile Lys Arg
            100                 105

<210> SEQ ID NO 210
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 210

Glu Ile Val Leu Thr Gln Ser Pro Ser Ser Leu Ser Ala Thr Val Gly
1               5                   10                  15

Asp Arg Val Thr Ile Thr Cys Arg Ala Ser Gln Gly Ile Arg Asn Asp
            20                  25                  30

Leu Val Trp Tyr Gln Gln Lys Pro Gly Lys Ala Pro Lys Arg Leu Thr
        35                  40                  45

Tyr Ala Ala Ser Ser Leu Leu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

```
Thr Phe Gly Gly Gly Thr Lys Leu Glu Ile Lys Arg
            100                 105
```

<210> SEQ ID NO 211
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 211

```
Asp Ile Glu Met Thr Gln Ser Pro Ser Leu Ser Ala Ser Val Arg
  1               5                  10                  15

Asp Lys Val Thr Ile Ser Cys Arg Ala Ser Gln Gly Ile Ser Ser Trp
             20                  25                  30

Leu Thr Trp Tyr Gln Gln Lys Pro Gly Lys Ala Pro Lys Leu Leu Ile
         35                  40                  45

Tyr Lys Ala Ser Thr Leu Gln Ser Gly Val Pro Ser Arg Phe Arg Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Gly Ser Phe Pro Leu
                 85                  90                  95

Thr Phe Gly Gln Gly Thr Lys Leu Glu Ile Lys Arg
            100                 105
```

<210> SEQ ID NO 212
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 212

```
Asp Ile Val Met Thr Gln Ser Pro Ser Ser Leu Ser Ala Ser Val Gly
  1               5                  10                  15

Asp Arg Val Thr Ile Ser Cys Arg Ala Ser Gln Asp Ile Arg Asn Asp
             20                  25                  30

Leu Asn Trp Tyr Gln Gln Lys Pro Gly Lys Ala Pro Lys Leu Leu Ile
         35                  40                  45

Tyr Ala Ser Thr Leu Gln Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ile Asn Ser Phe Pro Leu Thr
                 85                  90                  95

Phe Gly Gly Gly Thr Lys Val Glu Ile Lys Arg
            100                 105
```

<210> SEQ ID NO 213
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 213

```
Asp Ile Val Met Thr Gln Ser Pro Ser Ser Leu Ala Ala Ser Val Gly
```

```
                1               5                  10                 15
            Asp Arg Val Thr Ile Thr Cys Arg Ala Ser Gln Ser Ile Ser Gly Tyr
                            20                  25                 30

Leu Asn Trp Tyr Gln Gln Lys Pro Gly Lys Ala Pro Asn Leu Leu Ile
                        35                  40                  45

Tyr Ala Ala Ser Ser Leu Gln Ser Gly Val Pro Ser Arg Phe Ser Gly
                        50                  55                  60

Ser Gly Ser Gly Thr Asp Phe Thr Leu Thr Ile Ser Ser Leu Gln Pro
             65                 70                  75                  80

Asp Asp Phe Ala Ser Tyr Tyr Cys Gln Gln Ser Tyr Asp Ile Pro Arg
                            85                  90                  95

Thr Phe Gly Gln Gly Thr Lys Val Glu Ile Lys Arg
                            100                 105
```

<210> SEQ ID NO 214
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 214

```
            Asp Ile Val Met Thr Gln Ser Pro Ser Ser Leu Ser Ala Ser Val Gly
             1               5                  10                 15

Asp Arg Val Thr Ile Thr Cys Arg Ala Ser Gln Ser Ile Asn Ser Tyr
                            20                  25                 30

Leu Asn Trp Tyr Gln Gln Lys Pro Gly Lys Val Pro Arg Leu Leu Ile
                        35                  40                  45

Tyr Ser Ala Ser Ser Leu Gln Ser Gly Val Pro Ser Arg Phe Ser Gly
                        50                  55                  60

Ser Gly Ser Gly Thr Asp Phe Thr Leu Thr Ile Ser Ser Leu Gln Pro
             65                 70                  75                  80

Asp Asp Phe Ala Thr Tyr Tyr Cys Gln Gln Tyr Lys Arg Tyr Ser Ser
                            85                  90                  95

Phe Gly Gln Gly Thr Lys Val Glu Ile Lys Arg
                        100                 105
```

<210> SEQ ID NO 215
<211> LENGTH: 111
<212> TYPE: PRT
<213> ORGANISM: Artificial Sequence
<220> FEATURE:
<223> OTHER INFORMATION: Single chain antibody or single chain antibody
      domain

<400> SEQUENCE: 215

```
            Gln Ser Val Pro Thr Gln Pro Ala Ser Val Ser Gly Ser Pro Gly Gln
             1               5                  10                 15

Ser Ile Thr Ile Ser Cys Thr Gly Thr Ser Ser Asp Val Gly Ala Tyr
                            20                  25                 30

Asn Tyr Val Ser Trp Tyr Gln Gln His Pro Gly Lys Ala Pro Lys Leu
                        35                  40                  45

Met Ile Tyr Asp Val Ser Asp Arg Pro Ser Gly Val Ser Asn Arg Phe
                        50                  55                  60

Ser Gly Ser Lys Ser Gly Asn Thr Ala Ser Leu Thr Ile Ser Gly Leu
             65                 70                  75                  80

Gln Ala Glu Asp Glu Ala Asp Tyr Tyr Cys Ser Ser Tyr Thr Ser Ser
```

```
              85                  90                  95

Ser Thr Tyr Val Phe Gly Thr Gly Thr Lys Leu Thr Val Leu Gly
            100                 105                 110

<210> SEQ ID NO 216
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 216

Asp Ile Val Met Thr Gln Ser Pro Ser Ser Leu Ser Ala Ser Val Gly
  1               5                  10                  15

Asp Arg Val Thr Ile Thr Cys Arg Ala Ser Gln Asp Ile Asn Asn Arg
             20                  25                  30

Leu Ala Trp Tyr Gln Gln Lys Pro Gly Lys Ala Pro Lys Leu Leu Ile
         35                  40                  45

Tyr Gly Ala Thr Ser Leu Gln Ser Gly Val Pro Ser Arg Phe Ser Gly
 50                  55                  60

Ser Gly Ser Gly Thr Glu Phe Thr Leu Ala Ile Asn Asn Leu Gln Pro
 65                  70                  75                  80

Asp Asp Phe Ala Thr Tyr Tyr Cys Gln Gln Ala Asn Ser Leu Pro Leu
                 85                  90                  95

Thr Phe Gly Gly Gly Thr Lys Val Asp Ile Lys Arg
            100                 105

<210> SEQ ID NO 217
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 217

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Arg Tyr
             20                  25                  30

Asn Leu Val Ser Trp Tyr Gln Gln His Pro Gly Lys Pro Pro Lys Leu
         35                  40                  45

Met Ile Tyr Asp Val Ser Asn Arg Pro Ser Gly Val Ser Asn Arg Phe
 50                  55                  60

Ser Ala Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Gly
                 85                  90                  95

Asn Asn Leu Trp Val Phe Gly Gly Gly Thr Lys Val Thr Val Leu Gly
            100                 105                 110

<210> SEQ ID NO 218
<211> LENGTH: 111
<212> TYPE: PRT
<213> ORGANISM: Artificial Sequence
<220> FEATURE:
<223> OTHER INFORMATION: Single chain antibody or single chain antibody
      domain

<400> SEQUENCE: 218
```

Gln Pro Val Leu Thr Gln Pro Ser Ala Ser Gly Thr Pro Gly Gln
1               5                   10                  15

Arg Val Thr Ile Ser Cys Ser Gly Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Asn Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Gln Leu Thr Val Leu Gly
            100                 105                 110

<210> SEQ ID NO 219
<211> LENGTH: 111
<212> TYPE: PRT
<213> ORGANISM: Artificial Sequence
<220> FEATURE:
<223> OTHER INFORMATION: Single chain antibody or single chain antibody
      domain

<400> SEQUENCE: 219

Gln Pro Gly Leu Thr Gln Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Val Ser Leu
                85                  90                  95

Asn Ala Tyr Val Phe Gly Thr Gly Thr Lys Val Thr Val Leu Gly
            100                 105                 110

<210> SEQ ID NO 220
<211> LENGTH: 111
<212> TYPE: PRT
<213> ORGANISM: Artificial Sequence
<220> FEATURE:
<223> OTHER INFORMATION: Single chain antibody or single chain antibody
      domain

<400> SEQUENCE: 220

Ser Tyr Glu Leu Thr Gln Pro Ser Ala Ser Gly Thr Pro Gly Gln
1               5                   10                  15

Arg Val Ser Ile Ser Cys Ser Gly Ser Ser Ser Asn Ile Gly Ser Asn
                20                  25                  30

Pro Val Asn Trp Tyr Gln Gln Leu Pro Gly Thr Ala Pro Lys Leu Leu
            35                  40                  45

Ile Tyr Ser Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

```
Ser Glu Asp Glu Ala Asp Tyr Tyr Cys Ala Ala Trp Asp Asp Ser Leu
                85                  90                  95

Ser Thr Val Val Phe Gly Gly Gly Thr Lys Leu Thr Val Leu Gly
            100                 105                 110

<210> SEQ ID NO 221
<211> LENGTH: 111
<212> TYPE: PRT
<213> ORGANISM: Artificial Sequence
<220> FEATURE:
<223> OTHER INFORMATION: Single chain antibody or single chain antibody
      domain

<400> SEQUENCE: 221

Gln Pro Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
             35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                85                  90                  95

Asn Ala Tyr Val Phe Gly Thr Gly Thr Gln Leu Thr Val Leu Gly
            100                 105                 110

<210> SEQ ID NO 222
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 222

Asp Ile Val Met Thr Gln Thr Pro Ser Ser Leu Ser Ala Ser Val Gly
  1               5                  10                  15

Asp Arg Val Thr Ile Thr Cys Arg Thr Ser Gln Gly Phe Thr Ser Ala
             20                  25                  30

Leu Ala Trp Tyr Gln Gln Lys Ser Gly Glu Pro Pro Lys Leu Leu Ile
             35                  40                  45

Tyr Asp Ala Ser Arg Leu Glu Ser Gly Val Pro Ser Arg Phe Ser Gly
 50                  55                  60

Ser Gly Ser Gly Ser Asp Phe Ala Leu Ile Ile Ser Ser Leu Gln Pro
 65                  70                  75                  80

Glu Asp Phe Ala Thr Tyr Tyr Cys Gln Gln Ser Asn Ser Tyr Pro Leu
                85                  90                  95

Thr Phe Gly Gly Gly Thr Lys Val Asp Ile Lys Arg
            100                 105

<210> SEQ ID NO 223
<211> LENGTH: 108
<212> TYPE: PRT
<213> ORGANISM: Artificial Sequence
<220> FEATURE:
<223> OTHER INFORMATION: Single chain antibody or single chain antibody
      domain
```

<400> SEQUENCE: 223

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Ser Ser Ala
            20                  25                  30

Ser Trp Tyr Gln Gln Lys Pro Gly Gln Ala Pro Val Leu Val Ile Phe
        35                  40                  45

Gly Glu Asn Lys Arg Pro Ser Gly Ile Pro Asp Arg Phe Ser Gly Ser
    50                  55                  60

Thr Ser Gly Asn Thr Val Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Phe Gly Gly Gly Thr Lys Val Thr Val Leu Gly
            100                 105

<210> SEQ ID NO 224
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 224

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Leu Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Thr Pro Arg
                85                  90                  95

Thr Phe Gly Gln Gly Thr Lys Val Glu Ile Lys Arg
            100                 105

<210> SEQ ID NO 225
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 225

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Ser
            20                  25                  30

Leu Cys Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

```
Ser Gly Ser Gly Thr Asp Phe Ile Phe Thr Ile Ser Ser Leu Gln Pro
 65                  70                  75                  80

Glu Asp Ile Ala Thr Tyr Tyr Cys Gln Gln Tyr Asp Asn Leu Leu Arg
                 85                  90                  95

Val Phe Gly Gly Gly Thr Lys Leu Glu Ile Lys Arg
                100                 105
```

<210> SEQ ID NO 226
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 226

```
Glu Ile Val Leu Thr His Ser Pro Ser Ser Leu Ser Ala Ser Val Gly
  1               5                  10                  15

Asp Arg Ile Thr Ile Thr Cys Arg Ala Ser Gln Gly Ile Ser Asn Tyr
                 20                  25                  30

Leu Ala Trp Tyr Gln Gln Lys Pro Gly Lys Ala Pro Lys Val Leu Ile
             35                  40                  45

Tyr Lys Ala Ser Ser Leu Glu Asn Gly Val Pro Ser Arg Phe Ser Gly
 50                  55                  60

Ser Gly Ser Gly Thr Asp Phe Thr Leu Thr Ile Thr Ser Leu Gln Pro
 65                  70                  75                  80

Asp Asp Phe Ala Thr Tyr Tyr Cys Gln Gln Tyr Asn Ala Tyr Pro Leu
                 85                  90                  95

Thr Phe Gly Gly Gly Thr Lys Leu Glu Ile Lys Arg
                100                 105
```

<210> SEQ ID NO 227
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 227

```
Asp Ile Gln Met Thr Gln Ser Pro Ser Ser Leu Ser Ala Phe Val Gly
  1               5                  10                  15

Asp Arg Ile Thr Ile Thr Cys Arg Ala Ser Arg Gly Val Ser Asn Tyr
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Gly Leu Gln Pro
 65                  70                  75                  80

Asp Asp Phe Ala Thr Tyr Tyr Cys Gln Gln Tyr Asn Ala Tyr Pro Leu
                 85                  90                  95

Thr Phe Gly Gly Gly Thr Lys Leu Glu Ile Lys Arg
                100                 105
```

<210> SEQ ID NO 228
<211> LENGTH: 111
<212> TYPE: PRT
<213> ORGANISM: Artificial Sequence
<220> FEATURE:

```
<223> OTHER INFORMATION: Single chain antibody or single chain antibody
      domain

<400> SEQUENCE: 228

Ala Ser Val Leu Thr Gln Asp Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Glu Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Lys Arg Val Phe Gly Gly Gly Thr Lys Leu Thr Val Leu Gly
            100                 105                 110

<210> SEQ ID NO 229
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 229

Ala Glu Leu Thr Gln Asp Pro Ala Val Ser Val Ala Leu Gly Gln Thr
1               5                   10                  15

Val Arg Ile Thr Cys Gln Gly Asp Ser Leu Arg Asn Tyr Tyr Ala Ser
            20                  25                  30

Trp Tyr Gln Gln Lys Pro Gly Gln Ala Pro Val Leu Val Ile Tyr Gly
        35                  40                  45

Lys Asn Ile Arg Pro Ser Gly Ile Pro Asp Arg Phe Ser Gly Ser Ser
50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Asn Gly Asn His Tyr
                85                  90                  95

Val Phe Gly Thr Gly Thr Lys Val Thr Val Leu Gly
            100                 105

<210> SEQ ID NO 230
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 230

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Ser Gly Gly Thr Lys Val Thr Val Leu Gly
                100                 105

<210> SEQ ID NO 231
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 231

Glu Ile Val Leu Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
                 35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asn Thr Pro Leu
                 85                  90                  95

Thr Phe Gly Gly Gly Thr Lys Val Glu Ile Lys Arg
                100                 105

<210> SEQ ID NO 232
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 232

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
                 35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gly Gly Thr Lys Val Glu Ile Lys Arg
                100                 105

<210> SEQ ID NO 233
<211> LENGTH: 108
<212> TYPE: PRT
```

<213> ORGANISM: Artificial Sequence
<220> FEATURE:
<223> OTHER INFORMATION: Single chain antibody or single chain antibody domain

<400> SEQUENCE: 233

Asp Val Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Val Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys Arg
            100                 105

<210> SEQ ID NO 234
<211> LENGTH: 108
<212> TYPE: PRT
<213> ORGANISM: Artificial Sequence
<220> FEATURE:
<223> OTHER INFORMATION: Single chain antibody or single chain antibody domain

<400> SEQUENCE: 234

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln Ser Tyr Ser Thr Pro Phe
                85                  90                  95

Thr Phe Gly Gln Gly Thr Lys Val Glu Ile Lys Arg
            100                 105

<210> SEQ ID NO 235
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 235

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ile Trp
            20                  25                  30

Met Ala Trp Tyr Gln Gln Lys Pro Gly Lys Ala Pro Lys Leu Leu Val
        35                  40                  45

```
Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Gly Thr
                85                  90                  95

Phe Gly Lys Gly Thr Lys Val Glu Ile Lys Arg
            100                 105

<210> SEQ ID NO 236
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 236

Glu Ile Val Leu Thr Gln Ser Pro Ser Ser Val Ser Val Ser Val Gly
  1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Asp Ile Lys Arg
            100                 105

<210> SEQ ID NO 237
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 237

Glu Ile Val Leu Thr Gln Ser Pro Ser Phe Leu Ser Ala Ser Val Gly
  1               5                  10                  15

Asp Arg Val Thr Ile Thr Cys Arg Ala Ser Gln Gly Ile Arg Asn Asp
                20                  25                  30

Leu Ala Trp Phe Gln Gln Lys Pro Gly Lys Ala Pro Lys Leu Leu Ile
            35                  40                  45

Tyr Ala Thr Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Ala Ser Phe Pro Leu
                85                  90                  95

Thr Phe Gly Gly Gly Thr Lys Val Asp Ile Lys Arg
            100                 105

<210> SEQ ID NO 238
```

```
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 238

Asp Ile Val Met Thr Gln Ser Pro Ser Phe Leu Ser Ala Ser Ile Gly
 1               5                  10                  15

Asp Arg Val Thr Ile Thr Cys Arg Ala Ser Gln Ser Ile Ser Asn Trp
                20                  25                  30

Leu Ala Trp Tyr Gln Gln Lys Pro Gly Lys Ala Pro Lys Val Leu Val
            35                  40                  45

Tyr Lys Ala Ser Ser Leu Glu Asn Gly Val Pro Ser Arg Phe Ser Gly
 50                  55                  60

Ser Gly Ser Gly Thr Asp Phe Thr Leu Thr Ile Thr Ser Leu Gln Pro
 65                  70                  75                  80

Asp Asp Phe Ala Thr Tyr Tyr Cys Gln Gln Tyr Asn Ala Tyr Pro Leu
                85                  90                  95

Thr Phe Gly Gly Gly Thr Lys Val Glu Ile Lys Arg
                100                 105

<210> SEQ ID NO 239
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 239

Asp Ile Val Met Thr Gln Ser Pro Ser Thr Leu Ser Ala Ser Val Gly
 1               5                  10                  15

Ala Arg Val Thr Ile Thr Cys Arg Ala Ser Gln Asn Ile Asn Thr Tyr
                20                  25                  30

Leu Asn Trp Tyr His Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro His
                85                  90                  95

Thr Phe Gly Gly Gly Thr Lys Leu Glu Ile Lys Arg
                100                 105

<210> SEQ ID NO 240
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 240

Asp Ile Val Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30
```

```
Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Arg Leu Gln Pro
 65                  70                  75                  80

Glu Asp Val Ala Thr Tyr Tyr Cys Gln Arg Tyr Asn Ser Leu Pro Phe
                85                  90                  95

Thr Phe Gly Gly Gly Thr Lys Leu Glu Ile Lys Arg
            100                 105
```

<210> SEQ ID NO 241
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 241

```
Asp Ile Gln Met Thr Gln Ser Pro Ser Ser Leu Ser Ala Ser Val Gly
 1               5                  10                  15

Asp Arg Ile Thr Ile Thr Cys Arg Ala Ser Arg Asp Ile Arg Asp Asp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Asp Ile Lys Arg
            100                 105
```

<210> SEQ ID NO 242
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 242

```
Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
            35                  40                  45

Lys Asn Asn Arg Pro Ser Gly Ile Pro Asp Arg Phe Ser Gly Ser Ser
            50                  55                  60

Ser Gly Asn Thr Ala Ser Leu Thr Ile Thr Gly Ala Gln Ala Glu Asp
 65                  70                  75                  80

Glu Ala Asp Tyr Phe Cys Asn Ser Arg Asp Ser Asn Gly His Arg Ile
                85                  90                  95

Phe Gly Gly Gly Thr Lys Leu Thr Val Leu Gly
            100                 105
```

<210> SEQ ID NO 243
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 243

```
Glu Asn Val Leu Thr Gln Ser Pro Ala Ile Met Ser Ala Ser Leu Gly
 1               5                  10                  15

Glu Glu Ile Thr Leu Thr Cys Ser Ala Ser Ser Val Ser Tyr Met
                20                  25                  30

His Trp Tyr Gln Gln Lys Ser Gly Thr Ser Pro Lys Leu Trp Ile Tyr
             35                  40                  45

Tyr Thr Ser Asn Leu Ala Ser Gly Val Pro Ala Arg Phe Ser Gly Ser
         50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Tyr Thr
                 85                  90                  95

Phe Gly Gly Gly Thr Lys Leu Glu Ile Lys Arg
            100                 105
```

<210> SEQ ID NO 244
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 244

```
Gln Ile Val Leu Thr Gln Ser Pro Ala Thr Met Ser Ala Ser Pro Gly
 1               5                  10                  15

Glu Lys Val Thr Ile Thr Cys Ser Ala Ser Ser Ser Val Asn Tyr Met
                20                  25                  30

His Trp Tyr Gln Gln Lys Pro Gly Ser Ser Pro Lys Leu Trp Ile Tyr
             35                  40                  45

Asp Thr Ser Ser Leu Ala Pro Gly Val Pro Ala Arg Phe Ser Gly Ser
         50                  55                  60

Gly Ser Gly Thr Ser Tyr Ser Leu Thr Ile Ser Ser Met Glu Ala Glu
 65                  70                  75                  80

Asp Ala Ala Ser Tyr Phe Cys His Gln Trp Ser Ser Tyr Pro Tyr Thr
                 85                  90                  95

Phe Gly Gly Gly Thr Lys Leu Glu Ile Lys Arg
            100                 105
```

<210> SEQ ID NO 245
<211> LENGTH: 108
<212> TYPE: PRT
<213> ORGANISM: Artificial Sequence
<220> FEATURE:
<223> OTHER INFORMATION: Single chain antibody or single chain antibody domain

<400> SEQUENCE: 245

```
Asp Ile Glu Met Thr Gln Ser Pro Pro Ser Leu Ser Ala Ser Val Gly
 1               5                  10                  15

Asp Arg Val Ser Leu Thr Cys Arg Ala Ser Glu Tyr Ile Gly Thr Ser
```

```
                20                  25                  30

Leu Asn Trp Tyr Gln Gln Lys Pro Gly Lys Ala Pro Lys Leu Leu Ile
         35                  40                  45

Tyr Ala Ala Ser Ala Leu His Ser Gly Val Pro Ser Arg Phe Ser Gly
 50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Ala Asn Asp Leu Pro Leu
                 85                  90                  95

Thr Phe Gly Gly Gly Thr Lys Leu Glu Ile Lys Arg
            100                 105

<210> SEQ ID NO 246
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 246

Asp Ile Val Met Thr Gln Ser Pro Pro Ser Leu Ser Ala Ser Val Gly
 1               5                  10                  15

Asp Arg Val Ser Leu Thr Cys Arg Ala Ser Glu Tyr Ile Gly Thr Ser
                20                  25                  30

Leu Asn Trp Tyr Gln Gln Lys Pro Gly Lys Ala Pro Lys Leu Leu Ile
         35                  40                  45

Tyr Ala Ala Ser Ala Leu His Ser Gly Val Pro Ser Arg Phe Ser Gly
 50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Ala Asn Asp Leu Pro Leu
                 85                  90                  95

Thr Phe Gly Gly Gly Thr Lys Leu Glu Ile Lys Arg
            100                 105

<210> SEQ ID NO 247
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 247

Asp Ile Val Met Thr Gln Ser Pro Pro Ser Leu Ser Ala Ser Val Gly
 1               5                  10                  15

Asp Arg Val Ser Leu Thr Cys Arg Ala Ser Glu Tyr Ile Gly Thr Ser
                20                  25                  30

Leu Asn Trp Tyr Gln Gln Lys Pro Gly Lys Ala Pro Lys Leu Leu Ile
         35                  40                  45

Tyr Ala Ala Ser Ala Leu His Ser Gly Val Pro Ser Arg Phe Ser Gly
 50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Thr Asn Asp Leu Pro Leu
                 85                  90                  95

Thr Phe Gly Gly Gly Thr Lys Leu Glu Ile Lys Arg
```

```
                100                 105

<210> SEQ ID NO 248
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 248

Asp Ile Val Met Thr Gln Ser Pro Pro Ser Leu Ser Ala Ser Val Gly
 1               5                  10                  15

Asp Arg Val Ser Leu Thr Cys Arg Ala Ser Glu Tyr Ile Gly Thr Ser
                20                  25                  30

Leu Asn Trp Tyr Gln Gln Lys Pro Gly Lys Ala Pro Lys Leu Leu Ile
            35                  40                  45

Tyr Ala Ala Ser Ala Leu His Ser Gly Val Pro Ser Arg Phe Ser Gly
50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ala Asn Asp Leu Pro Leu
                85                  90                  95

Thr Phe Gly Gly Gly Thr Lys Leu Glu Asn Lys Arg
                100                 105

<210> SEQ ID NO 249
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 249

Asp Ile Val Met Thr Gln Ser Pro Pro Ser Leu Ser Ala Ser Val Gly
 1               5                  10                  15

Asp Arg Val Ser Leu Thr Cys Arg Ala Ser Glu Tyr Ile Gly Thr Ser
                20                  25                  30

Leu Asn Trp Tyr Gln Gln Lys Pro Gly Lys Ala Pro Lys Leu Leu Ile
            35                  40                  45

Tyr Ala Ala Ser Ala Leu His Ser Gly Val Pro Ser Arg Phe Ser Gly
50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ala Asn Asp Leu Pro Leu
                85                  90                  95

Thr Phe Gly Gly Gly Thr Lys Leu Glu Ile Lys Arg
                100                 105

<210> SEQ ID NO 250
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 250

Asp Ile Val Met Ile Gln Ser Pro Pro Ser Leu Ser Ala Ser Val Gly
 1               5                  10                  15
```

```
Asp Arg Val Ser Leu Thr Cys Arg Ala Ser Glu Tyr Ile Gly Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ala Leu His Ser Gly Val Pro Ser Arg Phe Ser Gly
 50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Ala Asn Asp Leu Pro Leu
                 85                  90                  95

Thr Phe Gly Gly Gly Thr Lys Leu Glu Ile Lys Arg
            100                 105
```

<210> SEQ ID NO 251
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 251

```
Asp Ile Leu Met Thr Gln Ser Pro Ser Leu Ser Ala Ser Val Gly
 1               5                  10                  15

Asp Arg Val Ser Leu Thr Cys Arg Ala Ser Glu Tyr Ile Gly Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ala Leu His Ser Gly Val Pro Ser Arg Phe Ser Gly
 50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Ala Asn Asp Leu Pro Leu
                 85                  90                  95

Thr Phe Gly Gly Gly Thr Lys Leu Glu Ile Lys Arg
            100                 105
```

<210> SEQ ID NO 252
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 252

```
Asp Ile Val Met Thr Gln Ser Pro Ser Leu Ser Ala Ser Val Gly
 1               5                  10                  15

Asp Arg Val Ser Leu Thr Cys Arg Ala Ser Glu Tyr Ile Gly Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ala Leu His Ser Gly Val Pro Ser Arg Phe Ser Gly
 50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Thr Asn Asp Leu Pro Leu
                 85                  90                  95
```

```
Thr Phe Gly Gly Gly Thr Lys Leu Glu Ile Lys Arg
            100                 105
```

<210> SEQ ID NO 253
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 253

```
Asp Ile Val Met Thr Gln Ser Pro Pro Ser Leu Ser Ala Ser Val Gly
 1               5                  10                  15

Asp Arg Val Ser Leu Thr Cys Arg Ala Ser Glu Tyr Ile Gly Thr Ser
                20                  25                  30

Leu Asn Trp Tyr Gln Gln Lys Pro Gly Lys Ala Pro Lys Leu Leu Ile
            35                  40                  45

Tyr Ala Ala Ser Ala Leu His Ser Gly Val Pro Ser Arg Phe Ser Gly
50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ala Asn Asp Leu Pro Leu
                85                  90                  95

Thr Phe Gly Gly Gly Thr Lys Leu Glu Ile Lys Arg
            100                 105
```

<210> SEQ ID NO 254
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 254

```
Asp Ile Val Met Thr Gln Ser Pro Pro Ser Leu Ser Ala Ser Val Gly
 1               5                  10                  15

Asp Arg Val Ser Leu Thr Cys Arg Ala Ser Glu Tyr Ile Gly Thr Ser
                20                  25                  30

Leu Asn Trp Tyr Gln Gln Lys Pro Gly Lys Ala Pro Lys Leu Leu Ile
            35                  40                  45

Tyr Ala Ala Ser Ala Leu His Ser Gly Val Pro Ser Arg Phe Ser Gly
50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Thr Asn Asp Leu Pro Leu
                85                  90                  95

Thr Phe Gly Gly Gly Thr Lys Leu Glu Ile Lys Arg
            100                 105
```

<210> SEQ ID NO 255
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 255

Asp Ile Val Met Thr Gln Ser Pro Pro Ser Leu Ser Ala Ser Val Gly
1               5                   10                  15

Asp Arg Val Ser Leu Thr Cys Arg Ala Ser Glu Tyr Ile Gly Thr Ser
            20                  25                  30

Leu Asn Trp Tyr Gln Gln Lys Pro Gly Thr Ala Pro Lys Leu Leu Ile
        35                  40                  45

Tyr Ala Ala Ser Ala Leu His Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ala Asn Asp Leu Pro Leu
                85                  90                  95

Thr Phe Gly Gly Gly Thr Lys Leu Glu Ile Lys Arg
            100                 105

<210> SEQ ID NO 256
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 256

Asp Ile Val Met Thr Gln Ser Pro Pro Ser Leu Ser Ala Ser Val Gly
1               5                   10                  15

Asp Arg Val Ser Leu Thr Cys Arg Ala Ser Glu Tyr Ile Gly Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ala Leu His Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ala Asn Asp Leu Pro Leu
                85                  90                  95

Thr Phe Gly Gly Gly Thr Lys Leu Glu Ile Lys Arg
            100                 105

<210> SEQ ID NO 257
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 257

Asp Ile Val Met Thr Gln Ser Pro Pro Ser Leu Ser Ala Ser Val Gly
1               5                   10                  15

Asp Arg Val Ser Leu Thr Cys Arg Ala Ser Glu Asn Ile Gly Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ala Leu His Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Thr Asn Asp Leu Pro Leu
                85                  90                  95

Thr Phe Gly Gly Gly Thr Lys Leu Glu Ile Lys Arg
            100                 105

<210> SEQ ID NO 258
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 258

Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys Arg
            100                 105                 110

<210> SEQ ID NO 259
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 259

Asp Ile Val Leu Thr Gln Thr Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Arg Leu Glu Ile Lys Arg
            100                 105

<210> SEQ ID NO 260
<211> LENGTH: 113
<212> TYPE: PRT
<213> ORGANISM: Artificial Sequence
<220> FEATURE:
<223> OTHER INFORMATION: Single chain antibody or single chain antibody
      domain

```
<400> SEQUENCE: 260

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Tyr Thr Phe Gly Gly Gly Thr Arg Leu Glu Ile Lys
                100                 105                 110

Ala

<210> SEQ ID NO 261
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 261

Asp Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
             20                  25                  30

Tyr Trp Tyr Gln Gln Lys Pro Gly Ser Ser Pro Lys Pro Trp Ile Tyr
         35                  40                  45

Arg Thr Ser Asn Leu Ala Ser Gly Val Pro Val Arg Phe Ser Gly Ser
     50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Tyr His Asn Phe Pro Pro Thr
                 85                  90                  95

Phe Gly Gly Gly Thr Lys Leu Glu Ile Lys Ala
                100                 105

<210> SEQ ID NO 262
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 262

Glu Ile Val Leu Thr Gln Ser Pro Ala Leu Met Ser Ala Ser Pro Gly
 1               5                  10                  15

Glu Lys Val Thr Met Thr Cys Ser Ala Ser Ser Ser Val Ser Tyr Met
             20                  25                  30

Tyr Trp Tyr Gln Gln Lys Pro Arg Ser Ser Pro Lys Pro Trp Ile Tyr
         35                  40                  45

Leu Thr Ser Asn Leu Ala Ser Gly Val Pro Ala Arg Phe Ser Gly Ser
     50                  55                  60
```

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Leu Lys Ala
            100                 105

<210> SEQ ID NO 263
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 263

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Asn Leu Ala Pro Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ser Tyr Phe Cys His Gln Trp Ser Ser Tyr Pro Tyr Thr
                85                  90                  95

Phe Gly Gly Gly Thr Lys Leu Glu Ile Lys Ala
            100                 105

<210> SEQ ID NO 264
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 264

Asp Val Val Met Thr Gln Thr Pro Ser Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Arg Leu Leu Ile Tyr Ala Ala Ser Asn Gln Gly Ser Gly Val Pro Ala
    50                  55                  60

Arg Phe Ser Gly Ser Gly Ser Gly Thr Asp Phe Arg Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys Arg
            100                 105                 110

<210> SEQ ID NO 265
<211> LENGTH: 112
<212> TYPE: PRT
<213> ORGANISM: Artificial Sequence

```
<220> FEATURE:
<223> OTHER INFORMATION: Single chain antibody or single chain antibody
      domain

<400> SEQUENCE: 265

Asp Val Val Met Thr Gln Ser Pro Leu Ser Leu Pro Val Thr Leu Gly
 1               5                  10                  15

Gln Pro Ala Ser Ile Ser Cys Arg Ala Ser Glu Ser Val Asp Asn Tyr
            20                  25                  30

Gly Ile Ser Phe Met Asn Trp Phe Gln Gln Arg Pro Gly Gln Pro Pro
        35                  40                  45

Arg Leu Leu Ile Tyr Ala Ala Ser Asn Gln Gly Ser Gly Val Pro Asp
 50                  55                  60

Arg Phe Ser Gly Ser Gly Ser Gly Thr Asp Phe Thr Leu Lys Ile Ser
 65                  70                  75                  80

Arg Met Glu Ala Glu Asp Val Ala Met Tyr Phe Cys Gln Gln Ser Lys
                 85                  90                  95

Glu Val Pro Trp Thr Phe Gly Gly Gly Thr Lys Leu Glu Ile Lys Arg
            100                 105                 110

<210> SEQ ID NO 266
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 266

Asp Val Val Met Thr Gln Ser Pro Lys Phe Met Ser Thr Ser Val Gly
 1               5                  10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Ser Asp Val Leu Ser
 65                  70                  75                  80

Glu Asp Leu Ala Asp Tyr Phe Cys Gln Gln Tyr Gly Ser Tyr Pro Thr
                 85                  90                  95

Phe Gly Gly Gly Thr Lys Leu Glu Ile Lys Arg
            100                 105

<210> SEQ ID NO 267
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 267

Asp Val Val Met Thr Gln Ser Pro Asp Ser Leu Ala Thr Ser Leu Gly
 1               5                  10                  15

Glu Arg Val Thr Ile Asn Cys Lys Ala Ser Gln Asp Val Gly Thr Ala
            20                  25                  30

Val Ala Trp Tyr Gln Gln Lys Pro Gly Gln Pro Pro Lys Leu Leu Ile
        35                  40                  45
```

```
Tyr Trp Ala Ser Thr Arg His Thr Gly Val Pro Asp Arg Phe Ser Gly
 50                  55                  60

Ser Gly Ser Gly Thr Asp Phe Thr Leu Thr Ile Ser Ser Val Gln Ala
 65                  70                  75                  80

Glu Asp Val Ala Asp Tyr Phe Cys Gln Gln Tyr Gly Gly Tyr Pro Thr
                 85                  90                  95

Phe Gly Gly Gly Thr Lys Leu Glu Ile Lys Arg
            100                 105
```

<210> SEQ ID NO 268
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 268

```
Asp Ile Val Leu Thr Gln Ser Pro Ala Ile Met Ser Ala Ser Leu Gly
 1               5                  10                  15

Glu Glu Ile Thr Leu Thr Cys Ser Ala Ser Ser Ser Val Ser Tyr Met
                 20                  25                  30

His Trp Tyr Gln Gln Lys Ser Gly Thr Ser Pro Lys Leu Leu Ile Tyr
             35                  40                  45

Ser Thr Ser Asn Leu Ala Ser Gly Val Pro Ser Arg Phe Ser Gly Ser
 50                  55                  60

Gly Ser Gly Thr Ser Tyr Ser Leu Thr Ile Ser Asn Met Glu Ala Glu
 65                  70                  75                  80

Asp Ala Ala Thr Tyr Tyr Cys Gln Gln Trp Ser Ser Asn Pro Tyr Thr
                 85                  90                  95

Phe Gly Gly Gly Thr Lys Leu Glu Leu Lys Ala
            100                 105
```

<210> SEQ ID NO 269
<211> LENGTH: 113
<212> TYPE: PRT
<213> ORGANISM: Artificial Sequence
<220> FEATURE:
<223> OTHER INFORMATION: Single chain antibody or single chain antibody
      domain

<400> SEQUENCE: 269

```
Asp Ile Val Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Thr Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
            100                 105                 110

Ala
```

```
<210> SEQ ID NO 270
<211> LENGTH: 106
<212> TYPE: PRT
<213> ORGANISM: Artificial Sequence
<220> FEATURE:
<223> OTHER INFORMATION: Single chain antibody or single chain antibody
      domain

<400> SEQUENCE: 270

Asp Ile Val Leu Thr Gln Ser Pro Ala Ile Thr Ala Ala Ser Leu Gly
1               5                   10                  15

Gln Lys Val Thr Ile Thr Cys Ser Ala Ser Ser Ser Gly Ser Tyr Ile
            20                  25                  30

His Trp Tyr Gln Gln Lys Ser Gly Thr Ser Pro Lys Leu Leu Ile Tyr
        35                  40                  45

Arg Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Phe Cys His Gln Trp Ser Ser Tyr Pro Thr Phe
                85                  90                  95

Gly Gly Gly Thr Lys Leu Glu Ile Lys Arg
            100                 105

<210> SEQ ID NO 271
<211> LENGTH: 106
<212> TYPE: PRT
<213> ORGANISM: Artificial Sequence
<220> FEATURE:
<223> OTHER INFORMATION: Single chain antibody or single chain antibody
      domain

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Gly Ser Tyr Ile
            20                  25                  30

His Trp Tyr Gln Gln Lys Pro Gly Lys Val Pro Lys Leu Leu Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Val Gln Pro Glu
65                  70                  75                  80

Asp Val Ala Asp Tyr Phe Cys His Gln Trp Ser Ser Tyr Pro Thr Phe
                85                  90                  95

Gly Gly Gly Thr Lys Leu Glu Ile Lys Arg
            100                 105

<210> SEQ ID NO 272
<211> LENGTH: 113
<212> TYPE: PRT
<213> ORGANISM: Artificial Sequence
<220> FEATURE:
<223> OTHER INFORMATION: Single chain antibody or single chain antibody
      domain

<400> SEQUENCE: 272

Gln Thr Val Val Thr Gln Glu Pro Ser Leu Thr Val Ala Pro Gly Gly
1               5                   10                  15

Thr Val Thr Leu Thr Cys Gly Ser Ser Ala Gly Ala Val Thr Thr Asp
            20                  25                  30
```

```
His Tyr Pro Ser Trp Phe Gln Lys Lys Pro Gly Gln Ala Pro Thr Thr
            35                  40                  45

Ile Ile Tyr Asp Thr Thr Asn Lys His Ser Met Thr Pro Gly Pro Ala
    50                  55                  60

Arg Phe Ser Gly Ser Leu Leu Gly Gly Lys Ala Ala Leu Thr Leu Ser
65                  70                  75                  80

Gly Ala Gln Pro Glu Asp Glu Ala Glu Tyr Tyr Cys Phe Leu Ser Tyr
                85                  90                  95

Arg Gly Ser Arg Pro Val Phe Gly Gly Gly Thr Lys Val Thr Val Leu
                100                 105                 110

Ala
```

<210> SEQ ID NO 273
<211> LENGTH: 104
<212> TYPE: PRT
<213> ORGANISM: Artificial Sequence
<220> FEATURE:
<223> OTHER INFORMATION: Single chain antibody or single chain antibody
      domain

<400> SEQUENCE: 273

```
Ser Ser Glu Leu Ser Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asp Pro
                85                  90                  95

Gly Thr Lys Leu Thr Val Leu Ala
                100
```

<210> SEQ ID NO 274
<211> LENGTH: 104
<212> TYPE: PRT
<213> ORGANISM: Artificial Sequence
<220> FEATURE:
<223> OTHER INFORMATION: Single chain antibody or single chain antibody
      domain

<400> SEQUENCE: 274

```
Ser Ser Glu Leu Ser Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asp Pro
                85                  90                  95
```

Gly Thr Lys Leu Thr Val Leu Ala
            100

<210> SEQ ID NO 275
<211> LENGTH: 104
<212> TYPE: PRT
<213> ORGANISM: Artificial Sequence
<220> FEATURE:
<223> OTHER INFORMATION: Single chain antibody or single chain antibody
      domain

<400> SEQUENCE: 275

Ser Ser Glu Leu Ser Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60
Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asp Pro
                85                  90                  95

Gly Thr Lys Leu Thr Val Leu Ala
            100

<210> SEQ ID NO 276
<211> LENGTH: 111
<212> TYPE: PRT
<213> ORGANISM: Artificial Sequence
<220> FEATURE:
<223> OTHER INFORMATION: Single chain antibody or single chain antibody
      domain

<400> SEQUENCE: 276

Gln Pro Gly Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Ala
            100                 105                 110

<210> SEQ ID NO 277
<211> LENGTH: 104
<212> TYPE: PRT
<213> ORGANISM: Artificial Sequence
<220> FEATURE:
<223> OTHER INFORMATION: Single chain antibody or single chain antibody
      domain

<400> SEQUENCE: 277

Ser Ser Glu Leu Ser Gln Asp Pro Ala Val Ser Val Ala Leu Gly Gln

```
                  1               5                  10                 15
Thr Val Arg Ile Thr Cys Gln Gly Asp Ser Leu Arg Ser Tyr Tyr Ala
                 20                 25                 30

Ser Trp Tyr Gln Gln Lys Pro Gly Gln Ala Pro Val Leu Val Ile Tyr
                 35                 40                 45

Gly Lys Asn Asn Arg Pro Ser Gly Ile Pro Asp Arg Phe Ser Gly Ser
    50                 55                 60

Ser Ser Gly Asn Thr Ala Ser Leu Thr Ile Thr Gly Ala Gln Ala Glu
65                 70                 75                 80

Asp Glu Ala Asp Tyr Tyr Cys Ser Ser Arg Asp Ser Ser Gly Asp Pro
                 85                 90                 95

Gly Thr Lys Leu Thr Val Leu Ala
                100

<210> SEQ ID NO 278
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 278

Gln Val Gln Leu Val Gln Ser Gly Ala Glu Val Lys Lys Pro Gly Ala
1               5                  10                 15

Ser Val Asn Val Ser Cys Lys Ala Ser Gly Tyr Thr Phe Thr Gly Tyr
                20                 25                 30

Tyr Ile Tyr Trp Val Arg Gln Ala Pro Gly Gln Gly Leu Glu Trp Met
                35                 40                 45

Gly Trp Ile Asn Pro Asn Ser Gly Val Thr Lys Tyr Ala Gln Lys Phe
    50                 55                 60

Gln Gly Arg Val Thr Met Thr Ile Asp Thr Ser Thr Asn Thr Ala Tyr
65                 70                 75                 80

Met Glu Leu Asn Arg Leu Arg Ala Asp Asp Thr Ala Val Tyr Tyr Cys
                85                 90                 95

Ala Arg Glu Trp Thr Gln Leu Trp Ser Pro Tyr Asp Tyr Trp Gly Gln
                100                105                110

Gly Thr Thr Val Thr Val Ser Ser
        115                120

<210> SEQ ID NO 279
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 279

Gln Val Gln Leu Val Gln Ser Gly Ala Glu Val Lys Lys Pro Gly Ala
1               5                  10                 15

Ser Val Asn Val Ser Cys Lys Ala Ser Gly Tyr Thr Phe Thr Gly Tyr
                20                 25                 30

Tyr Ile Tyr Trp Val Arg Gln Ala Pro Gly Gln Gly Leu Glu Trp Met
                35                 40                 45

Gly Trp Ile Asn Pro Asn Ser Gly Val Thr Lys Tyr Ala Gln Lys Phe
    50                 55                 60

Gln Gly Arg Val Thr Met Thr Ile Asp Thr Ser Thr Asn Thr Ala Tyr
```

```
                65                  70                  75                  80
Met Glu Leu Asn Arg Leu Arg Ala Asp Asp Thr Ala Val Tyr Tyr Cys
                    85                  90                  95

Ala Arg Glu Trp Thr Gln Leu Trp Ser Pro Tyr Asp Tyr Trp Gly Gln
                100                 105                 110

Gly Thr Thr Val Thr Val Ser Ser
                115                 120
```

<210> SEQ ID NO 280
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 280

```
Glu Ile Val Leu Thr Gln Ser Pro Ser Phe Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys Arg
                100                 105
```

<210> SEQ ID NO 281
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 281

```
Asp Ile Val Leu Thr Gln Ser Pro Ser Thr Leu Ser Ala Ser Val Gly
1               5                   10                  15

Asp Arg Val Thr Ile Ser Cys Arg Ala Ser Arg Ser Ile Gly Trp Tyr
                20                  25                  30

Leu Asn Trp Tyr Gln Gln Arg Pro Gly Lys Ala Pro Lys Leu Leu Ile
            35                  40                  45

Tyr Ala Ala Ser Ser Leu His Asn Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ala Phe Gly Phe Pro Arg
                85                  90                  95

Thr Phe Gly Gln Gly Thr Lys Val Glu Ile Lys Arg
                100                 105
```

<210> SEQ ID NO 282
<211> LENGTH: 122
<212> TYPE: PRT

```
<213> ORGANISM: Artificial Sequence
<220> FEATURE:
<223> OTHER INFORMATION: Single chain antibody or single chain antibody
      domain

<400> SEQUENCE: 282

Gln Val Gln Leu Val Gln Ser Gly Ala Glu Val Lys Arg Pro Gly Ala
1               5                   10                  15

Ser Val Lys Ile Ser Cys Lys Thr Ser Gly Tyr Ser Phe Asn Asp Tyr
            20                  25                  30

Ser Leu Gln Trp Val Arg Gln Ala Pro Gly Gln Gly Pro Glu Trp Met
        35                  40                  45

Gly Met Ile Ser Pro Ala Gly Thr Gly Pro Val Tyr Thr Lys Asn Phe
    50                  55                  60

Arg Asp Arg Val Thr Leu Thr Ser Asp Thr Ser Thr Gly Thr Ala Tyr
65                  70                  75                  80

Met Glu Leu Arg Ser Leu Thr Ser Gly Asp Thr Ala Ile Tyr Phe Cys
                85                  90                  95

Ala Arg Gly Ile His Arg Ser Gly Trp Arg Lys Phe Phe Asp Phe Trp
            100                 105                 110

Gly Gln Gly Thr Leu Val Thr Val Ser Ser
        115                 120

<210> SEQ ID NO 283
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 283

Gln Val Gln Leu Gln Gln Ser Gly Gly Gly Leu Ile Gln Pro Gly Gly
1               5                   10                  15

Ser Leu Arg Leu Ser Cys Val Ala Ser Gly Leu Thr Val Ser Ser Asn
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Asn Asn Gly Glu Tyr Asp Tyr Trp Gly Gln Gly Thr Leu
            100                 105                 110

Val Thr Val Ser Ser
115

<210> SEQ ID NO 284
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 284

Asp Ile Gln Met Thr Gln Ser Pro Ser Ser Val Ser Ala Ser Val Gly
1               5                   10                  15
```

```
Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105
```

<210> SEQ ID NO 285
<211> LENGTH: 108
<212> TYPE: PRT
<213> ORGANISM: Artificial Sequence
<220> FEATURE:
<223> OTHER INFORMATION: Single chain antibody or single chain antibody
    domain

<400> SEQUENCE: 285

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Val Pro Lys Arg Leu Ile
        35                  40                  45

Tyr Ala Ala Ser Ser Leu His Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Gln His Leu Asn Ser Tyr Pro Leu
                85                  90                  95

Thr Phe Gly Gly Gly Thr Lys Val Glu Ile Lys Arg
            100                 105
```

<210> SEQ ID NO 286
<211> LENGTH: 128
<212> TYPE: PRT
<213> ORGANISM: Artificial Sequence
<220> FEATURE:
<223> OTHER INFORMATION: Single chain antibody or single chain antibody
    domain

<400> SEQUENCE: 286

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Ala Trp Val
        35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95
```

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
            115                 120                 125

<210> SEQ ID NO 287
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 287

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Ala Trp Val
            35                  40                  45

Ser Ser Leu Thr Ala Ser Gly Asp Asn Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
            115                 120                 125

<210> SEQ ID NO 288
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 288

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Ala Trp Val
            35                  40                  45

Ser Ser Leu Thr Ala Ser Gly Asp Asn Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
            115                 120                 125

<210> SEQ ID NO 289

<211> LENGTH: 128
<212> TYPE: PRT
<213> ORGANISM: Artificial Sequence
<220> FEATURE:
<223> OTHER INFORMATION: Single chain antibody or single chain antibody domain

<400> SEQUENCE: 289

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Ala Trp Val
        35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
        115                 120                 125

<210> SEQ ID NO 290
<211> LENGTH: 128
<212> TYPE: PRT
<213> ORGANISM: Artificial Sequence
<220> FEATURE:
<223> OTHER INFORMATION: Single chain antibody or single chain antibody domain

<400> SEQUENCE: 290

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Ala Trp Val
        35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
        115                 120                 125

<210> SEQ ID NO 291
<211> LENGTH: 120
<212> TYPE: PRT
<213> ORGANISM: Artificial Sequence
<220> FEATURE:
<223> OTHER INFORMATION: Single chain antibody or single chain antibody domain

<400> SEQUENCE: 291

```
Glu Val Gln Leu Val Pro Ser Gly Gly Asn Leu Val Gln Pro Gly Gly
 1               5                  10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120
```

```
<210> SEQ ID NO 292
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 292
```

```
Gln Val Gln Leu Val Gln Ser Gly Ala Glu Val Lys Arg Pro Gly Ala
 1               5                  10                  15

Ser Val Lys Ile Ser Cys Lys Thr Ser Gly Tyr Ser Phe Asn Asp Tyr
            20                  25                  30

Ser Leu Gln Trp Val Arg Gln Ala Pro Gly Gln Gly Pro Glu Trp Met
        35                  40                  45

Gly Met Ile Ser Pro Ala Gly Thr Gly Pro Val Tyr Thr Lys Asn Phe
    50                  55                  60

Arg Asp Arg Val Thr Leu Thr Ser Asp Thr Ser Thr Gly Thr Ala Tyr
65                  70                  75                  80

Met Glu Leu Arg Ser Leu Thr Ser Gly Asp Thr Ala Ile Tyr Phe Cys
                85                  90                  95

Ala Arg Gly Ile His Arg Ser Gly Trp Arg Lys Phe Phe Asp Phe Trp
            100                 105                 110

Gly Gln Gly Thr Leu Val Thr Val Ser Ser
        115                 120
```

```
<210> SEQ ID NO 293
<211> LENGTH: 117
<212> TYPE: PRT
<213> ORGANISM: Artificial Sequence
<220> FEATURE:
<223> OTHER INFORMATION: Single chain antibody or single chain antibody
      domain

<400> SEQUENCE: 293
```

```
Gln Val Gln Leu Gln Gln Ser Gly Gly Gly Leu Ile Gln Pro Gly Gly
 1               5                  10                  15

Ser Leu Arg Leu Ser Cys Val Ala Ser Gly Leu Thr Val Ser Ser Asn
            20                  25                  30

Tyr Met Ser Trp Val Arg Gln Ala Pro Gly Lys Gly Leu Glu Trp Val
        35                  40                  45
```

```
Ser Ala Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Asn Asn Gly Glu Tyr Asp Tyr Trp Gly Gln Gly Thr Leu
            100                 105                 110

Val Thr Val Ser Ser
            115

<210> SEQ ID NO 294
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 294

Gln Val Thr Leu Lys Glu Ser Gly Ala Glu Val Lys Lys Pro Gly Ser
1               5                   10                  15

Ser Val Lys Val Ser Cys Lys Ala Ser Gly Gly Thr Phe Ser Arg His
                20                  25                  30

Gly Ile Ser Trp Val Arg Gln Val Pro Gly Gln Gly Leu Glu Trp Met
            35                  40                  45

Gly Gly Ile Ile Pro Ile Phe Gly Thr Ala Lys Tyr Ala Gln Lys Phe
        50                  55                  60

Gln Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Arg Asp Gly Arg Trp Leu Ala Leu Arg Arg Phe Asp Tyr Trp Gly
            100                 105                 110

Gln Gly Thr Leu Val Thr Val Ser Ser
        115                 120

<210> SEQ ID NO 295
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 295

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Ala Asn Glu
                20                  25                  30

Trp Ile Ala Trp Val Arg Gln Met Pro Gly Lys Gly Leu Asp Tyr Met
            35                  40                  45

Gly Met Ile Trp Pro Gly Val Ser Glu Thr Arg Tyr Ser Pro Ser Phe
        50                  55                  60

Gln Gly Gln Val Thr Ile Ser Ala Asp Lys Ser Ser Asn Thr Ala Tyr
65                  70                  75                  80

Leu His Trp Ser Ser Leu Lys Ala Ser Asp Ser Ala Met Tyr Tyr Cys
                85                  90                  95
```

-continued

Val Arg Arg Pro Ser Met Trp Tyr Arg His Pro Phe Asp Phe Trp Gly
            100                 105                 110

Gln Gly Thr Leu Val Thr Val Ser Ser
        115                 120

<210> SEQ ID NO 296
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 296

Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ser Pro Leu Leu Asp Tyr Gly Tyr Arg Asp Tyr Trp
            100                 105                 110

Gly Gln Gly Thr Leu Val Thr Val Ser Ser
        115                 120

<210> SEQ ID NO 297
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 297

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Leu Tyr Ser Ser Ser Val Asp Ala Phe Asp Ile Trp Gly Gln Gly Thr
            100                 105                 110

Thr Val Thr Val Ser Ser
        115

<210> SEQ ID NO 298
<211> LENGTH: 120

```
<212> TYPE: PRT
<213> ORGANISM: Artificial Sequence
<220> FEATURE:
<223> OTHER INFORMATION: Single chain antibody or single chain antibody
      domain

<400> SEQUENCE: 298

Glu Val Gln Leu Val Gln Ser Gly Ala Glu Val Arg Lys Pro Gly Ala
1               5                   10                  15

Ser Val Lys Leu Ser Cys Lys Ala Ser Gly Tyr Thr Phe Thr Asp Tyr
            20                  25                  30

Tyr Val His Trp Met Arg Gln Ala Pro Gly Gln Gly Leu Glu Trp Met
        35                  40                  45

Gly Trp Ile Asp Pro Asn Gly Gly Thr Asn Ser Ala Gln Lys Phe
    50                  55                  60

Arg Gly Arg Val Thr Leu Thr Arg Asp Thr Ser Ile Ser Thr Ala Tyr
65                  70                  75                  80

Met Glu Leu Arg Arg Leu Lys Ser Asp Asp Thr Ala Val Tyr Tyr Cys
                85                  90                  95

Ala Arg Lys Leu Gly Gly Ser Tyr Asn Ala Asn Asp Tyr Trp Gly Gln
            100                 105                 110

Gly Thr Thr Val Thr Val Ser Ser
        115                 120

<210> SEQ ID NO 299
<211> LENGTH: 122
<212> TYPE: PRT
<213> ORGANISM: Artificial Sequence
<220> FEATURE:
<223> OTHER INFORMATION: Single chain antibody or single chain antibody
      domain

<400> SEQUENCE: 299

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Phe Met Asp Gly Tyr
            20                  25                  30

Phe Leu Asn Trp Ile Arg Gln Thr Pro Gly Lys Gly Leu Glu Trp Ile
        35                  40                  45

Gly Tyr Ile Tyr Tyr Thr Gly Arg Thr Ser Tyr Ser Pro Ser Leu Asn
    50                  55                  60

Ser Arg Leu Thr Met Ser Val Asp Thr Ser Lys Thr Gln Phe Ser Leu
65                  70                  75                  80

Lys Leu Thr Ser Met Ala Ala Ala Asp Thr Ala Ile Tyr Tyr Cys Ala
                85                  90                  95

Arg Gly Arg Gln Leu Trp Pro Thr Ala Gln Tyr Tyr Leu Asp Tyr Trp
            100                 105                 110

Gly Pro Gly Thr Thr Val Thr Val Ser Ser
        115                 120

<210> SEQ ID NO 300
<211> LENGTH: 125
<212> TYPE: PRT
<213> ORGANISM: Artificial Sequence
<220> FEATURE:
<223> OTHER INFORMATION: Single chain antibody or single chain antibody
      domain

<400> SEQUENCE: 300

Glu Val Gln Leu Val Gln Ser Gly Ala Glu Val Lys Lys Pro Gly Ser
```

```
                1               5                  10                 15
            Ser Val Lys Val Ser Cys Arg Ala Ser Gly Gly Ala Phe Ser Thr Tyr
                         20                  25                  30

Thr Phe Asn Trp Val Arg Gln Ala Pro Gly Gln Gly Leu Glu Trp Ile
                         35                  40                  45

Gly Gly Ile Ile Pro Leu Phe Arg Thr Ser His Tyr Ala Gln Lys Phe
                         50                  55                  60

Gln Gly Arg Val Thr Ile Ser Ala Asp Glu Ser Thr Ser Thr Ala Tyr
             65                  70                  75                  80

Met Glu Leu Thr Ser Leu Arg Pro Glu Asp Thr Ala Val Tyr Tyr Cys
                         85                  90                  95

Ala Arg Val Ala Leu Gly Tyr Cys Ser Ser Pro Thr Cys Ala His Phe
                        100                 105                 110

Asp Tyr Trp Gly Gln Gly Thr Leu Val Thr Val Ser Ser
                        115                 120                 125

<210> SEQ ID NO 301
<211> LENGTH: 126
<212> TYPE: PRT
<213> ORGANISM: Artificial Sequence
<220> FEATURE:
<223> OTHER INFORMATION: Single chain antibody or single chain antibody
      domain
<220> FEATURE:
<221> NAME/KEY: VARIANT
<222> LOCATION: 18
<223> OTHER INFORMATION: Xaa = any amino acid

<400> SEQUENCE: 301

Gln Val Gln Leu Val Gln Ser Gly Gly Gly Val Val Gln Pro Gly Arg
             1               5                  10                  15

Ser Xaa Arg Leu Ser Cys Ala Ala Ser Gly Phe Thr Phe Ser Lys Tyr
                         20                  25                  30

Val Met His Trp Val Arg Gln Ala Pro Gly Lys Gly Leu Glu Trp Val
                         35                  40                  45

Ala Val Ile Trp His Asp Gly Ser His Arg Phe Tyr Gly Asp Ser Val
                         50                  55                  60

Lys Gly Arg Phe Thr Ile Ser Arg Asp Asn Ser Lys Asn Thr Val Tyr
             65                  70                  75                  80

Leu Gln Met Asn Ser Leu Arg Ala Glu Asp Thr Ala Val Tyr Tyr Cys
                         85                  90                  95

Ala Arg Asp Pro Gly Phe Thr Asn Gly Ser His Phe Tyr Tyr Tyr Tyr
                        100                 105                 110

Met Asp Val Trp Gly Lys Gly Thr Leu Val Thr Val Ser Ser
                        115                 120                 125

<210> SEQ ID NO 302
<211> LENGTH: 124
<212> TYPE: PRT
<213> ORGANISM: Artificial Sequence
<220> FEATURE:
<223> OTHER INFORMATION: Single chain antibody or single chain antibody
      domain

<400> SEQUENCE: 302

Glu Val Gln Leu Val Gln Ser Gly Ala Glu Val Lys Lys Pro Gly Ser
             1               5                  10                  15

Ser Val Lys Val Ser Cys Lys Ala Ser Gly Asp Thr Phe Thr Asn Tyr
                         20                  25                  30
```

Ala Ile Ser Trp Val Arg Gln Ala Pro Gly Gln Gly Leu Glu Trp Met
            35                  40                  45

Gly Gly Phe Ile Pro Met Phe Ala Thr Ala Asn His Ala Gln Lys Phe
 50                  55                  60

Gln Gly Arg Leu Ser Ile Thr Ala Asp Lys Ser Thr Ser Thr Ala Tyr
 65                  70                  75                  80

Met Glu Leu Ser Gly Leu Arg Ser Asp Asp Thr Ala Val Tyr Tyr Cys
                 85                  90                  95

Ala Gly Ala Arg Lys Ile Tyr His Gly Ser Gly Ser Tyr Pro Phe Asn
            100                 105                 110

Tyr Trp Gly Gln Gly Thr Leu Val Thr Val Ser Ser
            115                 120

<210> SEQ ID NO 303
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 303

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Pro Met Ser Trp Val Arg Gln Ala Pro Gly Lys Gly Leu Glu Trp Val
            35                  40                  45

Ser Ser Leu Thr Ala Ser Gly Asp Asn Thr Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met His Ser Leu Arg Ala Glu Asp Thr Ala Val Tyr Tyr Cys
                 85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
            115                 120                 125

<210> SEQ ID NO 304
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 304

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Pro Met Ser Trp Val Arg Gln Ala Pro Gly Lys Gly Leu Glu Trp Val
            35                  40                  45

Ser Ser Leu Thr Ala Ser Gly Asp Asn Thr Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

```
Leu Gln Met His Ser Leu Arg Ala Glu Asp Thr Ala Val Tyr Tyr Cys
            85                   90                   95

Ala Lys Ala Leu Val Gly Arg Tyr Asp Ile Ser Thr Gly Tyr Tyr Arg
            100                  105                  110

Pro Val Met Asp Ser Trp Gly Gln Gly Thr Leu Val Thr Val Ser Ser
            115                  120                  125

<210> SEQ ID NO 305
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 305

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Glu Trp Val
            35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
            85                  90                   95

Ala Lys Ala Leu Val Gly Arg Tyr Asp Ile Ser Thr Gly Tyr Tyr Arg
            100                 105                  110

Pro Val Met Asp Ser Trp Gly Gln Gly Thr Leu Val Thr Val Ser Ser
            115                 120                  125

<210> SEQ ID NO 306
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 306

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Glu Trp Val
            35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
            85                  90                  95

Ala Lys Ala Leu Val Gly Arg Tyr Asp Ile Ser Thr Gly Tyr Tyr Arg
            100                 105                  110

Pro Val Met Asp Ser Trp Gly Gln Gly Thr Leu Val Thr Val Ser Ser
            115                 120                  125
```

<210> SEQ ID NO 307
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 307

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Glu Trp Val
        35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
        115                 120                 125

<210> SEQ ID NO 308
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 308

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Glu Trp Val
        35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
        115                 120                 125

<210> SEQ ID NO 309
<211> LENGTH: 128
<212> TYPE: PRT
<213> ORGANISM: Artificial Sequence
<220> FEATURE:
<223> OTHER INFORMATION: Single chain antibody or single chain antibody
      domain -continued

<400> SEQUENCE: 309

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Glu Trp Val
        35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
        115                 120                 125

<210> SEQ ID NO 310
<211> LENGTH: 128
<212> TYPE: PRT
<213> ORGANISM: Artificial Sequence
<220> FEATURE:
<223> OTHER INFORMATION: Single chain antibody or single chain antibody
      domain

<400> SEQUENCE: 310

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Glu Trp Val
        35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
        115                 120                 125

<210> SEQ ID NO 311
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 311

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Phe
            20                  25                  30

Trp Ile Gly Trp Val Arg Gln Met Pro Gly Lys Gly Leu Glu Trp Met

```
                      35                  40                  45
Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Val Ser Tyr Ser Ser Leu Asp Ala Phe Asp Ile Trp Gly Gln Gly Thr
                100                 105                 110

Met Val Thr Val Ser Ser
                115

<210> SEQ ID NO 312
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 312

Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Val Ser Tyr Ser Ser Leu Asp Ala Phe Asp Ile Trp Gly Gln Gly Thr
                100                 105                 110

Met Val Thr Val Ser Ser
                115

<210> SEQ ID NO 313
<211> LENGTH: 124
<212> TYPE: PRT
<213> ORGANISM: Artificial Sequence
<220> FEATURE:
<223> OTHER INFORMATION: Single chain antibody or single chain antibody
      domain

<400> SEQUENCE: 313

Gln Val Gln Leu Val Gln Ser Arg Gly Gly Leu Val Lys Pro Gly Gly
  1               5                  10                  15

Ser Leu Arg Leu Ser Cys Ala Ala Ser Gly Phe Thr Phe Ser Ser His
                 20                  25                  30

Ser Met Asn Trp Val Arg Gln Ala Pro Gly Lys Gly Leu Glu Trp Val
             35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ser Lys Asn Ser Leu Tyr
 65                  70                  75                  80

Leu Gln Leu Asn Ser Leu Arg Ala Glu Asp Thr Ala Val Tyr Tyr Cys
```

85                  90                  95

Ala Arg Asp Gln Gly Gly Gly Ser Val Val Gly Thr Asn Trp Phe Asp
            100                 105                 110

Pro Trp Gly Gln Gly Thr Leu Val Thr Val Ser Ser
        115                 120

<210> SEQ ID NO 314
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 314

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Ser Ile Ser Ser Ala
            20                  25                  30

Gly Tyr Ser Trp Ser Trp Ile Arg Gln Ser Pro Gly Lys Gly Leu Glu
        35                  40                  45

Cys Leu Gly Tyr Ile Tyr Gln Thr Gly Ser Thr Phe Tyr Asn Leu Ser
    50                  55                  60

Leu Lys Gly Arg Val Thr Met Ser Leu Asp Arg Ser Lys Asn Gln Ile
65                  70                  75                  80

Ser Leu Arg Leu Thr Ser Val Val Ala Ala Asp Thr Ala Val Tyr Tyr
                85                  90                  95

Cys Ala Arg Val Val Gly Val Tyr Pro Gly Trp Phe Asp Ser Trp Gly
            100                 105                 110

Gln Gly Thr Leu Val Thr Val Ser Ser
        115                 120

<210> SEQ ID NO 315
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 315

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Ser Ile Ser Ser Ala
            20                  25                  30

Gly Tyr Ser Trp Ser Trp Ile Arg Gln Ser Pro Gly Lys Gly Leu Glu
        35                  40                  45

Cys Leu Gly Tyr Ile Tyr Gln Thr Gly Ser Thr Phe Tyr Asn Leu Ser
    50                  55                  60

Leu Lys Gly Arg Val Thr Met Ser Leu Asp Arg Ser Lys Asn Gln Ile
65                  70                  75                  80

Ser Leu Arg Leu Thr Ser Val Val Ala Ala Asp Thr Ala Val Tyr Tyr
                85                  90                  95

Cys Ala Arg Val Val Gly Val Tyr Pro Gly Trp Phe Asp Ser Trp Gly
            100                 105                 110

Gln Gly Thr Leu Val Thr Val Ser Ser
        115                 120

```
<210> SEQ ID NO 316
<211> LENGTH: 111
<212> TYPE: PRT
<213> ORGANISM: Artificial Sequence
<220> FEATURE:
<223> OTHER INFORMATION: Single chain antibody or single chain antibody
      domain

<400> SEQUENCE: 316

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Gly Glu Val Gln
65                  70                  75                  80

Ser Glu Asp Glu Ala Asp Tyr Tyr Cys Ala Ala Trp Asp Asn Asn Val
                85                  90                  95

Arg Gly Pro Val Phe Gly Gly Gly Thr Lys Leu Thr Ile Lys Pro
            100                 105                 110

<210> SEQ ID NO 317
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 317

Asp Val Val Met Thr Gln Ser Pro Ala Thr Leu Ser Leu Ser Pro Gly
1               5                   10                  15

Glu Arg Ala Thr Leu Ser Cys Arg Ala Ser Gln Asn Val Asn Ser His
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg
            100                 105

<210> SEQ ID NO 318
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 318

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30
```

```
Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Leu
                 85                  90                  95

Thr Phe Gly Gln Gly Thr Arg Leu Glu Ile Asn Val
            100                 105
```

<210> SEQ ID NO 319
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 319

```
Glu Thr Thr Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser His
                 20                  25                  30

Val Ala Trp Tyr Gln Gln Lys Pro Gly Gln Ala Pro Arg Leu Leu Ile
            35                  40                  45

Tyr Asp Ala Ser Asn Arg Ala Thr Gly Val Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Leu Glu Ile Lys Arg
            100                 105
```

<210> SEQ ID NO 320
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 320

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Ile Ser Asn Asn
                 20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Pro Thr Gly Ile Pro Asp Arg Phe Ser
 50                  55                  60

Gly Gly Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Arg Asn Leu Pro
                 85                  90                  95

Leu Thr Phe Gly Gly Gly Thr Lys Ala Glu Ile Lys Arg
            100                 105
```

<210> SEQ ID NO 321
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 321

Asp Ile Val Met Thr Gln Ser Pro Pro Ser Leu Ser Ala Ser Val Gly
1               5                   10                  15

Asp Arg Val Ser Leu Thr Cys Arg Ala Ser Glu Tyr Ile Gly Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ala Leu His Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Thr Asn Asp Leu Pro Leu
                85                  90                  95

Thr Phe Gly Gly Gly Thr Lys Leu Glu Ile Lys Arg
            100                 105

<210> SEQ ID NO 322
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 322

Glu Ile Val Leu Thr Gln Ser Pro Ser Ser Leu Ser Ala Ser Val Gly
1               5                   10                  15

Asp Gly Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Asn Ser Phe Pro Leu
                85                  90                  95

Thr Phe Gly Gly Gly Thr Lys Val Glu Ile Lys Arg
            100                 105

<210> SEQ ID NO 323
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 323

Glu Ile Val Leu Thr Gln Ser Pro Ser Ser Leu Ser Ala Ser Val Gly
1               5                   10                  15

```
Asp Arg Val Thr Thr Thr Cys Gln Ala Ser Gln Asp Ile Ser Asn Tyr
            20                  25                  30

Leu Asn Trp Tyr Gln Gln Lys Pro Gly Thr Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Thr Tyr Tyr Cys Gln Gln Ser Tyr Ser Thr Pro Arg
                85                  90                  95

Thr Phe Gly Gly Gly Thr Lys Val Glu Ile Lys Arg
                100                 105
```

<210> SEQ ID NO 324
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 324

```
Asp Val Val Met Thr Gln Ser Pro Pro Tyr Leu Ser Ala Ser Val Gly
1               5                   10                  15

Asp Arg Val Thr Ile Thr Cys Arg Ala Ser Gln Ala Phe Thr Ser Ala
            20                  25                  30

Leu Ala Trp Tyr Gln Gln Lys Ala Gly Glu Pro Pro Lys Leu Leu Ile
        35                  40                  45

Tyr Asp Ala Ser Arg Leu Glu Ser Gly Val Pro Ser Arg Phe Ser Gly
    50                  55                  60

Ser Gly Ser Gly Thr Asp Phe Thr Leu Ser Ile Ser Ser Leu Gln Pro
65                  70                  75                  80

Glu Asp Phe Ala Thr Tyr Tyr Cys Gln Gln Phe Asn Thr Tyr Pro Leu
                85                  90                  95

Thr Phe Gly Gly Gly Thr Lys Val Glu Ile Lys Arg
                100                 105
```

<210> SEQ ID NO 325
<211> LENGTH: 112
<212> TYPE: PRT
<213> ORGANISM: Artificial Sequence
<220> FEATURE:
<223> OTHER INFORMATION: Single chain antibody or single chain antibody
      domain

<400> SEQUENCE: 325

```
Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Pro Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95
```

Asn Gly His Val Val Phe Gly Gly Thr Lys Val Thr Val Leu Gly
            100                 105                 110

<210> SEQ ID NO 326
<211> LENGTH: 113
<212> TYPE: PRT
<213> ORGANISM: Artificial Sequence
<220> FEATURE:
<223> OTHER INFORMATION: Single chain antibody or single chain antibody
      domain

<400> SEQUENCE: 326

Asp Ile Gln Met Thr Gln Ser Pro Leu Ser Leu Pro Val Thr Pro Gly
 1               5                  10                  15

Glu Pro Ala Ser Ile Ser Cys Arg Ser Gly Gln Ser Leu Met Gln Ser
             20                  25                  30

Pro Gly Tyr Asp Cys Leu His Trp Tyr Leu Gln Lys Pro Gly Arg Ser
         35                  40                  45

Pro Gln Leu Leu Ile Ser Phe Gly Ser Ser Arg Ala Ser Gly Val Pro
     50                  55                  60

Asp Arg Phe Ser Ala Ser Gly Ser Gly Thr Asp Phe Thr Leu Lys Ile
 65                  70                  75                  80

Ser Arg Val Glu Ala Asp Asp Val Gly Ile Tyr Tyr Cys Met Gln Thr
                 85                  90                  95

Arg Glu Thr Pro Trp Thr Phe Gly Gln Gly Thr Lys Val Glu Ile Lys
            100                 105                 110

Arg

<210> SEQ ID NO 327
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 327

Asp Ile Val Met Thr Gln Ser Pro Ser Thr Leu Ser Ala Ser Val Gly
 1               5                  10                  15

Asp Thr Val Thr Ile Ala Cys Arg Ala Ser Arg Asp Ile Arg Asn Asp
             20                  25                  30

Leu Gly Trp Tyr Gln Gln Lys Pro Gly Arg Ala Pro Lys Leu Leu Ile
         35                  40                  45

His Pro Ala Ser Thr Leu Gln Thr Gly Val Pro Ser Arg Phe Ser Gly
     50                  55                  60

Ser Gly Ser Gly Thr Asp Phe Thr Leu Thr Ile Thr Ser Leu Gln Pro
 65                  70                  75                  80

Glu Asp Ser Ala Thr Tyr Tyr Cys Leu Gln Asp Tyr Asn Ser Tyr Thr
                 85                  90                  95

Phe Gly Pro Gly Thr Lys Val Asp Ile Lys Arg
            100                 105

<210> SEQ ID NO 328
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 328

```
Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Gly Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Lys Phe Thr Phe Thr Ile Ser Ser Leu Gln Pro
65                  70                  75                  80

Glu Asp Phe Ala Thr Tyr Tyr Cys Gln Gln Leu Gly Ser Tyr Pro Leu
                 85                  90                  95

Thr Phe Gly Gln Gly Thr Arg Leu Gly Ile Lys Arg
            100                 105
```

<210> SEQ ID NO 329
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 329

```
Glu Ile Val Leu Thr Gln Ser Pro Ser Leu Ser Ala Ser Met Gly
 1               5                  10                  15

Asp Thr Val Thr Ile Thr Cys Gln Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Met Ala Ser Thr Leu Glu Thr Gly Val Pro Ser Arg Phe Ser Gly
 50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Thr Ala Pro Cys
                 85                  90                  95

Thr Phe Gly Gln Gly Thr Lys Val Asp Ile Lys Arg
            100                 105
```

<210> SEQ ID NO 330
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 330

```
Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
             20                  25                  30

Trp Tyr Gln Gln Lys Pro Gly Gln Ala Pro Val Leu Val Ile Tyr Gly
         35                  40                  45

Lys Asn Asn Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
65                  70                  75                  80
```

```
Glu Ala Asp Tyr Tyr Cys Asn Ser Arg Asp Ser Ser Gly Asn His Val
                85                  90                  95

Val Phe Gly Gly Gly Thr Lys Leu Thr Val Leu Gly
            100                 105
```

<210> SEQ ID NO 331
<211> LENGTH: 110
<212> TYPE: PRT
<213> ORGANISM: Artificial Sequence
<220> FEATURE:
<223> OTHER INFORMATION: Single chain antibody or single chain antibody
      domain

<400> SEQUENCE: 331

```
His Val Ile Leu Thr Gln Asp Pro Ala Val Ser Val Ala Leu Gly Gln
 1               5                  10                  15

Thr Val Arg Ile Thr Cys Gln Gly Asp Ser Leu Gly Thr Tyr Tyr Ala
            20                  25                  30

Asn Trp Tyr Gln Gln Lys Pro Gly Gln Ala Pro Ile Leu Val Met Phe
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Ser Thr His
                85                  90                  95

Arg Gly Val Phe Gly Gly Gly Thr Lys Leu Thr Val Leu Gly
            100                 105                 110
```

<210> SEQ ID NO 332
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 332

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
            20                  25                  30

Tyr Leu Ala Trp Tyr Gln Lys Lys Pro Asp Gln Ala Pro Arg Leu Leu
        35                  40                  45

Ile Tyr Gly Thr Ser Ser Arg Ala Thr Gly Val Thr Asp Arg Phe Thr
    50                  55                  60

Gly Ser Gly Ser Gly Thr Asp Phe Thr Leu Thr Ile Ser Gly Leu Glu
65                  70                  75                  80

Pro Glu Asp Leu Ala Val Tyr Tyr Cys Gln Gln Tyr Asp Thr Ser Pro
                85                  90                  95

Trp Thr Phe Gly Gln Gly Thr Lys Val Glu Ile Lys Arg
            100                 105
```

<210> SEQ ID NO 333
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 333

Glu Ile Val Leu Thr Gln Ser Pro Gly Thr Leu Ser Leu Ser Pro Gly
1               5                   10                  15

Glu Arg Ala Thr Leu Phe Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gln Gly Thr Arg Leu Glu Ile Asn Val
            100                 105

<210> SEQ ID NO 334
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 334

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Lys Pro Asp Gln Ala Pro Arg Leu Leu
        35                  40                  45

Ile Tyr Gly Thr Ser Ser Arg Ala Thr Gly Val Thr Asp Arg Phe Thr
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asn Asn Trp Pro
                85                  90                  95

Leu Thr Phe Gly Gly Gly Thr Lys Ala Glu Ile Lys Arg
            100                 105

<210> SEQ ID NO 335
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 335

Asp Ile Val Met Thr Gln Thr Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Leu Ala Pro Arg Leu Leu Ile
        35                  40                  45

Tyr Gly Ala Ser Thr Arg Ala Thr Gly Ile Pro Ala Arg Phe Ser Gly
    50                  55                  60

```
Ser Gly Phe Gly Lys Glu Phe Thr Leu Thr Ile Ser Ser Leu Gln Ser
 65                  70                  75                  80

Glu Asp Phe Ala Val Tyr Tyr Cys Gln Gln Tyr Asn Ser Tyr Pro Leu
                 85                  90                  95

Thr Phe Gly Gly Gly Thr Lys Val Glu Ile Lys Arg
            100                 105
```

<210> SEQ ID NO 336
<211> LENGTH: 107
<212> TYPE: PRT
<213> ORGANISM: Artificial Sequence
<220> FEATURE:
<223> OTHER INFORMATION: Single chain antibody or single chain antibody domain

<400> SEQUENCE: 336

```
Ser Tyr Glu Leu Thr Gln Pro Pro Ser Val Ser Val Ala Leu Gly Gln
 1               5                  10                  15

Thr Ala Arg Ile Thr Cys Gly Gly Asn Asn Ile Gly Ser Lys Asn Val
                 20                  25                  30

His Trp Tyr Gln Gln Lys Pro Gly Gln Ala Pro Val Leu Val Ile Tyr
             35                  40                  45

Arg Asp Ser Asn Arg Pro Ser Gly Ile Pro Glu Arg Phe Ser Gly Ser
 50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Gln Val Trp Asp Ser Ser Thr Val Val
                 85                  90                  95

Phe Gly Gly Gly Thr Gln Leu Thr Leu Lys Arg
            100                 105
```

<210> SEQ ID NO 337
<211> LENGTH: 108
<212> TYPE: PRT
<213> ORGANISM: Artificial Sequence
<220> FEATURE:
<223> OTHER INFORMATION: Single chain antibody or single chain antibody domain

<400> SEQUENCE: 337

```
Glu Thr Thr Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys Arg
            100                 105
```

<210> SEQ ID NO 338
<211> LENGTH: 109
<212> TYPE: PRT
<213> ORGANISM: Artificial Sequence
<220> FEATURE:

<223> OTHER INFORMATION: Single chain antibody or single chain antibody
      domain

<400> SEQUENCE: 338

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Ala Arg Phe Ser
    50                  55                  60

Gly Ser Gly Ser Gly Thr Asp Phe Thr Leu Thr Ile Ser Arg Leu Glu
65                  70                  75                  80

Pro Glu Asp Val Ala Val Tyr Tyr Cys Gln Gln Tyr Arg Asn Leu Pro
                85                  90                  95

Leu Thr Phe Gly Gly Gly Thr Lys Val Asp Ile Lys Arg
            100                 105

<210> SEQ ID NO 339
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 339

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Asp Ile Pro Ala Arg Phe Ser
    50                  55                  60

Gly Ser Gly Ser Gly Thr Glu Phe Thr Leu Ser Ile Ser Ser Leu Glu
65                  70                  75                  80

Pro Glu Asp Phe Ala Val Tyr Tyr Cys Gln Gln Ala Ser Ser Phe Pro
                85                  90                  95

Leu Thr Phe Gly Gly Gly Thr Lys Leu Glu Ile Lys Arg
            100                 105

<210> SEQ ID NO 340
<211> LENGTH: 107
<212> TYPE: PRT
<213> ORGANISM: Artificial Sequence
<220> FEATURE:
<223> OTHER INFORMATION: Single chain antibody or single chain antibody
      domain

<400> SEQUENCE: 340

Asp Ile Gln Met Thr Gln Ser Pro Ser Ser Val Ser Ala Ser Val Gly
1               5                   10                  15

Asp Thr Val Ser Ile Thr Cys Arg Ala Ser Gln Gly Ile Gly Asn Leu
            20                  25                  30

Leu Ala Trp Tyr Gln Gln Lys Pro Gly Lys Ala Pro Asn Leu Leu Ile
        35                  40                  45

Tyr Ala Ser Thr Leu Gln Ser Gly Val Pro Ser Arg Phe Ser Gly Ser

-continued

```
                50                  55                  60
Gly Ser Gly Thr Asp Phe Thr Leu Thr Ile Ser Ser Leu Gln Ser Glu
 65                  70                  75                  80

Asp Phe Ala Thr Tyr Phe Cys Gln Gln Ala Lys Arg Leu Pro Leu Thr
                 85                  90                  95

Phe Gly Gly Gly Thr Lys Val Asp Ile Lys Arg
            100                 105
```

<210> SEQ ID NO 341
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 341

```
Asp Ile Val Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Leu Arg
                 85                  90                  95

Thr Phe Gly Gly Gly Thr Lys Val Asp Ile Lys Arg
            100                 105
```

<210> SEQ ID NO 342
<211> LENGTH: 108
<212> TYPE: PRT
<213> ORGANISM: Artificial Sequence
<220> FEATURE:
<223> OTHER INFORMATION: Single chain antibody or single chain antibody
      domain

<400> SEQUENCE: 342

```
Glu Ile Val Leu Thr Gln Ser Pro Ser Ser Val Ser Ala Ser Val Gly
 1               5                  10                  15

Asp Arg Val Thr Ile Thr Cys Arg Ala Ser Gln Ser Ile Gly Thr Tyr
                20                  25                  30

Leu Ser Trp Tyr Gln Gln Lys Pro Gly Lys Ala Pro Lys Leu Leu Ile
            35                  40                  45

Tyr Asp Ala Ser Lys Leu Glu Leu Gly Val Pro Ser Arg Phe Ser Gly
        50                  55                  60

Ser Gly Ser Gly Thr Asp Phe Thr Leu Thr Ile Thr Asp Leu Gln Pro
 65                  70                  75                  80

Asp Asp Leu Ala Thr Tyr Tyr Cys Gln Gln Tyr Leu Thr Tyr Phe Arg
                 85                  90                  95

Thr Phe Gly Gln Gly Thr Lys Val Asp Ile Lys Ser
            100                 105
```

<210> SEQ ID NO 343
<211> LENGTH: 110
<212> TYPE: PRT

```
<213> ORGANISM: Artificial Sequence
<220> FEATURE:
<223> OTHER INFORMATION: Single chain antibody or single chain antibody
      domain

<400> SEQUENCE: 343

Ser Ala Leu Thr Gln Pro Ala Ser Val Ser Gly Ser Pro Gly Gln Ser
1               5                   10                  15

Val Thr Ile Ser Cys Thr Gly Thr Ser Ser Asp Val Gly Gly Tyr Asn
            20                  25                  30

Tyr Val Ser Trp Tyr Gln Gln His Pro Gly Lys Ala Pro Lys Leu Met
        35                  40                  45

Ile Tyr Asp Val Ser Lys Arg Pro Ser Gly Val Pro Asp Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Cys Ser Tyr Ala Gly Arg Tyr
                85                  90                  95

Thr Tyr Val Phe Gly Thr Gly Thr Lys Val Thr Val Leu Gly
            100                 105                 110

<210> SEQ ID NO 344
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 344

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Val Ser Arg Trp
            20                  25                  30

Leu Ala Trp Tyr Gln Gln Lys Pro Gly Lys Pro Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Tyr Glu Asn Leu Pro Pro
                85                  90                  95

Ser Thr Phe Gly Gly Gly Thr Lys Leu Glu Ile Lys Arg
            100                 105

<210> SEQ ID NO 345
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 345

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Ser Thr Asp
            20                  25                  30

Leu Ala Trp Tyr Gln Gln Lys Pro Gly Arg Ala Pro Lys Leu Leu Ile
        35                  40                  45
```

```
Tyr Arg Ala Ser Ser Leu Gln Ser Gly Val Pro Ser Arg Phe Ser Gly
            50                  55                  60
Ser Gly Ser Gly Thr Asp Phe Thr Leu Thr Ile Ser Ser Leu Gln Pro
 65                  70                  75                  80
Asp Asp Leu Ala Thr Tyr Tyr Cys Gln His Tyr Glu Ser Tyr Ser Pro
                 85                  90                  95
Trp Thr Phe Gly Gln Gly Thr Gln Gly Glu Ile Lys Arg
            100                 105
```

<210> SEQ ID NO 346
<211> LENGTH: 8
<212> TYPE: PRT
<213> ORGANISM: Artificial Sequence
<220> FEATURE:
<223> OTHER INFORMATION: Synthetic peptide

<400> SEQUENCE: 346

```
Thr Ala Gly Phe Tyr Phe Asp Tyr
 1               5
```

<210> SEQ ID NO 347
<211> LENGTH: 9
<212> TYPE: PRT
<213> ORGANISM: Artificial Sequence
<220> FEATURE:
<223> OTHER INFORMATION: Synthetic peptide

<400> SEQUENCE: 347

```
Tyr Ser Gly Pro Tyr Ala Met Asp Tyr
 1               5
```

<210> SEQ ID NO 348
<211> LENGTH: 8
<212> TYPE: PRT
<213> ORGANISM: Artificial Sequence
<220> FEATURE:
<223> OTHER INFORMATION: Synthetic peptide

<400> SEQUENCE: 348

```
Gly Ser Ser Gly Tyr Val Asn Tyr
 1               5
```

<210> SEQ ID NO 349
<211> LENGTH: 14
<212> TYPE: PRT
<213> ORGANISM: Artificial Sequence
<220> FEATURE:
<223> OTHER INFORMATION: Synthetic peptide

<400> SEQUENCE: 349

```
Asp Trp Asp Tyr Tyr Tyr Gly Ser Tyr Trp Tyr Phe Asp Val
 1               5                  10
```

<210> SEQ ID NO 350
<211> LENGTH: 8
<212> TYPE: PRT
<213> ORGANISM: Artificial Sequence
<220> FEATURE:
<223> OTHER INFORMATION: Synthetic peptide

<400> SEQUENCE: 350

```
Gly Gly Thr Gly Tyr Phe Asp Val
 1               5
```

```
<210> SEQ ID NO 351
<211> LENGTH: 8
<212> TYPE: PRT
<213> ORGANISM: Artificial Sequence
<220> FEATURE:
<223> OTHER INFORMATION: Synthetic peptide

<400> SEQUENCE: 351

Gly Tyr Tyr Asp Thr Met Asp Tyr
 1               5

<210> SEQ ID NO 352
<211> LENGTH: 12
<212> TYPE: PRT
<213> ORGANISM: Artificial Sequence
<220> FEATURE:
<223> OTHER INFORMATION: Synthetic peptide

<400> SEQUENCE: 352

Gly Gly Trp Leu Gly Asn Tyr Tyr Ala Met Asp Tyr
 1               5                  10

<210> SEQ ID NO 353
<211> LENGTH: 8
<212> TYPE: PRT
<213> ORGANISM: Artificial Sequence
<220> FEATURE:
<223> OTHER INFORMATION: Synthetic peptide

<400> SEQUENCE: 353

Arg Arg Asn Tyr Gly Met Asp Tyr
 1               5

<210> SEQ ID NO 354
<211> LENGTH: 9
<212> TYPE: PRT
<213> ORGANISM: Artificial Sequence
<220> FEATURE:
<223> OTHER INFORMATION: Synthetic peptide

<400> SEQUENCE: 354

Gly Gly Gly Arg Ser Ser Leu Asp Tyr
 1               5

<210> SEQ ID NO 355
<211> LENGTH: 12
<212> TYPE: PRT
<213> ORGANISM: Artificial Sequence
<220> FEATURE:
<223> OTHER INFORMATION: Synthetic peptide

<400> SEQUENCE: 355

Leu Asn Tyr Asp Tyr Pro Tyr Trp Tyr Phe Asp Val
 1               5                  10

<210> SEQ ID NO 356
<211> LENGTH: 12
<212> TYPE: PRT
<213> ORGANISM: Artificial Sequence
<220> FEATURE:
<223> OTHER INFORMATION: Synthetic peptide

<400> SEQUENCE: 356

Arg Glu Gly His Tyr Tyr Gly Lys Ala Met Asp Tyr
 1               5                  10

<210> SEQ ID NO 357
```

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 357

Gly Gly Asn Gly Phe Phe Asp Tyr
1               5

<210> SEQ ID NO 358
<211> LENGTH: 9
<212> TYPE: PRT
<213> ORGANISM: Artificial Sequence
<220> FEATURE:
<223> OTHER INFORMATION: Synthetic peptide

<400> SEQUENCE: 358

Tyr Pro Gly Asn Arg Ala Met Asp Tyr
1               5

<210> SEQ ID NO 359
<211> LENGTH: 10
<212> TYPE: PRT
<213> ORGANISM: Artificial Sequence
<220> FEATURE:
<223> OTHER INFORMATION: Synthetic peptide

<400> SEQUENCE: 359

Asp Asp Gly Tyr Tyr Glu Ala Leu Asp Tyr
1               5                   10

<210> SEQ ID NO 360
<211> LENGTH: 7
<212> TYPE: PRT
<213> ORGANISM: Artificial Sequence
<220> FEATURE:
<223> OTHER INFORMATION: Synthetic peptide

<400> SEQUENCE: 360

Ile Tyr Tyr Gly His Asp Tyr
1               5

<210> SEQ ID NO 361
<211> LENGTH: 9
<212> TYPE: PRT
<213> ORGANISM: Artificial Sequence
<220> FEATURE:
<223> OTHER INFORMATION: Synthetic peptide

<400> SEQUENCE: 361

Asn Leu Gly Leu Trp Tyr Phe Asp Val
1               5

<210> SEQ ID NO 362
<211> LENGTH: 10
<212> TYPE: PRT
<213> ORGANISM: Artificial Sequence
<220> FEATURE:
<223> OTHER INFORMATION: Synthetic peptide

<400> SEQUENCE: 362

Asp Pro Tyr Tyr Tyr Ser Tyr Met Asp Val
1               5                   10

<210> SEQ ID NO 363
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 363

Asn Met Gly Leu Trp Tyr Phe Asp Val
1               5

<210> SEQ ID NO 364
<211> LENGTH: 17
<212> TYPE: PRT
<213> ORGANISM: Artificial Sequence
<220> FEATURE:
<223> OTHER INFORMATION: Synthetic peptide

<400> SEQUENCE: 364

Glu Ala Ser Phe Gly Trp Ser Tyr Leu Gly His Asp Asp Ala Phe Asp
1               5                   10                  15

Ile

<210> SEQ ID NO 365
<211> LENGTH: 7
<212> TYPE: PRT
<213> ORGANISM: Artificial Sequence
<220> FEATURE:
<223> OTHER INFORMATION: Synthetic peptide

<400> SEQUENCE: 365

Tyr Gly Ser Asn Phe Asp Tyr
1               5

<210> SEQ ID NO 366
<211> LENGTH: 7
<212> TYPE: PRT
<213> ORGANISM: Artificial Sequence
<220> FEATURE:
<223> OTHER INFORMATION: Synthetic peptide

<400> SEQUENCE: 366

Thr Gly Thr Gly Phe Asp Tyr
1               5

<210> SEQ ID NO 367
<211> LENGTH: 9
<212> TYPE: PRT
<213> ORGANISM: Artificial Sequence
<220> FEATURE:
<223> OTHER INFORMATION: Synthetic peptide

<400> SEQUENCE: 367

Tyr Gly Tyr Tyr Gly Tyr Phe Asp Tyr
1               5

<210> SEQ ID NO 368
<211> LENGTH: 9
<212> TYPE: PRT
<213> ORGANISM: Artificial Sequence
<220> FEATURE:
<223> OTHER INFORMATION: Synthetic peptide

<400> SEQUENCE: 368

Val Asn Phe Tyr Val Ser Trp Asp Tyr
1               5

<210> SEQ ID NO 369
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 369

Val Gly Phe Arg Val Asn Phe Asp Tyr
 1               5

<210> SEQ ID NO 370
<211> LENGTH: 9
<212> TYPE: PRT
<213> ORGANISM: Artificial Sequence
<220> FEATURE:
<223> OTHER INFORMATION: Synthetic peptide

<400> SEQUENCE: 370

Trp Gly Tyr Tyr Gly Ser Leu Ala Tyr
 1               5

<210> SEQ ID NO 371
<211> LENGTH: 9
<212> TYPE: PRT
<213> ORGANISM: Artificial Sequence
<220> FEATURE:
<223> OTHER INFORMATION: Synthetic peptide

<400> SEQUENCE: 371

Ser Tyr Tyr Arg Ala Trp Phe Asp Tyr
 1               5

<210> SEQ ID NO 372
<211> LENGTH: 11
<212> TYPE: PRT
<213> ORGANISM: Artificial Sequence
<220> FEATURE:
<223> OTHER INFORMATION: Synthetic peptide

<400> SEQUENCE: 372

Ser Glu Gly Tyr Tyr His Asn Leu Gly Ala Tyr
 1               5                   10

<210> SEQ ID NO 373
<211> LENGTH: 12
<212> TYPE: PRT
<213> ORGANISM: Artificial Sequence
<220> FEATURE:
<223> OTHER INFORMATION: Synthetic peptide

<400> SEQUENCE: 373

Asp Phe Tyr Asp Tyr Asp Gly Gly Gly Arg Gly Tyr
 1               5                   10

<210> SEQ ID NO 374
<211> LENGTH: 11
<212> TYPE: PRT
<213> ORGANISM: Artificial Sequence
<220> FEATURE:
<223> OTHER INFORMATION: Synthetic peptide

<400> SEQUENCE: 374

Tyr Gly Gln Val Gly Ser Tyr Ala Met Asp Tyr
 1               5                   10

<210> SEQ ID NO 375
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 375

Ser Gly Gly Thr Gly Tyr Tyr Phe Asp Tyr
1               5                   10

<210> SEQ ID NO 376
<211> LENGTH: 14
<212> TYPE: PRT
<213> ORGANISM: Artificial Sequence
<220> FEATURE:
<223> OTHER INFORMATION: Synthetic peptide

<400> SEQUENCE: 376

Gly Pro Ile Tyr Tyr Gly Thr Ser Tyr Arg Phe Phe Asp Val
1               5                   10

<210> SEQ ID NO 377
<211> LENGTH: 8
<212> TYPE: PRT
<213> ORGANISM: Artificial Sequence
<220> FEATURE:
<223> OTHER INFORMATION: Synthetic peptide

<400> SEQUENCE: 377

Trp Ser Asn Trp Tyr Phe Asp Val
1               5

<210> SEQ ID NO 378
<211> LENGTH: 10
<212> TYPE: PRT
<213> ORGANISM: Artificial Sequence
<220> FEATURE:
<223> OTHER INFORMATION: Synthetic peptide

<400> SEQUENCE: 378

Trp Leu Leu Tyr Tyr Tyr Ala Met Asp Tyr
1               5                   10

<210> SEQ ID NO 379
<211> LENGTH: 11
<212> TYPE: PRT
<213> ORGANISM: Artificial Sequence
<220> FEATURE:
<223> OTHER INFORMATION: Synthetic peptide

<400> SEQUENCE: 379

Tyr Tyr Asp Tyr Asp Gly Asp Tyr Phe Asp Tyr
1               5                   10

<210> SEQ ID NO 380
<211> LENGTH: 8
<212> TYPE: PRT
<213> ORGANISM: Artificial Sequence
<220> FEATURE:
<223> OTHER INFORMATION: Synthetic peptide

<400> SEQUENCE: 380

Glu Phe Tyr Tyr Tyr Phe Asp Val
1               5

<210> SEQ ID NO 381
<211> LENGTH: 12
<212> TYPE: PRT
```

```
<213> ORGANISM: Artificial Sequence
<220> FEATURE:
<223> OTHER INFORMATION: Synthetic peptide

<400> SEQUENCE: 381

Asn Asp Tyr Asp Pro Tyr Tyr Tyr Ala Leu Asp Tyr
1               5                   10

<210> SEQ ID NO 382
<211> LENGTH: 8
<212> TYPE: PRT
<213> ORGANISM: Artificial Sequence
<220> FEATURE:
<223> OTHER INFORMATION: Synthetic peptide

<400> SEQUENCE: 382

Asp Gly Tyr Tyr Val Tyr Asp Tyr
1               5

<210> SEQ ID NO 383
<211> LENGTH: 12
<212> TYPE: PRT
<213> ORGANISM: Artificial Sequence
<220> FEATURE:
<223> OTHER INFORMATION: Synthetic peptide

<400> SEQUENCE: 383

Asp Tyr Gly Asn Ser Tyr Pro Tyr Tyr Phe Asp Phe
1               5                   10

<210> SEQ ID NO 384
<211> LENGTH: 10
<212> TYPE: PRT
<213> ORGANISM: Artificial Sequence
<220> FEATURE:
<223> OTHER INFORMATION: Synthetic peptide

<400> SEQUENCE: 384

Ile Gly Pro Arg Leu Gly Tyr Phe Asp Val
1               5                   10

<210> SEQ ID NO 385
<211> LENGTH: 14
<212> TYPE: PRT
<213> ORGANISM: Artificial Sequence
<220> FEATURE:
<223> OTHER INFORMATION: Synthetic peptide

<400> SEQUENCE: 385

Glu Tyr Asp Gly Arg Tyr Pro Tyr Tyr Ser Thr Leu Asp Tyr
1               5                   10

<210> SEQ ID NO 386
<211> LENGTH: 14
<212> TYPE: PRT
<213> ORGANISM: Artificial Sequence
<220> FEATURE:
<223> OTHER INFORMATION: Synthetic peptide

<400> SEQUENCE: 386

Glu Tyr Asp Gly Ser Tyr Pro Tyr Tyr Asp Thr Leu Asp Tyr
1               5                   10

<210> SEQ ID NO 387
<211> LENGTH: 16
<212> TYPE: PRT
<213> ORGANISM: Artificial Sequence
```

```
<220> FEATURE:
<223> OTHER INFORMATION: Synthetic peptide

<400> SEQUENCE: 387

Glu Gly Val Tyr Tyr Asp Gly Ser Tyr Met Arg Ala Met Asp Tyr
 1               5                   10                  15

<210> SEQ ID NO 388
<211> LENGTH: 11
<212> TYPE: PRT
<213> ORGANISM: Artificial Sequence
<220> FEATURE:
<223> OTHER INFORMATION: Synthetic peptide

<400> SEQUENCE: 388

Ser Phe Tyr Asp Gly Tyr Leu Tyr Phe Asp Tyr
 1               5                  10

<210> SEQ ID NO 389
<211> LENGTH: 8
<212> TYPE: PRT
<213> ORGANISM: Artificial Sequence
<220> FEATURE:
<223> OTHER INFORMATION: Synthetic peptide

<400> SEQUENCE: 389

Leu Arg Val Val Pro Glu Ala Tyr
 1               5

<210> SEQ ID NO 390
<211> LENGTH: 7
<212> TYPE: PRT
<213> ORGANISM: Artificial Sequence
<220> FEATURE:
<223> OTHER INFORMATION: Synthetic peptide

<400> SEQUENCE: 390

Ser Arg Ala Gly Ala Val Tyr
 1               5

<210> SEQ ID NO 391
<211> LENGTH: 9
<212> TYPE: PRT
<213> ORGANISM: Artificial Sequence
<220> FEATURE:
<223> OTHER INFORMATION: Synthetic peptide

<400> SEQUENCE: 391

Gly Asp Tyr Tyr Gly Ser Leu Asp Tyr
 1               5

<210> SEQ ID NO 392
<211> LENGTH: 14
<212> TYPE: PRT
<213> ORGANISM: Artificial Sequence
<220> FEATURE:
<223> OTHER INFORMATION: Synthetic peptide

<400> SEQUENCE: 392

Glu Tyr Gly Gly Ser Tyr Pro Tyr Tyr Ser Thr Leu Asp Tyr
 1               5                   10

<210> SEQ ID NO 393
<211> LENGTH: 14
<212> TYPE: PRT
<213> ORGANISM: Artificial Sequence
<220> FEATURE:
```

```
<223> OTHER INFORMATION: Synthetic peptide

<400> SEQUENCE: 393

Asp Arg Ser His Tyr Gly Asp Tyr Val Gly Tyr Leu Asp Tyr
 1               5                  10

<210> SEQ ID NO 394
<211> LENGTH: 13
<212> TYPE: PRT
<213> ORGANISM: Artificial Sequence
<220> FEATURE:
<223> OTHER INFORMATION: Synthetic peptide

<400> SEQUENCE: 394

Val Thr Met Val Glu Ser Gly Asp Trp Tyr Phe Asp Val
 1               5                  10

<210> SEQ ID NO 395
<211> LENGTH: 7
<212> TYPE: PRT
<213> ORGANISM: Artificial Sequence
<220> FEATURE:
<223> OTHER INFORMATION: Synthetic peptide

<400> SEQUENCE: 395

Gly Pro Tyr Phe Phe Asp Phe
 1               5

<210> SEQ ID NO 396
<211> LENGTH: 5
<212> TYPE: PRT
<213> ORGANISM: Artificial Sequence
<220> FEATURE:
<223> OTHER INFORMATION: Synthetic peptide

<400> SEQUENCE: 396

Asp Arg Asp Tyr Asp
 1               5

<210> SEQ ID NO 397
<211> LENGTH: 7
<212> TYPE: PRT
<213> ORGANISM: Artificial Sequence
<220> FEATURE:
<223> OTHER INFORMATION: Synthetic peptide

<400> SEQUENCE: 397

Gly Thr Trp Val Phe Asp Tyr
 1               5

<210> SEQ ID NO 398
<211> LENGTH: 8
<212> TYPE: PRT
<213> ORGANISM: Artificial Sequence
<220> FEATURE:
<223> OTHER INFORMATION: Synthetic peptide

<400> SEQUENCE: 398

Asn Trp Asp Trp Tyr Phe Asp Val
 1               5

<210> SEQ ID NO 399
<211> LENGTH: 10
<212> TYPE: PRT
<213> ORGANISM: Artificial Sequence
<220> FEATURE:
<223> OTHER INFORMATION: Synthetic peptide
```

<400> SEQUENCE: 399

His Gly Tyr Tyr Ile Tyr Ala Leu Asp Tyr
1               5                   10

<210> SEQ ID NO 400
<211> LENGTH: 11
<212> TYPE: PRT
<213> ORGANISM: Artificial Sequence
<220> FEATURE:
<223> OTHER INFORMATION: Synthetic peptide

<400> SEQUENCE: 400

Leu Leu Arg Ser Arg Thr Gly Tyr Phe Asp Tyr
1               5                   10

<210> SEQ ID NO 401
<211> LENGTH: 13
<212> TYPE: PRT
<213> ORGANISM: Artificial Sequence
<220> FEATURE:
<223> OTHER INFORMATION: Synthetic peptide

<400> SEQUENCE: 401

Ile Ile Met Val Glu Ser Gly Asp Trp Tyr Phe Asp Val
1               5                   10

<210> SEQ ID NO 402
<211> LENGTH: 11
<212> TYPE: PRT
<213> ORGANISM: Artificial Sequence
<220> FEATURE:
<223> OTHER INFORMATION: Synthetic peptide

<400> SEQUENCE: 402

Ser Ser Asn Tyr Phe Phe His Val Leu Asp Tyr
1               5                   10

<210> SEQ ID NO 403
<211> LENGTH: 12
<212> TYPE: PRT
<213> ORGANISM: Artificial Sequence
<220> FEATURE:
<223> OTHER INFORMATION: Synthetic peptide

<400> SEQUENCE: 403

Arg Arg Val Tyr Tyr Gly Ser Ser Tyr Glu Asp Tyr
1               5                   10

<210> SEQ ID NO 404
<211> LENGTH: 13
<212> TYPE: PRT
<213> ORGANISM: Artificial Sequence
<220> FEATURE:
<223> OTHER INFORMATION: Synthetic peptide

<400> SEQUENCE: 404

Arg Arg Ser Tyr Asp Ser Val Tyr Trp Tyr Phe Asp Val
1               5                   10

<210> SEQ ID NO 405
<211> LENGTH: 6
<212> TYPE: PRT
<213> ORGANISM: Artificial Sequence
<220> FEATURE:
<223> OTHER INFORMATION: Synthetic peptide

```
<400> SEQUENCE: 405

Ala Ser Asp Phe Asp Val
1               5

<210> SEQ ID NO 406
<211> LENGTH: 6
<212> TYPE: PRT
<213> ORGANISM: Artificial Sequence
<220> FEATURE:
<223> OTHER INFORMATION: Synthetic peptide

<400> SEQUENCE: 406

Tyr Ser Asp Leu Ala Tyr
1               5

<210> SEQ ID NO 407
<211> LENGTH: 12
<212> TYPE: PRT
<213> ORGANISM: Artificial Sequence
<220> FEATURE:
<223> OTHER INFORMATION: Synthetic peptide

<400> SEQUENCE: 407

Leu Gln Trp Gly Gly Tyr Asn Gly Trp Leu Ser Pro
1               5                   10

<210> SEQ ID NO 408
<211> LENGTH: 13
<212> TYPE: PRT
<213> ORGANISM: Artificial Sequence
<220> FEATURE:
<223> OTHER INFORMATION: Synthetic peptide

<400> SEQUENCE: 408

Asp Glu Asp Tyr Tyr Asp Ser Ser Gly Tyr Tyr Asp Tyr
1               5                   10

<210> SEQ ID NO 409
<211> LENGTH: 13
<212> TYPE: PRT
<213> ORGANISM: Artificial Sequence
<220> FEATURE:
<223> OTHER INFORMATION: Synthetic peptide

<400> SEQUENCE: 409

Gly Gly Gly Gln Trp Trp Gln Asn Asp Ala Phe Asp Val
1               5                   10

<210> SEQ ID NO 410
<211> LENGTH: 17
<212> TYPE: PRT
<213> ORGANISM: Artificial Sequence
<220> FEATURE:
<223> OTHER INFORMATION: Synthetic peptide

<400> SEQUENCE: 410

Gly Pro Asn Pro Gly Lys Lys Trp Gly Ala Glu Trp Gly Ala Ser Gly
1               5                   10                  15

Asn

<210> SEQ ID NO 411
<211> LENGTH: 10
<212> TYPE: PRT
<213> ORGANISM: Artificial Sequence
<220> FEATURE:
<223> OTHER INFORMATION: Synthetic peptide
```

<400> SEQUENCE: 411

Pro His Arg Ser Asp Tyr Gly Leu Gly Val
1               5                   10

<210> SEQ ID NO 412
<211> LENGTH: 15
<212> TYPE: PRT
<213> ORGANISM: Artificial Sequence
<220> FEATURE:
<223> OTHER INFORMATION: Synthetic peptide

<400> SEQUENCE: 412

Asp Lys Gly Trp Glu Leu Met Thr Asn Thr Asp Ala Phe Asp Ile
1               5                   10                  15

<210> SEQ ID NO 413
<211> LENGTH: 11
<212> TYPE: PRT
<213> ORGANISM: Artificial Sequence
<220> FEATURE:
<223> OTHER INFORMATION: Synthetic peptide

<400> SEQUENCE: 413

Val Ala Gly Thr Ser Arg Ser Ala Phe Asp Ile
1               5                   10

<210> SEQ ID NO 414
<211> LENGTH: 12
<212> TYPE: PRT
<213> ORGANISM: Artificial Sequence
<220> FEATURE:
<223> OTHER INFORMATION: Synthetic peptide

<400> SEQUENCE: 414

Thr Lys Met Gly Ala Ala Glu Gly Val Phe Asp Tyr
1               5                   10

<210> SEQ ID NO 415
<211> LENGTH: 10
<212> TYPE: PRT
<213> ORGANISM: Artificial Sequence
<220> FEATURE:
<223> OTHER INFORMATION: Synthetic peptide

<400> SEQUENCE: 415

Gly Gly Leu Pro Tyr Gln Gln Leu Pro Leu
1               5                   10

<210> SEQ ID NO 416
<211> LENGTH: 11
<212> TYPE: PRT
<213> ORGANISM: Artificial Sequence
<220> FEATURE:
<223> OTHER INFORMATION: Synthetic peptide

<400> SEQUENCE: 416

Gly Ala Thr Asn Ile Pro Tyr Gly Met Ser Val
1               5                   10

<210> SEQ ID NO 417
<211> LENGTH: 14
<212> TYPE: PRT
<213> ORGANISM: Artificial Sequence
<220> FEATURE:
<223> OTHER INFORMATION: Synthetic peptide

```
<400> SEQUENCE: 417

Ala Ile Lys Ser Tyr Ser Thr Ile Gly Gly Ala Cys Asn Leu
1               5                   10

<210> SEQ ID NO 418
<211> LENGTH: 11
<212> TYPE: PRT
<213> ORGANISM: Artificial Sequence
<220> FEATURE:
<223> OTHER INFORMATION: Synthetic peptide

<400> SEQUENCE: 418

Thr Leu Lys Phe Gly Leu Asn Tyr Met Asp Val
1               5                   10

<210> SEQ ID NO 419
<211> LENGTH: 16
<212> TYPE: PRT
<213> ORGANISM: Artificial Sequence
<220> FEATURE:
<223> OTHER INFORMATION: Synthetic peptide

<400> SEQUENCE: 419

Ala Ile Lys Ala Phe Arg Pro Val Pro Pro Ser Phe His Met Asp Val
1               5                   10                  15

<210> SEQ ID NO 420
<211> LENGTH: 17
<212> TYPE: PRT
<213> ORGANISM: Artificial Sequence
<220> FEATURE:
<223> OTHER INFORMATION: Synthetic peptide

<400> SEQUENCE: 420

Gly Gln Asp Thr Ser Met Val Thr Arg Asn Phe Tyr Tyr Gly Leu Asp
1               5                   10                  15

Val

<210> SEQ ID NO 421
<211> LENGTH: 16
<212> TYPE: PRT
<213> ORGANISM: Artificial Sequence
<220> FEATURE:
<223> OTHER INFORMATION: Synthetic peptide

<400> SEQUENCE: 421

Glu Thr Trp Glu Val Leu Gly His Leu Gly Tyr Glu Val Leu Asp His
1               5                   10                  15

<210> SEQ ID NO 422
<211> LENGTH: 8
<212> TYPE: PRT
<213> ORGANISM: Artificial Sequence
<220> FEATURE:
<223> OTHER INFORMATION: Synthetic peptide

<400> SEQUENCE: 422

Gly Ala Phe Thr Asn Tyr Pro Phe
1               5

<210> SEQ ID NO 423
<211> LENGTH: 15
<212> TYPE: PRT
<213> ORGANISM: Artificial Sequence
<220> FEATURE:
<223> OTHER INFORMATION: Synthetic peptide
```

<400> SEQUENCE: 423

Asp Gln Gly Gly Gly Thr Val Val Lys Glu Asn Trp Phe Asp Pro
1               5                   10                  15

<210> SEQ ID NO 424
<211> LENGTH: 14
<212> TYPE: PRT
<213> ORGANISM: Artificial Sequence
<220> FEATURE:
<223> OTHER INFORMATION: Synthetic peptide

<400> SEQUENCE: 424

Val Lys Leu Thr Thr Met Val Arg Gly Gly Pro Phe Asp Tyr
1               5                   10

<210> SEQ ID NO 425
<211> LENGTH: 13
<212> TYPE: PRT
<213> ORGANISM: Artificial Sequence
<220> FEATURE:
<223> OTHER INFORMATION: Synthetic peptide

<400> SEQUENCE: 425

Val Lys Leu Asn Ser Val Arg Gly Gly Pro Phe Asp Leu
1               5                   10

<210> SEQ ID NO 426
<211> LENGTH: 17
<212> TYPE: PRT
<213> ORGANISM: Artificial Sequence
<220> FEATURE:
<223> OTHER INFORMATION: Synthetic peptide

<400> SEQUENCE: 426

Glu Lys Ala Ile Lys Gly Tyr Ser Ser Arg Pro Val Arg Ala Tyr Glu
1               5                   10                  15
Met

<210> SEQ ID NO 427
<211> LENGTH: 12
<212> TYPE: PRT
<213> ORGANISM: Artificial Sequence
<220> FEATURE:
<223> OTHER INFORMATION: Synthetic peptide

<400> SEQUENCE: 427

Gly Gly Lys Tyr Ser Asn Ser Ser Ala Met Tyr Gln
1               5                   10

<210> SEQ ID NO 428
<211> LENGTH: 9
<212> TYPE: PRT
<213> ORGANISM: Artificial Sequence
<220> FEATURE:
<223> OTHER INFORMATION: Synthetic peptide

<400> SEQUENCE: 428

Ser Val Ser Gly Gly Ala Phe Asp Leu
1               5

<210> SEQ ID NO 429
<211> LENGTH: 13
<212> TYPE: PRT
<213> ORGANISM: Artificial Sequence
<220> FEATURE:

```
<223> OTHER INFORMATION: Synthetic peptide

<400> SEQUENCE: 429

Asp Arg Trp Arg Ser Gly Ser Tyr Pro Ala Phe Glu Lys
1               5                   10

<210> SEQ ID NO 430
<211> LENGTH: 8
<212> TYPE: PRT
<213> ORGANISM: Artificial Sequence
<220> FEATURE:
<223> OTHER INFORMATION: Synthetic peptide

<400> SEQUENCE: 430

Ser Thr Arg Gly Pro Phe Asp Ile
1               5

<210> SEQ ID NO 431
<211> LENGTH: 13
<212> TYPE: PRT
<213> ORGANISM: Artificial Sequence
<220> FEATURE:
<223> OTHER INFORMATION: Synthetic peptide

<400> SEQUENCE: 431

Gly Thr Arg Asn Gly Ser Leu Arg Asp Ala Phe Asp Ile
1               5                   10

<210> SEQ ID NO 432
<211> LENGTH: 14
<212> TYPE: PRT
<213> ORGANISM: Artificial Sequence
<220> FEATURE:
<223> OTHER INFORMATION: Synthetic peptide

<400> SEQUENCE: 432

Gly Asp His Asp Phe Arg Ser Gly Tyr Tyr Gly Met Asp Val
1               5                   10

<210> SEQ ID NO 433
<211> LENGTH: 13
<212> TYPE: PRT
<213> ORGANISM: Artificial Sequence
<220> FEATURE:
<223> OTHER INFORMATION: Synthetic peptide

<400> SEQUENCE: 433

Glu Arg Leu Pro Pro Gly Arg Gly Tyr Asp Met Asp Val
1               5                   10

<210> SEQ ID NO 434
<211> LENGTH: 13
<212> TYPE: PRT
<213> ORGANISM: Artificial Sequence
<220> FEATURE:
<223> OTHER INFORMATION: Synthetic peptide

<400> SEQUENCE: 434

Gly Gly Phe Trp Gly Thr Trp Arg Asp Asn Met Asp Val
1               5                   10

<210> SEQ ID NO 435
<211> LENGTH: 15
<212> TYPE: PRT
<213> ORGANISM: Artificial Sequence
<220> FEATURE:
<223> OTHER INFORMATION: Synthetic peptide
```

<400> SEQUENCE: 435

Ala Ile Lys Gly Tyr Ser Ser Arg Pro Val Arg Ala Tyr Glu Met
1               5                   10                  15

<210> SEQ ID NO 436
<211> LENGTH: 15
<212> TYPE: PRT
<213> ORGANISM: Artificial Sequence
<220> FEATURE:
<223> OTHER INFORMATION: Synthetic peptide

<400> SEQUENCE: 436

Asp Gln Gly Gly Gly Ser Val Val Gly Thr Asn Trp Phe Asp Pro
1               5                   10                  15

<210> SEQ ID NO 437
<211> LENGTH: 12
<212> TYPE: PRT
<213> ORGANISM: Artificial Sequence
<220> FEATURE:
<223> OTHER INFORMATION: Synthetic peptide

<400> SEQUENCE: 437

Gly Gly Tyr Tyr Thr Arg Pro Leu Ala Phe Asp Thr
1               5                   10

<210> SEQ ID NO 438
<211> LENGTH: 12
<212> TYPE: PRT
<213> ORGANISM: Artificial Sequence
<220> FEATURE:
<223> OTHER INFORMATION: Synthetic peptide

<400> SEQUENCE: 438

Glu Gly Gln Leu Asp Ser Lys Tyr Tyr Phe Asp Ser
1               5                   10

<210> SEQ ID NO 439
<211> LENGTH: 8
<212> TYPE: PRT
<213> ORGANISM: Artificial Sequence
<220> FEATURE:
<223> OTHER INFORMATION: Synthetic peptide

<400> SEQUENCE: 439

Val Tyr Pro Gly Trp Phe Tyr Ser
1               5

<210> SEQ ID NO 440
<211> LENGTH: 11
<212> TYPE: PRT
<213> ORGANISM: Artificial Sequence
<220> FEATURE:
<223> OTHER INFORMATION: Synthetic peptide

<400> SEQUENCE: 440

Val Val Gly Val Tyr Pro Gly Trp Phe Asp Ser
1               5                   10

<210> SEQ ID NO 441
<211> LENGTH: 10
<212> TYPE: PRT
<213> ORGANISM: Artificial Sequence
<220> FEATURE:
<223> OTHER INFORMATION: Synthetic peptide

<400> SEQUENCE: 441

Glu Gly Ser Tyr Ile Asp Ser Phe Asp Met
1               5                   10

<210> SEQ ID NO 442
<211> LENGTH: 9
<212> TYPE: PRT
<213> ORGANISM: Artificial Sequence
<220> FEATURE:
<223> OTHER INFORMATION: Synthetic peptide

<400> SEQUENCE: 442

Val Tyr Tyr Tyr Tyr Gly Met Asp Val
1               5

<210> SEQ ID NO 443
<211> LENGTH: 18
<212> TYPE: PRT
<213> ORGANISM: Artificial Sequence
<220> FEATURE:
<223> OTHER INFORMATION: Synthetic peptide

<400> SEQUENCE: 443

Glu Gly Ala Arg Gly Tyr Cys Ser Ser Thr Ser Cys His Asp Ala Phe
1               5                   10                  15

Asp Ile

<210> SEQ ID NO 444
<211> LENGTH: 12
<212> TYPE: PRT
<213> ORGANISM: Artificial Sequence
<220> FEATURE:
<223> OTHER INFORMATION: Synthetic peptide

<400> SEQUENCE: 444

Gly Glu His Phe Val Val Val Thr Ala Phe Ala Thr
1               5                   10

<210> SEQ ID NO 445
<211> LENGTH: 16
<212> TYPE: PRT
<213> ORGANISM: Artificial Sequence
<220> FEATURE:
<223> OTHER INFORMATION: Synthetic peptide

<400> SEQUENCE: 445

Arg Arg Ala Val Ala Asn Leu Asp Tyr His Tyr Tyr Gly Met Asp Val
1               5                   10                  15

<210> SEQ ID NO 446
<211> LENGTH: 13
<212> TYPE: PRT
<213> ORGANISM: Artificial Sequence
<220> FEATURE:
<223> OTHER INFORMATION: Synthetic peptide

<400> SEQUENCE: 446

Ala Asn Tyr His Phe Ile Leu Ala Thr Thr Phe His Ser
1               5                   10

<210> SEQ ID NO 447
<211> LENGTH: 9
<212> TYPE: PRT
<213> ORGANISM: Artificial Sequence
<220> FEATURE:
<223> OTHER INFORMATION: Synthetic peptide

<400> SEQUENCE: 447

Ala Ile Trp Gly Gly Tyr Phe Asp Leu
1               5

<210> SEQ ID NO 448
<211> LENGTH: 10
<212> TYPE: PRT
<213> ORGANISM: Artificial Sequence
<220> FEATURE:
<223> OTHER INFORMATION: Synthetic peptide

<400> SEQUENCE: 448

Ile Leu Ala Gly Ser Trp Cys Phe Asp Leu
1               5                   10

<210> SEQ ID NO 449
<211> LENGTH: 9
<212> TYPE: PRT
<213> ORGANISM: Artificial Sequence
<220> FEATURE:
<223> OTHER INFORMATION: Synthetic peptide

<400> SEQUENCE: 449

Tyr Ser Ser Leu Asp Ala Phe Asp Ile
1               5

<210> SEQ ID NO 450
<211> LENGTH: 15
<212> TYPE: PRT
<213> ORGANISM: Artificial Sequence
<220> FEATURE:
<223> OTHER INFORMATION: Synthetic peptide

<400> SEQUENCE: 450

Gly Gly Gly Gly Ser Gly Gly Gly Ser Gly Gly Gly Gly Ser
1               5                   10                  15

<210> SEQ ID NO 451
<211> LENGTH: 5
<212> TYPE: PRT
<213> ORGANISM: Artificial Sequence
<220> FEATURE:
<223> OTHER INFORMATION: Synthetic peptide

<400> SEQUENCE: 451

Ser Ser Ser Ser Gly
1               5

<210> SEQ ID NO 452
<211> LENGTH: 15
<212> TYPE: PRT
<213> ORGANISM: Artificial Sequence
<220> FEATURE:
<223> OTHER INFORMATION: Synthetic peptide

<400> SEQUENCE: 452

Ser Ser Ser Ser Gly Ser Ser Ser Gly Ser Ser Ser Ser Gly
1               5                   10                  15

<210> SEQ ID NO 453
<211> LENGTH: 23
<212> TYPE: DNA
<213> ORGANISM: Artificial Sequence
<220> FEATURE:
<223> OTHER INFORMATION: Synthetic Oligonucleotide

```
<210> SEQ ID NO 454
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 454
gaggtgcagc tggtgcagtc tgg                                          23

<210> SEQ ID NO 455
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 455
caggtgcagc tggtgcaatc tgg                                          23

<210> SEQ ID NO 456
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 456
gatattgtga tgactcagtc tcc                                          23

<210> SEQ ID NO 457
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 457
gatattgtga tgacccagat ccc                                          23

<210> SEQ ID NO 458
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 458
gtggtggtgg ttctgctagc ggggccatgg ccaccctggt caccgtctcc tca         53

<210> SEQ ID NO 459
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 459
ggtggtggtt ctgctagcgg ggccatggcg acaatggtca ccgtctcttc a           51

<210> SEQ ID NO 460
<211> LENGTH: 51
```

<400> SEQUENCE: 453
caggtcacct tgaaggagtc tgg                                          23

<212> TYPE: DNA
<213> ORGANISM: Artificial Sequence
<220> FEATURE:
<223> OTHER INFORMATION: Synthetic Oligonucleotide

<400> SEQUENCE: 460
ggtggtggtt ctgctagcgg ggccatggca accctggtca ccgtctcctc a    51

<210> SEQ ID NO 461
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 461
ggtggtggtt ctgctagcgg ggccatggcg accacggtca ccgtctcctc a    51

<210> SEQ ID NO 462
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 462
gtcgattttg ttacatctac ac    22

<210> SEQ ID NO 463
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 463
gactatgcag ctagcggtgc catggcagag gtgcagcttc aggagtcagg    50

<210> SEQ ID NO 464
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 464
gactatgcag ctagcggtgc catggcagat gtgcagcttc aggagtcrgg    50

<210> SEQ ID NO 465
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 465
gactatgcag ctagcggtgc catggcacag gtgcagctga agsagtcagg    50

<210> SEQ ID NO 466
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 466
gactatgcag ctagcggtgc catggcagag gtycagctgc arcartctgg                50

<210> SEQ ID NO 467
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 467
gactatgcag ctagcggtgc catggcacag gtycarctgc agcagyctgg                50

<210> SEQ ID NO 468
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 468
gactatgcag ctagcggtgc catggcagar gtgaagctgg tggartctgg                50

<210> SEQ ID NO 469
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 469
gactatgcag ctagcggtgc catggcagag gttcagcttc agcagtctgg                50

<210> SEQ ID NO 470
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 470
gactatgcag ctagcggtgc catggcagaa gtgcagctgk tggagwctgg                50

<210> SEQ ID NO 471
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 471
gactatgcag ctagcggtgc catggcacag atccagttgc tgcagtctgg                50

<210> SEQ ID NO 472
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 472
gttgagcctc cggacttaag gtcgactgag gagacggtga ccgtggtccc                50

<210> SEQ ID NO 473
<211> LENGTH: 50
<212> TYPE: DNA
<213> ORGANISM: Artificial Sequence

```
<220> FEATURE:
<223> OTHER INFORMATION: Synthetic Oligonucleotide

<400> SEQUENCE: 473
gttgagcctc cggacttaag gtcgactgag gagactgtga gagtggtgcc         50

<210> SEQ ID NO 474
<211> LENGTH: 50
<212> TYPE: DNA
<213> ORGANISM: Artifical Sequence
<220> FEATURE:
<223> OTHER INFORMATION: Synthetic Oligonucleotide

<400> SEQUENCE: 474
gttgagcctc cggacttaag gtcgactgca gagacagtga ccagagtccc         50

<210> SEQ ID NO 475
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 475
gttgagcctc cggacttaag gtcgactgag gagacggtga ctgaggttcc         50

<210> SEQ ID NO 476
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 476
ggagaaggta gtagtggatc cgcgcgcgac attgtgatgw cacagtctcc         50

<210> SEQ ID NO 477
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 477
ggagaaggta gtagtggatc cgcgcgcgat gttktgatga cccaaactcc         50

<210> SEQ ID NO 478
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 478
ggagaaggta gtagtggatc cgcgcgcgat attgtgatra cbcaggcwgc         50

<210> SEQ ID NO 479
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 479
ggagaaggta gtagtggatc cgcgcgcgac attgtgctga cmcartctcc         50
```

<210> SEQ ID NO 480
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 480
ggagaaggta gtagtggatc cgcgcgcsaa awtgtkctca cccagtctcc            50

<210> SEQ ID NO 481
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 481
ggagaaggta gtagtggatc cgcgcgcgay atyvwgatga cmcagwctcc            50

<210> SEQ ID NO 482
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 482
ggagaaggta gtagtggatc cgcgcgccaa attgttctca cccagtctcc            50

<210> SEQ ID NO 483
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 483
ggagaaggta gtagtggatc cgcgcgctca ttattgcagg tgcttgtggg            50

<210> SEQ ID NO 484
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 484
ggcttacctt cgaagggccc gcctgcggcc gctttbakyt ccaryytkgt ccchbm            56

<210> SEQ ID NO 485
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 485
ggcttacctt cgaagggccc gcctgcggcc gctttgattt ccagcttggt gcctcc            56

<210> SEQ ID NO 486
<211> LENGTH: 56
<212> TYPE: DNA
<213> ORGANISM: Artificial Sequence
<220> FEATURE:
<223> OTHER INFORMATION: Synthetic Oligonucleotide -continued

<400> SEQUENCE: 486
ggcttacctt cgaagggccc gcctgcggcc gcttttattt ccagcttggt cccccc    56

<210> SEQ ID NO 487
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 487
ggcttacctt cgaagggccc gcctgcggcc gcttttattt ccagtctggt cccatc    56

<210> SEQ ID NO 488
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 488
ggcttacctt cgaagggccc gcctgcggcc gcttttattt ccaactttgt ccccga    56

<210> SEQ ID NO 489
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 489
ggcttacctt cgaagggccc gcctgcggcc gctttcagct ccagcttggt cccagc    56

<210> SEQ ID NO 490
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 490
agtaacgttt gtcagtaatt gc    22

<210> SEQ ID NO 491
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 491
cgacccgcca ccgccagagc cacctccgcc    30

<210> SEQ ID NO 492
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 492
atatataatc catggctcca ggaatctgta tcgacgtcga c    41

<210> SEQ ID NO 493

```
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 493
tgtataattg cggccgccag gatttcggaa ttgtatttgt tg                    42

<210> SEQ ID NO 494
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 494
atatataatc catggccaac aatatcatcc tgaacctgcg ttac                  44

<210> SEQ ID NO 495
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 495
tgtataattg cggccgcttc ggtccaacct tcgtctttcg g                     41

<210> SEQ ID NO 496
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 496
atatataatc catggcccca gttaccatca acaacttcaa ctac                  44

<210> SEQ ID NO 497
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 497
tgtataattg cggccgcctt aacagactta cacatttgaa tcttg                 45

<210> SEQ ID NO 498
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 498 gtcgaccta agtccggagg ttctacttcc ggttccggta agccaggttc tggtgaaggt   60
tcttctggat ccgcgcgc                                                78

<210> SEQ ID NO 499
<211> LENGTH: 46
<212> TYPE: DNA
<213> ORGANISM: Artificial Sequence
<220> FEATURE:
<223> OTHER INFORMATION: Synthetic Oligonucleotide
```

<400> SEQUENCE: 499
tatccatacg atgttcctga ctatgcagct agcggtgcca tggcac 46

<210> SEQ ID NO 500
<211> LENGTH: 12
<212> TYPE: Protein
<213> ORGANISM: Artificial Sequence
<220> FEATURE:
<223> OTHER INFORMATION: Synthetic Peptide

<400> SEQUENCE: 500
dyydyagggr gy 12

<210> SEQ ID NO 501
<211> LENGTH: 120
<212> TYPE: PRT
<213> ORGANISM: Artificial Sequence
<220> FEATURE:
<223> OTHER INFORMATION: Single chain antibody or single chain antibody
      domain

<400> SEQUENCE: 501

Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Asn Trp Asn Gly Asn Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr His Cys
                85                  90                  95

Ala Arg Glu Gly Asp Tyr Gly Gly Leu Tyr Phe Asp Tyr Trp Gly Gln
            100                 105                 110

Gly Thr Leu Val Thr Val Ser Ser
        115                 120

<210> SEQ ID NO 502
<211> LENGTH: 121
<212> TYPE: PRT
<213> ORGANISM: Artificial Sequence
<220> FEATURE:
<223> OTHER INFORMATION: Single chain antibody or single chain antibody
      domain

<400> SEQUENCE: 502

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys 85                  90                  95

Ala Arg Gly Ala Val Ala Gly Gly Ser Tyr Gly Met Asp Val Trp Gly
            100                 105                 110

Gln Gly Thr Met Val Thr Val Ser Ser
            115                 120

<210> SEQ ID NO 503
<211> LENGTH: 118
<212> TYPE: PRT
<213> ORGANISM: Artificial Sequence
<220> FEATURE:
<223> OTHER INFORMATION: Single chain antibody or single chain antibody
      domain

<400> SEQUENCE: 503

Gln Val Gln Leu Gln Glu Ser Gly Gly Leu Val Gln Pro Gly Gly
  1               5                  10                  15

Ser Leu Arg Leu Ser Cys Ala Ala Ser Gly Phe Thr Phe Lys Tyr Asp
             20                  25                  30

Tyr Met Tyr Trp Phe Arg Gln Ala Pro Gly Lys Gly Leu Glu Trp Val
             35                  40                  45

Ala Thr Ile Ser Asp Gly Gly Ser Tyr Thr Tyr Tyr Ser Asp Ser Val
         50                  55                  60

Glu Gly Arg Phe Thr Thr Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ser Arg Tyr Arg Tyr Asp Asp Ala Met Asp Tyr Trp Gly Gln Gly Thr
            100                 105                 110

Leu Val Thr Val Ser Ser
            115

<210> SEQ ID NO 504
<211> LENGTH: 109
<212> TYPE: PRT
<213> ORGANISM: Artificial Sequence
<220> FEATURE:
<223> OTHER INFORMATION: Single chain antibody or single chain antibody
      domain

<400> SEQUENCE: 504

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys Arg
            100                 105

<210> SEQ ID NO 505
<211> LENGTH: 114
<212> TYPE: PRT

```
<213> ORGANISM: Artificial Sequence
<220> FEATURE:
<223> OTHER INFORMATION: Single chain antibody or single chain antibody
      domain

<400> SEQUENCE: 505
```

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Leu Glu Ile
            100                 105                 110

Lys Arg

```
<210> SEQ ID NO 506
<211> LENGTH: 113
<212> TYPE: PRT
<213> ORGANISM: Artificial Sequence
<220> FEATURE:
<223> OTHER INFORMATION: Single chain antibody or single chain antibody
      domain

<400> SEQUENCE: 506
```

Glu Ile Val Leu Thr Gln Ser Pro Ala Thr Leu Ser Leu Ser Pro Gly
1               5                   10                  15

Glu Arg Ala Thr Ile Ser Cys Arg Ala Ser Glu Lys Leu Asn Ser Trp
            20                  25                  30

Gly His Ser Phe Met Gln Trp Tyr Gln Gln Lys Pro Gly Gln Ala Pro
        35                  40                  45

Arg Leu Leu Ile Tyr Arg Ala Ser Asn Leu Glu Pro Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Val Pro Phe Thr Phe Gly Gln Gly Thr Lys Val Glu Ile Lys
            100                 105                 110

Arg

```
<210> SEQ ID NO 507
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 507
```

Ser Gly Gly Ser Thr Ser Gly Ser Gly Lys Pro Gly Ser Gly Glu Gly
1               5                   10                  15

Ser Ser Gly Ser
            20

```
<210> SEQ ID NO 508
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 508

Asp Arg Trp Tyr Ser Gly Tyr Asp Phe Asp Tyr
 1               5                  10
```

ANTIBODIES FOR BOTULINUM NEUROTOXINS

CROSS-REFERENCE

This application claims the benefit of U.S. Provisional Patent Application No. 61/378,862, filed Aug. 31, 2010, U.S. Provisional Patent Application No. 61/430,084, filed Jan. 5, 2011, which applications are incorporated herein by reference in their entirety.

STATEMENT AS TO FEDERALLY SPONSORED RESEARCH

This invention was made with government support under Grant No. AI075443 awarded by the National Institutes of Health, Grant No. HDTRA1-07-C-0030 awarded by the Department of Defense, Defense Threat Reduction Agency, and Grant No. 200-2006-16697 awarded by the Centers for Disease Control. The government has certain rights in the invention.

INTRODUCTION

Botulism is caused by botulinum neurotoxin secreted by members of the genus *Clostridium* and is characterized by flaccid paralysis, which if not immediately fatal requires prolonged hospitalization in an intensive care unit and mechanical ventilation. Naturally occurring botulism is found in infants or adults whose gastrointestinal tracts become colonized by Clostridial bacteria (infant or intestinal botulism), after ingestion of contaminated food products (food botulism), or in anaerobic wound infections (wound botulism) (Center for Disease Control (1998) Botulism in the United States, 1899-1998. Handbook for epidemiologists, clinicians, and laboratory workers. Atlanta, Ga. U.S. Department of Health and Human Services, Public Health Service: downloadable at "bt.cdc.gov/agent/botulism/index.asp"). Botulinum neurotoxins (BoNTs) are also classified by the Centers for Disease Control (CDC) as one of the six highest-risk threat agents for bioterrorism (the "Category A agents"), due to their extreme potency and lethality, ease of production and transport, and need for prolonged intensive care (Amon et al. (2001) *JAMA* 285: 1059-1070). As a result of these threats, specific pharmaceutical agents are needed for prevention and treatment of intoxication.

No specific small molecule drugs exist for prevention or treatment of botulism, but an investigational pentavalent toxoid vaccine is available from the CDC (Siegel (1988) *J. Clin. Microbiol.* 26: 2351-2356) and a recombinant vaccine is under development (Smith (1998) *Toxicon* 36: 1539-1548). Regardless, mass civilian or military vaccination is unlikely due to the rarity of disease or exposure and the fact that vaccination would prevent subsequent medicinal use of BoNT. Toxin neutralizing antibody (Ab) can be used for pre- or post-exposure prophylaxis or for treatment (Franz et al. (1993) Pp. 473-476 In B. R. DasGupta (ed.), Botulinum and Tetanus Neurotoxins: Neurotransmission and Biomedical Aspects. Plenum Press, New York). Small quantities of both equine antitoxin and human botulinum immune globulin exist and are currently used to treat adult (Black and Gunn. (1980) *Am. J. Med.*, 69: 567-570; Hibbs et al. (1996) *Clin. Infect. Dis.*, 23: 337-340) and infant botulism (Amon (1993). Clinical trial of human botulism immune globulin, p. 477-482. In B. R. DasGupta (ed.), Botulinum and Tetanus Neurotoxins: Neurotransmission and Biomedical Aspects. Plenum Press, New York) respectively.

The development of monoclonal antibody (mAb) therapy for botulism is complicated by the fact that there are at least seven BoNT serotypes (A-G) (Hatheway (1995) *Curr. Top. Microbio. Immunol,* 195: 55-75) that show little, if any, antibody cross-reactivity. While only four of the BoNT serotypes routinely cause human disease (A, B, E, and F), there has been one reported case of infant botulism caused by BoNT/C (Oguma et al. (1990) *Lancet* 336: 1449-1450), one outbreak of foodborne botulism linked to BoNT/D (Demarchi, et al. (1958) *Bull. Acad. Nat. Med.,* 142: 580-582), and several cases of suspicious deaths where BoNT/G was isolated (Sonnabend et al. (1981) *J. Infect. Dis.,* 143: 22-27). Aerosolized BoNT/C, D, and G have also been shown to produce botulism in primates by the inhalation route (Middlebrook and Franz (1997) Botulinum Toxins, chapter 33. In F. R. Sidell, E. T. Takafuji, D. R. Franz (eds.), Medical Aspects of Chemical and Biological Warfare. TMM publications, Washington, D.C.), and would most likely also affect humans. Thus, it is likely that any one of the seven BoNT serotypes can be used as a biothreat agent.

Variability of the BoNT gene and protein sequence within serotypes has also been reported and there is evidence that such variability can affect the binding of monoclonal antibodies to BoNT/A (Kozaki et al. (1998) *Infect. Immun.,* 66: 4811-4816; Kozaki et al. (1995) *Microbiol. Immunol.,* 39: 767-774).

SUMMARY

Antibodies that bind to and neutralize and/or otherwise clear botulinum neurotoxin(s) are disclosed herein. Particularly effective neutralization of a BoNT serotype can be achieved by the use of neutralizing antibodies that bind two or more subtypes of the particular neurotoxin serotype with particularly high affinity and/or by combinations of such antibodies. The present disclosure provides antibodies that bind BoNT serotypes BoNT/A, BoNT/B, BoNT/C, BoNT/D, BoNT/E, BoNT/F, BoNT/G, or mosaics. BoNT subtypes include pure BoNT/A1 (Hall hyper), BoNT/A2 (FRI-H1A2), BoNT/B1, BoNT/B2, BoNT/B3, BoNT/B4, BoNT/C1, BoNT/F1, BoNT/F2, BoNT/F3, BoNT/F4, BoNT/F5, BoNT/F6, BoNT/F7, BoNT/202F. BoNT mosaics include BoNT/CD and BoNT/DC. Compositions comprising neutralizing antibodies that bind two or more BoNT subtypes (e.g., BoNT/F1, BoNT/F2, BoNT/F3, etc.) with high affinity are also provided herein.

An antibody for Botulinum neurotoxin (BoNT) is provided herein. The antibody typically comprises at least one $V_H$ complementarity determining region (CDR) selected from an antibody from a clone listed in FIG. 4 or FIG. 5, and/or at least one $V_L$ complementarity determining region selected from an antibody from a clone listed in FIG. 4 or FIG. 5.

The antibody may be a single chain Fv (scFv), a Fab, a (Fab')$_2$, an (ScFv)$_2$, and the like. The antibody may be an IgG. The antibody may also be in a pharmaceutically acceptable excipient (e.g., in a unit dosage formulation).

Methods of inhibiting and/or neutralizing the activity of BoNT in a mammal may involve administering to a mammal in need thereof a composition comprising at least one neutralizing anti-BoNT antibody as described herein. The composition may include at least two different antibodies, each of which binds to different BoNT subtypes. The composition may also include at least three, at least four, or more different antibodies, each of which may bind to different BoNT epitopes.

Compositions provided herein may partially or fully neutralize a BoNT. The compositions typically include a first antibody that binds one or more serotypes, e.g., one or more antibodies as described above, can optionally include a second antibody, a third antibody, or a fourth antibody, or more that bind one or more BoNT serotypes.

Nucleic acids provided herein encode one or more antibodies that are described herein. Cells containing such nucleic acids are also provided herein. Kits provided for neutralizing a BoNT may include a composition containing one or more antibodies as described herein. The kits optionally also include instructional materials teaching the use of the composition to neutralize a BoNT. The composition may be stored in a disposable syringe.

BRIEF DESCRIPTION OF THE DRAWINGS

FIG. 2. Schematic of the method used to construct yeast displayed light chain shuffled scFv antibody libraries. Panel A, $V_L$ gene repertoires were amplified by using a polymerase chain reaction (PCR) from donor cDNA or cloned scFv gene repertoires. Panel B, $V_L$ gene repertoires are reamplified to append the $V_H$ framework 4, scFv linker, and cloning sites at the 5' and 3' end of the genes. C. The $V_L$ gene repertoire is cloned into the yeast display vector pYD2. D. The $V_H$ gene of a binding scFv is PCR amplified using primers that append overhangs complementary to Nco1-NotI or HindIII-NotI digested pYD2-$V_L$ gene repertoire vector DNA. E. The $V_H$ gene is cloned into the pYD-$V_L$ repertoire vector to create a light chain shuffled library. Gal1-10 promoter=galactose promoter; syn prepro leader=synthetic leader sequence; Aga1=Aga1 surface protein; Aga2=Aga2 surface protein gene; trp=tryptophan selectable marker.

FIGS. 4A-L. Amino acid sequences of monoclonal antibodies against different serotypes of BoNT.

FIGS. 5A-D. Amino acid sequences of monoclonal antibodies to various serotypes of BoNT.

FIGS. 6A and 6B. Amino acid identities among BoNT/F subtypes (FIG. 6A) and among BoNT/C and BoNT/D toxins (FIG. 6B). HT=complete holotoxin; LC=light chain, or enzymatic domain; Hn=translocation domain; Hc=C-terminal third of the protein, including the receptor-binding domain.

DEFINITIONS

Figure 1:
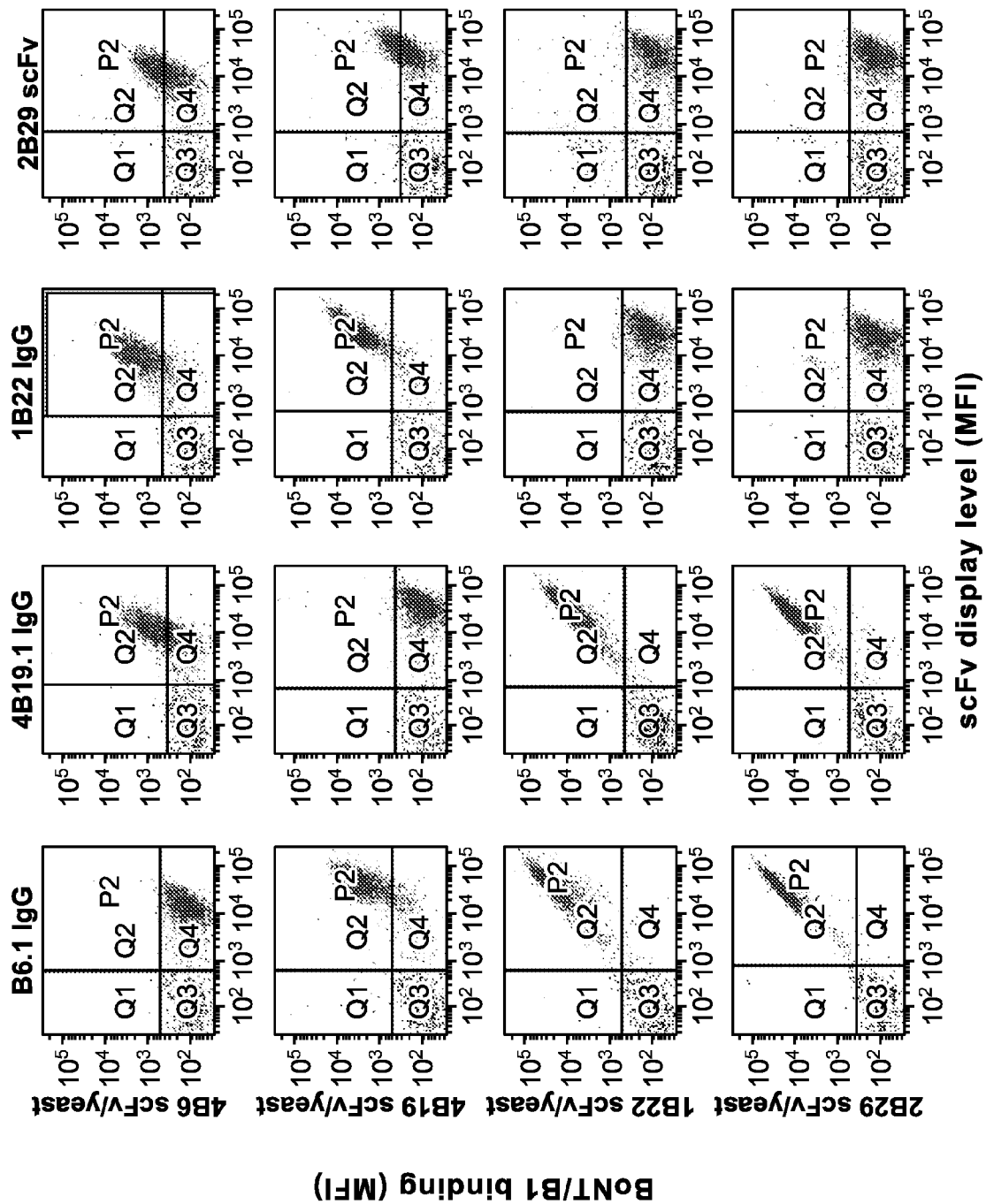
FIG. 1. Mapping whether mAb epitopes overlap by using yeast displayed and soluble antibodies. Yeast displayed scFv were incubated with BoNT/B1 followed by incubation with purified IgG (B6.1, 4B19.1, or 1B22) or soluble scFv (2B29). The level of scFv yeast display was quantitated using anti-SV5-Alexa647 (APC channel) and the level of scFv or IgG binding quantitated by using anti-mouse IgG1-phycoerythrin (IgG1-PE) or anti-human-PE (PE channel). scFv or IgG binding an epitope that overlapped with the yeast displayed scFv had no PE binding signal, while non-overlapping scFv or IgG had a positive PE binding signal.

A "BoNT polypeptide" refers to a Botulinum neurotoxin polypeptide (e.g., a BoNT/A polypeptide, a BoNT/B polypeptide, a BoNT/C polypeptide, and so forth). The BoNT polypeptide can refer to a full-length polypeptide or to a fragment thereof. Thus, for example, the term "BoNT/A polypeptide" refers to either a full-length BoNT/A (a neurotoxin produced by *Clostridium botulinum* of the type A serotype) or a fragment thereof (e.g. the $H_C$ fragment). The $H_C$ fragment of BoNT/A is an approximately 50 kDa C-terminal fragment (residues 873-1296) of BoNT/A (Lacy and Stevens (1999) *J. Mol. Biol.,* 291: 1091-1104).

A "BoNT serotype" refers one of the standard known BoNT serotypes (e.g. BoNT/A, BoNT/B, BoNT/C, BoNT/D, BoNT/E, BoNT/F, BoNT/G etc.).

The term "BoNT subtype" (e.g., a BoNT/A1 subtype) refers to botulinum neurotoxin gene sequences of a particular serotype (e.g., A, B, C, D, E, F, G etc.) that differ from each other sufficiently to produce differential antibody binding.

A "mosaic BoNT", as used herein, refers to a BoNT polypeptide that contains at least two contiguous amino acid sequences, each of which is derived from a different serotype or subtype.

"Derived from" in the context of an amino acid sequence or polynucleotide sequence (e.g., an amino acid sequence "derived from" BoNT/F) is meant to indicate that the polypeptide or nucleic acid has a sequence that is based on that of a reference polypeptide or nucleic acid (e.g., a naturally occurring BoNT/F or encoding nucleic acid), and is not meant to be limiting as to the source or method in which the protein or nucleic acid is made.

An "anti-BoNT antibody" refers to an antibody that binds a BoNT polypeptide, specifically binds a BoNT polypeptide with a $K_D$ less than about $10^{-7}$, less than about $10^{-8}$, less than about $10^{-9}$, less than about $10^{-10}$, less than about $10^{-11}$, or less than about $10^{-12}$ or less.

"Neutralization" refers to a measurable decrease in the toxicity and/or circulating level of a Botulinum neurotoxin (e.g., BoNT/C) in in vitro testing, animals, or human patient.

By "treatment" it is meant that at least an amelioration of the symptoms associated with the condition afflicting the host is achieved, where amelioration refers to at least a reduction in the magnitude of a parameter, e.g. symptom, associated with the condition being treated. As such, treatment includes situations where the condition, or at least symptoms associated therewith, are reduced or avoided. Thus treatment includes: (i) prevention, that is, reducing the risk of development of clinical symptoms, including causing the clinical symptoms not to develop, e.g., preventing disease progression to a harmful or otherwise undesired state; (ii) inhibition, that is, arresting the development or further development of clinical symptoms, e.g., mitigating or completely inhibiting an active disease.

"Potency" refers to the degree of protection from challenge with BoNT. This can be measured/quantified for example, as an increase in the $LD_{50}$ of a Botulinum neurotoxin (BoNT). In toxicology, the median lethal dose, $LD_{50}$ (abbreviation for "Lethal Dose, 50%"), or $LCt_{50}$ (Lethal Concentration & Time) of a toxic substance or radiation is the dose required to kill half the members of a tested population. The $LD_{50}$ usually expressed as the mass of substance administered per unit mass of test subject, such as grams of substance per kilogram of body mass. Stating it this way allows the relative toxicity of different substances to be compared, and normalizes for the variation in the size of the animals exposed (although toxicity does not always scale simply with body mass). Typically, the $LD_{50}$ of a substance is given in milligrams per kilogram of body weight. In the case of some toxins, the $LD_{50}$ may be more conveniently expressed as micrograms per kilogram (μg/kg) of body mass.

The term "high affinity" when used with respect to an antibody refers to an antibody that specifically binds to its target(s) with an affinity ($K_D$) of at least about $10^{-7}$ M at least about $10^{-8}$ M, preferably at least about $10^{-9}$ M, at least about $10^{-10}$ M, and at least about $10^{-11}$ M. "High affinity" antibodies may have a $K_D$ that ranges from about 1 nM to about 0.01 pM.

The following abbreviations are used herein: BoNT; Botulinum neurotoxin, BoNT/A; BoNT serotype A, BoNT/B; BoNT serotype B, BoNT/C; BoNT serotype C, BoNT/D; BoNT serotype D, BoNT/F; BoNT serotype F, BoNT/G; BoNT serotype G, Fc; fragment crystallizable, Fab'$_2$; fragment, antigen binding, mAb; monoclonal antibody, IgG; immunoglobulin G, $LD_{50}$; lethal dose 50%, scFv; single chain variable fragment, $V_H$; heavy chain variable region, $V_k$; kappa light chain variable region, PCR; polymerase chain reaction, AgaII or Aga2; yeast agglutinin receptor II, BoNT/A $L_C$; BoNT/A light chain, BoNT/B $L_C$; BoNT/B light chain, BoNT/B $H_C$; C-terminal domain of the BoNT/B heavy chain, pM; picomolar, fM; femtomolar, IU; International Unit, SD-CAA; selective dextrose casamino acids media, SG-CAA; selective galactose casamino acids media, CHO; Chinese hamster ovary cells, FACS; fluorescent activated cell sorting, $K_D$; equilibrium dissociation constant, $k_{on}$; association rate constant, $k_{off}$; dissociation rate constant, MFI: mean fluorescent intensity The terms "polypeptide", "peptide", and "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids, which include, but are not limited to those listed in 37 CFR (§1.822(b)(4)). Furthermore, it should be noted that a dash at the beginning or end of an amino acid residue sequence indicates either a peptide bond to a further sequence of one or more amino acid residues or a covalent bond to a carboxyl or hydroxyl end group. However, the absence of a dash should not be taken to mean that such peptide bonds or covalent bond to a carboxyl or hydroxyl end group is not present, as it is conventional in representation of amino acid sequences to omit such.

The term "antibody" (also used interchangeably with "immunoglobulin") encompasses polyclonal and monoclonal antibody preparations where the antibody may be of any class of interest (e.g., IgM, IgG, and subclasses thereof), as well as preparations including hybrid antibodies, altered antibodies, F(ab')$_2$ fragments, F(ab) molecules, Fv fragments, scFv fragments, single chain antibodies, single domain antibodies, chimeric antibodies, humanized antibodies, and functional fragments thereof which exhibit immunological binding properties of the parent antibody molecule. The antibodies may be conjugated to other moieties, and/or may be bound to a support (e.g., a solid support), such as a polystyrene plate or bead, test strip, and the like.

Immunoglobulin polypeptides include the kappa and lambda light chains and the alpha, gamma (IgG$_1$, IgG$_2$, IgG$_3$, IgG$_4$), delta, epsilon and mu heavy chains or equivalents in other species. Full-length immunoglobulin "light chains" (usually of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

An immunoglobulin light or heavy chain variable region is composed of a "framework" region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, (1991 and Lefranc et al. IMGT, the international ImMunoGeneTics information System®. Nucl. Acids Res., 2005, 33, D593-D597)). A detailed discussion of the IMGTS system, including how the IMGTS system was formulated and how it compares to other systems, is provided on the World Wide Web at imgt.cines.fr/textes/IMGTScientificChart/Numbering/IM-GTnumberingsTable.html. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. All CDRs and framework provided by the present disclosure are defined according to Kabat et al, supra, unless otherwise indicated.

An "antibody" thus encompasses a protein having one or more polypeptides that can be genetically encodable, e.g., by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (V$_L$) and variable heavy chain (V$_H$) refer to these light and heavy chains respectively.

Antibodies encompass intact immunoglobulins as well as a number of well characterized fragments produced by digestion with various peptidases. Thus, for example, pepsin digests an antibody below the disulfide linkages in the hinge region to produce F(ab)'$_2$, a dimer of Fab which itself is a light chain joined to VH-CHI by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'$_2$, IgG, IgM, IgA, scFv, dAb, nanobodies, unibodies, and diabodies.

Antibodies and fragments of the present disclosure encompass those that are bispecific. Bispecific antibodies or fragments can be of several configurations. For example, bispecific antibodies may resemble single antibodies (or antibody fragments) but have two different antigen binding sites (variable regions). Bispecific antibodies may be produced by chemical techniques (Kranz et al. (1981) Proc. Natl. Acad. Sci., USA, 78: 5807), by "polydoma" techniques (see, e.g., U.S. Pat. No. 4,474,893), or by recombinant DNA techniques. Bispecific antibodies may have binding specificities for at least two different epitopes, at least one of which is an epitope of BoNT. The BoNT binding antibodies and fragments can also be heteroantibodies. Heteroantibodies are two or more antibodies, or antibody binding fragments (e.g., Fab) linked together, each antibody or fragment having a different specificity.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

A 4C4.1 antibody refers to an antibody expressed by clone 4C4.1 or to an antibody synthesized in other manners, but having the same CDRs and optionally, the same framework regions as the antibody expressed by clone 4C4.1. Similarly, antibody 4C4.2 and any other shown in FIG. 4 or FIG. 5 and the like refer to antibodies expressed by the corresponding clone(s) and/or to antibodies synthesized in other manners, but having the same CDRs and optionally, the same framework regions as the referenced antibodies.

As used herein, the terms "immunological binding" and "immunological binding properties" refer to the non-covalent interactions of the type which occur between an immunoglobulin molecule and an antigen for which the immunoglobulin is specific. The strength or affinity of immunological binding interactions can be expressed in terms of the dissociation constant ($K_D$) of the interaction, wherein a smaller $K_D$ represents a greater affinity. Immunological binding properties of selected polypeptides can be quantified using methods well known in the art. One such method entails measuring the rates of antigen binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity and is thus equal to the equilibrium dissociation constant $K_D$ (see, generally, Davies et al. Ann. Rev. Biochem. 1990, 59: 439-15 473).

An "anti-BoNT antibody" refers to an antibody that binds to one or more Botulinum neurotoxin(s) (e.g., BoNT/C, BoNT/CD, etc.) Thus, for example the term "anti-BoNT/F—antibody", as used herein refers to an antibody that specifically binds to a BoNT/F polypeptide (e.g., a BoNT/F1 polypeptide). An example of an antibody of the present disclosure may bind to an $H_C$ domain of a BoNT/C1 polypeptide.

Antibodies derived from anti-BoNT antibodies have a binding affinity of about $1.6 \times 10^{-8}$ or better and can be derived by screening libraries of single chain Fv fragments displayed on phage or yeast constructed from heavy ($V_H$) and light ($V_L$) chain variable region genes obtained from mammals, including mice and humans, immunized with botulinum toxoid, toxin, or BoNT fragments. Antibodies can also be derived by screening phage or yeast display libraries in which a known BoNT-neutralizing variable heavy ($V_H$) chain is expressed in combination with a multiplicity of variable light ($V_L$) chains or conversely a known BoNT-neutralizing variable light chain is expressed in combination with a multiplicity of variable heavy ($V_H$) chains. BoNT-neutralizing antibodies also include those antibodies produced by the introduction of mutations into the variable heavy or variable light complementarity determining regions (CDR1, CDR2 or CDR3) as described herein. Finally BoNT-neutralizing antibodies include those antibodies produced by any combination of these modification methods as applied to the BoNT-neutralizing antibodies described herein and their derivatives.

An "epitope" is a site on an antigen (e.g. BoNT) to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

A neutralizing epitope refers to the epitope specifically bound by a neutralizing antibody.

"Isolated" refers to an entity of interest that is in an environment different from that in which the compound may naturally occur. An "isolated" compound (e.g., an "isolated" antibody) is separated from all or some of the components that accompany it in nature and may be substantially enriched, e.g., may be purified so that the compound is at least about 70% pure, at least about 80% pure, at least about 90% pure, at least about 95% pure, at least about 98% pure, at least about 99%, or greater than 99% pure, or free of impurities, contaminants, and/or components other than the compound. "Isolated" also refers to the state of a compound separated from all or some of the components that accompany it during manufacture (e.g., chemical synthesis, recombinant expression, culture medium, and the like).

A single chain Fv ("scFv") polypeptide is a covalently linked $V_H$::$V_L$ heterodimer which may be expressed from a nucleic acid including $V_H$- and $V_L$-encoding sequences either joined directly or joined by a peptide-encoding linker (Huston, et al. (1988) *Proc. Nat. Acad. Sci. USA*, 85: 5879-5883). A number of structures are available for converting the light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

Recombinant design methods may be used to develop suitable chemical structures (linkers) for converting two heavy and light polypeptide chains from an antibody variable region into a scFv molecule which will fold into a three-dimensional structure that is substantially similar to native antibody structure.

Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which will result in the minimum loss of residues from the polypeptide domains, and which will necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and may be free of residues having large side groups which might interfere with proper folding of the $V_H$ and $V_L$ chains. Thus, suitable linkers generally comprise polypeptide chains of alternating sets of glycine and serine residues, and may include glutamic acid and lysine residues inserted to enhance solubility. One particular linker has the amino acid sequence (Gly$_4$Ser)$_3$ (SEQ ID NO:450). Another particularly preferred linker has the amino acid sequence comprising 2 or 3 repeats of [(Ser)$_4$Gly] (SEQ ID NO:451), such as [(Ser)$_4$Gly]$_3$ (SEQ ID NO:452), and the like. Nucleotide sequences encoding such linker moieties can be readily provided using various oligonucleotide synthesis techniques known in the art (see, e.g., Sambrook, supra.).

The phrase "specifically binds to" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, BoNT/F-neutralizing antibodies can be raised to BoNT/F protein(s) that specifically bind to BoNT/F protein(s), and not to other proteins present in a tissue sample. A variety of immunoassay formats may be used to select antibodies specifically immunoreactive with a particular protein. For example, solid-phase enzyme-linked immunosorbent assay (ELISA) immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The term "conservative substitution" is used in reference to proteins or peptides to reflect amino acid substitutions that do not substantially alter the activity (specificity or binding affinity) of the molecule. Typically conservative amino acid substitutions involve substituting one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

DETAILED DESCRIPTION

This disclosure provides antibodies that specifically bind to botulinum neurotoxin. Botulinum neurotoxin is produced by the anaerobic bacterium *Clostridium botulinum*. Botulinum neurotoxin poisoning (botulism) arises in a number of contexts including, but not limited to food poisoning (food borne botulism), infected wounds (wound botulism), "infant botulism" from ingestion of spores and production of toxin in the intestine of infants, and as a chemical/biological warfare agent. Botulism is a paralytic disease that typically begins with cranial nerve involvement and progresses caudally to involve the extremities. In acute cases, botulism can prove fatal.

For each BoNT serotype, there can be multiple subtypes of BoNT. Antibodies of the present disclosure encompass antibodies that specifically bind one subtype (e.g. the BoNT/A1 subtype) but not a different subtype (BoNT/A2 subtype) and also antibodies that can bind more than one subtype/serotype.

The present disclosure is related to the discovery of high affinity antibodies. The antibodies are particularly efficient in the neutralization of a botulism neurotoxin (BoNT) subtype. The antibodies have a high affinity for BoNT and each of the various antibodies is either highly specific for a serotype/subtype or can cross-react with two, three, or more serotypes/subtypes.

Neutralizations of BoNT may also be accomplished by using one, two, three, four, or more different antibodies directed against each of the subtypes, or alternatively, by the use of antibodies that are cross-reactive for different BoNT subtypes, or by bispecific or polyspecific antibodies with specificities for two, three, or four or more BoNT epitopes, and/or serotypes, and/or subtypes.

Compositions containing at least two, or at least three high affinity antibodies that bind overlapping (partial or complete overlapping) or non-overlapping epitopes on the BoNT are contemplated herein.

Thus, compositions contemplated herein may include one, two or more, three or more, four or more, five or more different antibodies selected from the antibodies described herein (see, e.g., FIG. 4 and FIG. 5) and/or antibodies comprising one or more CDRs from these antibodies, and/or one or more antibodies comprising mutants or derivatives of these antibodies.

Compositions contemplated herein may include antitoxins for BoNT/A, BoNT/B, BoNT/C, BoNT/D, BoNT/E, BoNT/

F, and/or BoNT/G (or mosaics thereof). Compositions containing trivalent BoNT/A, BoNT/B, BoNT/C, BoNT/D, BoNT/E, BoNT/F, and/or BoNT/G antibodies (e.g. comprising antibodies selected from those described in PCT Pub. Nos. WO 07/094,754, WO 05/016232, WO 09/008,916, and WO 2010/014854) are also contemplated.

As indicated above, the antibodies provided by the present disclosure bind to one or more botulinum neurotoxin serotypes B, C, D, E, F, G (or mosaics thereof) and in certain instances Bont/A subtypes, and, in some embodiments, can neutralize the neurotoxin. Neutralization, in this context, refers to a measurable decrease in the toxicity and/or circulating level of the target neurotoxin. Such a decrease in toxicity can also be measured in vitro by a number of methods well known to those of skill in the art. One such assay involves measuring the time to a given percentage (e.g., 50%) twitch tension reduction in a hemidiaphragm preparation. Toxicity reduction can be determined in vivo, e.g. as an $LD_{50}$ in a test animal (e.g. mouse) BoNT in the presence of one or more putative neutralizing antibodies. The neutralizing antibody or antibody combination can be combined with the botulinum neurotoxin prior to administration, or the animal can be administered the antibody prior to, simultaneous with, or after administration of the neurotoxin. The rate of clearance of BoNT mediated by a test antibody, or combination of test antibodies, can be measured (e.g. in mice) by administering labeled BoNT (e.g. radiolabeled BoNT) and measuring the levels of BoNT in the serum and the liver and other organs over time in the presence or absence of test antibody or antibodies (see, e.g., Ravichandran et al. (2006) *J Pharmacol Exp Ther* 318: 1343-1351 (2006).

The present disclosure also contemplates an antibody that specifically binds an epitope shared by two or more (e.g., two, three, four, five, six, or seven) BoNT serotypes and/or subtypes and/or mosaics, e.g., BoNT polypeptides that share at least about 45%, at least about 50%, at least about 60%, at least about 70%, at least about 80%, at least about 90%, at least about 95%, at least about 98%, or at least about 99%, amino acid sequence identity over the complete holotoxin, over the light chain only, over the translocation domain only, or over the C-terminal third of the protein that includes the receptor-binding domain. See, e.g., FIGS. 6A and 6B.

As the antibodies of the present disclosure act to neutralize botulinum neurotoxins, they are useful in the treatment of pathologies associated with botulinum neurotoxin poisoning. The treatments essentially comprise administering to the poisoned organism (e.g. human or non-human mammal) a quantity of one or more neutralizing antibodies sufficient to neutralize (e.g. mitigate or eliminate) symptoms of BoNT poisoning.

Such treatments are most desired and efficacious in acute cases (e.g. where vital capacity is less than 30-40 percent of predicted and/or paralysis is progressing rapidly and/or hypoxemia with absolute or relative hypercarbia is present. These antibodies can also be used to treat early cases with symptoms milder than indicated (to prevent progression) or even prophylactically (a use the military envisions for soldiers going in harm's way). Treatment with the neutralizing antibody can be provided as an adjunct to other therapies (e.g. antibiotic treatment).

The antibodies provided by this disclosure can also be used for the rapid detection/diagnosis of botulism and thereby supplement and/or replace previous laboratory diagnostics.

This disclosure also provides the epitopes specifically bound by botulinum neurotoxin antibodies described herein. These epitopes can be used to isolate, and/or identify and/or screen for other antibodies BoNT neutralizing antibodies as described herein.

I. Botulinum Neurotoxin (BoNT)-Binding Antibodies.

Anti-BoNT antibodies may be selected based on their affinity to one or more BoNT serotypes/subtypes. Numbering system used herein for toxins is based on Lacy et al. (1999) *J. Mol. Biol.* 291:1091-1104. A number of subtypes are known for each BoNT serotype. Thus, for example, BoNT/A subtypes include, but are not limited to, BoNT/A1, BoNT/A2, BoNT/A3, and the like. It is also noted, for example, that the BoNT/A1 subtype includes, but is not limited to 62A, NCTC 2916, ATCC 3502, and Hall hyper (Hall Allergan) and are identical (99.9-100% identity at the amino acid level.) and have been classified as subtype A1. The BoNT/A2 sequences (Kyoto-F and FRI-A2H) (Willems, et al. (1993) *Res. Microbiol.* 144:547-556) are 100% identical at the amino acid level. Another BoNT/A subtype, e.g. A3, is produced by a strain called Loch Maree that killed a number of people in an outbreak in Scotland.

Similarly, a number of subtypes are also known for BoNT/B, BoNT/E and BoNT/F and there exist mosaics of BoNT/C and of BoNT/D. The subject antibodies encompass high affinity antibodies that are cross-reactive with two or more subtypes within a serotype. The disclosure further provides antibodies that are cross-reactive with two or more serotypes (such as BoNT/E and BoNT/F). For example, antibody from clone 4E17.2 binds all subtypes of BoNT/A, BoNT/B, BoNT/E, BoNT/F).

Serotypes that can be bound by the subject antibodies include BoNT/A, BoNT/B, BoNT/C, BoNT/D, BoNT/E, BoNT/F, BoNT/G, or mosaics thereof. Other BoNT subtypes/serotypes include pure BoNT/A1 (Hall hyper), BoNT/A2 (FRI-H1A2), BoNT/B1, BoNT/B2, BoNT/B3, BoNT/B4, BoNT/C1, BoNT/CD, BoNT/DC, BoNT/F1, BoNT/F2, BoNT/F3, BoNT/F4, BoNT/F5, BoNT/F6, and BoNT/F7. Moreover, without being bound to a particular theory, these cross-reactive antibodies can be more efficient in neutralizing Botulinum neurotoxin, particularly when used in combination one or more different neutralizing antibodies.

The sequences of the variable heavy ($V_H$) and variable light ($V_L$) domains for a number of BoNT (e.g. BoNT/A, BoNT/B, BoNT/C, BoNT/D, BoNT/F, BoNT/G) antibodies are illustrated in FIG. 4, FIG. 5, and Tables 1-4 and 8. Some antibodies of interest as seen in FIG. 4 encompass antibodies from clones 1C1.1, 87C78, 4C1, 4C2, 4C4.1, 4C4.2, 4C4, 4C5, 4C10, 4C10.1, 4C10.2, 8DC1, 8DC1.2, 8DC2, 8DC4, 8DC4.1, 6F1, 6F3, 4E17.2, 6F8, Hu6F8, 6F9, Hu6F9, 6F10, and Hu6F10. Antibodies of interest, as depicted in FIG. 5, include antibodies from clones 2B23K1, 2B23K2, 2B23K4, 2B23K7, 2B23K11, 6F5.1, 7G1.1, 7G2.1, 7G3, 7G4, 7G5, 7G6, 7G7, 7G8, 7G9, 7G10, 7G11, 2B23EK1, 2B23EK4, 2B23EK5, 2B23EK6, 2B23EK7, 2B23EK10, 2B23EK11, 2B23EK12, 8D2.2, 8D2.3, 8DC3.1, 8DC8.3, 8DC8.6, B4, A9, and A2S.

The relationship of certain antibodies specific for each subtype from each serotype is described in the example section below.

The antibodies of the present disclosure can be used individually, and/or in combination with each other, and/or in combination with other known anti-BoNT antibodies (see, e.g., Application Pub. No: 20080124328, 20020155114, 20040175385, 20020155114, and PCT Pub. Nos. WO 07/094,754, WO 05/016232, WO 09/008,916, and WO 2010/014854, which are incorporated herein by reference for all purposes). These antibodies can be used individually, and/or in combination with each other, and/or in combination with other known anti-BoNT antibodies to form bispecific or polyspecific antibodies.

Amino acid sequences of various antibodies, as well as each CDR and framework region, are shown in FIG. 4 and FIG. 5. It will be appreciated that the amino acid sequence of a CDR can also be defined using alternative systems, which will be readily apparent to and applied by the ordinarily skilled artisan (see, "Sequences of Proteins of Immunological Interest," E. Kabat et al., U.S. Department of Health and Human Services, (1991 and Lefranc et al. IMGT, the international ImMunoGeneTics information system. Nucl. Acids Res., 2005, 33, D593-D597)). A detailed discussion of the IMGTS system, including how the IMGTS system was formulated and how it compares to other systems, is provided on the World Wide Web at imgt.cines.fr/textes/IMGTScientific-Chart/Numbering/IMGTnumberingsTable.html. As seen in FIG. 4 and FIG. 5, CDRs are demarcated for each antibody in their respective columns and labels. All amino acid sequences of CDR in the present disclosure are defined according to Kabat et al., supra, unless otherwise indicated.

Using the teachings and the sequence information provided herein, the variable light and variable heavy chains can be joined directly or through a linker (e.g., (Gly$_4$Ser)$_3$, SEQ ID NO:450) to form a single-chain Fv antibody. The various CDRs and/or framework regions can be used to form human antibodies, chimeric antibodies, antibody fragments, polyvalent antibodies, and the like.

Anti-BoNT antibodies of the present disclosure have a binding affinity ($K_D$) for a BoNT protein of at most $10^{-7}$, of at most $10^{-8}$, at most $10^{-9}$, at most $10^{-10}$, and most preferably at most $10^{-11}$, $10^{-12}$ M or less. Some examples of $K_D$s (M$^{-1}$) for BoNT/C or BoNT/D fall in the following ranges: between about $2\times10^{-12}$ to about $5\times10^{-10}$, between about $5\times10^{-10}$ to about $1\times10^{-9}$, between $1\times10^{-9}$ to $5\times10^{-9}$, between $5\times10^{-9}$ to $1\times10^{-8}$, between $4\times10^{-9}$ to $2\times10^{-8}$. Certain antibodies (e.g. 8DC4) have a $K_D$ of more than 20 nM.

Some examples of $K_D$s (M$^{-1}$) for BoNT/F fall in the following ranges: between about $5\times10^{-11}$ to about $1\times10^{-10}$, between about $1\times10^{-10}$ to about $5\times10^{-10}$, between about $5\times10^{-10}$ to about $1\times10^{-9}$, between $1\times10^{-9}$ to about $5\times10^{-9}$. Certain antibodies can have a $K_D$ for BoNT/F in the range between about $1\times10^{-8}$ to about $4\times10^{-8}$. For example, antibody from clone 4E17.2, also referred herein as 6F5, can be described as having a $K_D$ of about 0.39 nM for BoNT/F.

As noted above, the antibody may also be defined by the serotypes and/or subtypes with which it is cross-reactive. Some antibodies have an affinity that is specific for only one serotype or subtype. Others are cross-reactive for two or more subtypes and/or serotypes. Examples of cross-reactive antibodies include 4C4.1, 4C4.2, 4C4, 4C10, 4C10.1, 4C10.2, 8DC1, 8DC1.2, 8DC2, 8DC4, and 8DC4.1. Other antibodies that are cross-reactive for two or more subtypes include certain antibodies designated as BoNT/F binders: 4E17.2 (also referred herein as 6F5), 6F8, 6F10, 38B8, 38F8, 39A1, 39D1.1, 41C2, etc. See Tables 1-8 for more details. Antibodies can also be reactive across two or more serotypes. For example, antibodies from clone 4E17.2 binds all subtypes of BoNT/A, BoNT/B, BoNT/E, and BoNT/F.

The antibody of the present disclosure may be defined by the epitope or the domain of BoNT bound by the antibody. The antibodies provided here may encompass those that bind to one or more epitopes or a specific domain of a BoNT to which an antibody containing one or more of the CDRs set forth in FIG. 4 or FIG. 5 bind. Epitopes bound by an antibody may be described by a specific BoNT domain and/or the residues therein that contribute to the interaction between the antibody and a BoNT protein. Domains bound by the certain antibodies are identified in the Table 8 and in the example section.

For example, based on Table 8, an antibody such as 4C4, may be described by its affinity to the $H_N$ domain and its cross reactivity with BoNT/C1, BoNT/CD, BoNT/D, and BoNT/DC.

The subject antibody may also be defined by the epitope shared by one or more antibodies. The ability of a particular antibody to recognize the same and/or overlapping epitope as another antibody can be determined by the ability of one antibody to competitively inhibit binding of the second antibody to the antigen. Competitive inhibition of binding may also be referred to as cross-reactivity of antibodies. For example, 4C4 also binds to an epitope that overlaps with 4C10. Any of a number of competitive binding assays can be used to measure competition between two antibodies to the same antigen. For example, a sandwich ELISA assay can be used for this purpose. Additional methods for assaying for cross-reactivity are described later below.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays used to assess competitive binding.

Accordingly, antibodies provided by the present disclosure encompass those that compete for binding to a BoNT with an antibody that includes one or more of the $V_H$ CDRs set forth in FIG. 4 or FIG. 5 and/or one or more of the $V_L$ CDRs set forth in FIG. 4 or FIG. 5.

For example, an antibody may have the binding specificity (i.e., in this context, the same CDRs, or substantially the same CDRs) of an antibody having one or more $V_H$ and $V_L$ CDRs or full length $V_H$ and/or $V_L$ as set forth in FIG. 4 or FIG. 5. An antibody of the present disclosure may therefore contain one or more CDR as set forth in a $V_H$ or $V_L$ sequence shown in FIG. 4 or FIG. 5 and, additionally, may have at least 80% identity, 85%, 90%, or 95% identity up to 100% identity of a full-length $V_H$ or $V_L$ sequence. For example, an antibody may contain the CDRs of a $V_H$ and a $V_L$ sequence and human framework sequences set forth in FIG. 4 or FIG. 5. Each CDR in a subject antibody may also be independently selected from any CDR shown in FIG. 4 or FIG. 5.

Examples of antibodies of the present disclosure are presented in Table 6 below. Although classified as a binder for a serotype, each antibody may be cross-reactive with more than one subtype/serotype, as described above. Details of cross-reactive antibodies can be found in Tables 1-5, 7, and 8.

TABLE 6

List of antibody clone names

| Type | Original organism | antibody clone name |
|---|---|---|
| BoNT/A LC binders (17 clones): | mouse | 6A1M |
| | mouse | 6A2M |
| | mouse | 6A3M |
| | mouse | 6A4M |
| | mouse | 6A5M |
| | mouse | 6A6M |
| | mouse | 6A7M |
| | mouse | 6A8M |
| | mouse | 6A9M |
| | mouse | 1C7 |
| | mouse | 1C10 |
| | mouse | 1D8 |

TABLE 6-continued

List of antibody clone names

| Type | Original organism | antibody clone name |
|---|---|---|
| | mouse | 1G11 |
| | mouse | 1H5 |
| | mouse | 9B2 |
| | mouse | 10C9 |
| | mouse | 10H10 |
| BoNT/A HC binders (3 clones): | Human | B4 |
| | Human | A9 |
| | Human | A2S |
| BoNT/B LC binders (37 clones): | mouse | 16B3 |
| | mouse | 16D5 |
| | mouse | 18A6 |
| | mouse | 18D10 |
| | mouse | 18E5 |
| | mouse | 18F2 |
| | mouse | 19A9 |
| | mouse | 19B6 |
| | mouse | 19D2 |
| | mouse | 19D22 |
| | mouse | 19D22.4 |
| | mouse | 19G6 |
| | mouse | 31A5 |
| | mouse | 31A5.1 |
| | mouse | 31C3 |
| | mouse | 31C3.6 |
| | mouse | 31E2 |
| | mouse | 31E2.20 |
| | mouse | 31G2 |
| | mouse | 31H3 |
| | mouse | 34E8 |
| | mouse | 34E8B12 |
| | human | 4B19 |
| | human | 4B19.1 |
| | human | 2B23K1 |
| | human | 2B23K2 |
| | human | 2B23K4 |
| | human | 2B23K7 |
| | human | 2B23K11 |
| | human | 2B23EK1 |
| | human | 2B23EK4 |
| | human | 2B23EK5 |
| | human | 2B23EK6 |
| | human | 2B23EK7 |
| | human | 2B23EK10 |
| | human | 2B23EK11 |
| | human | 2B23EK12 |
| BoNT/B Hc binders (16 clones): | mouse | 26A10 |
| | mouse | 26B2 |
| | mouse | 26C2 |
| | mouse | 26C4 |
| | mouse | 26D1 |
| | mouse | 26D9 |
| | mouse | 26D10 |
| | mouse | 26D11 |
| | mouse | 26E1 |
| | mouse | 26E2 |
| | mouse | 26E6 |
| | mouse | 26G5 |
| | mouse | 26G11 |
| | mouse | 26H11 |
| | human | 1B12.3 |
| | human | 1B12.4 |
| BoNT/C, BoNT/CD, BoNT/DC or BoNT/D binders (52 clones): | human | 1C1 |
| | human | 1C1.1 |
| | human | 1C2 |
| | human | 1C3 |
| | human | 1C4 |
| | human | 1C8 |
| | human | 87C1 |
| | human | 87C2 |
| | human | 87C78 |
| | human | 4C1 |
| | human | 4C2 |
| | human | 4C3 |
| | human | 4C4.1 |
| | human | 4C4.2 |
| | human | 4C4 |
| | human | 4C5 |
| | human | 4C6 |
| | human | 4C7 |
| | human | 4C8 |
| | human | 4C9 |
| | human | 4C10 |
| | human | 4C10.1 |
| | human | 4C10.2 |
| | human | 8C1 |
| | human | 8C2 |
| | human | 8C3 |
| | human | 8C4 |
| | human | 8C5 |
| | human | 8C6 |
| | human | 8D1 |
| | human | 8D2 |
| | human | 8D2.2 |
| | human | 8D2.3 |
| | human | 8DC1.2 |
| | human | 8DC2 |
| | human | 8DC3 |
| | human | 8DC3.1 |
| | human | 8DC4 |
| | human | 8DC4.1 |
| | human | 8DC5 |
| | human | 8DC6 |
| | human | 8DC7 |
| | human | 8DC8 |
| | human | 8DC8.3 |
| | human | 8DC8.6 |
| | human | 8DC10 |
| | human | 8DC11 |
| | human | 8DC12 |
| | human | 8DC13 |
| | human | 8DC14 |
| | human | 8DC15 |
| BoNT/F binders (37 clones): | human | 6F1 |
| | mouse | 6F3 |
| | mouse | 6F4 |
| | human | 4E17.2 (= 6F5) |
| | human | 6F5.1 |
| | human | 39A1 |
| | human | 41C2 |
| | human | 43D3 |
| | human | 39H6 |
| | human | 41E2 |
| | human | 41F7 |
| | human | 42G8(=6F5.1) |
| | human | 39D1.1 |
| | human | 41A4 |
| | human | 41B7 |
| | human | 39D5.1 |
| | human | 41G8 |
| | mouse | 6F6 |
| | mouse | 6F7 |
| | mouse | 6F8 |
| | humanized | Hu6F8 |
| | mouse | 6F9 |
| | humanized | Hu6F9 |
| | mouse | 6F10 |
| | humanized | Hu6F10 |
| | mouse | 28C9 |
| | mouse | 28H4 |
| | mouse | 29A2 |
| | mouse | 29B8 |
| | mouse | 30C8 |
| | mouse | 32G2 |
| | human | 37B4 |
| | human | 37B6 |
| | human | 38B8 |
| | human | 38C1 |
| | human | 38D11 |
| | human | 38F8 |

TABLE 6-continued

List of antibody clone names

| Type | Original organism | antibody clone name |
| --- | --- | --- |
| BoNT/G binders (13 clones) | Human | 7G1 |
| | Human | 7G2 |
| | Human | 7G1.1 |
| | Human | 7G2.1 |
| | Human | 7G3 |
| | Human | 7G4 |
| | Human | 7G5 |
| | Human | 7G6 |
| | Human | 7G7 |
| | Human | 7G8 |
| | Human | 7G9 |
| | Human | 7G10 |
| | Human | 7G11 |

II. Potency of Botulinum Neurotoxin (BoNT)-Binding Antibodies.

Without being bound to a particular theory, it is believed that the current antitoxins used to treat botulism (horse and human) have a potency of about 5000 mouse $LD_{50}$s/mg (human) and 55,000 mouse $LD_{50}$s/mg (horse).

Based on calculation, a commercially desirable antitoxin may generally have a potency greater than about 10,000 to 100,000 $LD_{50}$s/mg. Combinations of the antibodies described herein (e.g., two or three antibodies) can meet this potency. Thus, this disclosure provides antibodies and/or antibody combinations that neutralize at least about 10,000 mouse $LD_{50}$s/mg of antibody, preferably at least about 15,000 mouse $LD_{50}$s/mg of antibody, more preferably at least about 20,000 mouse $LD_{50}$s/mg of antibody, and most preferably at least about 25,000 or more mouse $LD_{50}$s/mg of antibody.

III. Preparation of Anti-BoNT Antibodies.

A) Recombinant Expression of Anti-BoNT Antibodies.

Using the information provided herein, the botulinum neurotoxin binding antibodies of the present disclosure are prepared using standard techniques well known to those of skill in the art.

For example, the polypeptide sequences provided herein (see, e.g., FIG. 4, FIG. 5, and/or Table 8) can be used to determine appropriate nucleic acid sequences encoding the anti-BoNT antibodies and the nucleic acids sequences then used to express one or more BoNT-neutralizing antibodies. The nucleic acid sequence(s) can be optimized to reflect particular codon "preferences" for various expression systems according to standard methods well known to those of skill in the art.

Using the sequence information provided, the nucleic acids may be synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12:6159-6168) or manually synthesized using, for example, the solid phase phosphoramidite triester method described by Beaucage et. al. (1981) *Tetrahedron Letts.* 22(20): 1859-1862.

Once a nucleic acid encoding an anti-BoNT antibody is synthesized it can be amplified and/or cloned according to standard methods. Molecular cloning techniques to achieve these ends are known in the art. A wide variety of cloning and in vitro amplification methods suitable for the construction of recombinant nucleic acids are known to persons of skill Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Nat'l Acad. Sci. USA* 86: 10029-10033.

Examples of techniques sufficient to direct persons of skill through in vitro amplification methods, including the polymerase chain reaction (PCR), the ligase chain reaction (LCR), Qβ-replicase amplification and other RNA polymerase mediated techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

Once the nucleic acid for an anti-BoNT antibody is isolated and cloned, one can express the gene in a variety of recombinantly engineered cells known to those of skill in the art. Examples of such cells include bacteria, yeast, filamentous fungi, insect (especially employing baculoviral vectors), plant, and mammalian cells. It is expected that those of skill in the art are knowledgeable in the numerous expression systems available for expression of antibodies.

In brief summary, the expression of natural or synthetic nucleic acids encoding anti-BoNT antibodies will typically be achieved by operably linking a nucleic acid encoding the antibody to a promoter (which is either constitutive or inducible), and incorporating the construct into an expression vector. The vectors can be suitable for replication and integration in prokaryotes, eukaryotes, or both. Typical cloning vectors contain transcription and translation terminators, initiation sequences, and promoters useful for regulation of the expression of the nucleic acid encoding the anti-BoNT antibody. The vectors optionally comprise generic expression cassettes containing at least one independent terminator sequence, sequences permitting replication of the cassette in both eukaryotes and prokaryotes, i.e., shuttle vectors, and selection markers for both prokaryotic and eukaryotic systems. See Sambrook et al (1989) supra.

To obtain high levels of expression of a cloned nucleic acid it is common to construct expression plasmids which typically contain a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky (1984) *J. Bacteriol.*, 158:1018-1024, and the leftward promoter of phage lambda ($P_L$) as described by Herskowitz and Hagen (1980) *Ann. Rev. Genet.*, 14:399-445 and the L-arabinose (araBAD) operon (Better (1999) *Gene Exp Systems* pp 95-107 Academic Press, Inc., San Diego, Calif.). The inclusion of selection markers in DNA vectors transformed in *E. coli* is also useful. Examples of such markers include genes specifying resistance to ampicillin, tetracycline, or chloramphenicol. See Sambrook et al (1989) supra for details concerning selection markers, e.g., for use in *E. coli*.

Expression systems for expressing anti-BoNT antibodies are available using, for example, *E. coli*, *Bacillus* sp. (see, e.g., Palva, et al. (1983) *Gene* 22:229-235; Mosbach et al. (1983) *Nature*, 302: 543-545), and *Salmonella*. *E. coli* systems may also be used.

The anti-BoNT antibodies produced by prokaryotic cells may require exposure to chaotropic agents for proper folding. During purification from, e.g., *E. coli*, the expressed protein is optionally denatured and then renatured. This can be accomplished, e.g., by solubilizing the bacterially produced antibodies in a chaotropic agent such as guanidine HCl. The antibody is then renatured, either by slow dialysis or by gel filtration (see, e.g., U.S. Pat. No. 4,511,503). Alternatively, nucleic acid encoding the anti-BoNT antibodies may be operably linked to a secretion signal sequence such as pelB so that the anti-BoNT antibodies are secreted into the medium in correctly-folded form (Better et al (1988) *Science* 240: 1041-1043).

Methods of transfecting and expressing genes in mammalian cells are known in the art (see e.g. Birch and Racher *Adv. Drug Deliv. Rev.* 2006, 58: 671-685). Transducing cells with nucleic acids can involve, for example, incubating viral vectors containing anti-BoNT nucleic acids with cells within the host range of the vector (see, e.g., Goeddel (1990) *Methods in Enzymology*, vol. 185, Academic Press, Inc., San Diego, Calif. or Krieger (1990) *Gene Transfer and Expression—A Laboratory Manual*, Stockton Press, New York, N.Y. and the references cited therein).

The culture of cells used in the present disclosure, including cell lines and cultured cells from tissue or blood samples is well known in the art (see, e.g., Freshney (1994) *Culture of Animal Cells, a Manual of Basic Technique, third edition*, Wiley-Liss, N.Y. and the references cited therein).

Techniques for using and manipulating antibodies are found in Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497.

The anti-BoNT antibody gene(s) (e.g. anti-BoNT scFv gene) may be subcloned into the expression vector pUC119mycHis (Tomlinson et al. (1996) *J. Mol. Biol.*, 256: 813-817) or pSYN3, resulting in the addition of a hexahistidine tag at the C-terminal end of the scFv to facilitate purification. Detailed protocols for the cloning and purification of certain anti-BoNT antibodies are found, for example, in Amersdorfer et al. (1997) *Infect. Immunity*, 65(9): 3743-3752, and the like.

B) Preparation of Whole Polyclonal or Monoclonal Antibodies.

The anti-BoNT antibodies of the present disclosure include individual, allelic, strain, or species variants, and fragments thereof, both in their naturally occurring (full-length) forms and in recombinant forms. Certain antibodies may be selected to bind one or more epitopes bound by the antibodies described herein (as seen in FIG. 4 or FIG. 5). The antibodies can be raised in their native configurations or in non-native configurations. Anti-idiotypic antibodies can also be generated. Many methods of making antibodies that specifically bind to a particular epitope are known to persons of skill. The following discussion is presented as a general overview of the techniques available; however, one of skill will recognize that many variations upon the following methods are known.

1) Polyclonal Antibody Production.

Methods of producing polyclonal antibodies are known to those of skill in the art. In brief, an immunogen (e.g., BoNT/A, BoNT/B, BoNT/E, etc.), subsequences including, but not limited to subsequences comprising epitopes specifically bound by antibodies expressed by clones disclosed herein, preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the BoNT polypeptide is performed where desired (see, e.g., Coligan (1991) *Current Protocols in Immunology* Wiley/Greene, NY; and Harlow and Lane (1989) *Antibodies: A Laboratory Manual* Cold Spring Harbor Press, NY).

Antibodies that specifically bind to the epitopes described herein can be selected from polyclonal sera using the selection techniques described herein.

2) Monoclonal Antibody Production.

In some instances, it is desirable to prepare monoclonal antibodies from various mammalian hosts, such as mice, rodents, primates, humans, etc. Descriptions of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, supra; Goding (1986) *Monoclonal Antibodies: Principles and Practice* (2d ed.) Academic Press, New York, N.Y.; and Kohler and Milstein (1975) *Nature* 256: 495-497.

Summarized briefly, monoclonal antibody production using hybridomas may proceed by injecting an animal with an immunogen (e.g., BoNT/A, BoNT/B, BoNT/E, etc.) subsequences including, but not limited to subsequences comprising epitopes specifically bound by antibodies expressed by clones disclosed herein. The animal is then sacrificed and cells taken from its spleen, which are fused with myeloma cells. The result is a hybrid cell or "hybridoma" that is capable of reproducing antibodies in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the BoNT antigen, and yield of the monoclonal antibodies produced by such cells is enhanced by various techniques, including injection into the peritoneal cavity of a vertebrate (preferably mammalian) host. The antibodies of the present disclosure are used with or without modification, and include chimeric antibodies such as humanized murine antibodies.

Techniques for creating recombinant DNA versions of the antigen-binding regions of antibody molecules which bypass the generation of hybridomas are contemplated for the present BoNT binding antibodies and fragments. DNA is cloned into a bacterial expression system. One example of a suitable technique uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind BoNT. Such BoNT binding agents (Fab fragments with specificity for a BoNT polypeptide) are specifically encompassed within the BoNT binding antibodies and fragments of the present disclosure. Other methods for screening and production of antibodies may employ one or more of display systems such as phage display, yeast display, ribosome, etc., and an antibody production system such as that derived from transgenic mice.

The present disclosure provides an isolated nucleic acid comprising a nucleotide sequence encoding an amino acid sequence of a $V_H$ of a subject antibody. The present disclosure provides an isolated nucleic acid comprising a nucleotide sequence encoding an amino acid sequence of a $V_L$ of a subject antibody. The present disclosure provides an isolated nucleic acid comprising a nucleotide sequence encoding an amino acid sequence of a $V_H$ and a $V_L$ of a subject antibody. In some instances, a subject nucleic acid comprises a nucleotide sequence encoding $V_H$ CDR1, CDR2, and CDR3 of a subject antibody and/or a $V_L$ CDR1, CDR2, and CDR3 of a subject antibody.

The present disclosure provides an isolated nucleic acid comprising a nucleotide sequence encoding an amino acid sequence of a $V_H$ of an antibody selected from the group consisting of a $V_H$ comprising a CDR1, CDR2 and CDR3, wherein the CDR1, CDR2 and CDR3 are selected from a $V_H$ of an antibody selected from the group consisting of 4C4.2, 8DC1.2, 4C10.2, 8DC4.1, 4C2, 8DC2, 8D1, 87C78, 8DC8, 4C10.1, 2B23EK4, 6F5, 6F5.1, hu6F8, hu6F10, 7G1.1, 7G2.1, 6A1M, 6A2M, 6A3M, 6A4M, 6A5M, 6A6M, 6A7M, 6A8M, 6A9M, 1C7, 1C10, 1D8, 1G11, 1H5, 9B2, 10C9, 10H10, 16B3, 16D5, 18A6, 18D10, 18E5, 18F2, 19A9, 19B6, 19D2, 19D22, 19D22.4, 19G6, 31A5, 31A5.1, 31C3, 31C3.6, 31E2, 31E2.20, 31G2, 31H3, 34E8, 34E8B12, 26A10, 26B2, 26C2, 26C4, 26D1, 26D9, 26D10, 26D11, 26E1, 26E2, 26E6, 26G5, 26G11, 26H11, 1B12.3, 1B12.4, 1C1, 1C1.1, 1C2, 1C3, 1C4, 1C8, 87C1, 87C2, 87C78, 4C1, 4C3, 4C4.1, 4C4, 4C5, 4C6, 4C7, 4C8, 4C9, 4C10, 8C1, 8C2, 8C3, 8C4, 8C5, 8C6, 8D2, 8DC1, 8DC3, 8DC4, 8DC5, 8DC6, 8DC7, 8DC10, 8DC11, 8DC12, 8DC13, 8DC14, 8DC15, 6F1, 6F3, 6F4, 39A1, 41C2, 43D3, 39H6, 41E2, 41F7, 42G8, 39D1.1, 41A4, 41B7, 39D5.1, 41G8, 6F6, 6F7, 6F8, 6F9, hu6F9, 6F10, 28C9, 28H4, 29A2, 29B8, 30C8, 32G2, 37B4, 37B6, 38B8, 38C1, 38D11, 38F8, 4B19, 4B19.1, 7G1, 7G2, 2B23K1, 2B23K2, 2B23K4, 2B23K7, 2B23K11, 7G3, 7G4, 7G5, 7G6, 7G7, 7G8, 7G9, 7G10, 7G11, 2B23EK1, 2B23EK5, 2B23EK6, 2B23EK7, 2B23EK10, 2B23EK11, 2B23EK12, 8D2.2, 8D2.3, 8DC3.1, 8DC8.3, 8DC8.6, B4, A9, and/or A2S; and/or a $V_L$ comprising a CDR1, CDR2 and CDR3, wherein the CDR1, CDR2 and CDR3 are selected from a $V_L$ of an antibody selected from the group consisting of 4C4.2, 8DC1.2, 4C10.2, 8DC4.1, 4C2, 8DC2, 8D1, 87C78, 8DC8, 4C10.1, 2B23EK4, 6F5, 6F5.1, hu6F8, hu6F10, 7G1.1, 7G2.1, 6A1M, 6A2M, 6A3M, 6A4M, 6A5M, 6A6M, 6A7M, 6A8M, 6A9M, 1C7, 1C10, 1D8, 1G11, 1H5, 9B2, 10C9, 10H10, 16B3, 16D5, 18A6, 18D10, 18E5, 18F2, 19A9, 19B6, 19D2, 19D22, 19D22.4, 31A5, 31A5.1, 31C3, 31C3.6, 31E2, 31E2.20, 31G2, 31H3, 34E8B12, 26A10, 26B2, 26C2, 26C4, 26D1, 26D9, 26D10, 26D11, 26E2, 26E6, 26G5, 26G11, 26H11, 1B12.3, 1B12.4, 1C1, 1C1.1, 1C2, 1C3, 1C4, 1C8, 87C1, 87C2, 87C78, 4C1, 4C3, 4C4.1, 4C4, 4C5, 4C6, 4C7, 4C8, 4C9, 4C10, 4C10.2, 8C1, 8C2, 8C3, 8C4, 8C5, 8C6, 8D1, 8D2, 8DC1, 8DC3, 8DC4, 8DC5, 8DC6, 8DC7, 8DC10, 8DC11, 8DC12, 8DC13, 8DC14, 8DC15, 6F1, 6F3, 6F4, 39A1, 41C2, 43D3, 39H6, 41E2, 41F7, 42G8, 39D1.1, 41A4, 41B7, 39D5.1, 41G8, 6F6, 6F7, 6F8, 6F9, hu6F9, 6F10, 28C9, 28H4, 29A2, 29B8, 30C8, 32G2, 37B4, 37B6, 38B8, 38C1, 38D11, 38F8, 4B19, 4B19.1, 7G1, 7G2, 7G7, 7G8, 7G9, 7G10, 7G11, 2B23EK1, 2B23EK4, 2B23EK5, 2B23EK6, 2B23EK7, 2B23EK10, 2B23EK11, 2B23EK12, 8D2.2, 8D2.3, 8DC3.1, 8DC8.3, 8DC8.6, B4, A9, and/or A2S.

The nucleic acid can be a recombinant vector, as described above, which provides for amplification and/or expression (synthesis) of the encoded antibody. The recombinant vector can be suitable for expression in prokaryotic and/or eukaryotic cells.

The present disclosure also provides a cell, e.g., a genetically modified cell, that comprises a subject nucleic acid. A subject genetically modified cell can be a prokaryotic cell (e.g., a bacterial cell); or a eukaryotic cell (e.g., an insect cell; a mammalian cell, such as a mammalian cell line suitable for in vitro cell culture; a yeast cell; etc.), where the cell may produce the encoded antibody.

IV. Modification of Anti-BoNT Antibodies.

A) Display Techniques can be Used to Increase Antibody Affinity.

To create higher affinity antibodies, mutant scFv gene repertories, based on the sequence of a binding scFv (see, e.g., FIG. 4 and FIG. 5), can be created and expressed on the surface of phage. Display of antibody fragments on the surface of viruses which infect bacteria (bacteriophage or phage) makes it possible to produce human or other mammalian antibodies (e.g., scFvs) with a wide range of affinities and kinetic characteristics. To display antibody fragments on the surface of phage (phage display), an antibody fragment gene is inserted into the gene encoding a phage surface protein (e.g., pIII) and the antibody fragment-pIII fusion protein is expressed on the phage surface (McCafferty et al. (1990) *Nature,* 348: 552-554; Hoogenboom et al. (1991) *Nucleic Acids Res.,* 19: 4133-4137).

Since the antibody fragments on the surface of the phage are functional, those phage bearing antigen binding antibody fragments can be separated from non-binding or lower affinity phage by antigen affinity chromatography (McCafferty et al. (1990) *Nature,* 348: 552-554). Mixtures of phage are allowed to bind to the affinity matrix, non-binding or lower affinity phage are removed by washing, and bound phage are eluted by treatment with acid or alkali.

By infecting bacteria with the eluted phage or modified variants of the eluted phage as described below, more phage can be grown and subjected to another round of selection. In this way, an enrichment of 1000 fold in one round may become 1,000,000 fold in two rounds of selection (see, e.g., McCafferty et al. (1990) *Nature,* 348: 552-554). Thus, even when enrichments in each round are low, multiple rounds of affinity selection leads to the isolation of rare phage and the genetic material contained within which encodes the sequence of the binding antibody (see, e.g., Marks et al. (1991) *J. Mol. Biol.,* 222: 581-597). The physical link between genotype and phenotype provided by phage display makes it possible to test every member of an antibody fragment library for binding to antigen, even with libraries as large as 100,000,000 clones. For example, after multiple rounds of selection on antigen, a binding scFv that occurred with a frequency of only 1/30,000,000 clones was recovered (Marks et al. (1991) *J. Mol. Biol.*, 222: 581-597.).

Yeast display may also be utilized to increase antibody affinity and has the ability to finely discriminate between mutants of close affinity. Antibody variable region genes (V-genes) may be diversified either randomly or using spiked oligonucleotides, and higher affinity mutants selected using various types of affinity chromatography or flow cytometry (see, e.g., Razai A. et al. (2005) *J. Mol. Biol.* 351:158-169. Lou J. et al. (2010). Protein Engineering, Design & Selection, 23(4):311-319).

1) Chain Shuffling.

One approach for creating mutant scFv gene repertoires involves replacing either the $V_H$ or $V_L$ gene from a binding scFv with a repertoire of $V_H$ or $V_L$ genes (chain shuffling) (see, e.g., Clackson et al. (1991) *Nature*, 352: 624-628). Such gene repertoires contain numerous variable genes derived from the same germline gene as the binding scFv, but with point mutations (see, e.g., Marks et al. (1992) *Bio/Technology*, 10: 779-783, Lou J. et al. (2010). Protein Engineering, Design & Selection, 23(4):311-319). Using light or heavy chain shuffling and phage display or yeast display, the binding avidities of, e.g., BoNT/E or BoNT/B binding antibody fragment can be dramatically increased (see, e.g., Marks et al. (1992) *Bio/Technology*, 10: 779-785).

Thus, to alter the affinity of anti-BoNT antibody a mutant scFv gene repertoire may be created containing the $V_H$ gene of a known anti-BoNT antibody and a $V_L$ gene repertoire (light chain shuffling). Alternatively, an scFv gene repertoire is created containing the $V_L$ gene of a known anti-BoNT antibody and a $V_H$ gene repertoire (heavy chain shuffling). The scFv gene repertoire may be cloned into a phage display vector (e.g., pHEN-1, Hoogenboom et al. (1991) *Nucleic Acids Res.*, 19: 4133-4137) or yeast display vector (e.g., pYD2. Razai A. et al. (2005) *J. Mol. Biol.* 351:158-169), and after transformation a library of transformants is obtained. Phage or yeasts are prepared and selections are performed accordingly. In addition to chain shuffling, it is also possible to shuffle individual complementarity determining regions (CDRs).

The antigen concentration may be decreased in each round of selection, reaching a concentration less than the desired $K_d$ by the final rounds of selection. This results in the selection of phage or yeast clones which expressed antibody on the basis of affinity with the antigen (Hawkins et al. (1992) *J. Mol. Biol.* 226: 889-896).

Chain shuffling may be combined with the stringent selections made possible by yeast display and flow cytometry. This novel approach was found to be particularly powerful for increasing antibody affinity (see example 1).

2) Increasing the Affinity of Anti-BoNT Antibodies by Site Directed Mutagenesis.

The majority of antigen contacting amino acid side chains are located in the complementarity determining regions (CDRs), three in the $V_H$ (CDR1, CDR2, and CDR3) and three in the $V_L$ (CDR1, CDR2, and CDR3) (see, e.g., Chothia et al. (1987) *J. Mol. Biol.*, 196: 901-917; Chothia et al. (1986) *Science*, 233: 755-8; Nhan et al. (1991) *J. Mol. Biol.*, 217: 133-151). Without being bound to a theory, it is believed that these residues contribute the majority of binding energetics responsible for antibody affinity for antigen. In other molecules, mutating amino acids that contact ligand has been shown to be an effective means of increasing the affinity of one protein molecule for its binding partner (Lowman et al. (1993) *J. Mol. Biol.*, 234: 564-578; Wells (1990) *Biochemistry*, 29: 8509-8516). Thus mutation (randomization) of the CDRs and screening against, for example, BoNT/A, BoNT/B, BoNT/F, or the epitopes thereof, can be used to generate anti-BoNT antibodies having improved binding affinity.

Each CDR is randomized in a separate library, using a selected antibody as a template. To simplify affinity measurement, a lower affinity anti-BoNT antibody is used as a template, rather than a higher affinity scFv. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (see, e.g., Lowman et al. (1993) *J. Mol. Biol.*, 234: 564-578).

To increase the affinity of anti-BoNT antibodies, amino acid residues located in one or more CDRs (e.g., 9 amino acid residues located in $V_L$ CDR3) are partially randomized by synthesizing a "doped" oligonucleotide in which the wild type nucleotide occurred with a frequency of, e.g. 49%. The oligonucleotide is used to amplify the remainder of the anti-BoNT scFv gene(s) using PCR.

For example, to create a library in which $V_H$ CDR3 is randomized, an oligonucleotide is synthesized which anneals to the anti-BoNT antibody $V_H$ framework 3 and encodes $V_H$ CDR3 and a portion of framework 4. At the four positions to be randomized, the sequence NNS can be used, where N is any of the 4 nucleotides, and S is "C" or "T". The oligonucleotide is used to amplify the anti-BoNT antibody $V_H$ gene using PCR, creating a mutant anti-BoNT antibody $V_H$ gene repertoire. PCR is used to splice the $V_H$ gene repertoire with the anti-BoNT antibody light chain gene, and the resulting scFv gene repertoire cloned into a phage display vector (e.g., pHEN-1 or pCANTAB5E). Ligated vector DNA is used to transform electrocompetent *E. coli* to produce a phage antibody library.

To select higher affinity mutant scFv, each round of selection of the phage antibody libraries is conducted on decreasing amounts of one or more BoNT subtypes. Clones from the third and fourth round of selection can be screened for binding to the desired antigen(s) (e.g., BoNT/B, BoNT/F, BoNT/G, etc.) by ELISA on 96 well plates. The scFv from, e.g., twenty to forty ELISA positive clones can be expressed, e.g. in 10 ml cultures, the periplasm harvested, and the scFv $k_{off}$ determined by BIAcore. Clones with the slowest $k_{off}$ are sequenced, and each unique scFv subcloned into an appropriate vector (e.g., pUC119 mycHis). The scFv are expressed in culture, and purified. Affinities of purified scFv can be determined by BIAcore.

Instead of using phage display, yeast display can also be used for affinity maturation. By way of illustration, FIG. 2 shows a scheme used to construct yeast displayed light chain shuffled scFv antibody libraries.

3) Creation of Anti-BoNT (scFv')$_2$ Homodimers.

To create anti-BoNT (scFv')$_2$ antibodies, two anti-BoNT scFvs are joined, either through a linker (e.g., a carbon linker, a peptide, etc.) or through a disulfide bond between, for example, two cysteines. Thus, for example, to create disulfide linked scFv, a cysteine residue can be introduced by site directed mutagenesis between a myc tag and a hexahistidine tag at the carboxy-terminus of an anti-BoNT/B. Introduction of the correct sequence can be verified by DNA sequencing. The construct may be in pUC119, so that the pelB leader directs expressed scFv to the periplasm and cloning sites (NcoI and NotI) exist to introduce anti-BoNT mutant scFv. Expressed scFv has the myc tag at the C-terminus, followed by two glycines, a cysteine, and then 6 histidines to facilitate purification by IMAC. After disulfide bond formation between the two cysteine residues, the two scFv can be separated from each other by 26 amino acids (two 11 amino acid myc tags and three repeats of a unit with 4 glycines plus one serine). An scFv expressed from this construct, purified by IMAC may predominantly comprise monomeric scFv. To produce (scFv')$_2$ dimers, the cysteine can be reduced by incubation with 1 mM beta-mercaptoethanol, and half of the scFv blocked by the addition of DTNB. Blocked and unblocked scFvs can be incubated together to form (scFv')$_2$ and the resulting material can optionally be analyzed by gel filtration. The affinity of the anti-BoNT scFv' monomer and (scFv')$_2$ dimer can optionally be determined by BIAcore.

The (scFv')$_2$ dimer may be created by joining the scFv fragments through a linker, more preferably through a peptide linker. This can be accomplished by a wide variety of means well known to those of skill in the art. For example, one preferred approach is described by Holliger et al. (1993) *Proc. Natl. Acad. Sci. USA*, 90: 6444-6448 (see also WO 94/13804).

Typically, linkers are introduced by PCR cloning. For example, synthetic oligonucleotides encoding the 5 amino acid linker (Gly$_4$Ser, SEQ ID NO:451) can be used to PCR amplify the anti-BoNT antibody $V_H$ and $V_L$ genes which are then spliced together to create the anti-BoNT diabody gene. The gene can then be cloned into an appropriate vector, expressed, and purified according to standard methods well known to those of skill in the art.

4) Preparation of Anti-BoNT (scFv)$_2$, Fab, and (Fab')$_2$ Molecules.

Anti-BoNT antibodies such as anti-BoNT/F or anti-BoNT/B scFv, or variant(s) with higher affinity, are suitable templates for creating size and valency variants. For example, an anti-BoNT (scFv')$_2$ can be created from the parent scFv as described above. An scFv gene can be excised using appropriate restriction enzymes and cloned into another vector as described herein.

Expressed scFv may include a myc tag at the C-terminus, followed by two glycines, a cysteine, and six histidines to facilitate purification. After disulfide bond formation between the two cystine residues, the two scFv may be separated from each other by 26 amino acids (e.g., two eleven amino acid myc tags and four glycines). Single-chain Fv (scFv) can be expressed from this construct and purified.

To produce (scFv')$_2$ dimers, the cysteine is reduced by incubation with 1 mM β-mercaptoethanol, and half of the scFv blocked by the addition of DTNB. Blocked and unblocked scFv are incubated together to form (scFv')$_2$, which is purified. As higher affinity scFv are isolated, their genes are similarly used to construct (scFv')$_2$.

Anti-BoNT Fab may also be expressed in *E. coli* using an expression vector similar to the one described by Better et. al. (1988) *Science*, 240: 1041-1043. For example, to create a BoNT/B or BoNT/F binding Fab, the $V_H$ and $V_L$ genes are amplified from the scFv using PCR. The $V_H$ gene is cloned into an expression vector (e.g., a pUC119 based bacterial expression vector) that provides an IgG $C_H1$ domain downstream from, and in frame with, the $V_H$ gene. The vector also contains the lac promoter, a pelB leader sequence to direct expressed $V_H$-$C_H1$ domain into the periplasm, a gene 3 leader sequence to direct expressed light chain into the periplasm, and cloning sites for the light chain gene. Clones containing the correct $V_H$ gene are identified, e.g., by PCR fingerprinting. The $V_L$ gene is spliced to the $C_L$ gene using PCR and cloned into the vector containing the $V_H C_H1$ gene.

B) Selection of Antibodies.

Selection of anti-BoNT antibodies (whether produced by phage display, yeast display, immunization methods, hybridoma technology, etc.) involves screening the resulting antibodies for specific binding to an appropriate antigen(s). In the instant case, suitable antigens can include, but are not limited to BoNT/G, BoNT/F1, BoNT/F3, BoNT/E1, BoNT/E2, BoNT/E3, BoNT/B1, BoNT/B2, BoNT/B3, BoNT/B4, BoNT/A1, BoNT/A2, BoNT/A3, a C-terminal domain of BoNT heavy chain (binding domain) of BoNT holotoxins, recombinant BoNT domains such as $H_C$ (binding domain), $H_N$ (translocation domain), or $L_C$ (light chain), and the like. The antibodies may be selected for specific binding of an epitope recognized by one or more of the antibodies described herein.

Selection can be by any of a number of methods well known to those of skill in the art. In one example, selection is by immunochromatography (e.g., using immunotubes, Maxisorp, Nunc) against the desired target, e.g., BoNT/G, BoNT/B, etc. In a related example, selection is against a BoNT protein in a surface plasmon resonance system (e.g., BIAcore, Pharmacia) either alone or in combination with an antibody that binds to an epitope specifically bound by one or more of the antibodies described herein. Selection can also be done using flow cytometry for yeast display libraries. Yeast display libraries are sequentially selected, first on BoNT/B1, then on other BoNT/B subtypes (BoNT/B2, B3 and B4) to obtain antibodies that bind with high affinity to all subtypes of BoNT/B. This can be repeated for other subtypes.

For phage display, analysis of binding can be simplified by including an amber codon between the antibody fragment gene and gene III. This makes it possible to easily switch between displayed and soluble antibody fragments simply by changing the host bacterial strain. When phage are grown in a supE suppresser strain of *E. coli*, the amber stop codon between the antibody gene and gene III is read as glutamine and the antibody fragment is displayed on the surface of the phage. When eluted phage are used to infect a non-suppressor strain, the amber codon is read as a stop codon and soluble antibody is secreted from the bacteria into the periplasm and culture media (Hoogenboom et al. (1991) *Nucleic Acids Res.*, 19: 4133-4137). Binding of soluble scFv to antigen can be detected, e.g., by ELISA using a murine IgG monoclonal antibody (e.g., 9E10) which recognizes a C-terminal myc peptide tag on the scFv (Evan et al. (1985) *Mol. Cell. Biol.*, 5: 3610-3616; Munro et al. (1986) *Cell*, 46: 291-300), e.g., followed by incubation with polyclonal anti-mouse Fc conjugated to a detectable label (e.g., horseradish peroxidase).

As indicated above, purification of the anti-BoNT antibody can be facilitated by cloning of the scFv gene into an expression vector (e.g., expression vector pUC119mycHIS) that results in the addition of the myc peptide tag followed by a hexahistidine tag at the C-terminal end of the scFv. The vector also preferably encodes the pectate lyase leader sequence that directs expression of the scFv into the bacterial periplasm where the leader sequence is cleaved. This makes it possible to harvest native properly folded scFv directly from the bacterial periplasm. The anti-BoNT antibody is then expressed and purified from the bacterial supernatant using immobilized metal affinity chromatography.

C) Measurement of Anti-BoNT Antibody Affinity for One or More BoNT Subtypes.

As explained above, selection for increased avidity involves measuring the affinity of an anti-BoNT antibody (e.g. a modified anti-BoNT antibody) for one or more targets of interest (e.g. BoNT/E subtype(s) or domains thereof. For example, the $K_D$ of a BoNT/F-binding antibody and the kinetics of binding to BoNT/F are determined in a BIAcore, a biosensor based on surface plasmon resonance. For this technique, antigen is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ M and $k_{off}$ in the range $1.0 \times 10^{-1}$ to $1.0 \times 10^{-6}$ M. The equilibrium constant $K_d$ is then calculated as $k_{off}/k_{on}$ and thus is typically measured in the range $10^{-5}$ to $10^{-12}$ M. Affinities measured in this manner usually correlate well with affinities measured in solution by fluorescence quench titration.

Phage display and selection generally results in the selection of higher affinity mutant scFvs (Marks et al. (1992) *Bio/Technology*, 10: 779-783; Hawkins et al. (1992) *J. Mol. Biol.* 226: 889-896; Riechmann et al. (1993) *Biochemistry*, 32: 8848-8855; Clackson et al. (1991) *Nature*, 352: 624-628), but probably does not result in the separation of mutants with less than a 6 fold difference in affinity (Riechmann et al. (1993) *Biochemistry*, 32: 8848-8855). Thus a rapid method can be used to estimate the relative affinities of mutant scFvs isolated after selection. Since increased affinity results primarily from a reduction in the $k_{off}$, measurement of $k_{off}$ should identify higher affinity scFv. $k_{off}$ can be measured in the BIAcore on unpurified scFv in bacterial periplasm, since expression levels are high enough to give an adequate binding signal and $k_{off}$ is independent of concentration. The value of $k_{off}$ for periplasmic and purified scFv is typically in close agreement.

V. Humanized, Human Engineered or Human Antibody Production.

The present BoNT binding antibodies and fragments can be humanized or human engineered antibodies. As used herein, a humanized antibody, or antigen binding fragment thereof, is a recombinant polypeptide that comprises a portion of an antigen binding site from a non-human antibody and a portion of the framework and/or constant regions of a human antibody. A human engineered antibody or antibody fragment may be derived from a human or non-human (e.g., mouse) source that has been engineered by modifying (e.g., deleting, inserting, or substituting) amino acids at specific positions so as to alter certain biophysical properties or to reduce any detectable immunogenicity of the modified antibody in a human.

Humanized antibodies also encompass chimeric antibodies and CDR-grafted antibodies in which various regions may be derived from different species. Chimeric antibodies may be antibodies that include a non-human antibody variable region linked to a human constant region. Thus, in chimeric antibodies, the variable region is mostly non-human, and the constant region is human. Chimeric antibodies and methods for making them are described in Morrison, et al., *Proc. Natl. Acad. Sci. USA,* 81: 6841-6855 (1984), Boulianne, et al., *Nature,* 312: 643-646 (1984), and PCT Application Publication WO 86/01533. Although, they can be less immunogenic than a mouse monoclonal antibody, administrations of chimeric antibodies have been associated with human anti-mouse antibody responses (HAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate ADCC. Morrison et al. (1984), *Proc. Natl. Acad. Sci.,* 81: 6851; Neuberger et al. (1984), *Nature,* 312: 604. One example is the replacement of an Fc region with that of a different isotype.

CDR-grafted antibodies are antibodies that include the CDRs from a non-human "donor" antibody linked to the framework region from a human "recipient" antibody. Generally, CDR-grafted antibodies include more human antibody sequences than chimeric antibodies because they include both constant region sequences and variable region (framework) sequences from human antibodies. Thus, for example, a CDR-grafted humanized antibody may comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in, Jones et al., *Nature,* 321: 522-525 (1986), Riechmann et al., *Nature,* 332: 323-327 (1988), and Verhoeyen et al., *Science,* 239: 1534-1536 (1988)). Methods that can be used to produce humanized antibodies also are described in U.S. Pat. Nos. 4,816,567, 5,721,367, 5,837,243, and 6,180,377. CDR-grafted antibodies are considered less likely than chimeric antibodies to induce an immune reaction against non-human antibody portions. However, it has been reported that framework sequences from the donor antibodies are required for the binding affinity and/or specificity of the donor antibody, presumably because these framework sequences affect the folding of the antigen-binding portion of the donor antibody. Therefore, when donor, non-human CDR sequences are grafted onto unaltered human framework sequences, the resulting CDR-grafted antibody can exhibit, in some cases, loss of binding avidity relative to the original non-human donor antibody. See, e.g., Riechmann et al., *Nature,* 332: 323-327 (1988), and Verhoeyen et al., *Science,* 239: 1534-1536 (1988).

Human engineered antibodies include for example "veneered" antibodies and antibodies prepared using HUMAN ENGINEERING™ technology (U.S. Pat. No. 5,869,619). HUMAN ENGINEERING™ technology is commercially available, and involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Techniques for making human engineered proteins are described in Studnicka et al., *Protein Engineering,* 7: 805-814 (1994), U.S. Pat. Nos. 5,766,886, 5,770,196, 5,821,123, and 5,869,619, and PCT Application Publication WO 93/11794.

"Veneered" antibodies are non-human or humanized (e.g., chimeric or CDR-grafted antibodies) antibodies that have been engineered to replace certain solvent-exposed amino acid residues so as to further reduce their immunogenicity or enhance their function. As surface residues of a chimeric antibody are presumed to be less likely to affect proper antibody folding and more likely to elicit an immune reaction, veneering of a chimeric antibody can include, for instance, identifying solvent-exposed residues in the non-human framework region of a chimeric antibody and replacing at least one of them with the corresponding surface residues from a human framework region. Veneering can be accomplished by any suitable engineering technique, including the use of the above-described HUMAN ENGINEERING™ technology.

In a different approach, a recovery of binding avidity can be achieved by "de-humanizing" a CDR-grafted antibody. De-humanizing can include restoring residues from the donor antibody's framework regions to the CDR grafted antibody, thereby restoring proper folding. Similar "de-humanization" can be achieved by (i) including portions of the "donor" framework region in the "recipient" antibody or (ii) grafting portions of the "donor" antibody framework region into the recipient antibody (along with the grafted donor CDRs).

For a further discussion of antibodies, humanized antibodies, human engineered, and methods for their preparation, see Kontermann and Dubel, eds., *Antibody Engineering*, Springer, New York, N.Y., 2001.

The present antibodies and fragments encompass human antibodies, such as antibodies which bind BoNT polypeptides and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art, such as through the use of transgenic mammals (such as transgenic mice) in which the native immunoglobulin repertoire has been replaced with human V-genes in the mammal chromosome. Such mammals appear to carry out VDJ recombination and somatic hypermutation of the human germline antibody genes in a normal fashion, thus producing high affinity antibodies with completely human sequences.

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598, 6,657,103 and 6,833,268.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851, 1996), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (*Cloning Stem Cells.* 4:91-102, 2002) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TC MOUSE™ with various human antigens produces antibody responses comprising human antibodies. See also Jakobovits et al., *Proc. Natl. Acad. Sci. USA,* 90:2551 (1993); Jakobovits et al., *Nature,* 362:255-258 (1993); Bruggermann et al., *Year in Immunol.,* 7:33 (1993); and U.S. Pat. Nos. 5,591,669; 5,589,369; 5,545,807; and U.S. Patent Publication Nos. 20020199213 and 20030092125, which describe methods for biasing the immune response of an animal to the desired epitope. Human antibodies may also be generated by in vitro activated B cells (see U.S. Pat. Nos. 5,567,610 and 5,229,275).

Human antibodies can also be generated through the in vitro screening of antibody display libraries. See Hoogenboom et al. (1991), *J. Mol. Biol.* 227: 381; and Marks et al. (1991), *J. Mol. Biol.* 222: 581. Various antibody-containing phage display libraries have been described and may be readily prepared. Libraries may contain a diversity of human antibody sequences, such as human Fab, Fv, and scFv fragments that may be screened against an appropriate target. Phage display libraries may comprise peptides or proteins other than antibodies which may be screened to identify selective binding agents of BoNT.

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Methods for display of peptides on the surface of yeast and microbial cells have also been used to identify antigen specific antibodies. See, for example, U.S. Pat. No. 6,699,658. Antibody libraries may be attached to yeast proteins, such as agglutinin, effectively mimicking the cell surface display of antibodies by B cells in the immune system.

In addition to phage display methods, antibodies may be isolated using ribosome mRNA display methods and microbial cell display methods. Selection of polypeptide using ribosome display is described in Hanes et al., (*Proc. Natl. Acad. Sci. USA,* 94:4937-4942, 1997) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Human BoNT-binding antibodies of the present disclosure may be produced in trioma cells. Genes encoding the antibodies are then cloned and expressed in other cells, particularly, nonhuman mammalian cells.

The general approach for producing human antibodies by trioma technology has been described by Ostberg et al. (1983) *Hybridoma* 2: 361-367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Other approaches to antibody production include in vitro immunization of human blood. In this approach, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody (see U.S. Pat. No. 4,716,111).

In another approach, mouse-human hybridomas which produce human anti-BoNT antibodies are prepared (see, e.g., U.S. Pat. No. 5,506,132). Other approaches include immunization of murines transformed to express human immunoglobulin genes, and phage display screening (Vaughan et al. supra.).

VI. Other Antibody Forms.

Sequence provided herein can be used to generate other antibody forms, including but not limited to nanobodies, UniBodies, and/or affibodies.

VHH and/or Nanobodies.

The Camelidae heavy chain antibodies are found as homodimers of a single heavy chain, dimerized via their constant regions. The variable domains of these camelidae heavy chain antibodies are referred to as VHH domains or VHH, and can be either used per se as nanobodies and/or as a starting point for obtaining nanobodies. Isolated VHH retain the ability to bind antigen with high specificity (see, e.g., Hamers-Casterman et al. (1993) Nature 363: 446-448). VHH domains, or nucleotide sequences encoding them, can be derived from antibodies raised in Camelidae species, for example in camel, dromedary, llama, alpaca and guanaco. Other species besides Camelidae (e.g., shark, pufferfish) can produce functional antigen-binding heavy chain antibodies, from which (nucleotide sequences encoding) such naturally occurring VHH can be obtained, e.g. using the methods described in U.S. Patent Publication US 2006/0211088.

Human proteins may be used in therapy primarily because they are not as likely to provoke an immune response when administered to a patient. Comparisons of camelid VHH with the $V_H$ domains of human antibodies reveals several key differences in the framework regions of the camelid VHH domain corresponding to the $V_H/V_L$ interface of the human $V_H$ domains. Mutation of these human residues to VHH resembling residues has been performed to produce "camelized" human $V_H$ domains that retain antigen binding activity, yet have improved expression and solubility.

Libraries of single $V_H$ domains have also been derived for example from $V_H$ genes amplified from genomic DNA or from mRNA came from the spleens of immunized mice and expressed in E. coli (Ward et al. (1989) Nature 341: 544-546) and similar approaches can be performed using the $V_H$ domains and/or the $V_L$ domains described herein. The isolated single $V_H$ domains are called "dAbs" or domain antibodies. A "dAb" is an antibody single variable domain ($V_H$ or $V_L$) polypeptide that specifically binds antigen. A "dAb" binds antigen independently of other V domains; however, as the term is used herein, a "dAb" can be present in a homo- or heteromultimer with other $V_H$ or $V_L$ domains where the other domains are not required for antigen binding by the dAb, i.e., where the dAb binds antigen independently of the additional $V_H$ or $V_L$ domains.

As described in U.S. Patent Publication No. 2006/0211088 methods are known for the cloning and direct screening of immunoglobulin sequences (including but not limited to multivalent polypeptides comprising: two or more variable domains—or antigen binding domains—and in particular $V_H$ domains or VHH domains; fragments of $V_L$, $V_H$ or VHH domains, such as CDR regions, for example CDR3 regions; antigen-binding fragments of conventional 4-chain antibodies such as Fab fragments and scFv's, heavy chain antibodies and domain antibodies; and in particular of VH sequences, and more in particular of VHH sequences) that can be used as part of and/or to construct such nanobodies.

Methods and procedures for the production of VHH/nanobodies can also be found for example in WO 94/04678, WO 96/34103, WO 97/49805, WO 97/49805 WO 94/25591, WO 00/43507 WO 01/90190, WO 03/025020, WO 04/062551, WO 04/041863, WO 04/041865, WO 04/041862, WO 04/041867, PCT/BE2004/000159, Hamers-Casterman et al. (1993) Nature 363: 446; Riechmann and Muyldermans (1999) J. Immunological Meth., 231: 25-38; Vu et al. (1997) Molecular Immunology, 34(16-17): 1121-1131; Nguyen et al. (2000) EMBO J., 19(5): 921-930; Arbabi Ghahroudi et al. (19997) FEBS Letters 414: 521-526; van der Linden et al. (2000) J. Immunological Meth., 240: 185-195; Muyldermans (2001) Rev. Molecular Biotechnology 74: 277-302; Nguyen et al. (2001) Adv. Immunol. 79:261, and the like, which are all incorporated herein by reference.

UniBodies.

UniBodies are generated by an antibody technology that produces a stable, smaller antibody format with an anticipated longer therapeutic window than certain small antibody formats. UniBodies may be produced from IgG4 antibodies by eliminating the hinge region of the antibody. Unlike the full size IgG4 antibody, the half molecule fragment is very stable and is termed a UniBody. Halving the IgG4 molecule left only one area on the UniBody that can bind to a target. Methods of producing UniBodies are described in detail in PCT Publication WO2007/059782, which is incorporated herein by reference in its entirety (see, also, Kolfschoten et al. (2007) Science 317: 1554-1557).

Affibodies.

Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g., Nord et al. (1997) Nat. Biotechnol. 15: 772-777; Ronmark et al. (2002) Eur. J. Biochem., 269: 2647-2655.). Details of affibodies and methods of production are known to those of skill (see, e.g., U.S. Pat. No. 5,831,012 which is incorporated herein by reference in its entirety).

VI. Assaying for Cross-Reactivity at an Epitope.

The antibodies of the present disclosure encompass those that specifically bind to one or more epitopes recognized by antibodies described herein (as seen in FIG. 4 and FIG. 5). In other words, antibodies are cross-reactive with one or more of these epitopes but may have different sequences. Means of assaying for cross-reactivity are well known to those of skill in the art (see, e.g., Dowbenko et al. (1988) J. Virol. 62: 4703-4711).

This can be ascertained by providing one or more isolated target BoNT polypeptide(s) (e.g. BoNT/B1 and/or BoNT/B2, or recombinant domains of said toxin, such as H$_C$) attached to a solid support and assaying the ability of a test antibody to compete with, an antibody described herein for binding to the target BoNT peptide. Thus, immunoassays in a competitive binding format are preferably used for cross-reactivity determinations. For example, a BoNT/E and/or BoNT/B polypeptide may be immobilized to a solid support. Antibodies to be tested (e.g. generated by selection from a phage-display library) added to the assay compete with any antibody from clones as shown in FIG. 4 and FIG. 5 for binding to the immobilized BoNT polypeptide(s). The ability of test antibodies to compete with the binding of one or more antibodies listed in FIG. 4 or FIG. 5 to the immobilized protein(s) are compared. The percent cross-reactivity above proteins is then calculated, using standard calculations.

If the test antibody competes with one or more of the antibodies listed in FIG. 4 or FIG. 5 and has a binding affinity comparable to or greater than a threshold (such as having a K$_D$ equal or less than about $1 \times 10^{-8}$ M) with the same target then the test antibody is expected to be an anti-BoNT antibody. In some cases, a subject antibody competes for binding to a Botulinum neurotoxin epitope with an antibody comprising VH and/or VL CDRs (e.g., V$_H$ CDR1, CDR2, and CDR3; and/or V$_L$ CDR1, CDR2, and CDR3) of an antibody depicted in FIG. 4 or FIG. 5. As one non-limiting example, in some instances, a subject antibody competes for binding to a Botulinum neurotoxin epitope with an antibody comprising VH CDR1, VH CDR2, and VH CDR3 of the antibody designated 4C4.1. In some instances, a subject antibody competes for binding to a Botulinum neurotoxin epitope with an antibody comprising VL CDR1, VL CDR2, and VL CDR3 of the antibody designated 4C4.1. As another example, in some cases, a subject antibody competes for binding to a Botulinum neurotoxin epitope with an antibody comprising VH CDR1, VH CDR2, VH CDR3, VL CDR1, VL CDR2, VL CDR3 of the antibody designated 4C4.1.

Cross-reactivity may be performed by using surface plasmon resonance in a BIAcore. In a BIAcore flow cell, the BoNT polypeptide(s) (e.g., BoNT/C and/or BoNT/F) are coupled to a sensor chip (e.g. CM5) as described in WO 09/008,916, disclosure of which is incorporated herein by reference. With a flow rate of 5 µl/min, a titration of 100 nM to 1 µM antibody is injected over the flow cell surface for about 5 minutes to determine an antibody concentration that results in near saturation of the surface. Epitope mapping or cross-reactivity is then evaluated using pairs of antibodies at concentrations resulting in near saturation and at least 100 relative units (RU) of antibody bound. The amount of antibody bound is determined for each member of a pair, and then the two antibodies are mixed together to give a final concentration equal to the concentration used for measurements of the individual antibodies. Antibodies recognizing different epitopes show an essentially additive increase in the RU bound when injected together, while antibodies recognizing identical epitopes show only a minimal increase in RU. Antibodies may be said to be cross-reactive if, when "injected" together they show an essentially additive increase (e.g., an increase by at least a factor of about 1.4, an increase by at least a factor of about 1.6, or an increase by at least a factor of about 1.8 or 2).

Cross-reactivity may also be determined by incubating a yeast displayed scFv with a BoNT domain polypeptide followed by incubation with an epitope-tagged scFv. Bound scFv is detected with an antibody recognizing the epitope tag and the level of BoNT domain display quantitated by incubation with anti-SV5 (see example 1).

Cross-reactivity at the desired epitopes can be ascertained by a number of other standard techniques (see, e.g., Geysen et al (1987) *J. Immunol. Meth.* 102, 259-274). This technique involves the synthesis of large numbers of overlapping BoNT peptides. The synthesized peptides are then screened against one or more of the prototypical antibodies (e.g., 4C10.1, 8DC1.2, etc.) and the characteristic epitopes specifically bound by these antibodies can be identified by binding specificity and affinity. The epitopes thus identified can be conveniently used for competitive assays as described herein to identify cross-reacting antibodies.

The peptides for epitope mapping can be conveniently prepared using "Multipin" peptide synthesis techniques (see, e.g., Geysen et al (1987) *Science,* 235: 1184-1190). Using the known sequence of one or more BoNT subtypes (see, e.g., Atassi et al. (1996) *J. Prot. Chem.,* 7: 691-700 and references cited therein), overlapping BoNT polypeptide sequences can be synthesized individually in a sequential manner on plastic pins in an array of one or more 96-well microtest plate(s).

The procedure for epitope mapping using this multipin peptide system is described in U.S. Pat. No. 5,739,306. Briefly, the pins are first treated with a pre-coat buffer containing 2% bovine serum albumin and 0.1% Tween 20 in phosphate-buffered saline (PBS) for 1 hour at room temperature. Then the pins are then inserted into the individual wells of 96-well microtest plate containing the antibodies in the pre-coat buffer, e.g. at 2 µg/ml. The incubation is preferably for about 1 hour at room temperature. The pins are washed in PBST (e.g., 3 rinses for every 10 minutes), and then incubated in the wells of a 96-well microtest plate containing 100 of horse radish peroxidase (HRP)-conjugated goat anti-mouse IgG (Fc) (Jackson ImmunoResearch Laboratories) at a 1:4, 000 dilution for 1 hour at room temperature. After the pins are washed as before, the pins are put into wells containing peroxidase substrate solution of diammonium 2,2'-azino-bis[3-ethylbenzthiazoline-b-sulfonate] (ABTS) and H$_2$O$_2$ (Kirkegaard & Perry Laboratories Inc., Gaithersburg, Md.) for 30 minutes at room temperature for color reaction. The plate is read at 405 nm by a plate reader (e.g., BioTek ELISA plate reader) against a background absorption wavelength of 492 nm. Wells showing color development indicate reactivity of the BoNT peptides in such wells with the test antibodies.

VII. Assaying for Neutralizing Activity of Anti-BoNT Antibodies

Preferred antibodies of the present disclosure act, individually or in combination, to neutralize (reduce or eliminate) the toxicity of botulinum neurotoxin type. Neutralization can be evaluated in vivo or in vitro. In vivo neutralization measurements simply involve measuring changes in the lethality (e.g., LD$_{50}$ or other standard metric) due to a BoNT neurotoxin administration with the presence of one or more antibodies being tested for neutralizing activity. The neurotoxin can be directly administered to the test organism (e.g. mouse) or the organism can harbor a botulism infection (e.g., be infected with *Clostridium botulinum*). The antibody can be administered before, during, or after the injection of BoNT neurotoxin or infection of the test animal. A decrease in the rate of progression, or mortality rate indicates that the antibody(s) have neutralizing activity.

One suitable in vitro assay for neutralizing activity uses a hemidiaphragm preparation (Deshpande et al. (1995) *Toxicon,* 33: 551-557). Briefly, left and right phrenic nerve hemidiaphragm preparations are suspended in physiological solution and maintained at a constant temperature (e.g. 36° C.). The phrenic nerves are stimulated supramaximally (e.g. at 0.05 Hz with square waves of 0.2 ms duration). Isometric twitch tension is measured with a force displacement transducer (e.g., GrassModel FT03) connected to a chart recorder.

Purified antibodies are incubated with purified BoNT (e.g. BoNT/A1, BoNT/C, BoNT/F1, etc.) for 30 min at room temperature and then added to the tissue bath, resulting in a final antibody concentration of about $2.0 \times 10^{-8}$ M and a final BoNT concentration of about $2.0 \times 10^{-11}$ M. For each antibody studied, time to 50% twitch tension reduction is determined (e.g., three times for BoNT alone and three times for antibody plus BoNT). Differences between times to a given (arbitrary) percentage (e.g. 50%) twitch reduction are determined by standard statistical analyses (e.g. two-tailed t test) at standard levels of significance (e.g., a P value of <0.05 considered significant).

VIII. Diagnostic Assays.

As explained above, the anti-BoNT antibodies of the present disclosure can be used for the in vivo or in vitro detection of BoNT toxin and thus, are useful in the diagnosis (e.g. confirmatory diagnosis) of botulism. The detection and/or quantification of BoNT in a biological sample obtained from an organism is indicative of a *Clostridium botulinum* infection of that organism.

The BoNT antigen can be quantified in a biological sample derived from a patient such as a cell, or a tissue sample derived from a patient. As used herein, a biological sample is a sample of biological tissue or fluid that contains a BoNT concentration that may be correlated with and indicative of a *Clostridium botulinum* infection. Preferred biological samples include blood, urine, saliva, and tissue biopsies.

Although the sample is typically taken from a human patient, the assays can be used to detect BoNT antigen in samples from mammals in general, such as dogs, cats, sheep, cattle and pigs, and most particularly primates such as humans, chimpanzees, gorillas, macaques, and baboons, and rodents such as mice, rats, and guinea pigs.

Tissue or fluid samples are isolated from a patient according to standard methods well known to those of skill in the art, most typically by biopsy or venipuncture. The sample is optionally pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

A) Immunological Binding Assays

The BoNT polypeptide (e.g., BoNT/C, BoNT/F, etc.) can be detected in an immunoassay utilizing only one or more than one of the anti-BoNT antibodies of the present disclosure as a capture agent that specifically binds to the BoNT polypeptide.

As used herein, an immunoassay is an assay that utilizes only one or more than one antibody (e.g. one or more anti-BoNT/F antibodies listed in FIG. 4 or FIG. 5) to specifically bind an analyte. The immunoassay is characterized by the binding of only one or more than one type of anti-BoNT antibody to a target (e.g. one or more BoNT/F subtypes) as opposed to other physical or chemical properties to isolate, target, and quantify the BoNT analyte.

The BoNT marker can be detected and quantified using any of a number of well recognized immunological binding assays. For example, the antibody of the present disclosure may be immobilized on a substrate (e.g. bead) and/or be the capture antibody in an ELISA. The detection step may take one of many formats known in the art, such as using a labeled secondary antibody or PCR amplification. Where PCR amplification is the method of detection, the antibody is conjugated to a nucleic acid, the antigen may optionally be first attached to a substrate, and the antibody is allowed to be bound to the antigen. The bound antibody-nucleic acid fusion then undergoes PCR amplification of the nucleic acid sequence attached to the antibody. The amplified sequences can in turn be detected via a fluorophore bound to the incorporated nucleotides. The amplified sequences can also be first hybridized to an array before fluorescence is measured to enable multiplexing. Multiplexing encompasses processing and detecting two or more samples and/or two or more analytes in parallel. Details of an assay using antibody-nucleic acid fusion may be found in US 20060141505, disclosure of which is incorporated by reference.

Single assay or multiplex assay can also take the form of an array where signal is detected only by electro-stimulation. In this format, the antibody of the present disclosure is conjugated to an electrochemiluminescent moiety and immobilized on an electrode. A signal (e.g. fluorescence) is emitted due to electrical stimulation at a particular electrode. Details of an assay using electrochemiluminescent moiety in an array may be found in US 20100140086, disclosure of which is incorporated by reference.

A fluorescent compound may be also added later to the assay for visualization by either Luminex type or other type of detection (see, e.g., U.S. Pat. Nos. 4,366,241; 4,376,110; 4,517,288; and 4,837,168, and the like). For a review of the general immunoassays, see also *Methods in Cell Biology Volume* 37: *Antibodies in Cell Biology*, Asai, ed. Academic Press, Inc. New York (1993); *Basic and Clinical Immunology* 7th Edition, Stites & Terr, eds. (1991)).

The immunoassays of the present disclosure can be performed in any of a number of configurations (see, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non isotopic Immunoassays* Plenum Press, NY).

Immunoassays often utilize a labeling agent to specifically bind to and label the binding complex formed by the capture agent and the analyte (e.g., an anti-BoNT/F antibody/BoNT/F complex). The labeling agent can itself be one of the moieties comprising the antibody/analyte complex. Thus, for example, the labeling agent can be a labeled BoNT/F polypeptide or a labeled anti-BoNT/F antibody. Alternatively, the labeling agent is optionally a third moiety, such as another antibody, that specifically binds to the BoNT antibody, the BoNT peptide(s), the antibody/polypeptide complex, or to a modified capture group (e.g., biotin) which is covalently linked to BoNT polypeptide or to the anti-BoNT antibody.

The labeling agent encompasses an antibody that specifically binds to the anti-BoNT antibody. Such agents are well known to those of skill in the art, and most typically comprise labeled antibodies that specifically bind antibodies of the particular animal species from which the anti-BoNT antibody is derived (e.g., an anti-species antibody). Thus, for example, where the capture agent is a human derived BoNT/F antibody, the label agent may be a mouse anti-human IgG, i.e., an antibody specific to the constant region of the human antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong non immunogenic reactivity with immunoglobulin constant regions from a variety of species (see generally Kronval, et al., (1973) *J. Immunol.*, 111: 1401-1406, and Akerstrom, et al., (1985) *J. Immunol.*, 135: 2589-2542, and the like).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays are carried out at ambient temperature, although they can be conducted over a range of temperatures, such as 5° C. to 45° C.

1) Non Competitive Assay Formats.

Immunoassays for detecting BoNT neurotoxins (e.g. BoNT serotypes and/or subtypes) may be either competitive or noncompetitive. Noncompetitive immunoassays are assays in which the amount of captured analyte (in this case, BoNT polypeptide) is directly measured. In one preferred "sandwich" assay, for example, the capture agent (e.g., an anti-BoNT antibody) is bound directly or indirectly to a solid substrate where it is immobilized. These immobilized anti-BoNT antibodies capture BoNT polypeptide(s) present in a test sample (e.g., a blood sample). The BoNT polypeptide(s) thus immobilized are then bound by a labeling agent, e.g., an anti-BoNT antibody bearing a label. Alternatively, the second antibody may lack a label, but it may, in turn, be bound by a labeled third antibody specific to antibodies of the species from which the second antibody is derived. Free labeled antibody is washed away and the remaining bound labeled antibody is detected (e.g., using a gamma detector where the label is radioactive).

2) Competitive Assay Formats.

In competitive assays, the amount of analyte (e.g., BoNT) present in the sample is measured indirectly by measuring the amount of an added (exogenous) analyte displaced (or competed away) from a capture agent (e.g., anti-BoNT antibody) by the analyte present in the sample. For example, in one competitive assay, a known amount of BoNT is added to a test sample with an unquantified amount of BoNT, and the sample is contacted with a capture agent, e.g., an anti-BoNT antibody that specifically binds BoNT/F. The amount of added BoNT that binds to the anti-BoNT antibody is inversely proportional to the concentration of BoNT/F present in the test sample.

The anti-BoNT antibody can be immobilized on a solid substrate. The amount of BoNT bound to the anti-BoNT antibody is determined either by measuring the amount of BoNT present in a BoNT-anti-BoNT antibody complex, or alternatively by measuring the amount of remaining uncomplexed BoNT.

B) Reduction of Non Specific Binding.

One of skill will appreciate that it is often desirable to reduce non specific binding in immunoassays and during analyte purification. Where the assay involves, for example BoNT/E polypeptide(s), BoNT/E-binding antibody, or other capture agent(s) immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

C) Substrates.

As mentioned above, depending upon the assay, various components, including the BoNT polypeptide(s), anti-BoNT antibodies, etc., are optionally bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, and enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, (1970) *J. Biol. Chem.* 245 3059.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082, which is incorporated herein by reference.

D) Other Assay Formats

BoNT polypeptides or anti-BoNT antibodies (e.g. BoNT neutralizing antibodies) can also be detected and quantified by any of a number of other means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Western blot analysis and related methods can also be used to detect and quantify the presence of BoNT polypeptides in a sample. The technique generally comprises separating sample products by gel electrophoresis on the basis of molecular weight, transferring the separated products to a suitable solid support, (such as a nitrocellulose filter, a nylon filter, or derivatized nylon filter), and incubating the sample with the antibodies that specifically bind either the BoNT polypeptide. The antibodies specifically bind to the biological agent of interest on the solid support. These antibodies are directly labeled or alternatively are subsequently detected using labeled antibodies (e.g., labeled sheep anti-human antibodies where the antibody to a marker gene is a human antibody) which specifically bind to the antibody which binds the BoNT polypeptide.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34-41).

E) Labeling of Anti-BoNT Antibodies.

Anti-BoNT antibodies can be labeled by any of a number of methods known to those of skill in the art. Thus, for example, the labeling agent can be, e.g., a monoclonal antibody, a polyclonal antibody, a protein or complex such as those described herein, or a polymer such as an affinity matrix, carbohydrate or lipid. Detection proceeds by any known method, including immunoblotting, western analysis, gel-mobility shift assays, tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The detectable group can be any material having a detectable physical or chemical property. Such detectable labels have been well-developed in the field of immunoassays and, in general, any label useful in such methods can be applied in the various embodiments of the present disclosure. Thus, a label is any composition detectable by spectroscopic, photochemical, biochemical, immunochemical, electrical, optical or chemical means. Useful labels in the present disclosure include magnetic beads (e.g. Dynabeads™), fluorescent dyes (e.g., fluorescein isothiocyanate, Texas red, rhodamine, Alexa fluor dyes and the like), radiolabels (e.g., $^3$H, $^{125}$I, $^{35}$S, $^{14}$C, or $^{32}$P), enzymes (e.g., LacZ, CAT, horse radish peroxidase, luciferase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads. For example, an antibody can include a fluorescent label, a chemiluminescent label, a radiolabel, a chromogenic label, or other suitable label.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of BoNT peptides. In this case, antigen-coated particles are agglutinated by samples comprising the target antibodies. In this format, none of the components need be labeled and the presence of the target antibody is detected by simple visual inspection.

IX. Compositions.

The BoNT-binding antibodies of this disclosure are useful in preventing or mitigating the progression of botulism produced, e.g., by endogenous disease processes or by chemical/biological warfare agents. Typically compositions containing one, two, or more different antibodies can be provided as a pharmaceutical composition and administered to a mammal (e.g., to a human) in need thereof.

As disclosed herein, particularly efficient neutralization of a botulism neurotoxin (BoNT) can be achieved by the use of antibodies that bind two or more BoNT subtypes/serotypes/mosaics with high affinity. This can be accomplished by using one, two or more different antibodies. Where there is more than one type of antibody, each can be directed against a different subtype. One or more of the antibodies can also be cross-reactive. Cross-reactive antibodies can bind two or more BoNT serotypes/subtypes (e.g., BoNT/CD, BoNT/D, BoNT/DC, BoNT/G etc.) with high affinity.

Different neutralizing antibodies when combined, exhibit a potency that is increased dramatically. This increase makes it possible to generate a botulinum antibody composition of the required potency for therapeutic use. Compositions comprising at least two, at least three, or more high affinity antibodies that bind overlapping or non-overlapping epitopes on the BoNT are contemplated herein.

Compositions contemplated herein may contain two, three, or more different antibodies selected from antibodies of the present disclosure (e.g. any of the clones as shown in FIG. 4 or FIG. 5). For example, the composition may include antibodies comprising one or more CDRs from these antibodies, and/or one or more antibodies comprising mutants or derivatives of these antibodies. Examples of compositions of the present disclosure contain one, at least 2, at least 3, or at least 4 of the antibodies: 1C1.1, 87C78, 4C1, 4C2, 4C4.1, 4C4.2, 4C4, 4C5, 4C10, 4C10.1, 4C10.2, 8D1, 8D2, 8DC1, DC1.2, 8DC2, 8DC4, 8DC4.1, 6F1, 6F3, 4E17.2, 42G8, 43D3, 6F8, hu6F8, 6F9, hu6F9, 6F10, hu6F10, which antibodies can be provided in combination with a pharmaceutical carrier. Other antibodies that may be included in the composition may be selected from: 39A1, 41C2, 43D3, 39H6, 41E2, 41F7, 39D5.1, 41G8, 7G1, 7G1.1, 7G2, 7G2.1, 7G3, 7G4, 7G5, 7G6, 7G7, 7G8, 7G9, 7G10, 7G11, 2B23EK1, 2B23EK4, 2B23EK5, 2B23EK6, 2B23EK7, 2B23EK10, 2B23EK11, 2B23EK12, 6F5.1, 8D2.2, 8D2.3, 8DC3.1, 8DC8.3, 8DC8.6, B4, A9, and A2S (e.g., any of the clones listed in Table 6).

The subject composition encompasses compositions that specifically bind to one or more serotypes/subtypes/mosaics. The composition can contain one or more antibodies that are cross-reactive. The composition may also contain any first combination of antibodies described above that specifically bind to one serotype together with a second combination of antibodies that specifically neutralizes a different serotype. The subject composition may contain multiple combinations such that that composition may bind and/or neturalize two, three, or more serotypes/subtypes (e.g. BoNT/CD, BoNT/D, BoNT/DC, etc.).

A composition that neutralizes multiple serotypes may include any of the combinations described above or one or more of the antibodies disclosed in Tables 1-8 and/or FIG. 4 and/or FIG. 5.

Where combinations of antibodies are disclosed herein, such combinations can be provided in a single formulation or can be provided as separate formulations in a kit, where the separate formulations may contain a single antibody or two antibodies. Such separate formulations of a kit may be combined prior to administration or administered by separate injection.

The anti-BoNT antibodies provided by the present disclosure are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. The antibodies comprising the pharmaceutical compositions of the present disclosure, when administered orally, are preferably protected from digestion. This is typically accomplished either by complexing the antibodies with a composition to render them resistant to acidic and enzymatic hydrolysis or by packaging the antibodies in an appropriately resistant carrier such as a liposome. Means of protecting proteins from digestion are well known in the art.

The pharmaceutical compositions of the present disclosure are particularly useful for parenteral administration, such as intravenous administration or administration into a body cavity or lumen of an organ. The compositions for administration can comprise a solution of one or more anti-BoNT antibody dissolved in a pharmaceutically acceptable carrier, which may be an aqueous carrier. A variety of aqueous carriers can be used, e.g., buffered saline and the like.

Non-aqueous pharmaceutically acceptable carriers (excipients) are known to those of skill in the art. Such excipients can comprise any substance that is biocompatible and liquid or soft enough at the subject's body temperature to release the active agent(s) (e.g., Anti-BoNT antibodies) into the subject's bloodstream at a desired rate. Non-aqueous carriers are usually hydrophobic and commonly organic, e.g., an oil or fat of vegetable, animal, mineral or synthetic origin or derivation. The carrier may include at least one chemical moiety of the kind that typifies "fatty" compounds, e.g., fatty acids, alcohols, esters, etc., i.e., a hydrocarbon chain, an ester linkage, or both. "Fatty" acids in this context include, but are not limited to, acetic, propionic and butyric acids through straight- or branched-chain organic acids containing up to 30 or more carbon atoms. The non-aqueous carrier may be immiscible in water and/or soluble in the substances commonly known as fat solvents. The non-aqueous carrier can correspond to a reaction product of a "fatty" compound or compounds with a hydroxy compound, e.g., a mono-hydric, di-hydric, trihydric or other polyhydric alcohol, e.g., glycerol, propanediol, lauryl alcohol, polyethylene or -propylene glycol, etc. These compounds include, but are not limited to, the fat-soluble vitamins, e.g., tocopherols and their esters, e.g., acetates sometimes produced to stabilize tocopherols. Sometimes, for economic reasons, the carrier can comprise a natural, unmodified vegetable oil such as sesame oil, soybean oil, peanut oil, palm oil, or an unmodified fat. Alternatively the vegetable oil or fat may be modified by hydrogenation or other chemical means which is compatible with the present disclosure. The appropriate use of hydrophobic substances prepared by synthetic means is also envisioned. Non-aqueous excipient compositions can also comprise, in addition to a biocompatible oil, an "antihydration agent" which term as used herein means a substance that retards hydration of the active agent(s) and/or the biocompatible oil or fat and thereby further decreases and/or stabilizes the rate of release of the active agent(s) from that composition following administration to an animal (e.g. human). A great variety of non-toxic antihydration agents are known. By way of example there are "gelling" agents that, when dispersed, and in some cases heated to dissolve them in the oil, give the body of oil greater visco-elasticity (and therefore greater structural stability) and thereby slow down penetration of the oil by body fluids.

Illustrative antihydration agents include various polyvalent metal salts or complexes of organic acids, for instance fatty acids having from about 8 or 10 to about 20 or 22 carbon atoms, e.g. aluminum, zinc, magnesium or calcium salts of lauric acid, palmitic acid, stearic acid and the like. Such salts can be mono-, di- or tri-substituted, depending on the valence of the metal and the degree of oxidation of the metal by the acid. Of common usage are the aluminum salts of such fatty acids. Aluminum monostearate and distearate are frequently used anti-hydration agents. Others that are useful include aluminum tristearate, calcium mono- and distearate, magnesium mono- and distearate and the corresponding palmitates, laurates and the like. The concentration of such an antihydration agent, based on the weight of the oil plus that agent, may be between about 1% and about 10% (most typically between about 2% and about 5%), although other concentrations may be suitable in some cases.

The various solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of anti-BoNT antibody in these formulations can vary widely, and will be selected primarily based on fluid volumes, viscosities, body weight and the like in accordance with the particular mode of administration selected and the patient's needs. In some instances, the solutions may be stored in lyophilized or frozen form. Examples of suitable anti-BoNT antibody formulations are described in WO 2011/028961.

Thus, a typical pharmaceutical composition for intravenous administration would be about 0.1 to 10 mg per patient per day. Dosages from about 1 mg up to about 200 mg per patient per day can be used. Methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the anti-BoNT antibodies of the present disclosure or a cocktail thereof can be administered for therapeutic and/or prophylactic treatments. Preferred pharmaceutical compositions are administered in a dosage sufficient to neutralize (mitigate or eliminate) the BoNT toxin(s) (i.e., reduce or eliminate a symptom of BoNT poisoning (botulism)). An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the antibodies of the present disclosure to effectively treat the patient.

The present disclosure thus provides a method of neutralizing a Botulinum neurotoxin in an individual (e.g., a human; or a non-human mammal), the method generally involving administering to the individual an effective amount of a subject anti-BoNT antibody, or an effective amount of a subject composition comprising a subject anti-BoNT antibody. The treatments essentially comprise administering to the poisoned organism (e.g. human or non-human mammal) a quantity of one or more neutralizing antibodies sufficient to neutralize (e.g. mitigate or eliminate) symptoms of BoNT poisoning. Administering the antibody, or the composition comprising the antibody, provides for neutralization of Botulinum neurotoxin present in the individual. The BoNT poisoning can be due to ingestion of contaminated food products (food botulism), can result from an anaerobic wound infection (wound botulism), or can result from an act of biological warfare or bioterrorism.

The present disclosure also provides methods of reducing the likelihood that an individual at risk of exposure to Botulinum neurotoxin will experience symptoms of Botulinum neurotoxin poisoning following exposure to the Botulinum neurotoxin (e.g., where the exposure is via inhalation, via ingestion, via a wound infection, or via another route/mode of exposure). Administration of a subject antibody or subject composition reduces the likelihood that the individual will experience symptoms of Botulinum neurotoxin poisoning. Thus, e.g., a subject anti-BoNT antibody, or a subject composition comprising a subject anti-BoNT antibody, can be administered to an individual before the individual has Botulinum neurotoxin poisoning, e.g., before a BoNT is present in the individual. For example, a subject anti-BoNT antibody, or a subject composition comprising a subject anti-BoNT antibody, can be administered to an individual who is at risk of BoNT exposure, e.g., an individual who is at greater risk than the general population of experiencing Botulinum neurotoxin exposure and poisoning. Such individuals include, e.g., military personnel, e.g., military personnel in a combat setting; personnel involved in investigation or clean up of a site suspected of involving Botulinum neurotoxin exposure (e.g., hazardous materials ("hazmat") personnel) and other individuals who are at risk of Botulinum neurotoxin exposure, either accidental or intentional.

X. Kits for Diagnosis or Treatment.

Kits for the treatment of botulism or for the detection/confirmation of a *Clostridium botulinum* infection are also provided. Kits will typically comprise one or more anti-BoNT antibodies (e.g., anti-BoNT antibodies in a composition for pharmaceutical use). For diagnostic purposes, the antibody(s) can optionally be labeled. In addition the kits will typically include instructional materials disclosing means of use anti-BoNT antibodies in the treatment of symptoms of botulism. The kits may also include additional components to facilitate the particular application for which the kit is designed. Thus, for example, where a kit contains one or more anti-BoNT antibodies for detection of diagnosis of BoNT subtype, the antibody can be labeled, and the kit can additionally contain means of detecting the label (e.g. enzyme substrates for enzymatic labels, filter sets to detect fluorescent labels, appropriate secondary labels such as a sheep anti-human antibody, or the like). The kits may additionally include buffers and other reagents routinely used for the practice of a particular method. Such kits and appropriate contents are well known to those of skill in the art.

Kits provided for the treatment of botulism may contain one or more anti-BoNT antibodies. The antibodies can be provided separately or mixed together. Typically the antibodies will be provided in a sterile pharmacologically acceptable excipient. The antibodies can also be provided pre-loaded into a delivery device (e.g., a disposable syringe).

The kits can optionally include instructional materials teaching the use of the antibodies, recommended dosages, contraindications, and the like.

EXAMPLES

The following examples are offered to illustrate, but not to limit any embodiments provided by the present disclosure.

Overview

The use of yeast display to generate and affinity or specificity mature antibodies from immunized humans or mice is reported herein. Repertoires of 6 human donor or 13 immunized mice antibody variable genes were displayed as single chain Fv (scFv) on the surface of yeast and a total of 175 scFv leads (17 specific for BoNT/A $L_C$, 3 for BoNT/A HC, 37 for BoNT/B $L_C$, 16 for BoNT/B $H_C$, 52 for BoNT/C, BoNT/D, BoNT/DC and BoNT/CD, 37 for BoNT/F, 13 for BoNT/G) isolated, engineered and characterized. These scFvs were epitopically diverse, binding one or more of the three different BoNT functional domains of each serotype with an average $K_D$ in the low nanomolar to picomolar range. The converted IgG antibodies from some of those scFv leads bound multiple subtypes of BoNT/A, BoNT/B, BoNT/C, BoNT/D, BoNT/E, BoNT/F, BoNT/G and should prove to be useful for the development of sensitive and specific diagnostics or potent therapeutics for botulism either in human or in animals.

Materials and Methods
Oligonucleotide Primers
Primary human library construction in pYD2 vector HuVH2bBACK:
(SEQ ID NO: 453)
5'-CAGGTCACCTTGAAGGAGTCTGG-3'

HuVH5bBACK:
(SEQ ID NO: 454)
5'-GAGGTGCAGCTGGTGCAGTCTGG-3'

HuVH7aBACK:
(SEQ ID NO: 455)
5'-CAGGTGCAGCTGGTGCAATCTGG-3'

HuVK2aBACK:
(SEQ ID NO: 456)
5'-GATATTGTGATGACTCAGTCTCC-3'

HuVK2bBACK:
(SEQ ID NO: 457)
5'-GATATTGTGATGACCCAGATCCC-3'

Light chain shuffled human library construction in pYD2 vector

GAP5-HuRJH1-2BACK:
(SEQ ID NO: 458)
5'-GTGGTGGTGGTTCTGCTAGCGGGGCCATGGCCACCCTGGTCACCGTCTCCTCA-3'

GAP5-HuRJH3BACK:
(SEQ ID NO: 459)
5'-GGTGGTGGTTCTGCTAGCGGGGCCATGGCGACAATGGTCACCGTCTCTTCA-3'

GAP5-HuRJH4-5 BACK:
(SEQ ID NO: 460)
5'-GGTGGTGGTTCTGCTAGCGGGGCCATGGCAACCCTGGTCACCGTCTCCTCA-3

GAP5-HuRJH6 BACK:
(SEQ ID NO: 461)
5'-GGTGGTGGTTCTGCTAGCGGGGCCATGGCGACCACGGTCACCGTCTCCTCA-3

PYDFOR1:
(SEQ ID NO: 462)
5'-GTCGATTTTGTTACATCTACAC-3'

Underlined region anneals to $J_H$ gene, bolded sequence is the NcoI restriction site
Primers for Mouse scfv Library Construction with pYD4 Vector MMVH1pYD4Gap5 ':
(SEQ ID NO: 463)
5'-GACTATGCAGCTAGCGGTGCCATGGCAGAGGTGCAGCTTCAGGAGTCAGG-3'

MMVH2pYD4Gap5':
(SEQ ID NO: 464)
5'-GACTATGCAGCTAGCGGTGCCATGGCAGATGTGCAGCTTCAGGAGTCRGG-3'

MMVH3pYD4Gap5':
(SEQ ID NO: 465)
5'-GACTATGCAGCTAGCGGTGCCATGGCACAGGTGCAGCTGAAGSAGTCAGG-3'

MMVH4pYD4Gap5':
(SEQ ID NO: 466)
5'-GACTATGCAGCTAGCGGTGCCATGGCAGAGGTYCAGCTGCARCARTCTGG-3'

MMVH5pYD4Gap5':
(SEQ ID NO: 467)
5'-GACTATGCAGCTAGCGGTGCCATGGCACAGGTYCARCTGCAGCAGYCTGG-3'

MMVH7pYD4Gap5':
(SEQ ID NO: 468)
5'-GACTATGCAGCTAGCGGTGCCATGGCAGARGTGAAGCTGGTGGARTCTGG-3'

MMVH8pYD4Gap5':
(SEQ ID NO: 469)
5'-GACTATGCAGCTAGCGGTGCCATGGCAGAGGTTCAGCTTCAGCAGTCTGG-3'

MMVH10pYD4Gap5':
(SEQ ID NO: 470)
5'-GACTATGCAGCTAGCGGTGCCATGGCAGAAGTGCAGCTGKTGGAGWCTGG-3'

MMVH11pYD4Gap5':
(SEQ ID NO: 471)
5'-GACTATGCAGCTAGCGGTGCCATGGCACAGATCCAGTTGCTGCAGTCTGG-3'

MMVH1pYD4Gap3':
(SEQ ID NO: 472)
5'-GTTGAGCCTCCGGACTTAAGGTCGACTGAGGAGACGGTGACCGTGGTCCC-3'

MMVH2pYD4Gap3':
(SEQ ID NO: 473)
5'-GTTGAGCCTCCGGACTTAAGGTCGACTGAGGAGACTGTGAGAGTGGTGCC-3'

MMVH3pYD4Gap3':
(SEQ ID NO: 474)
5'-GTTGAGCCTCCGGACTTAAGGTCGACTGCAGAGACAGTGACCAGAGTCCC-3'

MMVH4pYD4Gap3':
(SEQ ID NO: 475)
5'-GTTGAGCCTCCGGACTTAAGGTCGACTGAGGAGACGGTGACTGAGGTTCC-3'

MMVK1pYD4Gap5':
(SEQ ID NO: 476)
5'-GGAGAAGGTAGTAGTGGATCCGCGCGCGACATTGTGATGWCACAGTCTCC-3'

MMVK2pYD4Gap5':
(SEQ ID NO: 477)
5'-GGAGAAGGTAGTAGTGGATCCGCGCGCGATGTTKTGATGACCCAAACTCC-3'

MMVK3pYD4Gap5':
(SEQ ID NO: 478)
5'-GGAGAAGGTAGTAGTGGATCCGCGCGCGATATTGTGATRACBCAGGCWGC-3'

MMVK4pYD4Gap5':
(SEQ ID NO: 479)
5'-GGAGAAGGTAGTAGTGGATCCGCGCGCGACATTGTGCTGACMCARTCTCC-3'

MMVK5pYD4Gap5':
(SEQ ID NO: 480)
5'-GGAGAAGGTAGTAGTGGATCCGCGCGCSAAAWTGTKCTCACCCAGTCTCC-3'

MMVK6pYD4Gap5':
(SEQ ID NO: 481)
5'-GGAGAAGGTAGTAGTGGATCCGCGCGCGAYATYVWGATGACMCAGWCTCC-3'

-continued

MMVK7pYD4Gap5':
(SEQ ID NO: 482)
5'-GGAGAAGGTAGTAGTGGATCCGCGCGCCAAATTGTTCTCACCCAGT
CTCC-3'

MMVK8pYD4Gap5':
(SEQ ID NO: 483)
5'-GGAGAAGGTAGTAGTGGATCCGCGCGCTCATTATTGCAGGTGCTTG
TGGG-3'

MMGap3 VKdeg:
(SEQ ID NO: 484)
5'-GGCTTACCTTCGAAGGGCCCGCCTGCGGCCGCTTTBAKYTCCARYYT
KGTCCCHBM-3'

MMGap3 Vkprimer1:
(SEQ ID NO: 485)
5'-GGCTTACCTTCGAAGGGCCCGCCTGCGGCCGCTTTGATTTCCAGCT
TGGTGCCTCC-3'

MMGap3 Vkprimer2:
(SEQ ID NO: 486)
5'-GGCTTACCTTCGAAGGGCCCGCCTGCGGCCGCTTTTATTTCCAGCTT
GGTCCCCCC-3'

MMGap3 Vkprimer3:
(SEQ ID NO: 487)
5'-GGCTTACCTTCGAAGGGCCCGCCTGCGGCCGCTTTTATTTCCAGTC
TGGTCCCATC-3'

MMGap3 Vkprimer4:
(SEQ ID NO: 488)
5'-GGCTTACCTTCGAAGGGCCCGCCTGCGGCCGCTTTTATTTCCAACTT
TGTCCCCGA-3'

MMGap3 Vkprimer5:
(SEQ ID NO: 489)
5'-GGCTTACCTTCGAAGGGCCCGCCTGCGGCCGCTTTCAGCTCCAGCTT
GGTCCCAGC-3'

For $V_H$ gene amplification from pYD2 vector pYDFOR:
(SEQ ID NO: 490)
5'-AGTAACGTTTGTCAGTAATTGC-3'

LinkRev:
(SEQ ID NO: 491)
5'-CGACCCGCCACCGCCAGAGCCACCTCCGCC-3'

As an example for toxin epitope mapping for selected antibodies, BoNT/B domains are subcloned in pYD2 vector and expressed on the yeast surface. The following primers are used for PCR amplification of each domain before they were subcloned into pYD2 vector. Each underlined segment corresponds to the DNA sequence of each BoNT/B toxin domain. Similar primers with the underlined DNA sequence changed to match the sequence of other BoNT serotypes (e.g., BoNT/C, BoNT/D, BoNT/F, BoNT/G, etc) could be used to get their toxin domain expressed on the yeast surface. These yeast displayed toxin domains could be used for epitope mapping the selected antibodies.

BoNTB1-HN5-NcoI:
(SEQ ID NO: 492)
5'-ATATATAATCCATGGCTCCAGGAATCTGTATCGACGTCGAC-3'

BoNTB1-HN3-NotI
(SEQ ID NO: 493)
5'-TGTATAATTGCGGCCGCCAGGATTTCGGAATTGTATTTGTTG-3'

BoNTB1-HC5-NcoI
(SEQ ID NO: 494)
5'-ATATATAATCCATGGCCAACAATATCATCCTGAACCTGCGTTAC-3'

BoNTB1-HC3-NotI
(SEQ ID NO: 495)
5'-TGTATAATTGCGGCCGCTTCGGTCCAACCTTCGTCTTTCGG-3'

BoNT B1-LC5-NcoI
(SEQ ID NO: 496)
5'-ATATATAATCCATGGCCCCAGTTACCATCAACAACTTCAACTAC-3

BoNT B1-LC3-NotI
(SEQ ID NO: 497)
5'-TGTATAATTGCGGCCGCCTTAACAGACTTACACATTTGAATCT
TG-3'

Unique linker sequence between $V_H$ and $V_L$ with designed cutting sites in pYD4 vector (SEQ ID NO: 498)
GTCGACCTTAAGTCCGGAGGTTCTACTTCCGGTTCCGGTAAGCCAGGTT
CTGGTGAAGGTTCTTCTGGATCCGCGCGC The sequence of HA tag (underlined) between Aga2 linker and VH in pYD4 vector (SEQ ID NO: 499)
TATCCATACGATGTTCCTGACTATGCAGCTAGCGGTGCCATGGCAC Strains, Media, Antibodies, and Toxins Yeast strain *Saccharomyces cerevisiae* EBY100 (GAL1-AGA1TURA3 ura3-52 trp1 leu2Δ1 his3Δ200 pep4::HIS3 prb1Δ1.6R can1) was maintained in YPD medium (1% yeast extract, 2% peptone, 2% dextrose) (Current Protocols in Molecular Biology, John Wiley and Sons, Chapter 13.1.2). EBY100 transformed with expression vector pYD2 (Razai A et al. (2005) *J. Mol. Biol.* 351:158-169) was selected on SD-CAA medium (0.7% yeast nitrogen base, 0.1M Sodium phosphate, 0.5% casamino acids, 2% dextrose, 0.006% Leucine). ScFv yeast surface display was induced by transferring yeast cultures from SD-CAA to SG-CAA medium (identical to SD-CAA medium except the glucose was replaced by galactose) and growing at 18° C. for 24~48 hr as described previously (Feldhaus, M J et al. (2003) *Nature Biotechnol.* 21:163-170). Bacteria strain *E. coli* DH5α, (K12, Δ(lac-pro), supE, thi, hsdD5/F' traD36, proA+B+, lacIq, lacZΔM15) was used for cloning and preparation of plasmid DNA. Pure or Crude BoNT/A1 (Hall hyper), BoNT/A2 (FRI-H1A2), BoNT/B1, BoNT/B2, BoNT/B3, BoNT/B4, BoNT/C1, BoNT/CD, BoNT/DC, BoNT/D, BoNT/F1, BoNT/F6, BoNT/G were either purchased from Metabiologics (Madison, Wis.) or purified from their respective strains by researchers at USARMIID. Mouse anti-SV5 and anti-myc 9E10 antibody and BoNT/A antibodies 7C1 and 9D8 were purified from hybridoma supernatant using Protein G and directly labeled with Alexa-488 or Alexa-647 using a kit provided by the manufacturer (Molecular Probes). Other recombinant human antibodies (Razai A et al. (2005) *J. Mol. Biol.* 351:158-169; Nowakowski A et al. (2002) *Proc. Natl. Acad. Sci. USA* 99:11346-11350; Kalb S R et al. *International Journal of Mass Spectrometry* 278:101-108; Kalb S R et al. *PLoS ONE* 4(4): e5355. doi:10.1371/journal.pone.0005355; Lou J. et al (2010) *Protein Engineering, Design & Selection.* 23(4):311-319) specific for BoNT/A, BoNT/B, BoNT/C, BoNT/D, BoNT/E, BoNT/F or BoNT/G were prepared from stable cell line production of Chinese hamster ovary cells (CHO) supernatants as described before ((Razai A et al. (2005) *J. Mol. Biol.* 351:158-169; Nowakowski A et al. (2002) *Proc. Natl. Acad. Sci. USA* 99:11346-11350). For flow cytometry (FACS), purified human or mouse IgGs were directly labeled with either Alexa-647 or Alexa-488 using a kit provided by the manufacturer (Molecular Probes).

Immune scFv Yeast Antibody Library Generation in Bacteria and in Yeast

Six scFv yeast libraries were constructed in pYD2 vector using V-genes isolated from human volunteers immunized with pentavalent toxoid, and thirteen scFv yeast libraries were constructed in pYD4 vector with V-genes from mice immunized either with purified recombinant toxin domain (ALC, BLC, FHC) or with monovalent toxin of BoNT/F. For human scFv library construction, briefly, approximately 25 ml of blood was drawn 7 days after immunization and PBLs isolated using Lymphoprep tubes (Axis-Shield PoC AS, Norway). Blood was drawn after obtaining informed consent and under a protocol reviewed and approved by the USAMRIID and UCSF IRBs. Total RNA was isolated from PBLs using an RNAgents® kit (Promega). cDNA was synthesized from total RNA by using AMV reverse transcriptase (Invitrogen) and HuIgG1-4-C1FOR, HuCK1FOR primers (Marks, J D et al. (1991) *J Mol Biol* 222:581-97; Amersdorfer P et al. (2002) *Vaccine.* 20: 1640-1648). $V_H$ and $V_K$ gene fragments were amplified by PCR from cDNA by using Pfu polymerase (Stratagene) and a mixture of HuVH1-6BACK, HuVH2bBACK, HuVH5bBACK, HuVH7aBACK and HuJH1-5FOR mix primers for the $V_H$ gene and HuVK1-6BACK, HuVK2aBACK, HuVK2bBACK and HuJK1-5FOR primers or the $V_k$ gene (Marks, J D et al. (1991) *Eur. J. Immunol.* 21:985-991). scFv linker DNA template for pYD2 vector was prepared as previously described (Marks, J D et al. (1991) *J Mol Biol* 222:581-97), but the unique linker with cloning sites designed was synthesized for pYD4 vector, and pYD4 vector was used for construction of 13 mouse immune libraries and for individual clone affinity or specificity maturation. The whole library construction process was very similar to the ones used for human library, except total RNA was prepared from mouse spleen instead of human PBL, and all the primers used are those for mouse V-gene amplification (described in the Material and Methods section with a name start as "MM", e.g, MMVH1pYD4Gap5'). PCR amplified $V_H$ or $V_K$ DNA fragments were gel purified, isolated from the gel using GENECLEAN® Turbo (Q.BIOgene). Human scFv gene repertoires were constructed by using PCR to splice together the $V_H$ and $V_K$ gene repertoires with scFv linker DNA (Marks, J D et al. (1991) *J Mol Biol* 222:581-97). The scFv genes were gel purified, isolated from the gel and reamplified using HuVHBACK and HuJkFOR primer mixes which appended NcoI and NotI site restriction sites (Marks, J D et al. (1991) *J Mol Biol* 222:581-97). scFv genes were digested with NcoI an NotI and ligated into NcoI-NotI digested pYD2 (Razai A et al. (2005) *J. Mol. Biol.* 351:158-169). For pYD2 gap-repair transformation, scFv gene repertoires were amplified from the ligation mixtures using primers GAP5 and GAP3 (Razai A et al. (2005) *J. Mol. Biol.* 351:158-169) to append homologous overlaps with pYD2. Appended scFv PCR products were ethanol precipitated, combined with NcoI-NotI digested pYD2 and used to transform EBY100 (Gietz, R D and Schiestl, R H (1991) *Yeast* 7:253-263; Orr-Weaver, T L et al. (1983) *Proc. Natl. Acad. Sci. USA* 80:4417-4421). The mouse scFv gene repertoires with the unique linker and HA tag at the N-terminal of scFv were prepared by two step sequential cloning into pYD4 vector, and the libraries were kept both in bacterial and in yeast. After PCR amplification of the mouse V-gene using the mouse primers with Gap tail, the 5' end of the amplified VL gene repertoire were cut with BamHI or BssHII, and the 3' end of the same VL gene repertoire cut with Not I, Apa I or BstBI, then the double cut VL genes were ligated into pYD4 vector which has been cut with the same sets of enzymes. The ligation product was used to transform *E. coli* DH5 cc to get a library with VL-only in pYD4 vector, this VL gene library is kept in bacteria. Alternatively the VL gene repertoire with the gap tail was used to transform yeast EBY100 directly to get a VL-only library in pYD4 vector, this library is created in yeast. The second cloning step is to insert the VH gene repertoire into this VL-only library. The VH gene repertoire is inserted into this VL library either by gap-repair or by cut and ligation. Using gap-repair method, the PCR amplified VH gene repertoire is mixed with the above mentioned VL library plasmids which was cut with Nco I and Sal I first, then the mixture used to transform yeast strain EBY 100 as described before (Gietz, R D and Schiestl, R H (1991) *Yeast* 7:253-263). So, the scFv display library is prepared and kept in yeast directly. Alternatively, based on the unique design, the VH gene repertoire was cut with NheI or NcoI at the 5' end, and with Afl II or BspE1 at the 3' end of the same VH, this double cut VH gene was then ligated into the VL-only library prepared with same double cutting method. The ligation product was used to transform *E. coli*, and a scFv yeast display library was created and kept in bacteria, milligram quantities of plasmid DNA covering the whole library was easily prepared from those transformed bacteria. These plasmid DNA was then used to transform yeast strain EBY100 to get a library in yeast. Transformed yeast were cultured and subcultured in SD-CAA and library size calculated by serially diluting and plating the transformed culture on SD-CAA plates. Final library size was calculated as the product of the number of transformants and the percentage of clones with full length scFv insert as determined by PCR (Razai A et al. (2005) *J. Mol. Biol.* 351:158-169). Library sizes of 4.1 to $25.7\times10^7$ were obtained for the 13 murine scFv libraries.

Selection and Characterization of scFv Antibodies for BoNT/A, BoNT/B, BoNT/C, BoNT/D, BoNT/E, BoNT/F or BoNT/G For antibody selection from yeast displayed library, a total amount of yeast that was ten to forty times the library size was grown and scFv display induced. For sorting, libraries were incubated with either recombinant produced toxin domain (ALC, BLC, BHC, etc) or holotoxin (BoNT/C, BoNT/D, BoNT/E, BoNT/F, BoNT/G, etc) in five times excess of antigen molecular, assuming each yeast expresses $1\times10^5$ scFv on the cell surface, at room temperature (RT) for 1 hr. The first two rounds were usually done by staining with 100-200 nM of each toxin or toxin domain, and the third and fourth round of staining were done by staining with lower (1-10 nM) concentration of the same toxin or another subtype of the same BoNT serotype. Libraries were washed once with ice cold FACS buffer (PBS (1.9 mM $NaH_2PO_4$, 8.1 mM $Na_2HPO_4$, 154 mM NaCl, pH7.4), 0.5% BSA, 1 mM $MgCl_2$, 0.5 mM $CaCl_2$) before reacting with the properly diluted toxin or toxin domain at room temperature for 1-2 hrs. BoNT binding was detected either by staining with Alexa-647 labeled human antibodies developed in the lab previously (such as ING2 for BoNT/A, B6.1 for BoNT/B, etc) or by using commercial polyclonal rabbit antibody before any human antibody was developed (such as for BoNT/C and BoNT/F, polyclonal rabbit antibody from Metabiologics (Madison, Wis.)). The staining reaction is normally performed at 4° C. for an hour, and simultaneously, scFv display level was quantitated by staining with 2.5 μg/ml anti-SV5 mAb labeled with Alexa-488. When rabbit polyclonal antibody was used for detection (i.e., to get the first human antibody for BoNT/C, BoNT/F, or BoNT/G), PE labeled goat anti-rabbit IgG (Jackson ImmunoResearch) is followed. Yeast libraries were washed as described, re-suspended in 200 to 700 μl of FACS buffer and were sorted on a FACS Aria (Becton-Dickinson) with sort gates set to collect all SV5 positive BoNT binding yeast. After the last round of sorting, yeast were plated on SD-CAA plates and individual clones grown and induced. Individual clones were screened to identify BoNT binding scFv and unique clones identified by DNA sequencing (Amersdorfer P et al. (2002) *Vaccine*. 20:1640-1648). For each unique clone, the affinity of the yeast displayed scFv for either the target toxin domain (ALC, BLC or BHC, etc) or for all the subtypes of the corresponding BoNT (BoNT/A1, A2, A3, BoNT/B1, B2, B3, B4, BoNT/C, CD, DC, D, BoNT/F1, 202F, BoNT/G etc) was determined exactly as previously described (Razai A et al. (2005) *J. Mol. Biol.* 351:158-169; Lou J. et al. (2010) *Protein Engineering, Design & Selection,* 23:311-319).

Construction and Expression of Yeast Displayed BoNT Domains and Mapping of Antibody Binding As an example for the BoNT toxin domain yeast display, primers BoNTB1-HC5-NcoI, BoNTB1-HC3-NotI, BoNTB1-HN5-NcoI, BoNTB1-HN3-NotI, and BoNTB1-LC5-NcoI and BoNTB1-LC3-NotI were designed to PCR amplify the BoNT/B1 (NCBI accession number YP_001693307) $H_C$ (amino acids N853-E1290) $H_N$ (amino acids P443-F854), or $L_C$ (amino acids M1-K441) gene fragment respectively adding the restriction sites NcoI and NotI. Each gene fragment was amplified by using PCR from a synthetic gene construct (Gilsdorf, J et al. (2006) *Protein Expr Purif* 46:256-67; Smith, L. A. & Henderson, I. (2006). Vaccines to protect against the neurotoxins. In *Treatments from Toxins: The therapeutic potential of Clostridial neurotoxins* (Foster, K., Hambleton, I. & Shone, C., eds.), pp. 75-106. CRC Press, Boca Raton, Fla.). Following digestion of both pYD2 and the resulting PCR amplification product with NcoI and Nod, the BoNT/B gene fragments were gel-purified and ligated into pYD2. Ligation mixtures were used to transform *E. coli* DH5α and correct transformed clones identified by DNA sequencing of the purified plasmid DNA. The same plasmid DNA was later used to transform LiAc-treated EBY100 cells. Yeast cultures were then grown and induced, as described above. Similarly primers HCFor, HCRev, HNFor, HNRev, and LCFor and LCRev were designed to PCR amplify the BoNT/A, BoNT/C, BoNT/D, BoNT/E, BoNT/F and BoNT/G $H_C$, $H_N$, or $L_C$ gene fragment respectively from synthetic gene constructs as reported (Levy R. et al. (2007) *J. Mol. Biol.* 365:196-210).

For mapping scFv binding to yeast displayed BoNT/A, BoNT/B, BoNT/C, BoNT/D, BoNT/E, BoNT/F or BoNT/G domains, scFv genes in pYD2 were excised by digestion with Ncol and Not1, ligated into pSYN1, and the ligation mixture used to transform *E. coli* DH5 cc. Soluble scFv expression was induced and the periplasmic fraction containing the scFv prepared as previously described (Schier, R et al. (1995) *Immunotechnology* 1:73-81). Periplasmic fractions containing scFv were incubated for 1 hour at RT with yeast displaying BoNT domains. After washing with phosphate buffered saline (PBS), yeast were incubated with 1 μg/ml of mAb 9E10 which recognizes an epitope tag at the scFv C-terminus. After washing, 9E10 binding was detected using 1 μg/ml anti-mouse gamma1 specific antibody (Jackson ImmunoResearch) and the level of BoNT domain display quantitated by incubation with 1 μg/ml of anti-SV5-Alexa-488. For some antibodies, mapping was performed by staining with 1 μg/ml of the respective IgG conjugated to Alexa-647. The IgG was converted from the scFv lead and produced in CHO cells as described below.

Mapping the Overlap of BoNT Antibodies

Each yeast displayed scFv was grown and induced and incubated with 20~100 nM BoNT/A, BoNT/B, BoNT/C, BoNT/D, BoNT/E, BoNT/F or BoNT/G for 1 hour at RT followed by washing with PBS. After re-suspension, yeasts were incubated with either scFv containing periplasmic preparations (see above) or purified IgG, followed by washing and then incubation with 1 μg/ml 9E10. After washing, 9E10 binding was detected using 1 μg/ml anti-mouse gamma1 specific antibody (Jackson ImmunoResearch) and the level of BoNT domain display quantitated by incubation with 1 μg/ml of anti-SV5-Alexa-488. For some antibodies, mapping was performed by staining with 1 μg/ml of the respective IgG conjugated to Alexa-647.

Affinity and Specificity Maturation of Selected Lead scFv by Chain Shuffling

Since the lead scFvs selected from the original library may not always have high enough affinity or broad enough specificity, we used chain shuffling to engineer the lead antibody before change them into full length IgG. Two different versions of a yeast display vector were created and used as: pYD2 and pYD4. The key differences between these two vectors are the linker between the VH and VL of the antibody and an HA tag following the leader sequence. The pYD2 vector has the traditional (G4S)$_3$ linker as reported (Schier, R et al. (1995) *Immunotechnology* 1:73-81), but the pYD4 has a new 20 amino acid linker (SGGSTSGSGKPGSGEGSSGS; SEQ ID NO:507) with 4 designed cloning sites (Afl II, BspE 1, BamHI and BssH II) integrated, and it has HA tag following the V gene leader sequence, so either the VH or the VL can easily shuffled by cloning. For a human library, a light chain library was created in the pYD2 by cloning in $V_L$ gene repertoires from donors six, nine, and ten. cDNA was synthesized from total RNA prepared from donor PBLs by using AMV reverse transcriptase (Invitrogen) and HuCK1FOR primers as published (Marks, J D et al. (1991). *J Mol Biol* 222:581-97; Amersdorfer P et al. (2002) *Vaccine*. 20: 1640-1648). $V_K$ gene fragments were amplified by PCR from cDNA by using Pfu polymerase (Stratagene) and an equimolar mixture of the four GAP5-HuRJHBACK primers and the primer pYDForVL (Marks, J D et al. (1991) *J Mol Biol* 222:581-97). To further increase light chain diversity, the light chain repertoire cloned into pYD2 from a large non-immune scFv phage antibody library was also utilized (Sheets, M D et al. (1998) *Proc Natl Acad Sci USA* 95:6157-62). PCR fragments were gel purified, digested with Ncol and NotI, and ligated into NcoI-NotI digested pYD2. The ligation mixture was used to transform *E. coli* DH5α, creating a light chain shuffling library of size 4.2×10$^7$ that was determined to be diverse by PCR fingerprinting and DNA sequencing, and it is created and kept in bacteria. To create light chain shuffled scFv libraries, light chain library DNA was prepared and digested with either NheI or HindIII and NcoI. It was determined that when cutting with NheI-Not1, recombination could occur between the scFv linker DNA and the Gly-Ser linker after the AgaII protein, resulting in approximately 1-20% of transformants having no light chain. Digesting with HindIII cuts in AgaII, eliminating this problem. The $V_H$ gene was amplified from its respective scFv gene in pYD2 using primers that annealed upstream of the $V_H$ gene (pYDFOR) and a primer than annealed in the framework 4 linker region (LinkRev). Gel purified $V_H$ gene was mixed with digested vector DNA and used to transform LiAc-treated EBY100 yeast cells. Alternatively, scFv chain shuffled libraries were created by amplifying the $V_H$ FR4-scFv linker-$V_L$ gene repertoire from pYD2 and splicing it to a specific $V_H$ gene by overlap extension. The chain shuffled scFv gene repertoire was then cloned into pYD2. A total of twenty chain shuffled libraries were created from the $V_H$ genes of scFv lead as previously described (Marks J D et al. (1992) *Bio/Technology* 10:779-783) to get the affinity and cross reactivity maturated clones of 1B12.3, 1B12.4, 1C1.1, 4C2, 4C4, 4C4.1, 4C4.2, 4C5, 4C10, 4C10.1, 4C10.2 87C78, 8DC1, 8DC1.2, 8DC2, 8DC3, 8DC4, 8DC4.1, 8DC5, 4E17.2, 43D3, etc. The library size ranged from $2.0 \times 10^6$ to $4.0 \times 10^7$. Owing to the unique design of pYD4 vector, it is relative easy to chain shuffle the lead scFv by either cut and ligation or gap-repair. So, all the lead scFv with double digit nM or worse affinity are chain shuffled similarly before they were converted into full length IgG, such as 6F8.

To select higher affinity scFv, light chain shuffled libraries were grown and scFv display on the yeast surface induced. Induced yeast were stained with BoNT/A1, BoNT/B1, BoNT/C, BoNT/D, BoNT/E, BoNT/F, or BoNT/G at a concentration 10 times greater than or equal to the $K_D$ for the first two rounds of sorting respectively with the majority of BoNT binding yeast collected. Subsequent rounds of sorting were increasingly stringent with the antigen concentration decreased and less than 1% of the yeast collected. A total of four to six rounds of sorting were performed for each chain shuffled library, after which the sort output was plated to allow for characterization of individual yeast displayed scFv. Ten individual clones were characterized by DNA sequencing of the scFv gene and the affinity for each serotype or subtype of BoNT determined as previously described (Razai A et al. (2005) *J. Mol. Biol.* 351:158-169; Lou J. et al. (2010) *Protein Engineering, Design & Selection*, 23:311-319).

Construction and Purification of IgG

The $V_H$ and $V_K$ genes of lead scFv were amplified with primers annealing to the 5' and 3' ends of the full length $V_H$ and $V_L$ genes, and then cloned into vectors for stable expression in CHO cells as previously described (Razai A et al. (2005) *J. Mol. Biol.* 351:158-169; Nowakowski A et al. (2002) *Proc. Natl. Acad. Sci. USA* 99:11346-11350). These vector results in expression of IgG of the γ1/kappa or γ1/lambda isotype from the transformed CHO cells. Clones containing the correct $V_H$ and $V_L$ genes were identified by DNA sequencing, and vector DNA was used to transfect CHO DG44 cells by electroporation. Stable cell lines were established by selection in G418 and expanded into 1 L spinner flasks or 10 L wavebags. Supernatant containing IgG were collected, concentrated by ultra filtration, and purified on Protein G (Pharmacia) column as described in Kehoe J et al. (2006) *Molecular & Cellular Proteomics* 5:2350-2362.

Measurement of Solution Phase Affinity at Equilibrium

Equilibrium binding studies were conducted at room temperature (~25° C.) using a KinExA 3000 flow fluorimeter to quantify the free BoNT/A, BoNT/B, BoNT/C, BoNT/D, BoNT/E, BoNT/F or BoNT/G at equilibrium using varying concentrations of antibody (Blake, R C et al. (1999) *Anal Biochem* 272:123-34; Ohmura, N et al. (2001) *Anal Chem* 73:3392-9) as previously described (Razai A et al. (2005) *J. Mol. Biol.* 351:158-169). Studies of antibody antigen reaction were performed in PBS (pH 7.4), with 1 mg/ml BSA and 0.02% (w/v) sodium azide as a preservative in the reaction mixture. Antibody was serially diluted into a constant concentration of pure BoNT/A, BoNT/B, BoNT/C, BoNT/D, BoNT/E, BoNT/F, or BoNT/G sufficient to produce a reasonable signal, where the antibody concentration was varied from less than 0.1 to greater than 10-fold above the value of the apparent $K_D$. The BoNT concentrations were no more than 4-fold above the $K_D$ to ensure a $K_D$ controlled experiment. Samples were allowed to reach equilibrium for as long as three days, then each of the 12 dilutions were passed over a flow cell with a 4 mm column of Azlactone beads (Sapidyne Instruments) covalently coated with the corresponding antibody to capture the free BoNT. Passing an Alexa-647 labeled BoNT antibody binding a non-overlapping epitope over the beads produced a signal relative to the amount of free BoNT bound to the beads. All data points were run in duplicate and sample volume varied from 4 to 25 ml depending on antibody affinity. The equilibrium titration data were fit to a 1:1 reversible binding model using KinExA Pro Software (version 1.0.2; Sapidyne Instruments) to determine the $K_D$ (Drake, A W et al. (2004) *Anal Biochem* 328:35-43).

Measurement of mAb Inhibition of SNAP25 Cleavage by BoNT/A Lc

Figure 3:
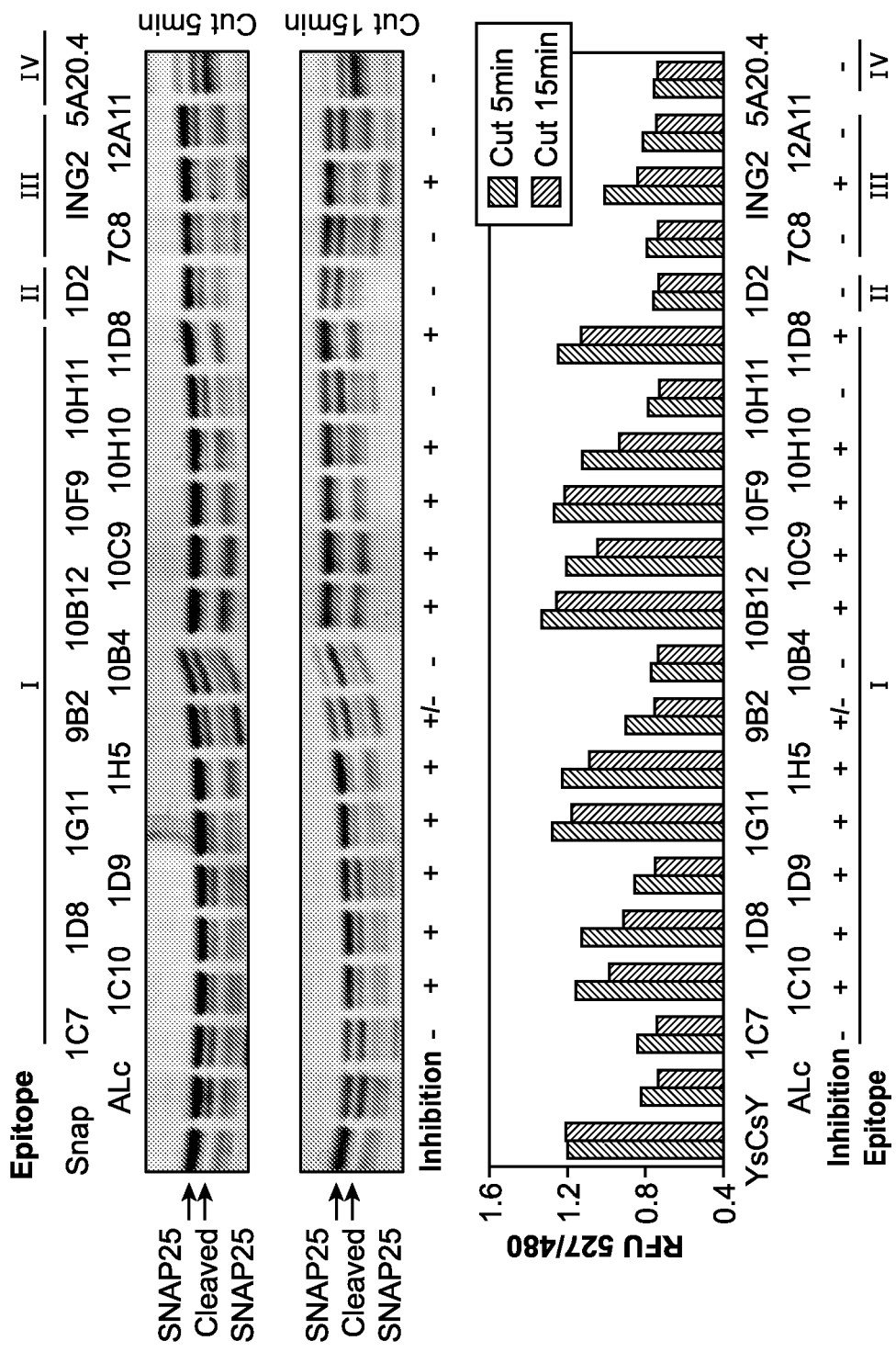
FIG. 3. Mab inhibition of SNAP25 cleavage by BoNT/A Lc. Inhibition of BoNT/A Lc activity by the 19 mAbs assayed by sodium dodecyl sulfate-polyacrylamide gel electrophoresis (SDS-PAGE) (A) and Förster resonance energy transfer (FRET) (B). 1 µM of single chain Ab or IgG (1C7 to 12A11, ING2 and 5A20.4) and 20 nM home-made BoNT/A Lc was used to start the reaction, digesting for 5 minutes and 15 minutes. For FRET assay, emission at 527 nm and 480 nM were recorded and then the ratio of 527 nM/480 nM was calculated to evaluate YsCsY cleavage. The results showed that mAbs with epitope I, 1C10, 1D8, 1D9, 1G11, 1H5, 10B12, 10C9, 10F9, 10H10 and 11D8 strongly inhibit BoNT/A Lc while 1C7, 10B4 and 10H11 do not. The colony 9B2 showed very weakly inhibition of BoNT/A Lc. The only mAb with epitope II, 1D2 does not inhibit BoNT/A LC. For mAbs with epitope III, 12A11 does not inhibit BoNT/A LC; 7C8 and ING2 conditionally inhibit BoNT/A LC dependent on the salt in the reaction buffer or on the different batch of substrate (SNAP25 or YsCsY). All the experiments were repeated at least three times.

As one of the many functional tests for the selected mAbs, an SDS-PAGE and a fluorescent resonance energy transfer (FRET) assay of ALC inhibition was performed as published (Dong, J., et al. (2010) *Journal of Molecular Biology* 397:1106-1118, Pires-Alves, M. et al. (2009) *Toxicon* 53:392-399). Briefly, for the SDS-PAGE assay, BoNT/A Lc 448 was mixed with or without testing mAb in 50 mM Tris buffer, pH 8.0. SNAP25 substrate as added into the mixture to initiate the reaction. The final volume was 40 µl, and final concentration was approximately 20 nM for BoNT/A Lc and 5 mM for SNAP25. The concentration of each mAb varies but was at least 1× fold higher than the BoNT/A Lc concentration. The reaction was run at room temperature for 1~30 min or for the indicated time, stopped by adding SDS-PAGE loading buffer and heated for 10 min at 99° C., then analyzed by SDS-PAGE. The gel was stained in 0.1% Coomassie Blue R-250 (see FIG. 3). For the FRET based cleavage assay with YsCsY as substrat, reactions were performed in black 96-well plates (Corning) in assay buffer (10 mM HEPES, 150 mM K glutamate, 0.01% Tween20, pH 7.2). YsCsY was mixed with two-fold serially dilution of each mAb, with the estimated $IC_{50}$ equal to the median mAb concentration. After pre-incubation at 30° C. for 15 min in a microplate fluorescence reader (Spectra Max Gemini, Molecular Devices), BoNT/A Lc was added to the wells by multi-channel pipet, to initiate the reaction. The total reaction volume was 1004 the final concentration was 0.5 mM for YsCsY and 400 pM for BoNT/A Lc. Fluorescence was measured in the monochromatic mode with excitation at 425 nm and emission at 525 nm. Initial rates were determined from the change in YFP fluorescence reading (525 nm); the fluorescent data from the first 40 sec was fit to a simple linear regression model Y=RX+C (where Y=YFP fluorescence, R=slope, X=time, and C=y-intercept) and the "−R" value was taken as the initial rate (the R value was negative since the signal at 525 nm gets weaker with substrate cleavage). The $IC_{50}$ of each mAb was determined by fitting the initial rate and log mAb concentration to a sigmoidal dose-response (variable slope) model (GraphPad Prism).

Example 1

Generation of Human or Mouse Yeast Displayed scFv Antibody Libraries

Yeast displayed scFv antibody libraries were constructed from V-genes isolated either from human volunteers immunized with pentavalent botulinum toxoid (serotypes BoNT/A1, BoNT/B1, BoNT/C, BoNT/D, and BoNT/E) or mice selectively immunized with monovalent toxin fragment (BoNT/A $L_C$, BoNT/B $L_C$, BoNT/B $H_C$, BoNT/F $H_C$, etc) or BoNT holotoxin. RNA was prepared from the peripheral blood lymphocytes of 6 different human donors or from the spleens of 13 immunized mice, and the immunoglobulin heavy ($V_H$) and light ($V_L$) chain variable regions amplified using the polymerase chain reaction (PCR) as previously described (Marks, J D et al. (1991) *J Mol Biol* 222, 581-97; Marks, J D et al. (1991) *Eur. J. Immunol.* 21, 985-991. Amersdorfer P et al. (1997) *Infection Immunity* 65: 3743-3752). $V_H$ and $V_L$ gene repertoires from each donor or mouse were spliced together to create scFv gene repertoires which were cloned for display as N-terminal fusions to the agglutinin receptor (Aga II) protein on the surface of yeast (Boder, E T (1997) *Nat. Biotechnol.* 15:553-557). A total of 19 yeast displayed scFv libraries (13 mouse V-gene+6 human V-gene) were generated, ranging in size from 4.1 to 25.7×10$^7$ members. Each library was diverse as determined by PCR fingerprinting and DNA sequencing of 10 randomly selected clones from the library. After induction of scFv display, the percentage of yeast displaying scFv ranged from 45-55% as determined by staining with SV5 antibody binding the C-terminal SV5 tag fused to each scFv.

Example 2

Generation of High Affinity Mouse Antibodies Specific to the Light Chain of Type A Botulinum Neurotoxins To generate BoNT/A $L_C$ specific mAbs, three different yeast displayed scFv libraries were constructed using pYD4 vector and V-genes from BoNT/A $L_C$-immunized mouse spleen RNA, and were subjected to several rounds of sorting using different concentrations of purified BoNT/A $L_C$. Sorts were performed using relatively high concentrations in the initial rounds (100-200 nM) to ensure collection of all antigen-binding scFv. In later rounds, the antigen concentration was decreased to between 1-10 nM to select higher affinity antibodies. Libraries were sorted a total of three to six rounds, and yeast displayed scFv from individual colonies were screened for binding to both the BoNT/A $L_C$ and BoNT/A1 holotoxin. Antigen-binding clones were further characterized with respect to the diversity of scFv present using colony PCR and DNA sequencing. In this manner, 17 scFv were isolated, each with a unique $V_H$ and/or $V_L$ (Table 1, FIG. 4). The equilibrium binding constant for BoNT/A $L_C$ was measured for each of the yeast displayed scFv (Table 1) and were in the range of 35.33 nM to 90 pM with an average $K_D$ of 6.58 nM. The inhibitory function of some mAbs against SNAP25 cleavage by BoNT/A was also characterized (Table 1, FIG. 3).

TABLE 1

Table 1. mAbs against BoNT/A Lc. All antibodies were isolated from BoNT/A Lc-immunized mouse scFv libraries except 5A20.4 and ING2, which were isolated from immunized human libraries. Characterization of the antibodies included sequencing, binding affinity for BoNT/A Lc (measured on yeast displayed scFv by flow cytometry or IgG by KinExA), cross reactivity with BoNT/A1, A2 or A3 holotoxin, ability to inhibit SNAP25 cleavage by BoNT/A Lc, and mapping of which overlapping epitopes. In Table 1, "−" means that a mAb does not bind the tested BoNT/BoNT fragment or does not inhibit BoNT/A Lc activity; "+" means a mAb binds the tested BoNT/BoNT fragment or inhibits BoNT/A Lc activity; "+/−, −;+" means inhibition observed using certain reaction buffer but not using all buffers. "NM" means "not measured."

| Initial scFv lead clone name | Converted IgG Name | H-CDR3 | Yeast $K_D$ (nM) ALc | A1 | A2 | IgG $K_D$ (nM) ALc | A1 | A2 | ALc enzyme Activity vitro Inhibition | Epitope Designation |
|---|---|---|---|---|---|---|---|---|---|---|
| 1C7 | | TAGFYFDY (SEQ ID NO: 346) | 35.33 | − | − | NM | NM | NM | − | I |
| 1C10 | | YSGPYAMDY (SEQ ID NO: 347) | 4.85 | − | − | NM | NM | NM | + | I |
| 1D8 | | GSSGYVNY (SEQ ID NO: 348) | 3.35 | − | − | NM | NM | NM | + | I |
| 1D9 | 6A7M | DWDYYYGSYWYFDV (SEQ ID NO: 349) | 9.13 | − | − | NM | NM | NM | + | I |
| 1G11 | | GGTGYFDV (SEQ ID NO: 350) | 0.114 | − | − | NM | NM | NM | + | I |
| 1H5 | | GYYDTMDY (SEQ ID NO: 351) | 10.62 | − | − | NM | NM | NM | + | I |
| 9B2 | | GGWLGNYYAMDY (SEQ ID NO: 352) | 0.67 | 232 | 154 | NM | NM | NM | +/− | I |
| 10C9 | | RRNYGMDY (SEQ ID NO: 353) | 0.36 | >500 | 112.5 | NM | NM | NM | + | I |
| 10H10 | | GGGRSSLDY (SEQ ID NO: 354) | 11.09 | − | − | NM | NM | NM | + | I |
| 10H11 | 6A9M | LNYDYPYWYFDV (SEQ ID NO: 355) | 0.92 | − | − | NM | NM | NM | − | I |
| 10B12 | 6A2M | REGHYYGKAMDY (SEQ ID NO: 356) | 0.53 | − | 140 | 45 | NM | NM | + | I |

TABLE 1-continued

Table 1. mAbs against BoNT/A Lc. All antibodies were isolated from BoNT/A
Lc-immunized mouse scFv libraries except 5A20.4 and ING2, which were isolated from
immunized human libraries. Characterization of the antibodies included sequencing, binding
affinity for BoNT/A Lc (measured on yeast displayed scFv by flow cytometry or IgG by
KinExA), cross reactivity with BoNT/A1, A2 or A3 holotoxin, ability to inhibit SNAP25
cleavage by BoNT/A Lc, and mapping of which overlapping epitopes. In Table 1, "−" means
that a mAb does not bind the tested BoNT/BoNT fragment or does not inhibit BoNT/A Lc
activity; "+" means a mAb binds the tested BoNT/BoNT fragment or inhibits BoNT/A Lc
activity; "+/−, −;+" means inhibition observed using certain reaction buffer but not using all
buffers. "NM" means "not measured."

| Initial scFv lead clone name | Converted IgG Name | H-CDR3 | Yeast $K_D$ (nM) ALc | A1 | A2 | IgG $K_D$ (nM) ALc | A1 | A2 | ALc enzyme Activity vitro Inhibition | Epitope Designation |
|---|---|---|---|---|---|---|---|---|---|---|
| 10F9 | 6A3M | GGNGFFDY (SEQ ID NO: 357) | 0.09 | >500 | >500 | 10 | NM | NM | + | I |
| 11D8 | 6A4M | YPGNRAMDY (SEQ ID NO: 358) | 0.22 | − | − | 21 | NM | NM | + | I |
| 10B4 | 6A8M | DDGYYEALDY (SEQ ID NO: 359) | 1.53 | >500 | 252 | 4.99 | 0.852 | NM | − | I |
| 1D2 | 6A6M | IYYGHDY (SEQ ID NO: 360) | 6.40 | − | − | NM | NM | NM | − | II |
| 7C8 | 6A1M | NLGLWYFDV (SEQ ID NO: 361) | 0.94 | 0.73 | 0.45 | 1.38 | 9.21pM | 2.89pM | −; + | III |
| ING2 | ING2* | DPYYYSYMDV (SEQ ID NO: 362) | >16.3 | 0.11 | 0.12 | 85.7 | 9.57pM | 7.42pM | −; + | III |
| 12A11 | 6A5M | NMGLWYFDV (SEQ ID NO: 363) | 25.8 | 0.66 | 2.08 | NM | NM | NM | − | III |
| 5A20.4 | 5A20.4* | EASFGWSYLGHDDAFDI (SEQ ID NO: 364) | 0.13 | 0.18 | − | 3.12pM | 13.6pM | − | − | IV |

Example 3

Generation of High Affinity Mouse or Human Antibodies Specific to the Light Chain of Type B Botulinum Neurotoxins Similar to the procedures used for BoNT/A $L_C$ specific mAbs generation, BoNT/B $L_C$ specific mAbs were screened and selected from three different yeast displayed scFv libraries which were constructed from BoNT/B $L_C$-immunized mouse spleen RNA and the yeast display vector pYD4. Each library was subjected to several rounds of sorting using different concentrations of purified BoNT/B $L_C$. 22 scFv were isolated, each with a unique $V_H$ and/or $V_L$ (Table 2, FIG. 4). The equilibrium binding constant for BoNT/B $L_C$ was measured for each of the yeast displayed scFv (Table 2) and were in the range of 0.75 to 17.1 nM, with an average $K_D$ of 5.01 nM. The cross reactivity with all four subtypes of BoNT/B was checked and the epitope overlap of each antibody corresponding to previously engineered human mAbs was identified (Table 2). Human MAbs 2B23K1, 2B23K2, 2B23K7, 2B23K11, 2B23EK1, 2B23EK4, 2B23EK5, 2B23EK6, 2B23EK7, 2B23EK10, 2B23EK11, and 2B23EK12 bind the same epitope as 2B23 on the B Lc domain of BoNT; they were generated by site-directed mutation and light chain shuffling as described above.

TABLE 2

Mouse mAbs against BoNT/B Lc. Clone name, VH CDR3 sequence,
epitope overlapping with known human antibodies for BoNT/B, equilibrium dissociation
constant ($K_D$) for B $L_C$ and four BoNT/B subtypes are shown. scFv $K_D$ measured on yeast
displayed scFv. In the table, + means non-overlapping epitope with the testing human mAb, −
means the lead shares an epitope with the tested human antibody. "ND" refers to no detectable
binding at the maximum toxin concentration tested (500 nM). "NM" means not measured for this
subtype of BoNT/B.

| scFv lead Clone Name | BLc Enzyme Activity Inhibition | VH CDR3 sequence | Epitope mapping with known human antibody 4B19 | 1B10.1 | 1B22 | B6.1 | 2B23 | BoNT/B Domain and subtype Cross Reactivity with $K_D$ (nM) BLC | BoNT/B1 | BoNT/B2 | BoNT/B3 | BoNT/B4 |
|---|---|---|---|---|---|---|---|---|---|---|---|---|
| 19G6 | + | YGSNFDY (SEQ ID NO: 365) | + | + | + | − | + | 4.76 | 6.22 | 3.44 | 5.41 | 5.84 |

TABLE 2-continued

Mouse mAbs against BoNT/B Lc. Clone name, VH CDR3 sequence, epitope overlapping with known human antibodies for BoNT/B, equilibrium dissociation constant ($K_D$) for B $L_C$ and four BoNT/B subtypes are shown. scFv $K_D$ measured on yeast displayed scFv. In the table, + means non-overlapping epitope with the testing human mAb, − means the lead shares an epitope with the tested human antibody. "ND" refers to no detectable binding at the maximum toxin concentration tested (500 nM). "NM" means not measured for this subtype of BoNT/B.

| scFv lead Clone Name | BLc Enzyme Activity Inhibition | VH CDR3 sequence | Epitope mapping with known human antibody | | | | | BoNT/B Domain and subtype Cross Reactivity with $K_D$ (nM) | | | | |
|---|---|---|---|---|---|---|---|---|---|---|---|---|
| | | | 4B19 | 1B10.1 | 1B22 | B6.1 | 2B23 | BLC | BoNT/B1 | BoNT/B2 | BoNT/B3 | BoNT/B4 |
| 18D10 | + | TGTGFDY (SEQ ID NO: 366) | + | + | + | − | + | 7.53 | 5.97 | 5.57 | 3.35 | 4.20 |
| 18E5 | ++ | YGYYGYFDY (SEQ ID NO: 367) | + | − | − | + | + | 1.00 | 1.33 | 2.66 | 2.56 | 1.36 |
| 18A6 | − | VNFYVSWDY (SEQ ID NO: 368) | + | + | + | + | + | 4.21 | 14.5 | 32.4 | 27.9 | 30.6 |
| 18A7 | + | TGTGFDY (SEQ ID NO: 366) | + | + | + | − | + | 13.5 | 69.3 | 139 | 24.9 | 43.9 |
| 19B6 | + | VGFRVNFDY (SEQ ID NO: 369) | + | + | − | + | + | 2.35 | 19.7 | 35.6 | 865.5 | 43.5 |
| 16B3 | ++ | WGYYGSLAY (SEQ ID NO: 370) | + | − | − | + | + | 0.84 | 1.01 | 0.75 | 0.49 | 0.71 |
| 16D5 | ++ | SYYRAWFDY (SEQ ID NO: 371) | + | + | + | + | + | 1.80 | 7.57 | ND | ND | ND |
| 18F2 | − | SEGYYHNLGAY (SEQ ID NO: 372) | + | + | + | + | + | 1.05 | >> | 8.75 | >> | ND |
| 19A9 | − | DYYDYAGGGRGY (SEQ ID NO: 500) | − | + | + | + | − | 3.16 | 1.98 | 0.88 | 1.18 | 1.04 |
| 19D2 | + | DFYDYDGGGRGY (SEQ ID NO: 373) | − | + | + | + | − | 5.69 | 2.95 | 1.85 | 1.47 | 1.84 |
| 19D22 | ++ | YGQVGSYAMDY (SEQ ID NO: 374) | + | + | + | − | + | 21.2 | 7.39 | 5 | 3.77 | 5.24 |
| 31A5 | ++ | SGGTGYYFDY (SEQ ID NO: 375) | + | + | + | + | + | 9.31 | NM | NM | NM | NM |
| 31A5.1 | ++ | SGGTGYYFDY (SEQ ID NO: 375) | + | + | + | + | + | 1.75 | NM | NM | NM | NM |
| 31C3 | − | GPIYYGTSYRFFDV (SEQ ID NO: 376) | + | + | + | + | + | 5.27 | NM | NM | NM | NM |
| 31C3.5 | − | GPIYYGTSYRFFDV (SEQ ID NO: 376) | + | + | + | + | + | 0.75 | NM | NM | NM | NM |
| 31E2 | − | WSNWYFDV (SEQ ID NO: 377) | + | + | + | + | + | 17.1 | NM | NM | NM | NM |
| 31E2.20 | − | WSNWYFDV (SEQ ID NO: 377) | + | + | + | + | + | 1.96 | NM | NM | NM | NM |
| 31G2 | − | WLLYYYAMDY (SEQ ID NO: 378) | + | + | + | + | + | 3.34 | NM | NM | NM | NM |
| 31H3 | | YGSNFDY (SEQ ID NO: 365) | + | + | + | + | + | 1.28 | NM | NM | NM | NM |
| 34E8B12 | + | YYDYDGDYFDY (SEQ ID NO: 379) | + | − | − | + | + | 2.44 | NM | NM | NM | NM |

Example 4

Generation of High Affinity Mouse and Human Antibodies Specific to the Heavy Chain of Type B Botulinum Neurotoxins Similar to the procedures used for BoNT/A $L_C$ specific mAb generation, BoNT/B $H_C$ specific mAbs were screened and selected from three different yeast displayed scFv libraries which were constructed from BoNT/B $H_C$ immunized mice spleen RNA using pYD4 vector. Each library was subjected to several rounds of sorting using different concentrations of purified BoNT/B $H_C$. 14 scFv were isolated, each with a unique $V_H$ CDR3 (Table 3, FIG. 4). Also, to switch the light chain from lambda to kappa for one unique BoNT/B binder, 1B12, originally selected from a human scFv library, another chain-shuffled library was created using human VK only, and sorting was performed similarly to that used for the mouse scFv library. The equilibrium binding constant for BoNT/B $H_C$ was measured for each of the yeast displayed scFv (Table 3, FIG. 4) and were in the range of 33 pM to 50.94 nM with an average $K_D$ of 5.48 nM. The cross reactivity with all four subtypes of BoNT/B was checked and the epitope relationships with the previously engineered human mAbs B8.1 and B12.1 were identified (Table 3).

TABLE 3

Mouse and Human mAbs against BoNT/B Hc.
Clone name, VH CDR3 sequence, epitope overlapping with known human antibodies for BoNT/B, equilibrium dissociation constant ($K_D$) for B $H_C$ and four BoNT/B subtypes are shown. scFv $K_D$ measured on yeast displayed scFv. + and ++ mean that the lead scFv has non-overlapping epitope with the testing human mAb; +/− means that the lead has detectable but weak cross reactivity with the tested subtype; − means that the lead shares epitope with the testing human antibody or has no cross reactivity with the tested subtype. "NM" means $K_D$ was not measured.

| scFv Lead Clone Name | VH-CDR3 | Cross reactivity &KD (nM) | | | | | overlap | |
|---|---|---|---|---|---|---|---|---|
| | | BoNT/B1 | BoNT/B2 | BoNT/B3 | BoNT/B4 | BHc | B8.1 | B12.1 |
| 26B2 | EFYYYFDV (SEQ ID NO: 380) | 0.276 | 5.433 | ++ | − | 0.086 | + | + |
| 26D9 | NDYDPYYYALDY (SEQ ID NO: 381) | 0.582 | 0.467 | ++ | − | 0.089 | + | + |
| 26C4 | DGYYVYDY (SEQ ID NO: 382) | 0.186 | 24.95 | + | − | 0.033 | + | + |
| 26G11 | DYGNSYPYYFDF (SEQ ID NO: 383) | 1.579 | 1.658 | − | − | 0.375 | + | − |
| 26D10 | IGPRLGYFDV (SEQ ID NO: 384) | 0.302 | 12.26 | ++ | − | 0.129 | + | + |
| 26D11 | EYDGRYPYYSTLDY (SEQ ID NO: 385) | 0.334 | 0.862 | − | − | 0.140 | + | − |
| 26A10 | EYDGSYPYYDTLDY (SEQ ID NO: 386) | 1.128 | 3.51 | + | ++ | 0.38 | + | − |
| 26E1 | EGVYYYDGSYMRAMDY (SEQ ID NO: 387) | 0.395 | − | − | − | 50.94 | + | + |
| 26E6 | EFYYYFDV (SEQ ID NO: 380) | 4.853 | 17.61 | +/− | − | 0.889 | + | + |
| 26G5 | SFYDGYLYFDY (SEQ ID NO: 388) | 3.912 | 30.48 | + | + | 1.788 | + | + |
| 26E2 | LRVVPEAY (SEQ ID NO: 389) | + | + | − | − | + | + | − |

TABLE 3-continued

Mouse and Human mAbs against BoNT/B Hc.
Clone name, VH CDR3 sequence, epitope overlapping with known
human antibodies for BoNT/B, equilibrium dissociation constant ($K_D$)
for B $H_C$ and four BoNT/B subtypes are shown. scFv $K_D$ measured
on yeast displayed scFv. + and ++ mean that the lead scFv has
non-overlapping epitope with the testing human mAb; +/- means that
the lead has detectable but weak cross reactivity with the tested
subtype; - means that the lead shares epitope with the testing human
antibody or has no cross reactivity with the tested subtype.
"NM" means $K_D$ was not measured.

| scFv Lead Clone Name | VH-CDR3 | Cross reactivity &KD (nM) | | | | | overlap | |
|---|---|---|---|---|---|---|---|---|
| | | BoNT/B1 | BoNT/B2 | BoNT/B3 | BoNT/B4 | BHc | B8.1 | B12.1 |
| 26D1 | SRAGAVY (SEQ ID NO: 390) | NM | NM | NM | NM | NM | NM | NM |
| 26C2 | GDYYGSLDY (SEQ ID NO: 391) | 23.66 | 4.772 | ++ | − | 7.765 | + | + |
| 26H11 | EYGGSYPYYSTLDY (SEQ ID NO: 392) | 2.7 | 0.424 | − | − | 0.168 | + | − |
| 1B12.3 | DRSHYGDYVGYLDY (SEQ ID NO: 393) | 75.73 pM | ++ | ++ | ++ | ++ | + | − |
| 1B12.4 | DRSHYGDYVGYLDY (SEQ ID NO: 393) | 15.6 pM | ++ | ++ | ++ | ++ | + | − |

Example 5

Generation of High Affinity Antibodies Specific for Type F Botulinum Neurotoxins To generate additional anti BoNT/F mAbs, procedures similar to those used for BoNT/A $L_C$ specific mAb generation were employed. BoNT/F specific mAbs were screened and selected from four different yeast displayed scFv libraries which were constructed from BoNT/F holotoxin-immunized mouse spleen RNA and pYD4 vector, and subjected to several rounds of sorting using different concentrations of BoNT/F. 36 scFv were isolated or engineered after the initial leads were found, each with a unique $V_H$ or $V_L$ (Table 4, FIG. 4). The equilibrium binding constant for BoNT/F was measured for each of the yeast displayed scFv (Table 4) and were in the range of 2.9 nM to 40 pM with an average $K_D$ of 6.22 nM. The epitope designation of each mAb was assigned (Table 4).

TABLE 4

Select mAbs specific for BoNT/F from mouse and human immune libraries.
Clone name, VH CDR3 sequence, kappa or lambda light chain, epitope
overlapping with known antibodies for BoNT/F, equilibrium dissociation
constant ($K_D$) for BoNT/F1 and cross reactivity with BoNT/F 202F
subtypes are shown. scFv $K_D$ measured on yeast displayed scFv.
+ means the lead scFv has non-overlapping epitope with the testing
human mAb, - means the lead shares an epitope with the testing
human antibody. "NM" means $K_D$ was not measured.

| scFv lead Colony name | Final IgG name | Species | Light Chain | VH_CDR3 | SEQ ID NO: | BoNT/F1 $K_D$ (nM) | Domain specificity | 202F binding | Epitope |
|---|---|---|---|---|---|---|---|---|---|
| 6F3 | 6F3 | Mouse | Kappa | VTMVESGDWYFDV | 394 | 0.765 | NM | No | 1 |
| 6F4 | 6F4 | Mouse | Kappa | GPYFFDF | 395 | 2.87 | NM | No | 2 |
| 29H11 | 6F8 | Mouse | Kappa | DRDYD | 396 | 0.30 | $H_C$ | Yes | 3 |
| 28B10 | 6F6 | Mouse | Kappa | GTWVFDY | 397 | 3.02 | NM | No | 4 |
| 30A7 | 6F9 | Mouse | Kappa | NWDWYFDV | 398 | 0.04 | $H_C$ | No | 5 |
| 28H4 | | Mouse | Kappa | HGYYIYALDY | 399 | 20.0 | NM | NM | 6 |
| 29B8 | | Mouse | Kappa | LLRSRTGYFDY | 400 | 35.8 | NM | NM | 8 |

TABLE 4-continued

Select mAbs specific for BoNT/F from mouse and human immune libraries. Clone name, VH CDR3 sequence, kappa or lambda light chain, epitope overlapping with known antibodies for BoNT/F, equilibrium dissociation constant ($K_D$) for BoNT/F1 and cross reactivity with BoNT/F 202F subtypes are shown. scFv $K_D$ measured on yeast displayed scFv. + means the lead scFv has non-overlapping epitope with the testing human mAb, − means the lead shares an epitope with the testing human antibody. "NM" means $K_D$ was not measured.

| scFv lead Colony name | Final IgG name | Species | Light Chain | VH_CDR3 | SEQ ID NO: | BoNT/F1 $K_D$ (nM) | Domain specificity | 202F binding | Epitope |
|---|---|---|---|---|---|---|---|---|---|
| 30C8 | | Mouse | Kappa | IIMVESGDWYFDV | 401 | 0.2 | NM | NM | 1 |
| 28H2 | 6F7 | Mouse | Kappa | SSNYFFHVLDY | 402 | 1.55 | NM | No | 7 |
| 29A2 | | Mouse | Kappa | RRVYYGSSYEDY | 403 | 0.99 | NM | NM | 4 |
| 28C11 | 6F10 | Mouse | Kappa | RRSYDSVYWYFDV | 404 | 0.12 | NM | Yes | 4 |
| 28C9 | | Mouse | Kappa | ASDFDV | 405 | NM | NM | NM | 5 |
| 32G2 | | Mouse | Kappa | YSDLAY | 406 | NM | NM | NM | 5 |
| 4E17.2 | 4E17.2 | Human | Kappa | LQWGGYNGWLSP | 407 | 0.39 | $H_N$ | Yes | 8 |
| 37B4 | | Human | Lamda | DEDYYDSSGYYDY | 408 | 10.14 | NM | NM | NM |
| 37B6 | | Human | Lamda | GGGQWWQNDAFDV | 409 | 23.75 | NM | NM | NM |
| 38B8 | | Human | Lamda | GPNPGKKWGAEWGASGN | 410 | 18.32 | NM | NM | NM |
| 38C1 | | Human | Lamda | PHRSDYGLGV | 411 | 30.26 | NM | NM | NM |
| 38D11 | | Human | Lamda | DKGWELMTN DAFDI | 412 | 29.13 | NM | NM | NM |
| 38F8 | | Human | Lamda | VAGTSRSAFDI | 413 | 29.36 | NM | NM | NM |
| 39A1 | | Human | Kappa | LQWGGYNGWLSP | 407 | 588.0 pM | Hn | Yes | 8 |
| 41C2 | | Human | Kappa | LQWGGYNGWLSP | 407 | 355.4 pM | Hn | Yes | 8 |
| 43D3 | | Human | Kappa | LQWGGYNGWLSP | 407 | 333.4 pM | Hn | Yes | 8 |
| 39H6 | | Human | Kappa | LQWGGYNGWLSP | 407 | 526.2 pM | Hn | Yes | 8 |
| 41E2 | | Human | Kappa | LQWGGYNGWLSP | 407 | 583.9 pM | Hn | Yes | 8 |
| 41F7 | | Human | Kappa | LQWGGYNGWLSP | 407 | 565.5 pM | Hn | Yes | 8 |
| 42G8 | | Human | Kappa | LQWGGYNGWLSP | 407 | 242.9 pM | Hn | Yes | 8 |
| 39D1.1 | | Human | Kappa | LQWGGYNGWLSP | 407 | 746.8 pM | Hn | Yes | 8 |
| 41A4 | | Human | Kappa | LQWGGYNGWLSP | 407 | 533.4 pM | Hn | Yes | 8 |
| 41B7 | | Human | Kappa | LQWGGYNGWLSP | 407 | 891.8 pM | Hn | Yes | 8 |
| 39D5.1 | | Human | Kappa | LQWGGYNGWLSP | 407 | 1775.0 pM | Hn | Yes | 8 |
| 41G8 | | Human | Kappa | LQWGGYNGWLSP | 407 | 612.4 pM | Hn | Yes | 8 |

A human BoNT/F antibody that binds a translocation domain epitope that is conserved in all BoNT/F subtypes was identified. Using chain shuffling, the affinity of this antibody for BoNT/F was increased from approximately 10 nM to less than 1 nM (scFv 4E17.2, Table 5). A fully human IgG (6F5) has been constructed from this scFv with a KD of 0.66 nM for BoNT/F1 and which binds all of the BoNT/F subtypes. To increase the potency of this mAb, the affinity of the scFv was further increased approximately 6 fold using error prone mutagenesis and an IgG (6F5.1) was constructed from the affinity matured scFv.

Table 5. Properties of BoNT/F Antibodies.

Antibody name and VH CDR3 sequence are provided. For cross reactivity, the $K_D$ of the yeast displayed scFv for BoNT/F1 (proteolytic BoNT/F) is indicated, as well as whether it binds the other BoNT/F subtypes. Epitope bound ($H_C$, $H_N$, or $L_C$) is indicated. Where IgG has been produced, the IgG $K_D$ for proteolytic BoNT/F1 is provided. "Yes" means binding; "No" means no clear binding at the maximum toxin concentration tested; "NM" means not measured.

TABLE 5

| mAb | $V_H$ CDR3 | yeast_$K_D$ (BoNT/F1) (nM) | IgG $K_D$ (BoNT/F1) (nM) | Binds BoNT/F2 | Binds BoNT/F3 | Binds BoNT/F4 | Binds BoNT/F5 | Binds BoNT/F6 | Binds BoNT/F7 |
|---|---|---|---|---|---|---|---|---|---|
| 6F1 | DRWYSGYDFDY (SEQ ID NO: 508) | 1.10 | NM | No | No | No | No | No | No |
| 6F3 | VTMVESGDWYFDV (SEQ ID NO: 394) | 0.76 | 2.39 | No | No | No | No | No | Yes |
| 6F4 | GPYFFDF (SEQ ID NO: 395) | 2.87 | 1.17 | No | No | No | No | No | No |
| 4E17.2 | LQWGGYNGWLSP (SEQ ID NO: 407) | 0.39 | 0.66 | Yes | Yes | Yes | Yes | Yes | Yes |
| 6F6 | GTWVFDY (SEQ ID NO: 397) | 0.55 | 0.048 | No | No | No | No | No | Yes |
| 6F7 | SSNYFFHVLDY (SEQ ID NO: 402) | 1.55 | 0.57 | No | No | Yes | No | No | No |
| 6F8 | DRDYD (SEQ ID NO: 396) | 0.30 | 0.22 | Yes | Yes | Yes | Yes | Yes | No |
| 6F9 | NWDWYFDV (SEQ ID NO: 398) | 0.04 | 0.26 | Yes | Yes | No | No | No | No |
| 6F10 | RRSYDSVYWYFDV (SEQ ID NO: 404) | 0.12 | 0.07 | No | No | No | No | Yes | No |
| 29B10 | GPYEEDF (SEQ ID NO: 395) | 0.14 | NM | NM | NM | NM | NM | NM | NM |
| 28H4 | HGYYIYALDY (SEQ ID NO: 399) | 20.0 | NM | NM | NM | NM | NM | NM | NM |
| 29B8 | LLRSRTGYFDY (SEQ ID NO: 400) | 35.8 | NM | NM | NM | NM | NM | NM | NM |
| 30C8 | IIMVESGDWYFDV (SEQ ID NO: 401) | 0.2 | NM | NM | NM | NM | NM | NM | NM |
| 29A2 | RRVYYGSSYEDY (SEQ ID NO: 403) | 0.99 | NM | NM | NM | NM | NM | NM | NM |

The antibodies were shown to have the requisite potency for development as a therapeutic antitoxin (Table 7). The combination of 6F5:6 F9:6 F10 protected 7/10 mice challenged with 40,000 mouse $LD_{50}$s of BoNT/F1.

Table 7. In Vivo Protection of Mice Challenged with the Indicated Number of Mouse $LD_{50}$s of BoNT/F1.

The combination of 6F5:6 F9:6 F10 protected 7/10 mice challenged with 40,000 mouse $LD_{50}$s of BoNT/F1. The number of mice surviving/number of mice challenged is indicated. "NM" means "not measured."

TABLE 7

| mAb combination | 5,000 $LD_{50}$ | 10,000 $LD_{50}$ | 20,000 $LD_{50}$ | 40,000 $LD_{50}$ |
|---|---|---|---|---|
| 6F3:6F4:6F5 | 4/10 | 1/10 | 0/10 | NM |
| 6F3:6F9:6F10 | NM | 7/10 | 2/10 | NM |
| 6F5:6F9:6F10 | NM | 9/10 | 7/10 | 7/10 |

Example 6

Generation of High Affinity Human Antibodies to Type C and D Botulinum Neurotoxins To generate a panel of human antibodies to type C and/or D botulinum neurotoxins, six different yeast displayed scFv libraries were constructed using pYD2 or pYD4 vectors and sorted separately on holotoxin BoNT/C, BoNT/D, BoNT/CD, or BoNT/DC. Those libraries were constructed with V-genes isolated from pentavalent botulinum toxoid (BoNT/A to BoNT/E alphabetically)-immunized human donors. Similar to the process used to select antibody leads for BoNT/A $L_C$, sorts were performed using relatively high concentrations of BoNT/C1 or other holotoxin in the initial rounds (100-200 nM) to ensure collection of all antigen binding scFv. In later rounds, the antigen concentration was decreased to between 1-25 nM to select for higher affinity antibodies, and sorts were also performed using other BoNT/C or BoNT/D or mosaic subtypes (BoNT/CD, BoNT/DC) to select cross reactive antibodies. Libraries were sorted using a total of three to six rounds until a positive binding population of over 10% was present during the sorting, and yeast displayed scFv from individual colonies were screened for binding to BoNT/C, BoNT/D, BoNT/CD or BoNT/DC. Antigen binding clones were further characterized with respect to the diversity of scFv present using colony PCR and DNA sequencing. In this manner, 47 scFv were isolated or engineered, each with a unique $V_H$ and/or $V_L$ (Table 8, FIG. 4). The equilibrium binding constant for BoNT/C1 or other subtypes was measured for each of the yeast displayed scFv, some data is included in Table 8. Affinities ranged from 51 to $0.14 \times 10^{-9}$ M, with a mean $K_D$ of $14.74 \times 10^{-9}$ M.

TABLE 8

Select mAbs specific for BoNT/C, BoNT/D, BoNT/CD or BoNT/DC from human libraries. Clone name, library source, VH CDR3 sequence, epitope overlapping with known antibodies for BoNT/C, equilibrium dissociation constant (KD) for BoNT/C1 and cross reactivity with BoNT/C1, BoNT/CD, BoNT/DC and BoNT/D subtypes are shown. scFv $K_D$ measured on yeast displayed scFv. + means the lead scFv has good binding with the tested subtype, − means the lead does not react with the tested subtype at the maximum concentration used for testing (~1 µM).

| Clone Name | Library source | KD nM | CDR H3 | Domain Specificity | Epitope Overlap with | Crossreactivity C1 | CD | D | DC |
|---|---|---|---|---|---|---|---|---|---|
| 1C1 | D6 | 0.50 | TKMGAAEGVFDY (SEQ ID NO: 414) | HN | 1C1.1 | + | − | − | − |
| 1C1.1 | D6 | 0.15 | TKMGAAEGVFDY (SEQ ID NO: 414) | HN | 1C1 | + | − | − | − |
| 1C2 | D6 | 24.0 | GGLPYQQLPL (SEQ ID NO: 415) | LCHN | | + | − | − | + |
| 1C8 | D6 | 42.0 | GATNIPYGMSV (SEQ ID NO: 416) | LCHN | | + | − | − | + |
| 87C1 | D9 | 2.0 | AIKSYSTIGGACNL (SEQ ID NO: 417) | LC | 4C1 | + | + | − | − |
| 87C2 | D9 | 7.0 | TLKFGLNYMDV (SEQ ID NO: 418) | LC | | + | − | − | − |
| 87C78 | D9 | 1.0 | AIKAFRPVPPSFHMDV (SEQ ID NO: 419) | LCHN | | + | + | − | − |
| 4C1 | D15 | 2.7 | GQDTSMVTRNFYYGLDV (SEQ ID NO: 420) | LC | 87C1 | + | + | − | − |
| 4C2 | D15 | 0.19 | ETWEVLGHLGYEVLDH (SEQ ID NO: 421) | HC | | + | − | − | + |
| 4C3 | D15 | 4.7 | GAFTNYPF (SEQ ID NO: 422) | LC | | + | + | − | − |

TABLE 8-continued

Select mAbs specific for BoNT/C, BoNT/D, BoNT/CD or BoNT/DC from human libraries. Clone name, library source, VH CDR3 sequence, epitope overlapping with known antibodies for BoNT/C, equilibrium dissociation constant (KD) for BoNT/C1 and cross reactivity with BoNT/C1, BoNT/CD, BoNT/DC and BoNT/D subtypes are shown. scFv $K_D$ measured on yeast displayed scFv. + means the lead scFv has good binding with the tested subtype, - means the lead does not react with the tested subtype at the maximum concentration used for testing (~1 μM).

| Clone Name | Library source | KD nM | CDR H3 | Domain Specificity | Epitope Overlap with | Crossreactivity C1 | CD | D | DC |
|---|---|---|---|---|---|---|---|---|---|
| 4C4 | D15 | 2.6 | DQGGGTVVKENWFDP (SEQ ID NO: 423) | HN | 4C10 | + | + | + | + |
| 4C5 | D10 | 0.143 | VKLTTMVRGGPFDY (SEQ ID NO: 424) | LC | | + | + | − | − |
| 4C6 | D10 | 4.01 | VKLNSVRGGPFDL (SEQ ID NO: 425) | | | + | + | − | − |
| 4C7 | D10 | 63.88 | EKAIKGYSSRPVRAYEM (SEQ ID NO: 426) | LC | | + | − | − | − |
| 4C8 | D10 | 51.07 | GGKYSNSSAMYQ (SEQ ID NO: 427) | LC | | + | − | − | − |
| 4C9 | D10 | 29.64 | SVSGGAFDL (SEQ ID NO: 428) | LC | | + | + | − | − |
| 4C10 | D12 | 0.39 | DRWRSGSYPAFEK (SEQ ID NO: 429) | HN | 4C4 | + | + | + | + |
| 8DC1 | D10 | 4.5 | STRGPFDI (SEQ ID NO: 430) | HN | | + | + | + | + |
| 8DC2 | D12 | 0.5 | GTRNGSLRDAFDI (SEQ ID NO: 431) | HC | | + | − | − | + |
| 8DC3 | D12 | >20 | GDHDFRSGYYGMDV (SEQ ID NO: 432) | LC | | − | − | + | + |
| 8DC4 | D15 | >20 | ERLPPGRGYDMDV (SEQ ID NO: 433) | HN | 8DC1 | + | + | + | + |
| 8DC5 | D15 | 15 | GGFWGTWRDNMDV (SEQ ID NO: 434) | LC | 4C4, 4C10 | − | − | + | + |

Example 7

Generation of High Affinity Human Antibodies to Type F or G Botulinum Neurotoxins Similar to the procedure used for the selection of human antibodies against BoNT/C and D, five of the same six human donor yeast displayed antibody libraries described in Example 1 were sorted with BoNT/F1 or BoNT/G toxin, and 8 scFv were isolated specific for BoNT/F, 11 scFv were isolate specific for BoNT/G, each with a unique $V_H$ CDR3 (Table 4, FIG. 4, FIG. 5). The equilibrium binding constant for BoNT/F1 or BoNT/G was measured for each of the yeast displayed scFv (Table 4). Affinities for BoNT/F ranged from 30.26 to $0.39 \times 10^{-9}$ M, with a mean $K_D$ of $17.99 \times 10^{-9}$ M. Affinities for BoNT/G ranged from 92.3 to $0.69 \times 10^{-9}$ M, with a mean $K_D$ of $30.51 \times 10^{-9}$ M.

Example 8

Characterization of Toxin Domain Specificity and BoNT Subtype Cross Reactivity of Selected Antibodies To determine which BoNT functional domains were bound by selected scFv leads, the $H_C$, $H_N$, and $L_C$ genes and some combination of them (e.g, $L_CH_N$) of BoNT/B, BoNT/C, BoNT/D, BoNT/E, BoNT/F, and BoNT/G were cloned into pYD2 and displayed on the surface of Saccharomyces cerevisiae using methods similar to those as previously reported for BoNT/A domains (Levy R. et al. (2007) *J. Mol. Biol.* 365:196-210). Each domain was well displayed on the yeast surface, as quantitated using a C-terminal SV5 tag fused to each domain. The domain recognized by each of the scFvs was determined by incubating yeast displayed BoNT domains with either native soluble scFv expressed in *E. coli*, or with whole IgG constructed from the scFv lead gene and produced from CHO cells (see below). Native scFv was generated by subcloning the scFv lead genes into the bacterial secretion vector pSYN1 (Schier, R. et al. (1995) *Immunotech-*

*nology* 1:73-81). To determine how many non-overlapping BoNT epitopes were recognized by all the lead antibodies, yeast displayed scFv were incubated with BoNT/A, BoNT/B, BoNT/C, BoNT/D, BoNT/E, BoNT/F, or BoNT/G holotoxin, followed by incubation with purified native scFv. scFv recognizing overlapping epitopes showed no yeast staining while scFv binding non-overlapping epitopes stained the yeast surface (FIG. 1). For some of these assays, purified IgG constructed from the scFv V-genes was used for yeast staining instead of the scFv (FIG. 1). Using these assays, it was determined (Tables 1 to 4 and 8) that some of the 175 scFv leads bind only one subtype of the selected BoNT serotype (e.g. mAb 4C8 binds BoNT/C1 only). Others bind more than one subtype or serotype (e.g., mAb 4C4 binds BoNT/C, BoNT/CD, BoNT/DC and BoNT/D; mAb 4E17.2 and 6F5.1 bind all subtypes of BoNT/A, BoNT/B, BoNT/E and BoNT/F).

Example 9

Characterization of Human Antibodies to Type C and D Botulinum Neurotoxins

A panel of 52 yeast-displayed scFv binding to BoNT/C, BoNT/D, BoNT/CD, or BoNT D/C was isolated (Table 6, 9). Yeast-displayed scFv were first selected with one serotype (BoNT/C or BoNT/CD), then screened for binding to pure or crude culture supernatants prepared from Clostridial strains producing BoNT/CD, BoNT/DC or BoNT/D (Table 6, 9). The results identified four lead antibodies, 4C4, 4C10, 8DC1, and 8DC4, that each bound to BoNT/C, CD, DC, and D. Other antibodies were generated (e.g. 4C2, 87C1, 8DC8) that each bound to a pair of BoNT's, such as C and CD, or DC and D. Using yeast-displayed domains of LC, $H_N$, and $H_C$, it proved possible to map the binding of most of these antibodies to their cognate BoNT domain (Table 9). 4C4, 4C10, and 8DC1 bind non-overlapping epitopes on the $H_N$, LC, and $H_N$, respectively. 8DC1 and 8DC4 bind overlapping epitopes on the $H_N$. These studies identified four antibodies binding three non-overlapping epitopes shared by BoNT/C, CD, DC and D that could serve as lead molecules for an antitoxin for BoNT/C and BoNT/D.

TABLE 9

Characteristics of lead yeast displayed scFv BoNT/C, CD, DC, D antibodies scFv $K_D$ measured on yeast displayed scFv. + means the lead scFv has good binding with the tested serotype or mosiac, − means the lead does not react with the tested serotype or mosiac at the maximum concentration used for testing (~1 μM).

| Clone | Epitope | $V_H$ CDR3 Sequence | BoNT ScFv $K_D$ by FACS ($\times 10^{-9}$ $M^{-1}$) | | | |
|---|---|---|---|---|---|---|
| | | | C1 | CD | DC | D |
| 4C4 | HN1 | DQGGGTVVKENWFDP (SEQ ID NO: 423) | 3.0 | + | 0.58 | + |
| 4C4.1 | HN1 | DQGGGTVVKENWFDP (SEQ ID NO: 423) | 1.5 | + | 0.06 | + |
| 4C4.2 | HN1 | DQGGGTVVKENWFDP (SEQ ID NO: 423) | 1.1 | + | 0.13 | + |
| 4C10 | LC1 | DRWRSGSYPAFEK (SEQ ID NO: 429) | 1.1 | + | 107 | + |
| 4C10.1 | LC1 | DRWRSGSYPAFEK (SEQ ID NO: 429) | 0.45 | + | + | + |
| 4C10.2 | LC1 | DRWRSGSYPAFEK (SEQ ID NO: 429) | 0.27 | + | 0.89 | + |
| 8DC1 | HN2 | STRGPFDI (SEQ ID NO: 430) | 11 | + | 5.2 | + |
| 8DC1.2 | HN2 | STRGPFDI (SEQ ID NO: 430) | 0.46 | + | 0.16 | + |
| 8DC4 | HN2 | ERLPPGRGYDMDV (SEQ ID NO: 433) | 3.0 | + | 39 | + |
| 8DC4.1 | HN2 | ERLPPGRGYDMDV (SEQ ID NO: 433) | 1.6 | + | 0.85 | + |
| 8DC4.2 | HN2 | ERLPPGRGYDMDV (SEQ ID NO: 433) | 1.5 | + | >20 | + |
| 1C1 | HN | TKMGAAEGVFDY (SEQ ID NO: 414) | 0.5 | − | − | − |
| 1C1.1 | HN | TKMGAAEGVFDY (SEQ ID NO: 414) | 0.15 | − | − | − |
| 1C2 | LCHN | GGLPYQQLPL (SEQ ID NO: 415) | 24 | − | − | − |
| 1C8 | LCHN | GATNIPYGMSV (SEQ ID NO: 416) | 42 | − | >200 | − |
| 87C1 | LC1 | AIKSYSTIGGACNL (SEQ ID NO: 417) | 2.0 | + | − | − |
| 87C2 | LC1 | TLKFGLNYMDV (SEQ ID NO: 418) | 7.0 | − | − | − |
| 87C78 | LCHN | AIKAFRPVPPSFHMDV (SEQ ID NO: 419) | 1.0 | + | − | − |
| 4C1 | LC1 | GQDTSMVTRNFYYGLDV (SEQ ID NO: 420) | 2.7 | + | − | − |
| 4C2 | HC | ETWEVLGHLGYEVLDH (SEQ ID NO: 421) | 0.19 | − | 0.5 | − |
| 4C3 | LC1 | GAFTNYPF (SEQ ID NO: 422) | 4.7 | + | − | − |
| 4C5 | LC1 | VKLTTMVRGGPFDY (SEQ ID NO: 424) | 0.14 | + | − | − |
| 4C7 | LC | AIKGYSSRPVRAYEM (SEQ ID NO: 435) | 64 | − | − | − |
| 4C8 | LC | GGKYSNSSAMYQ (SEQ ID NO: 427) | 51 | − | − | − |
| 4C9 | LC1 | SVSGGAFDL (SEQ ID NO: 428) | 30 | + | − | − |
| 8DC2 | HC | GTRNGSLRDAFDI (SEQ ID NO: 431) | 0.2 | − | 0.5 | − |
| 8DC3 | HC | GDHDFRSGYYGMDV (SEQ ID NO: 432) | − | − | 16.5 | + |

TABLE 9-continued

Characteristics of lead yeast displayed scFv BoNT/C, CD, DC, D antibodies scFv $K_D$ measured on yeast displayed scFv. + means the lead scFv has good binding with the tested serotype or mosiac, − means the lead does not react with the tested serotype or mosiac at the maximum concentration used for testing (~1 µM).

| Clone | Epitope | $V_H$ CDR3 Sequence | BoNT ScFv $K_D$ by FACS ($\times 10^{-9}$ M$^{-1}$) | | | |
|---|---|---|---|---|---|---|
| | | | C1 | CD | DC | D |
| 8DC3.1 | HC | DQGGGSVVGTNWFDP (SEQ ID NO: 436) | − | − | 2.4 | + |
| 8DC5 | LC2 | GGFWGTWRDNMDV (SEQ ID NO: 434) | − | − | 15 | + |
| 8DC6 | LC2 | GGYYTRPLAFDT (SEQ ID NO: 437) | − | − | 43 | + |
| 8DC7 | HC | EGQLDSKYYFDS (SEQ ID NO: 438) | − | − | 16 | + |
| 8DC8 | HC1 | VYPGWFYS (SEQ ID NO: 439) | − | − | 7.3 | 7.1 |
| 8DC8.3 | HC1 | VVGVYPGWFDS (SEQ ID NO: 440) | − | − | 0.85 | + |
| 8DC8.6 | HC1 | VVGVYPGWFDS (SEQ ID NO: 440) | − | − | 1.21 | + |
| 8DC9 | | EGSYIDSFDM (SEQ ID NO: 441) | − | − | 7.6 | + |
| 8DC10 | LC2 | VYYYYGMDV (SEQ ID NO: 442) | − | − | 12 | + |
| 8DC11 | HC1 | EGARGYCSSTSCHDAFDI (SEQ ID NO: 443) | − | − | 20 | + |
| 8DC12 | LC2 | GEHFVVVTAFAT (SEQ ID NO: 444) | − | − | 73 | + |
| 8DC13 | LC2 | RRAVANLDYHYYGMDV (SEQ ID NO: 445) | − | − | 182 | + |
| 8DC14 | LC2 | ANYHFILATTFHS (SEQ ID NO: 446) | − | − | >200 | + |
| 8DC15 | HC | AIWGGYFDL (SEQ ID NO: 447) | 3.3 | − | >200 | − |
| 8D1 | | ILAGSWCFDL (SEQ ID NO: 448) | − | + | − | + |
| 8D2 | | YSSLDAFDI (SEQ ID NO: 449) | − | + | − | 23.8 |
| 8D2.1 | | YSSLDAFDI (SEQ ID NO: 449) | − | + | − | 1.95 |
| 8D2.3 | | YSSLDAFDI (SEQ ID NO: 449) | − | + | − | 2.31 |

The affinities and cross-reactivities of antibodies 4C4, 4C10, 8DC1, and 8DC4 were increased by using yeast-displayed mutant scFv libraries and selecting for higher affinity and better cross-reactivity using previously described methods (Garcia et al. (2007) Nat. Biotechnol. 25:107; Razai A. et al. (2005) J. Mol. Biol. 351:158-169. Lou J. et al. (2010) Protein Engineering, Design & Selection, 23(4):311-319). For each antibody, these initial efforts resulted in an increase in scFv affinity of at least 10-fold. For animal studies, scFv were converted to full length human IgG1 molecules which were expressed from CHO cells and purified using protein G. Solution affinities of the affinity matured antibodies (and in some instances the parental antibody) were measured by using flow fluorimetry (Table 10).

TABLE 10

Affinities of antibodies to BoNT/C, BoNT/CD, BoNT/DC and BoNT/D. + or +++ or ++++ means the lead scFv has good binding with the tested serotype or mosaic in FACS, but the MFI signal strength varies at the same test concentration. --- means the lead does not react with the tested serotype or mosaic at the maximum concentration used for testing(~1 µM). All the KD values were obtained with KinExA measurement using IgG format of the indicated mAb, except the clone 8DC4.

| Antibody | KD BoNT/C ($\times 10^{-12}$ M$^{-1}$) | Binds BoNT/CD | KD BoNT/DC ($\times 10^{-12}$ M$^{-1}$) | Binds BoNT/D |
|---|---|---|---|---|
| 4C4 | 835 | +++ | 577 | +++ |
| 4C4.1 | 539 | +++ | 58 | +++ |
| 4C4.2 | 35 | +++ | 126 | +++ |
| 4C10 | 401 | +++ | --- | +++ |
| 4C10.2 | 34 | ++++ | 892 | ++++ |
| 8DC1 | 1809 | +++ | 95 | +++ |
| 8DC1.2 | 736 | ++++ | 162 | ++++ |
| 8DC4 | 3000 (as scFv) | + | >20,000 (as scFv) | + |
| 8DC4.1 | 397 | +++ | 854 | +++ |
| 8DC2 | 15.7 | --- | 7.0 | --- |
| 4C2 | 6.99 | --- | 9.7 | --- |
| 87C78 | 0.41 | +++ | --- | --- |
| 1C1.1 | 0.41 | --- | --- | --- |

The ability of selected antibodies to protect mice against challenge with BoNT was evaluated in vivo using a standard mouse neutralization assay. As observed with other BoNT serotypes, single antibodies only protected mice against very low dose challenge with toxin. BoNT/C or BoNT/DC toxins were used for challenge as they were the only commercially available BoNT/C or BoNT/D serotypes. A combination of three antibodies binding BoNT/C with very high affinity (1C1.1:4 C2:4 C10, see affinities in Table 10) at a dose of 50 µg of total antibody completely protected mice against challenge with 20,000 mouse LD$_{50}$ of BoNT/C (Table 11). This combination was not evaluated on BoNT/DC, since one of these antibodies (1C1.1) did not bind BoNT/DC. Using combinations of four antibodies (among 4C2, 4C4.2, 8DC1.2, 4C10.2, and 8DC4.1) binding both BoNT/C, BoNT/D and their mosaic toxins, comparable potencies could be achieved against both BoNT/C and BoNT/DC (Table 11). Note that the cross-reactive antibodies are of lower affinity than 1C1.1 and 4C2, which potently neutralize BoNT/C in a three antibody combination.

TABLE 11

Protection of mice against intraperitoneal challenge with BoNT/C or BoNT/DC

| Constituent of 50 µg of total antibody treatment | number of mice surviving/ number of mice studied | |
|---|---|---|
| | 20,000 LD$_{50}$ BoNT/C | 20,000 LD$_{50}$ BoNT/DC |
| 1C1.1:4C2:4C10 | 10/10 | ND |
| 4C2:4C4.2:8DC1.2:4C10.2 | 4/10 | 9/10 |
| 4C2:4C4.2:8DC4.1:4C10.2 | 9/10 | 5/10 |

Example 10

Characterization of Antibodies to Type A Botulinum Neurotoxins

Antibodies grouped together are clonally related, differing primarily by affinity for the different toxin subtypes. Epitopes are indicated as toxin domain bound and by unique epitope number. Subtype cross reactivity is indicated. A1>>>A2, significantly higher affinity for BoNT/A1 compared to BoNT/A2; A2>>A1, significantly higher affinity for BoNT/A2 compared to BoNT/A1. Antibodies shown as 'binding' BoNT/A4 are assumed to bind based on identity of the epitope in BoNT/A4 compared to the other subtypes.

Species: M=mouse; H=human; HZ=humanized, AM=affinity matured; SP=specificity improved

TABLE 12

| Antibody | Species | Antigen | $K_D$ | On Rate | Off Rate | Epitope | Subtype specificity |
|---|---|---|---|---|---|---|---|
| A2S | H | A1 | 7.21 nM | $1.002e^6$ | $7.228e^{-3}$ | SA | A2 >> A1 |
| A2S |   | A2 | 77.75 pM | $1.253e^7$ | $9.739e^{-4}$ | SA | A2 >> A1 |
| A9 | H | A1 | 77.14 pM | $1.642e^6$ | $1.267e^{-4}$ | $H_{CC}$ epitope 2 | A1 = A2 |
| A9 |   | A2 | 223.3 pM | $7.604e^5$ | $1.698e^{-4}$ | SA | A1 = A2 |
| B4 | H | A1 | 93.1 pM | $3.078e^6$ | $2.865e^{-4}$ | $H_{CC}$ epitope 3 | A1 only |
| 4E17.1 | H/AM | A1 | 1.83 pM | $2.811e^6$ | $5.144e^{-6}$ | $H_N$ epitope 4 | A1 = A2 = A3 = A4 |
| 4E17.1 |   | A2 | 7.98 pM | $2.456e^6$ | $1.96e^{-5}$ | SA | A1 = A2 = A3 = A4 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

While the subject antibody, method, and composition have been particularly shown and described with references to preferred embodiments thereof, it will be understood by those skilled in the art that various changes in form and details may be made therein without departing from the scope of the invention encompassed by the appended claims.

---

What is claimed is:

1. An isolated antibody, or antigen-binding fragment thereof, that competes for binding with, or specifically binds an epitope of a Botulinum neurotoxin that is specifically bound by, an antibody comprising:
   a) a $V_H$ CDR1 comprising the amino acid sequence of residues 31-35 of SEQ ID NO:68;
   b) a $V_H$ CDR2 comprising the amino acid sequence of residues 50-66 of SEQ ID NO:68;
   c) a $V_H$ CDR3 comprising the amino acid sequence of residues 99-114 of SEQ ID NO:68;
   d) a $V_L$ CDR1 comprising the amino acid sequence of residues 24-34 of SEQ ID NO:205;
   e) a $V_L$ CDR2 comprising the amino acid sequence of residues 50-56 of SEQ ID NO:205; and
   f) a $V_L$ CDR3 comprising the amino acid sequence of residues 89-97 of SEQ ID NO:205.

2. The isolated antibody, or antigen-binding fragment thereof, of claim 1, wherein said antibody, or antigen-binding fragment thereof, specifically binds an epitope of a Botulinum neurotoxin that is specifically bound by an antibody comprising:
   a) a $V_H$ CDR1 comprising the amino acid sequence of residues 31-35 of SEQ ID NO:68;
   b) a $V_H$ CDR2 comprising the amino acid sequence of residues 50-66 of SEQ ID NO:68;
   c) a $V_H$ CDR3 comprising the amino acid sequence of residues 99-114 of SEQ ID NO:68;
   d) a $V_L$ CDR1 comprising the amino acid sequence of residues 24-34 of SEQ ID NO:205;
   e) a $V_L$ CDR2 comprising the amino acid sequence of residues 50-56 of SEQ ID NO:205; and
   f) a $V_L$ CDR3 comprising the amino acid sequence of residues 89-97 of SEQ ID NO:205.

3. The isolated antibody, or antigen-binding fragment thereof, of claim 1, wherein said antibody, or antigen-binding fragment thereof, is a humanized antibody.

4. The isolated antibody, or antigen-binding fragment thereof, of claim 1, wherein said antibody is a single chain Fv (scFv), IgG, Fab, (Fab)$_2$, or (scFv')$_2$.

5. The isolated antibody, or antigen-binding fragment thereof, of claim 1, wherein said antibody, or antigen-binding fragment thereof, is a human monoclonal antibody.

6. The isolated antibody, or antigen-binding fragment thereof, of claim 1, wherein said antibody, or antigen-binding fragment thereof, comprises:
   a) a $V_H$ CDR1 comprising the amino acid sequence of residues 31-35 of SEQ ID NO:68;
   b) a $V_H$ CDR2 comprising the amino acid sequence of residues 50-66 of SEQ ID NO:68;
   c) a $V_H$ CDR3 comprising the amino acid sequence of residues 99-114 of SEQ ID NO:68;
   d) a $V_L$ CDR1 comprising the amino acid sequence of residues 24-34 of SEQ ID NO:205;
   e) a $V_L$ CDR2 comprising the amino acid sequence of residues 50-56 of SEQ ID NO:205; and
   f) a $V_L$ CDR3 comprising the amino acid sequence of residues 89-97 of SEQ ID NO:205.

7. The isolated antibody, or antigen-binding fragment thereof, of claim 1, wherein said antibody competes for binding to a Botulinum neurotoxin with an antibody comprising:
   a) a $V_H$ CDR1 comprising the amino acid sequence of residues 31-35 of SEQ ID NO:68;
   b) a $V_H$ CDR2 comprising the amino acid sequence of residues 50-66 of SEQ ID NO:68;
   c) a $V_H$ CDR3 comprising the amino acid sequence of residues 99-114 of SEQ ID NO:68;
   d) a $V_L$ CDR1 comprising the amino acid sequence of residues 24-34 of SEQ ID NO:205;
   e) a $V_L$ CDR2 comprising the amino acid sequence of residues 50-56 of SEQ ID NO:205; and
   f) a $V_L$ CDR3 comprising the amino acid sequence of residues 89-97 of SEQ ID NO:205.

8. A composition comprising:
a pharmaceutically acceptable carrier; and
the antibody, or antigen-binding fragment thereof, according to claim 1.

9. A kit comprising a composition of claim 8.

10. A method for detecting Botulinum neurotoxin in a sample, comprising:
contacting an antibody, or antigen-binding fragment thereof, of claim 1 with the sample,
detecting binding of said antibody to Botulinum neurotoxin in said sample.

11. The method of claim 10, wherein said antibody is labeled.

12. The method of claim 11, wherein said label is a fluorescent label, a chemiluminescent label, a radiolabel, an enzyme, or a chromogenic label.

13. The method of claim 10, wherein said sample is blood.

14. The method of claim 10, wherein said antibody is immobilized on a substrate.

15. The method of claim 10, wherein said antibody is conjugated to a nucleic acid and wherein said detecting comprises a polymerase chain reaction.

16. A method of reducing the likelihood that an individual at risk of exposure to Botulinum neurotoxin will experience symptoms of Botulinum neurotoxin poisoning following exposure, the method comprising administering to said individual an effective amount of an antibody of claim 1;
   wherein said administering provides for reducing the likelihood that the individual will experience symptoms of Botulinum neurotoxin poisoning.

17. The isolated antibody or antigen-binding fragment of claim 1, wherein said antibody comprises:
a heavy chain comprising the amino acid sequence of SEQ ID NO:68.

18. The isolated antibody or antigen-binding fragment of claim 1, wherein said antibody comprises:
a light chain comprising the amino acid sequence of SEQ ID NO:205.

19. The isolated antibody or antigen-binding fragment of claim 1, wherein said antibody comprises:
a) a heavy chain comprising the amino acid sequence of SEQ ID NO:68; and
b) a light chain comprising the amino acid sequence of SEQ ID NO:205.

20. The isolated antibody or antigen-binding fragment of claim 19, wherein said antibody is a human monoclonal antibody.

21. The isolated antibody or antigen-binding fragment of claim 19, wherein said antibody is a single chain Fv (scFv), Fab, (Fab')$_2$ or (scFv')$_2$.

22. The isolated antibody or antigen-binding fragment of claim 1, wherein said antibody is an IgG.

23. The isolated antibody or antigen-binding fragment of claim 19, wherein said antibody is an IgG.

* * * * *